US012336796B2

(12) United States Patent
Al-Ali et al.

(10) Patent No.: US 12,336,796 B2
(45) Date of Patent: Jun. 24, 2025

(54) WEARABLE DEVICE WITH PHYSIOLOGICAL PARAMETERS MONITORING

(71) Applicant: Masimo Corporation, Irvine, CA (US)

(72) Inventors: Ammar Al-Ali, San Juan Capistrano, CA (US); Stephen Scruggs, Newport Beach, CA (US); Richard Priddell, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 338 days.

(21) Appl. No.: 17/812,104

(22) Filed: Jul. 12, 2022

(65) Prior Publication Data
US 2023/0028745 A1    Jan. 26, 2023

Related U.S. Application Data

(60) Provisional application No. 63/252,893, filed on Oct. 6, 2021, provisional application No. 63/230,239, filed
(Continued)

(51) Int. Cl.
*A61B 5/024*    (2006.01)
*A61B 5/00*    (2006.01)
*A61B 5/1455*    (2006.01)

(52) U.S. Cl.
CPC ........ *A61B 5/02427* (2013.01); *A61B 5/6824* (2013.01)

(58) Field of Classification Search
CPC ..... A61B 5/0022; A61B 5/08; A61B 2503/06; A61B 2560/0242; A61B 2560/0252;
(Continued)

(56) References Cited

U.S. PATENT DOCUMENTS 3,139,086 A    6/1964    Botsch et al.
3,452,215 A    6/1969    Alessio
(Continued)

FOREIGN PATENT DOCUMENTS

AU    7426381    2/1983
AU    2014200060    10/2016
(Continued)

OTHER PUBLICATIONS

US 2022/0192529 A1, 06/2022, Al-Ali et al. (withdrawn)
(Continued)

*Primary Examiner* — Jon Eric C Morales
(74) *Attorney, Agent, or Firm* — Knobbe, Martens, Olson & Bear, LLP

(57) ABSTRACT

An optical physiological sensor can be integrated into a wearable device and can comprise a substrate having an optical center, a first emitter group of light emitting diodes (LEDs) positioned adjacent to the optical center of the substrate and spaced at an offset from the optical center, a second emitter group of LEDs positioned adjacent to the optical center of the substrate at an offset to the optical center and spaced at an offset from the optical center opposite the first emitter group of LEDs relative to the optical center, and a plurality of detectors arranged in a spatial configuration that surrounds the first and the second emitter group. Each of the plurality of detectors can be positioned on the substrate a same distance away from the optical center of the substrate.

28 Claims, 82 Drawing Sheets

Related U.S. Application Data on Aug. 6, 2021, provisional application No. 63/221,385, filed on Jul. 13, 2021.

(58) Field of Classification Search
CPC ..... A61B 2562/029; A61B 5/002; A61B 5/01; A61B 5/0205; A61B 5/02438; A61B 5/0816; A61B 5/1112; A61B 5/1123; A61B 5/117; A61B 5/14551; A61B 5/486; A61B 5/6898; A61B 5/7264; A61B 5/7267; A61B 5/7282; A61B 5/746; A61B 5/7465; A61B 2505/07; A61B 5/00; A61B 5/0008; A61B 5/021; A61B 5/024; A61B 5/103; A61B 5/14532; A61B 5/4803; A61B 5/4875; G16H 50/30; G16H 40/63; G16H 40/67; G16H 50/20; G06F 1/163
See application file for complete search history.

(56) References Cited

U.S. PATENT DOCUMENTS

| | | |
|---|---|---|
| 3,514,538 A | 5/1970 | Chadwick et al. |
| 3,535,067 A | 10/1970 | Lesher et al. |
| 3,638,640 A | 2/1972 | Shaw |
| 3,704,706 A | 12/1972 | Herczfeld et al. |
| 3,742,937 A | 7/1973 | Manuel et al. |
| 3,760,582 A | 9/1973 | Thiess et al. |
| 3,769,974 A | 11/1973 | Smart et al. |
| 3,789,601 A | 2/1974 | Bergey |
| 3,835,837 A | 9/1974 | Peek |
| 3,863,626 A | 2/1975 | Huber |
| 3,908,636 A | 9/1975 | Page |
| 3,910,701 A | 10/1975 | Henderson et al. |
| 3,978,849 A | 9/1976 | Geneen |
| 4,009,708 A | 3/1977 | Fay, Jr. |
| 4,015,595 A | 4/1977 | Benjamin |
| 4,030,483 A | 6/1977 | Stevens |
| 4,038,976 A | 8/1977 | Hardy et al. |
| 4,063,551 A | 12/1977 | Sweeny |
| 4,086,916 A | 5/1978 | Freeman et al. |
| 4,120,294 A | 10/1978 | Wolfe |
| 4,129,124 A | 12/1978 | Thalmann |
| 4,163,447 A | 8/1979 | Orr |
| 4,216,462 A | 8/1980 | McGrath et al. |
| 4,224,948 A | 9/1980 | Cramer et al. |
| 4,230,127 A | 10/1980 | Larson |
| 4,248,244 A | 2/1981 | Charnitski et al. |
| 4,295,472 A | 10/1981 | Adams |
| 4,375,219 A | 3/1983 | Schmid |
| 4,404,942 A | 9/1983 | Asami |
| 4,404,972 A | 9/1983 | Gordon et al. |
| 4,409,470 A | 10/1983 | Shepard et al. |
| 4,414,980 A | 11/1983 | Mott |
| 4,447,150 A | 5/1984 | Heinemann |
| 4,448,199 A | 5/1984 | Schmid |
| 4,541,439 A | 9/1985 | Hon |
| 4,547,075 A | 10/1985 | Fei |
| 4,606,352 A | 8/1986 | Geddes et al. |
| 4,621,643 A | 11/1986 | New, Jr. et al. |
| 4,625,733 A | 12/1986 | Saynajakangas |
| 4,635,646 A | 1/1987 | Gilles et al. |
| 4,648,892 A | 3/1987 | Kittrell et al. |
| 4,700,708 A | 10/1987 | New, Jr. et al. |
| 4,750,495 A | 6/1988 | Moore et al. |
| 4,759,369 A | 7/1988 | Taylor |
| 4,802,486 A | 2/1989 | Goodman et al. |
| 4,819,860 A | 4/1989 | Hargrove et al. |
| 4,827,943 A | 5/1989 | Bornn et al. |
| 4,859,057 A | 8/1989 | Taylor et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,880,304 A | 11/1989 | Jaeb et al. |
| 4,890,619 A | 1/1990 | Hatschek |
| 4,892,101 A | 1/1990 | Cheung et al. |
| 4,903,701 A | 2/1990 | Moore et al. |
| 4,928,692 A | 5/1990 | Goodman et al. |
| 4,933,545 A | 6/1990 | Saaski et al. |
| 4,938,218 A | 7/1990 | Goodman et al. |
| 4,941,236 A | 7/1990 | Sherman et al. |
| 4,945,239 A | 7/1990 | Wist et al. |
| 4,955,379 A | 9/1990 | Hall |
| 4,960,128 A | 10/1990 | Gordon et al. |
| 4,960,314 A | 10/1990 | Smith et al. |
| 4,964,408 A | 10/1990 | Hink et al. |
| 5,007,423 A | 4/1991 | Branstetter et al. |
| 5,014,703 A | 5/1991 | Alt |
| 5,025,791 A | 6/1991 | Niwa |
| 5,052,388 A | 10/1991 | Sivula et al. |
| 5,058,203 A | 10/1991 | Inagami |
| 5,069,214 A | 12/1991 | Samaras et al. |
| 5,069,680 A | 12/1991 | Grandjean |
| 5,099,842 A | 3/1992 | Mannheimer et al. |
| 5,137,364 A | 8/1992 | McCarthy |
| 5,158,082 A | 10/1992 | Jones |
| 5,158,091 A | 10/1992 | Butterfield et al. |
| 5,176,137 A | 1/1993 | Erickson et al. |
| 5,184,620 A | 2/1993 | Cudahy et al. |
| 5,190,038 A | 3/1993 | Polson et al. |
| 5,191,891 A | 3/1993 | Righter |
| 5,203,329 A | 4/1993 | Takatani et al. |
| 5,209,230 A | 5/1993 | Swedlow et al. |
| 5,218,962 A | 6/1993 | Mannheimer et al. |
| 5,228,449 A | 7/1993 | Christ et al. |
| 5,251,011 A | 10/1993 | Fujiwara et al. |
| 5,254,388 A | 10/1993 | Melby et al. |
| 5,254,992 A | 10/1993 | Keen et al. |
| 5,259,381 A | 11/1993 | Cheung et al. |
| 5,299,570 A | 4/1994 | Hatschek |
| 5,316,008 A | 5/1994 | Suga et al. |
| 5,319,355 A | 6/1994 | Russek |
| 5,323,309 A | 6/1994 | Taylor et al. |
| 5,334,916 A | 8/1994 | Noguchi |
| 5,337,744 A | 8/1994 | Branigan |
| 5,341,805 A | 8/1994 | Stavridi et al. |
| 5,342,404 A | 8/1994 | Alt et al. |
| 5,350,412 A | 9/1994 | Hoegnelid et al. |
| 5,351,695 A | 10/1994 | Mills et al. |
| 5,358,519 A | 10/1994 | Grandjean |
| 5,365,924 A | 11/1994 | Erdman |
| 5,368,224 A | 11/1994 | Richardson et al. |
| D353,195 S | 12/1994 | Savage et al. |
| D353,196 S | 12/1994 | Savage et al. |
| 5,372,135 A | 12/1994 | Mendelson et al. |
| 5,377,676 A | 1/1995 | Vari et al. |
| 5,413,100 A | 5/1995 | Barthelemy et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,461,365 A | 10/1995 | Schlager et al. |
| 5,462,051 A | 10/1995 | Oka et al. |
| 5,477,853 A | 12/1995 | Farkas et al. |
| 5,479,934 A | 1/1996 | Imran |
| 5,482,036 A | 1/1996 | Diab et al. |
| 5,490,505 A | 2/1996 | Diab et al. |
| 5,490,523 A | 2/1996 | Isaacson et al. |
| 5,494,043 A | 2/1996 | O'Sullivan et al. |
| 5,497,771 A | 3/1996 | Rosenheimer |
| 5,533,511 A | 7/1996 | Kaspari et al. |
| 5,542,146 A | 8/1996 | Hoekstra et al. |
| 5,544,661 A | 8/1996 | Davis et al. |
| 5,555,882 A | 9/1996 | Richardson et al. |
| 5,561,275 A | 10/1996 | Savage et al. |
| 5,564,429 A | 10/1996 | Bornn et al. |
| 5,581,069 A | 12/1996 | Shepard et al. |
| 5,584,296 A | 12/1996 | Cui et al. |
| 5,590,649 A | 1/1997 | Caro et al. |
| 5,601,079 A | 2/1997 | Wong et al. |
| 5,602,924 A | 2/1997 | Durand et al. |
| 5,610,590 A | 3/1997 | Johnson et al. |

(56) References Cited

U.S. PATENT DOCUMENTS

| | | |
|---|---|---|
| 5,623,432 A | 4/1997 | Degrauwe |
| 5,623,925 A | 4/1997 | Swenson et al. |
| 5,623,926 A | 4/1997 | Weiss |
| 5,626,620 A | 5/1997 | Kieval et al. |
| 5,632,272 A | 5/1997 | Diab et al. |
| 5,635,700 A | 6/1997 | Fazekas |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,673,692 A | 10/1997 | Shulze et al. |
| 5,699,808 A | 12/1997 | John |
| 5,702,429 A | 12/1997 | King |
| 5,719,557 A | 2/1998 | Rattman et al. |
| 5,720,284 A | 2/1998 | Aoyagi et al. |
| 5,726,440 A | 3/1998 | Kalkhoran et al. |
| 5,729,203 A | 3/1998 | Oka et al. |
| D393,830 S | 4/1998 | Tobler et al. |
| 5,738,104 A | 4/1998 | Lo et al. |
| 5,743,262 A | 4/1998 | Lepper, Jr. et al. |
| 5,746,697 A | 5/1998 | Swedlow et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,782,756 A | 7/1998 | Mannheimer |
| 5,782,757 A | 7/1998 | Diab et al. |
| 5,792,052 A | 8/1998 | Isaacson et al. |
| 5,797,841 A | 8/1998 | Delonzor et al. |
| 5,800,348 A | 9/1998 | Kaestle |
| 5,800,349 A | 9/1998 | Isaacson et al. |
| 5,817,008 A | 10/1998 | Rafert et al. |
| 5,830,137 A | 11/1998 | Scharf |
| 5,838,451 A | 11/1998 | McCarthy |
| 5,854,706 A | 12/1998 | Alb |
| 5,860,932 A | 1/1999 | Goto et al. |
| 5,867,561 A | 2/1999 | Strasser et al. |
| 5,890,929 A | 4/1999 | Mills et al. |
| 5,893,364 A | 4/1999 | Haar et al. |
| 5,911,689 A | 6/1999 | Smith et al. |
| 5,916,155 A | 6/1999 | Levinson et al. |
| 5,919,134 A | 7/1999 | Diab |
| 5,923,021 A | 7/1999 | Dvorkis et al. |
| 5,924,979 A | 7/1999 | Swedlow et al. |
| 5,936,986 A | 8/1999 | Cantatore et al. |
| 5,952,084 A | 9/1999 | Anderson et al. |
| 5,957,861 A | 9/1999 | Combs et al. |
| 5,963,333 A | 10/1999 | Walowit et al. |
| 5,964,701 A | 10/1999 | Asada et al. |
| 5,983,122 A | 11/1999 | Jarman et al. |
| 5,987,343 A | 11/1999 | Kinast |
| 5,991,467 A | 11/1999 | Kamiko |
| 5,997,343 A | 12/1999 | Mills et al. |
| 6,002,952 A | 12/1999 | Diab et al. |
| 6,005,658 A | 12/1999 | Kaluza et al. |
| 6,010,937 A | 1/2000 | Karam et al. |
| 6,014,576 A | 1/2000 | Raley |
| 6,018,403 A | 1/2000 | Shirakura et al. |
| 6,022,321 A | 2/2000 | Amano et al. |
| 6,027,452 A | 2/2000 | Flaherty et al. |
| 6,030,343 A | 2/2000 | Chechersky et al. |
| 6,035,223 A | 3/2000 | Baker |
| 6,040,578 A | 3/2000 | Malin et al. |
| 6,041,247 A | 3/2000 | Weckstrom et al. |
| 6,058,331 A | 5/2000 | King |
| 6,066,204 A | 5/2000 | Haven |
| 6,069,653 A | 5/2000 | Hudson |
| 6,070,092 A | 5/2000 | Kazama et al. |
| 6,075,755 A | 6/2000 | Zarchan |
| 6,083,156 A | 7/2000 | Lisiccki |
| 6,091,530 A | 7/2000 | Duckworth |
| 6,093,146 A | 7/2000 | Filangeri et al. |
| 6,102,856 A | 8/2000 | Groff et al. |
| 6,108,571 A | 8/2000 | Minoz et al. |
| 6,115,673 A | 9/2000 | Malin et al. |
| 6,124,597 A | 9/2000 | Shehada et al. |
| 6,126,595 A | 10/2000 | Amano et al. |
| 6,128,521 A | 10/2000 | Marro et al. |
| 6,129,675 A | 10/2000 | Jay |
| 6,133,871 A | 10/2000 | Krasner |
| 6,144,868 A | 11/2000 | Parker |
| 6,147,618 A | 11/2000 | Halleck et al. |
| 6,152,754 A | 11/2000 | Gerhardt et al. |
| 6,158,245 A | 12/2000 | Savant |
| 6,167,303 A | 12/2000 | Thompson |
| 6,178,343 B1 | 1/2001 | Bindszus et al. |
| 6,184,521 B1 | 2/2001 | Coffin, IV et al. |
| 6,185,454 B1 | 2/2001 | Thompson |
| 6,198,951 B1 | 3/2001 | Kosuda et al. |
| 6,212,210 B1 | 4/2001 | Serizawa |
| 6,212,641 B1 | 4/2001 | Frank et al. |
| 6,223,063 B1 | 4/2001 | Chaiken et al. |
| 6,226,539 B1 | 5/2001 | Potratz |
| 6,232,609 B1 | 5/2001 | Snyder et al. |
| 6,241,680 B1 | 6/2001 | Miwa |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,265,789 B1 | 7/2001 | Honda et al. |
| 6,270,223 B1 | 8/2001 | Del Bon et al. |
| 6,278,889 B1 | 8/2001 | Robinson |
| 6,280,381 B1 | 8/2001 | Malin et al. |
| 6,285,896 B1 | 9/2001 | Tobler et al. |
| 6,293,915 B1 | 9/2001 | Amano et al. |
| 6,297,906 B1 | 10/2001 | Allen et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,330,468 B1 | 12/2001 | Scharf |
| 6,331,063 B1 | 12/2001 | Kamada et al. |
| 6,334,065 B1 | 12/2001 | Al-Ali et al. |
| 6,343,223 B1 | 1/2002 | Chin et al. |
| 6,351,217 B1 | 2/2002 | Kuhn |
| 6,356,203 B1 | 3/2002 | Halleck et al. |
| 6,356,774 B1 | 3/2002 | Bernstein et al. |
| 6,360,114 B1 | 3/2002 | Diab et al. |
| 6,368,283 B1 | 4/2002 | Xu et al. |
| 6,374,311 B1 | 4/2002 | Mahany et al. |
| 6,393,311 B1 | 5/2002 | Edgar et al. |
| 6,396,873 B1 | 5/2002 | Goldstein et al. |
| 6,398,727 B1 | 6/2002 | Bui et al. |
| 6,402,690 B1 | 6/2002 | Rhee et al. |
| 6,411,373 B1 | 6/2002 | Garside et al. |
| 6,415,166 B1 | 7/2002 | Van hoy et al. |
| 6,415,167 B1 | 7/2002 | Blank et al. |
| 6,430,423 B2 | 8/2002 | DeLonzor et al. |
| 6,430,437 B1 | 8/2002 | Marro |
| 6,430,525 B1 | 8/2002 | Weber et al. |
| 6,434,421 B1 | 8/2002 | Taheri |
| 6,449,509 B1 | 9/2002 | Park et al. |
| 6,463,311 B1 | 10/2002 | Diab |
| 6,470,199 B1 | 10/2002 | Kopotic et al. |
| 6,473,008 B2 | 10/2002 | Kelly et al. |
| 6,483,976 B2 | 11/2002 | Shie et al. |
| 6,487,429 B2 | 11/2002 | Hockersmith et al. |
| 6,491,639 B1 | 12/2002 | Turcott |
| 6,505,059 B1 | 1/2003 | Kollias et al. |
| 6,505,061 B2 | 1/2003 | Larson |
| 6,522,915 B1 | 2/2003 | Ceballos et al. |
| 6,522,926 B1 | 2/2003 | Kieval et al. |
| 6,525,386 B1 | 2/2003 | Mills et al. |
| 6,526,300 B1 | 2/2003 | Kiani et al. |
| 6,527,711 B1 | 3/2003 | Stivoric et al. |
| 6,527,729 B1 | 3/2003 | Turcott |
| 6,529,754 B2 | 3/2003 | Kondo |
| 6,534,012 B1 | 3/2003 | Hazen et al. |
| 6,542,764 B1 | 4/2003 | Al-Ali et al. |
| 6,553,242 B1 | 4/2003 | Sarussi |
| 6,556,852 B1 | 4/2003 | Schulz et al. |
| 6,560,352 B2 | 5/2003 | Rowe et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |

(56) References Cited

U.S. PATENT DOCUMENTS

| | | |
|---|---|---|
| 6,595,316 B2 | 7/2003 | Cybulski et al. |
| 6,596,016 B1 | 7/2003 | Vreman et al. |
| 6,597,932 B2 | 7/2003 | Tian et al. |
| 6,605,045 B2 | 8/2003 | Ohsaki et al. |
| 6,606,511 B1 | 8/2003 | Ali et al. |
| 6,608,562 B1 | 8/2003 | Kimura et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,526 B1 | 12/2003 | Aoyagi et al. |
| 6,675,031 B1 | 1/2004 | Porges et al. |
| 6,697,656 B1 | 2/2004 | Al-Ali |
| 6,697,658 B2 | 2/2004 | Al-Ali |
| RE38,476 E | 3/2004 | Diab et al. |
| 6,707,476 B1 | 3/2004 | Hochstedler |
| 6,711,691 B1 | 3/2004 | Howard et al. |
| 6,714,803 B1 | 3/2004 | Mortz |
| RE38,492 E | 4/2004 | Diab et al. |
| 6,738,652 B2 | 5/2004 | Mattu et al. |
| 6,760,607 B2 | 7/2004 | Al-Ali |
| 6,775,566 B2 | 8/2004 | Nissilä |
| 6,785,568 B2 | 8/2004 | Chance |
| 6,788,965 B2 | 9/2004 | Ruchti et al. |
| 6,801,798 B2 | 10/2004 | Geddes et al. |
| 6,801,799 B2 | 10/2004 | Mendelson |
| 6,815,694 B2 | 11/2004 | Sfez et al. |
| 6,816,241 B2 | 11/2004 | Grubisic |
| 6,822,564 B2 | 11/2004 | Al-Ali |
| 6,831,266 B2 | 12/2004 | Paritsky et al. |
| 6,843,771 B2 | 1/2005 | Lo et al. |
| 6,847,836 B1 | 1/2005 | Sujdak |
| 6,850,787 B2 | 2/2005 | Weber et al. |
| 6,850,788 B2 | 2/2005 | Al-Ali |
| 6,853,304 B2 | 2/2005 | Reisman |
| 6,871,089 B2 | 3/2005 | Korzinov et al. |
| 6,876,931 B2 | 4/2005 | Lorenz et al. |
| 6,889,153 B2 | 5/2005 | Dietiker |
| 6,920,345 B2 | 7/2005 | Al-Ali et al. |
| 6,922,241 B2 | 7/2005 | Kramer |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,982,930 B1 | 1/2006 | Hung |
| 6,985,764 B2 | 1/2006 | Mason et al. |
| 6,990,364 B2 | 1/2006 | Ruchti et al. |
| 6,998,247 B2 | 2/2006 | Monfre et al. |
| 6,999,685 B1 | 2/2006 | Kawase et al. |
| 7,003,338 B2 | 2/2006 | Weber et al. |
| 7,008,380 B1 | 3/2006 | Rees et al. |
| 7,015,451 B2 | 3/2006 | Dalke et al. |
| 7,018,338 B2 | 3/2006 | Vetter et al. |
| 7,019,338 B1 | 3/2006 | Ballon |
| 7,027,849 B2 | 4/2006 | Al-Ali |
| 7,031,728 B2 | 4/2006 | Beyer, Jr. |
| 7,035,736 B2 | 4/2006 | Nissila |
| 7,060,963 B2 | 6/2006 | Maegawa et al. |
| 7,072,700 B2 | 7/2006 | Yamamoto et al. |
| D526,719 S | 8/2006 | Richie, Jr. et al. |
| 7,088,040 B1 | 8/2006 | Ducharme et al. |
| 7,092,735 B2 | 8/2006 | Osann, Jr. |
| 7,096,052 B2 | 8/2006 | Mason et al. |
| 7,096,054 B2 | 8/2006 | Abdul-Hafiz et al. |
| 7,107,706 B1 | 9/2006 | Bailey, Sr. et al. |
| D529,616 S | 10/2006 | Deros et al. |
| 7,130,672 B2 | 10/2006 | Pewzner et al. |
| 7,133,710 B2 | 11/2006 | Acosta et al. |
| 7,142,901 B2 | 11/2006 | Kiani et al. |
| 7,155,273 B2 | 12/2006 | Taylor |
| 7,171,251 B2 | 1/2007 | Sarussi et al. |
| 7,190,986 B1 | 3/2007 | Hannula et al. |
| 7,225,006 B2 | 5/2007 | Al-Ali et al. |
| RE39,672 E | 6/2007 | Shehada et al. |
| 7,227,156 B2 | 6/2007 | Colvin, Jr. et al. |
| 7,251,513 B2 | 7/2007 | Kondoh et al. |
| 7,252,385 B2 | 8/2007 | Engle et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,261,690 B2 | 8/2007 | Teller et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,285,090 B2 | 10/2007 | Stivoric et al. |
| 7,289,835 B2 | 10/2007 | Mansfield et al. |
| 7,292,883 B2 | 11/2007 | De Felice et al. |
| 7,315,632 B2 | 1/2008 | Spycher et al. |
| 7,341,559 B2 | 3/2008 | Schulz et al. |
| 7,341,560 B2 | 3/2008 | Henderson et al. |
| 7,343,186 B2 | 3/2008 | Lamego et al. |
| D566,282 S | 4/2008 | Al-Ali et al. |
| 7,355,284 B2 | 4/2008 | Negley |
| 7,356,365 B2 | 4/2008 | Schurman |
| 7,371,981 B2 | 5/2008 | Abdul-Hafiz |
| 7,372,778 B2 | 5/2008 | Klopfenstein et al. |
| 7,373,193 B2 | 5/2008 | Al-Ali et al. |
| 7,377,794 B2 | 5/2008 | Al-Ali et al. |
| 7,378,647 B2 | 5/2008 | Nishikawa et al. |
| 7,383,105 B2 | 6/2008 | Conroy |
| 7,385,874 B2 | 6/2008 | Vuilleumier et al. |
| 7,395,104 B2 | 7/2008 | Mouradian et al. |
| 7,395,158 B2 | 7/2008 | Monfre et al. |
| 7,399,277 B2 | 7/2008 | Saidara et al. |
| 7,415,297 B2 | 8/2008 | Al-Ali et al. |
| 7,415,298 B2 | 8/2008 | Casciani et al. |
| 7,438,683 B2 | 10/2008 | Al-Ali et al. |
| 7,455,423 B2 | 11/2008 | Takenaka |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,502,643 B2 | 3/2009 | Farringdon et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,327 B2 | 4/2009 | White |
| 7,519,406 B2 | 4/2009 | Blank et al. |
| D592,507 S | 5/2009 | Wachman et al. |
| 7,530,942 B1 | 5/2009 | Diab |
| 7,558,622 B2 | 7/2009 | Tran |
| 7,572,508 B2 | 8/2009 | Lutz et al. |
| 7,593,230 B2 | 9/2009 | Abul-Haj et al. |
| 7,596,398 B2 | 9/2009 | Al-Ali et al. |
| 7,601,123 B2 | 10/2009 | Tweed et al. |
| 7,606,608 B2 | 10/2009 | Blank et al. |
| 7,613,490 B2 | 11/2009 | Sarussi et al. |
| 7,613,504 B2 | 11/2009 | Rowe |
| 7,620,212 B1 | 11/2009 | Allen et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| D608,225 S | 1/2010 | Giroud |
| 7,647,083 B2 | 1/2010 | Al-Ali et al. |
| D609,193 S | 2/2010 | Al-Ali et al. |
| 7,656,393 B2 | 2/2010 | King et al. |
| 7,658,613 B1 | 2/2010 | Griffin et al. |
| 7,676,253 B2 | 3/2010 | Raridan, Jr. |
| 7,682,070 B2 | 3/2010 | Burton |
| 7,683,926 B2 | 3/2010 | Schechterman et al. |
| D614,305 S | 4/2010 | Al-Ali et al. |
| 7,695,680 B2 | 4/2010 | Unlu et al. |
| 7,697,966 B2 | 4/2010 | Monfre et al. |
| 7,698,105 B2 | 4/2010 | Ruchti et al. |
| 7,698,909 B2 | 4/2010 | Hannula et al. |
| RE41,317 E | 5/2010 | Parker |
| RE41,333 E | 5/2010 | Blank et al. |
| 7,726,209 B2 | 6/2010 | Ruotoistenmäki |
| 7,729,733 B2 | 6/2010 | Al-Ali et al. |
| 7,740,588 B1 | 6/2010 | Sciarra |

(56) References Cited

U.S. PATENT DOCUMENTS

| | | |
|---|---|---|
| 7,740,589 B2 | 6/2010 | Maschke et al. |
| 7,761,127 B2 | 7/2010 | Al-Ali et al. |
| 7,764,982 B2 | 7/2010 | Dalke et al. |
| D620,884 S | 8/2010 | Lee et al. |
| D621,516 S | 8/2010 | Kiani et al. |
| 7,778,118 B2 | 8/2010 | Lyons et al. |
| 7,791,155 B2 | 9/2010 | Diab |
| D626,147 S | 10/2010 | Goddard |
| RE41,912 E | 11/2010 | Parker |
| D628,110 S | 11/2010 | Boulangeot |
| D630,961 S | 1/2011 | Ciuchindel et al. |
| 7,862,523 B2 | 1/2011 | Ruotoistenmaki |
| 7,869,849 B2 | 1/2011 | Ollerdessen et al. |
| 7,876,274 B2 | 1/2011 | Hobson et al. |
| 7,880,626 B2 | 2/2011 | Al-Ali et al. |
| 7,890,158 B2 | 2/2011 | Rowe et al. |
| 7,899,510 B2 | 3/2011 | Hoarau |
| 7,904,130 B2 | 3/2011 | Raridan, Jr. |
| 7,909,772 B2 | 3/2011 | Popov et al. |
| 7,918,779 B2 | 4/2011 | Haber et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,946,758 B2 | 5/2011 | Mooring |
| 7,957,780 B2 | 6/2011 | Lamego et al. |
| 7,962,188 B2 | 6/2011 | Kiani et al. |
| 7,976,472 B2 | 7/2011 | Kiani |
| 7,978,062 B2 | 7/2011 | LaLonde et al. |
| 7,990,382 B2 | 8/2011 | Kiani |
| 8,008,088 B2 | 8/2011 | Bellott et al. |
| RE42,753 E | 9/2011 | Kiani-Azarbayjany et al. |
| D645,818 S | 9/2011 | Guccione et al. |
| 8,028,701 B2 | 10/2011 | Al-Ali et al. |
| 8,040,758 B1 | 10/2011 | Dickinson |
| 8,048,040 B2 | 11/2011 | Kiani |
| 8,050,728 B2 | 11/2011 | Al-Ali et al. |
| 8,071,935 B2 | 12/2011 | Besko et al. |
| 8,092,396 B2 | 1/2012 | Bagha |
| RE43,169 E | 2/2012 | Parker |
| 8,118,620 B2 | 2/2012 | Al-Ali et al. |
| 8,130,105 B2 | 3/2012 | Al-Ali et al. |
| 8,162,804 B2 | 4/2012 | Tagliabue |
| 8,177,720 B2 | 5/2012 | Nanba et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,535 B2 | 7/2012 | Mensinger et al. |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,469 B2 | 10/2012 | Baker, Jr. et al. |
| 8,280,473 B2 | 10/2012 | Al-Ali |
| 8,285,010 B2 | 10/2012 | Rowe |
| 8,289,130 B2 | 10/2012 | Nakajima et al. |
| 8,311,514 B2 | 11/2012 | Bandyopadhyay et al. |
| 8,315,682 B2 | 11/2012 | Such et al. |
| 8,315,683 B2 | 11/2012 | Al-Ali et al. |
| RE43,860 E | 12/2012 | Parker |
| 8,343,026 B2 | 1/2013 | Gardiner et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,364,389 B2 | 1/2013 | Dorogusker et al. |
| 8,374,665 B2 | 2/2013 | Lamego |
| 8,374,825 B2 | 2/2013 | Vock et al. |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,452,364 B2 | 5/2013 | Hannula et al. |
| 8,455,290 B2 | 6/2013 | Siskavich |
| 8,457,707 B2 | 6/2013 | Kiani |
| 8,463,345 B2 | 6/2013 | Kuhn et al. |
| 8,471,713 B2 | 6/2013 | Poeze et al. |
| 8,473,020 B2 | 6/2013 | Kiani et al. |
| D685,367 S | 7/2013 | Akana et al. |
| 8,487,256 B2 | 7/2013 | Kwong et al. |
| 8,496,595 B2 | 7/2013 | Jornod |
| 8,509,867 B2 | 8/2013 | Workman et al. |
| 8,515,509 B2 | 8/2013 | Bruinsma et al. |
| 8,515,511 B2 | 8/2013 | Boutelle |
| 8,515,515 B2 | 8/2013 | McKenna et al. |
| 8,523,781 B2 | 9/2013 | Al-Ali |
| D692,145 S | 10/2013 | Al-Ali et al. |
| 8,552,989 B2 | 10/2013 | Hotelling et al. |
| 8,562,489 B2 | 10/2013 | Burton et al. |
| 8,564,544 B2 | 10/2013 | Jobs et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| D694,182 S | 11/2013 | Lee et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,591,426 B2 | 11/2013 | Onoe et al. |
| D694,745 S | 12/2013 | Akana et al. |
| 8,600,494 B2 | 12/2013 | Schroeppel et al. |
| 8,611,095 B2 | 12/2013 | Kwong et al. |
| 8,615,290 B2 | 12/2013 | Lin et al. |
| D697,027 S | 1/2014 | Ho |
| 8,624,836 B1 | 1/2014 | Miller et al. |
| 8,626,256 B2 | 1/2014 | Fein et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,655,004 B2 | 2/2014 | Prest et al. |
| 8,666,468 B1 | 3/2014 | Al-Ali |
| 8,668,643 B2 | 3/2014 | Kinast |
| 8,670,811 B2 | 3/2014 | O'Reilly |
| 8,670,819 B2 | 3/2014 | Iwamiya et al. |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,111 B2 | 4/2014 | Leboeuf et al. |
| 8,702,627 B2 | 4/2014 | Telfort et al. |
| 8,712,494 B1 | 4/2014 | MacNeish, III et al. |
| D704,634 S | 5/2014 | Eidelman et al. |
| 8,715,206 B2 | 5/2014 | Telfort et al. |
| 8,723,677 B1 | 5/2014 | Kiani |
| 8,734,343 B2 | 5/2014 | Lin et al. |
| 8,740,792 B1 | 6/2014 | Kiani et al. |
| 8,755,535 B2 | 6/2014 | Telfort et al. |
| 8,755,872 B1 | 6/2014 | Marinow |
| 8,760,517 B2 | 6/2014 | Sarwar et al. |
| D709,873 S | 7/2014 | Aumiller et al. |
| D709,874 S | 7/2014 | Aumiller et al. |
| 8,764,671 B2 | 7/2014 | Kiani |
| 8,768,423 B2 | 7/2014 | Shakespeare et al. |
| 8,768,426 B2 | 7/2014 | Haisley et al. |
| 8,771,204 B2 | 7/2014 | Telfort et al. |
| 8,781,544 B2 | 7/2014 | Al-Ali et al. |
| 8,787,984 B2 | 7/2014 | Murakami et al. |
| 8,790,268 B2 | 7/2014 | Al-Ali |
| D711,372 S | 8/2014 | Aumiller et al. |
| D711,873 S | 8/2014 | Aumiller et al. |
| 8,801,613 B2 | 8/2014 | Al-Ali et al. |
| 8,814,802 B2 | 8/2014 | Iijima et al. |
| D712,930 S | 9/2014 | Lee et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,838,210 B2 | 9/2014 | Wood et al. |
| 8,840,549 B2 | 9/2014 | Al-Ali et al. |

(56) References Cited

U.S. PATENT DOCUMENTS

| | | |
|---|---|---|
| 8,852,094 B2 | 10/2014 | Al-Ali et al. |
| 8,852,994 B2 | 10/2014 | Wojtczuk et al. |
| D718,233 S | 11/2014 | Aumiller et al. |
| D718,234 S | 11/2014 | Rautiainen |
| D718,236 S | 11/2014 | Murray |
| D718,324 S | 11/2014 | Lee et al. |
| 8,888,701 B2 | 11/2014 | LeBoeuf et al. |
| 8,897,847 B2 | 11/2014 | Al-Ali |
| D720,289 S | 12/2014 | Chiang et al. |
| 8,911,377 B2 | 12/2014 | Al-Ali |
| 8,920,332 B2 | 12/2014 | Hong et al. |
| 8,929,967 B2 | 1/2015 | Mao et al. |
| 8,948,832 B2 | 2/2015 | Hong et al. |
| 8,954,135 B2 | 2/2015 | Yuen et al. |
| 8,958,859 B2 | 2/2015 | Petersen et al. |
| D724,103 S | 3/2015 | Akana et al. |
| 8,979,762 B2 | 3/2015 | Ma et al. |
| 8,989,831 B2 | 3/2015 | Al-Ali et al. |
| D727,316 S | 4/2015 | Song |
| 8,998,809 B2 | 4/2015 | Kiani |
| 8,998,815 B2 | 4/2015 | Venkatraman et al. |
| 9,001,047 B2 | 4/2015 | Forstall et al. |
| 9,005,129 B2 | 4/2015 | Venkatraman et al. |
| D729,238 S | 5/2015 | Song |
| D729,796 S | 5/2015 | Song |
| D730,347 S | 5/2015 | Jung et al. |
| 9,036,970 B2 | 5/2015 | Guyon et al. |
| D732,527 S | 6/2015 | Kim et al. |
| D732,528 S | 6/2015 | Kim et al. |
| D733,132 S | 6/2015 | Kim et al. |
| D733,133 S | 6/2015 | Kim et al. |
| 9,063,160 B2 | 6/2015 | Stamler et al. |
| 9,066,666 B2 | 6/2015 | Kiani |
| 9,066,680 B1 | 6/2015 | Al-Ali et al. |
| D735,131 S | 7/2015 | Akana et al. |
| D735,190 S | 7/2015 | Song |
| 9,072,437 B2 | 7/2015 | Paalasmaa |
| 9,081,889 B2 | 7/2015 | Ingrassia, Jr. et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,173,578 B2 | 11/2015 | Miettinen |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,513 S | 12/2015 | Jung et al. |
| D745,514 S | 12/2015 | Jung et al. |
| 9,210,566 B2 | 12/2015 | Ziemianska et al. |
| 9,211,095 B1 | 12/2015 | Al-Ali |
| 9,218,454 B2 | 12/2015 | Kiani et al. |
| D746,868 S | 1/2016 | Akana et al. |
| 9,245,668 B1 | 1/2016 | Vo et al. |
| 9,267,572 B2 | 2/2016 | Barker et al. |
| D751,069 S | 3/2016 | Choi et al. |
| D752,580 S | 3/2016 | Choi et al. |
| D752,582 S | 3/2016 | Jung et al. |
| 9,277,880 B2 | 3/2016 | Poeze et al. |
| D753,510 S | 4/2016 | Puttorngul et al. |
| 9,307,928 B1 | 4/2016 | Al-Ali et al. |
| 9,311,382 B2 | 4/2016 | Varoglu et al. |
| 9,314,173 B2 | 4/2016 | Gu et al. |
| 9,314,197 B2 | 4/2016 | Eisen et al. |
| 9,323,894 B2 | 4/2016 | Kiani |
| D755,176 S | 5/2016 | Jung et al. |
| D755,392 S | 5/2016 | Hwang et al. |
| D757,819 S | 5/2016 | Akana et al. |
| 9,326,712 B1 | 5/2016 | Kiani |
| 9,339,236 B2 | 5/2016 | Frix et al. |
| 9,351,645 B2 | 5/2016 | Irisawa |
| 9,357,665 B2 | 5/2016 | Myers et al. |
| D759,120 S | 6/2016 | Akana et al. |
| D760,220 S | 6/2016 | Aumiller et al. |
| 9,392,945 B2 | 7/2016 | Al-Ali et al. |
| 9,392,946 B1 | 7/2016 | Sarantos et al. |
| 9,392,976 B2 | 7/2016 | Rodriguez-Llorente et al. |
| 9,408,542 B1 | 8/2016 | Kinast et al. |
| 9,423,952 B2 | 8/2016 | Tamegai |
| D766,115 S | 9/2016 | Ma |
| D766,235 S | 9/2016 | Song |
| 9,436,645 B2 | 9/2016 | Al-Ali et al. |
| 9,445,759 B1 | 9/2016 | Lamego et al. |
| D768,622 S | 10/2016 | Kim et al. |
| D768,724 S | 10/2016 | Akana et al. |
| 9,460,846 B2 | 10/2016 | Graham et al. |
| 9,474,474 B2 | 10/2016 | Lamego et al. |
| D770,533 S | 11/2016 | Akana et al. |
| D771,624 S | 11/2016 | Aumiller et al. |
| D772,228 S | 11/2016 | Jung et al. |
| 9,480,435 B2 | 11/2016 | Olsen |
| 9,489,081 B2 | 11/2016 | Anzures et al. |
| 9,497,534 B2 | 11/2016 | Prest et al. |
| 9,504,405 B2 | 11/2016 | Conrad et al. |
| 9,510,779 B2 | 12/2016 | Poeze et al. |
| 9,517,024 B2 | 12/2016 | Kiani et al. |
| 9,526,430 B2 | 12/2016 | Srinivas et al. |
| 9,532,722 B2 | 1/2017 | Lamego et al. |
| 9,553,625 B2 | 1/2017 | Hatanaka et al. |
| D780,223 S | 2/2017 | Kim |
| 9,560,996 B2 | 2/2017 | Kiani |
| 9,579,039 B2 | 2/2017 | Jansen et al. |
| 9,583,256 B2 | 2/2017 | Lapetina et al. |
| D782,537 S | 3/2017 | Akana et al. |
| 9,593,969 B2 | 3/2017 | King |
| 9,622,692 B2 | 4/2017 | Lamego et al. |
| D787,714 S | 5/2017 | Wang et al. |
| D788,079 S | 5/2017 | Son et al. |
| D788,312 S | 5/2017 | Al-Ali et al. |
| 9,636,059 B2 | 5/2017 | Cinbis et al. |
| 9,649,054 B2 | 5/2017 | Lamego et al. |
| 9,651,405 B1 | 5/2017 | Gowreesunker et al. |
| 9,664,556 B2 | 5/2017 | Chu et al. |
| 9,666,764 B2 | 5/2017 | Bergmann et al. |
| 9,668,676 B2 | 6/2017 | Culbert |
| 9,681,812 B2 | 6/2017 | Presura |
| 9,683,894 B2 | 6/2017 | Uematsu et al. |
| 9,684,900 B2 | 6/2017 | Motoki et al. |
| 9,697,928 B2 | 7/2017 | Al-Ali et al. |
| 9,699,546 B2 | 7/2017 | Qian et al. |
| 9,700,249 B2 | 7/2017 | Johnson et al. |
| 9,716,937 B2 | 7/2017 | Qian et al. |
| 9,717,448 B2 | 8/2017 | Frix et al. |
| 9,717,458 B2 | 8/2017 | Lamego et al. |
| 9,723,997 B1 | 8/2017 | Lamego |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| D797,809 S | 9/2017 | Akana et al. |
| D797,810 S | 9/2017 | Akana et al. |
| 9,750,442 B2 | 9/2017 | Olsen |
| 9,750,461 B1 | 9/2017 | Telfort |
| 9,752,925 B2 | 9/2017 | Chu et al. |
| D800,172 S | 10/2017 | Akana et al. |
| 9,775,545 B2 | 10/2017 | Al-Ali et al. |
| 9,775,548 B2 | 10/2017 | Sarantos et al. |
| 9,778,079 B1 | 10/2017 | Al-Ali et al. |
| 9,781,984 B2 | 10/2017 | Baranski et al. |
| 9,782,077 B2 | 10/2017 | Lamego et al. |
| 9,787,568 B2 | 10/2017 | Lamego et al. |
| 9,801,547 B2 | 10/2017 | Yuen et al. |
| 9,808,188 B1 | 11/2017 | Perea et al. |
| 9,814,399 B2 | 11/2017 | Takahashi et al. |
| 9,820,658 B2 | 11/2017 | Tran |
| D806,063 S | 12/2017 | Kim |
| 9,838,775 B2 | 12/2017 | Qian et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,787 B2 | 12/2017 | White et al. |
| 9,848,800 B1 | 12/2017 | Lee et al. |
| 9,848,823 B2 | 12/2017 | Raghuram et al. |

(56) References Cited

U.S. PATENT DOCUMENTS

| | | |
|---|---|---|
| D807,351 S | 1/2018 | Bang et al. |
| 9,861,298 B2 | 1/2018 | Eckerbom et al. |
| 9,861,305 B1 | 1/2018 | Weber et al. |
| 9,866,671 B1 | 1/2018 | Thompson et al. |
| 9,867,575 B2 | 1/2018 | Maani et al. |
| 9,877,650 B2 | 1/2018 | Muhsin et al. |
| D809,512 S | 2/2018 | Mistry et al. |
| 9,883,824 B2 | 2/2018 | Tiao et al. |
| 9,891,079 B2 | 2/2018 | Dalvi |
| 9,891,590 B2 | 2/2018 | Shim et al. |
| 9,898,049 B2 | 2/2018 | Myers et al. |
| D812,607 S | 3/2018 | Mistry et al. |
| 9,918,646 B2 | 3/2018 | Singh alvarado et al. |
| 9,924,874 B2 | 3/2018 | Sato |
| 9,924,897 B1 | 3/2018 | Abdul-Hafiz |
| 9,936,917 B2 | 4/2018 | Poeze et al. |
| 9,952,095 B1 | 4/2018 | Hotelling et al. |
| D816,524 S | 5/2018 | Akana et al. |
| D819,021 S | 5/2018 | Mistry et al. |
| 9,955,919 B2 | 5/2018 | LeBoeuf et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| 9,993,200 B2 | 6/2018 | Jeong |
| D822,215 S | 7/2018 | Al-Ali et al. |
| D822,216 S | 7/2018 | Barker et al. |
| D823,301 S | 7/2018 | Bang et al. |
| 10,010,276 B2 | 7/2018 | Al-Ali et al. |
| 10,024,655 B2 | 7/2018 | Raguin et al. |
| 10,039,080 B2 | 7/2018 | Miller et al. |
| 10,039,491 B2 | 8/2018 | Thompson et al. |
| 10,052,850 B2 | 8/2018 | Weiss et al. |
| 10,055,121 B2 | 8/2018 | Chaudhri et al. |
| 10,058,254 B2 | 8/2018 | Fei |
| 10,060,788 B2 | 8/2018 | Fei |
| D827,831 S | 9/2018 | Fong et al. |
| 10,066,970 B2 | 9/2018 | Gowreesunker et al. |
| 10,076,257 B2 | 9/2018 | Lin et al. |
| 10,078,052 B2 | 9/2018 | Ness et al. |
| 10,080,499 B2 | 9/2018 | Kuhn |
| 10,085,656 B2 | 10/2018 | Sato |
| 10,086,138 B1 | 10/2018 | Novak, Jr. |
| 10,090,712 B2 | 10/2018 | Jabori et al. |
| 10,092,197 B2 | 10/2018 | Han |
| 10,092,244 B2 | 10/2018 | Chuang et al. |
| 10,104,219 B2 | 10/2018 | Thompson et al. |
| 10,108,151 B2 | 10/2018 | Cardinali et al. |
| 10,111,591 B2 | 10/2018 | Dyell et al. |
| D833,624 S | 11/2018 | DeJong et al. |
| 10,117,587 B2 | 11/2018 | Han |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,789 B2 | 12/2018 | Raghuram et al. |
| 10,154,815 B2 | 12/2018 | Al-Ali et al. |
| 10,159,412 B2 | 12/2018 | Lamego et al. |
| 10,164,688 B2 | 12/2018 | Rothkopf et al. |
| 10,165,954 B2 | 1/2019 | Lee |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| D839,753 S | 2/2019 | Domke et al. |
| 10,201,286 B2 | 2/2019 | Waydo |
| 10,205,291 B2 | 2/2019 | Scruggs et al. |
| 10,206,623 B2 | 2/2019 | Harrison-Noonan et al. |
| 10,215,698 B2 | 2/2019 | Han et al. |
| 10,219,754 B1 | 3/2019 | Lamego |
| 10,226,187 B2 | 3/2019 | Al-Ali et al. |
| 10,231,629 B1 | 3/2019 | Pei et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,244,948 B2 | 4/2019 | Pham et al. |
| 10,247,670 B2 | 4/2019 | Ness et al. |
| 10,265,024 B2 | 4/2019 | Lee et al. |
| 10,271,746 B2 | 4/2019 | Jeanne et al. |
| 10,279,247 B2 | 5/2019 | Kiani |
| 10,285,626 B1 | 5/2019 | Kestelli et al. |
| 10,285,645 B2 | 5/2019 | Bushnell et al. |
| 10,292,664 B2 | 5/2019 | Al-Ali |
| 10,299,720 B2 | 5/2019 | Brown et al. |
| 10,302,465 B2 | 5/2019 | Gowreesunker et al. |
| 10,303,219 B2 | 5/2019 | Myers et al. |
| 10,318,716 B2 | 6/2019 | Nakajima et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,368,799 B2 | 8/2019 | Sannholm et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,390,716 B2 | 8/2019 | Shimuta |
| 10,398,383 B2 | 9/2019 | Van dinther et al. |
| 10,406,445 B2 | 9/2019 | Vock et al. |
| 10,416,079 B2 | 9/2019 | Magnussen et al. |
| D861,676 S | 10/2019 | Mistry et al. |
| D864,120 S | 10/2019 | Forrest et al. |
| 10,433,043 B2 | 10/2019 | Hankey et al. |
| 10,441,181 B1 | 10/2019 | Telfort et al. |
| 10,441,196 B2 | 10/2019 | Eckerbom et al. |
| 10,447,844 B2 | 10/2019 | Ma et al. |
| 10,448,844 B2 | 10/2019 | Al-Ali et al. |
| 10,448,871 B2 | 10/2019 | Al-Ali et al. |
| 10,448,876 B2 | 10/2019 | Hutchinson |
| 10,456,038 B2 | 10/2019 | Lamego et al. |
| D866,350 S | 11/2019 | Park et al. |
| 10,463,340 B2 | 11/2019 | Telfort et al. |
| 10,466,889 B2 | 11/2019 | Tyler |
| 10,471,159 B1 | 11/2019 | Lapotko et al. |
| 10,478,075 B2 | 11/2019 | Martin et al. |
| 10,492,726 B2 | 12/2019 | Dusan et al. |
| 10,499,821 B2 | 12/2019 | Pi et al. |
| 10,503,254 B2 | 12/2019 | Allec et al. |
| 10,503,379 B2 | 12/2019 | Al-Ali et al. |
| 10,504,380 B2 | 12/2019 | Thompson et al. |
| 10,505,311 B2 | 12/2019 | Al-Ali et al. |
| 10,512,406 B2 | 12/2019 | Martinez et al. |
| 10,512,432 B2 | 12/2019 | Shahparnia et al. |
| 10,512,436 B2 | 12/2019 | Muhsin et al. |
| 10,517,489 B2 | 12/2019 | Narasimhan et al. |
| 10,521,900 B2 | 12/2019 | Bartula et al. |
| 10,524,670 B2 | 1/2020 | Raghuram et al. |
| 10,524,671 B2 | 1/2020 | Lamego |
| 10,524,706 B2 | 1/2020 | Telfort et al. |
| 10,524,735 B2 | 1/2020 | Waydo et al. |
| 10,524,738 B2 | 1/2020 | Olsen |
| 10,531,811 B2 | 1/2020 | Al-Ali et al. |
| 10,531,819 B2 | 1/2020 | Diab et al. |
| 10,531,835 B2 | 1/2020 | Al-Ali et al. |
| 10,532,174 B2 | 1/2020 | Al-Ali |
| 10,536,768 B2 | 1/2020 | Wagner et al. |
| 10,537,284 B1 | 1/2020 | Ruh et al. |
| 10,537,285 B2 | 1/2020 | Shreim et al. |
| 10,542,903 B2 | 1/2020 | Al-Ali et al. |
| 10,542,920 B2 | 1/2020 | Sato |
| D875,092 S | 2/2020 | Akana et al. |
| 10,548,561 B2 | 2/2020 | Telfort et al. |
| 10,555,678 B2 | 2/2020 | Dalvi et al. |
| 10,568,514 B2 | 2/2020 | Wojtczuk et al. |
| 10,568,516 B2 | 2/2020 | Yang et al. |
| 10,568,553 B2 | 2/2020 | O'Neil et al. |
| 10,575,766 B2 | 3/2020 | Sato |
| 10,575,779 B2 | 3/2020 | Poeze et al. |
| 10,588,518 B2 | 3/2020 | Kiani |
| 10,588,556 B2 | 3/2020 | Kiani et al. |
| 10,593,186 B2 | 3/2020 | Hankey et al. |
| 10,595,747 B2 | 3/2020 | Al-Ali et al. |
| 10,603,690 B2 | 3/2020 | Zadesky et al. |
| 10,608,817 B2 | 3/2020 | Haider et al. |

(56) References Cited

U.S. PATENT DOCUMENTS

| | | |
|---|---|---|
| D880,477 S | 4/2020 | Forrest et al. |
| D882,565 S | 4/2020 | Akana et al. |
| 10,610,157 B2 | 4/2020 | Pandya et al. |
| 10,617,302 B2 | 4/2020 | Al-Ali et al. |
| 10,617,335 B2 | 4/2020 | Al-Ali et al. |
| 10,617,912 B2 | 4/2020 | Narasimha Rao et al. |
| 10,620,591 B2 | 4/2020 | Rothkopf |
| 10,627,783 B2 | 4/2020 | Rothkopf |
| 10,637,181 B2 | 4/2020 | Al-Ali et al. |
| D883,279 S | 5/2020 | Akana et al. |
| 10,653,327 B2 | 5/2020 | Iijima |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| 10,687,707 B2 | 6/2020 | Tan et al. |
| 10,687,718 B2 | 6/2020 | Allec et al. |
| 10,687,752 B2 | 6/2020 | Pham et al. |
| 10,694,994 B2 | 6/2020 | Alvarado et al. |
| 10,699,594 B2 | 6/2020 | Mermel et al. |
| D890,708 S | 7/2020 | Forrest et al. |
| 10,702,171 B2 | 7/2020 | Narasimhan et al. |
| 10,702,211 B2 | 7/2020 | Clavelle et al. |
| 10,709,933 B2 | 7/2020 | Tan et al. |
| 10,721,785 B2 | 7/2020 | Al-Ali |
| 10,722,157 B2 | 7/2020 | Bower et al. |
| 10,726,731 B2 | 7/2020 | Arney et al. |
| 10,736,518 B2 | 8/2020 | Al-Ali et al. |
| 10,736,543 B2 | 8/2020 | Chen et al. |
| 10,750,984 B2 | 8/2020 | Pauley et al. |
| D897,098 S | 9/2020 | Al-Ali |
| 10,758,133 B2 | 9/2020 | Shapiro |
| 10,772,512 B2 | 9/2020 | Klaassen et al. |
| 10,779,098 B2 | 9/2020 | Iswanto et al. |
| 10,779,738 B2 | 9/2020 | Sullivan et al. |
| 10,799,128 B2 | 10/2020 | Paulussen et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,912,501 B2 | 2/2021 | Poeze et al. |
| 10,912,502 B2 | 2/2021 | Poeze et al. |
| 10,918,281 B2 | 2/2021 | Al-Ali et al. |
| 10,918,322 B2 | 2/2021 | Shao et al. |
| 10,930,452 B2 | 2/2021 | Weaver |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,942,491 B2 | 3/2021 | Rothkopf et al. |
| 10,945,648 B2 | 3/2021 | Poeze et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,054 B2 * | 4/2021 | Pandya .................. G06F 1/163 |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| 11,009,390 B2 | 5/2021 | Hotelling et al. |
| D921,202 S | 6/2021 | Al-Ali et al. |
| 11,024,064 B2 | 6/2021 | Muhsin et al. |
| 11,026,604 B2 | 6/2021 | Chen et al. |
| 11,033,189 B2 | 6/2021 | Verkruijsse et al. |
| 11,033,708 B2 | 6/2021 | Blahnik et al. |
| D925,597 S | 7/2021 | Chandran et al. |
| 11,069,255 B2 | 7/2021 | Blahnik et al. |
| D927,699 S | 8/2021 | Al-Ali et al. |
| 11,076,771 B2 | 8/2021 | Allec et al. |
| 11,076,777 B2 | 8/2021 | Lee et al. |
| 11,106,352 B2 | 8/2021 | Tyler |
| 11,107,578 B2 | 8/2021 | Nag |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,134,854 B2 | 10/2021 | Presura |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| 11,210,583 B2 | 12/2021 | Mathew et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| D947,842 S | 4/2022 | Akana et al. |
| D949,144 S | 4/2022 | Akana et al. |
| D949,145 S | 4/2022 | Akana et al. |
| 11,298,021 B2 | 4/2022 | Muhsin et al. |
| 11,298,075 B2 | 4/2022 | Paalasmaa et al. |
| D950,580 S | 5/2022 | Ahmed |
| D950,599 S | 5/2022 | Ahmed |
| D950,738 S | 5/2022 | Al-Ali et al. |
| D953,324 S | 5/2022 | Akana et al. |
| 11,331,013 B2 | 5/2022 | Al-ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| D962,933 S | 9/2022 | Akana et al. |
| D962,934 S | 9/2022 | Akana et al. |
| D962,936 S | 9/2022 | Akana et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,474,483 B2 | 10/2022 | Rothkopf et al. |
| 11,478,258 B2 | 10/2022 | Chien et al. |
| 11,504,057 B2 | 11/2022 | Clavelle et al. |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |

(56) References Cited

U.S. PATENT DOCUMENTS

| | | |
|---|---|---|
| 11,832,940 B2 | 12/2023 | Diab et al. |
| D1,013,179 S | 1/2024 | Al-Ali et al. |
| 11,857,298 B1 * | 1/2024 | Allec .................... G06F 1/163 |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,133,717 B2 | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 12,207,901 B1 | 1/2025 | Lapotko et al. |
| D1,060,680 S | 2/2025 | Al-Ali et al. |
| D1,063,893 S | 2/2025 | DeJong et al. |
| 12,235,941 B2 | 2/2025 | Kiani et al. |
| 12,236,767 B2 | 2/2025 | Muhsin |
| D1,066,244 S | 3/2025 | Lim et al. |
| D1,066,672 S | 3/2025 | Al-Ali et al. |
| 2001/0017970 A1 | 8/2001 | Shie et al. |
| 2001/0034477 A1 | 10/2001 | Mansfield et al. |
| 2001/0039483 A1 | 11/2001 | Brand et al. |
| 2001/0056243 A1 | 12/2001 | Ohsaki et al. |
| 2002/0010401 A1 | 1/2002 | Bushmakin et al. |
| 2002/0015034 A1 | 2/2002 | Malmborg |
| 2002/0019586 A1 | 2/2002 | Teller et al. |
| 2002/0042558 A1 | 4/2002 | Mendelson |
| 2002/0058864 A1 | 5/2002 | Mansfield et al. |
| 2002/0133080 A1 | 9/2002 | Apruzzese et al. |
| 2002/0156353 A1 | 10/2002 | Larson |
| 2002/0161291 A1 | 10/2002 | Kianl et al. |
| 2002/0184055 A1 | 12/2002 | Naghavi et al. |
| 2002/0188210 A1 | 12/2002 | Aizawa |
| 2003/0013975 A1 | 1/2003 | Kiani |
| 2003/0018243 A1 | 1/2003 | Gerhardt et al. |
| 2003/0033102 A1 | 2/2003 | Dietiker |
| 2003/0036689 A1 | 2/2003 | Diab et al. |
| 2003/0065269 A1 | 4/2003 | Vetter et al. |
| 2003/0088162 A1 | 5/2003 | Yamamoto et al. |
| 2003/0125612 A1 | 7/2003 | Fox et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2003/0212316 A1 | 11/2003 | Leiden et al. |
| 2004/0039272 A1 | 2/2004 | Abdul-Hafiz et al. |
| 2004/0054290 A1 | 3/2004 | Chance |
| 2004/0106163 A1 | 6/2004 | Workman, Jr. et al. |
| 2004/0138568 A1 | 7/2004 | Lo et al. |
| 2004/0152957 A1 | 8/2004 | Stivoric et al. |
| 2005/0007582 A1 | 1/2005 | Villers et al. |
| 2005/0007589 A1 | 1/2005 | Kramer |
| 2005/0030518 A1 | 2/2005 | Nishi et al. |
| 2005/0030629 A1 | 2/2005 | Kursawe et al. |
| 2005/0033284 A1 | 2/2005 | Hooven et al. |
| 2005/0047455 A1 | 3/2005 | Tanaka |
| 2005/0055276 A1 | 3/2005 | Kiani et al. |
| 2005/0116820 A1 | 6/2005 | Goldreich |
| 2005/0197555 A1 | 9/2005 | Mouradian et al. |
| 2005/0212405 A1 | 9/2005 | Negley |
| 2005/0234317 A1 | 10/2005 | Kiani |
| 2005/0274971 A1 | 12/2005 | Wang et al. |
| 2005/0276164 A1 | 12/2005 | Amron |
| 2005/0277819 A1 | 12/2005 | Kiani et al. |
| 2005/0279949 A1 | 12/2005 | Oldham et al. |
| 2006/0009698 A1 | 1/2006 | Banet et al. |
| 2006/0033724 A1 | 2/2006 | Chaudhri et al. |
| 2006/0073719 A1 | 4/2006 | Kiani |
| 2006/0115128 A1 | 6/2006 | Mainguet |
| 2006/0142654 A1 | 6/2006 | Rytky |
| 2006/0189871 A1 | 8/2006 | Al-Ali et al. |
| 2006/0226992 A1 | 10/2006 | Al-Ali et al. |
| 2007/0021677 A1 | 1/2007 | Markel |
| 2007/0073116 A1 | 3/2007 | Kiani et al. |
| 2007/0093717 A1 | 4/2007 | Nagar et al. |
| 2007/0093786 A1 | 4/2007 | Goldsmith et al. |
| 2007/0145255 A1 | 6/2007 | Nishikawa et al. |
| 2007/0180140 A1 | 8/2007 | Welch et al. |
| 2007/0228404 A1 | 10/2007 | Tran et al. |
| 2007/0232880 A1 | 10/2007 | Siddiqui et al. |
| 2007/0244377 A1 | 10/2007 | Cozad et al. |
| 2007/0276270 A1 | 11/2007 | Tran |
| 2007/0282478 A1 | 12/2007 | Al-Ali et al. |
| 2008/0030468 A1 | 2/2008 | Al-Ali et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0122796 A1 | 5/2008 | Jobs et al. |
| 2008/0147147 A1 | 6/2008 | Griffiths et al. |
| 2008/0165063 A1 | 7/2008 | Schlub et al. |
| 2008/0194932 A1 | 8/2008 | Ayers et al. |
| 2008/0208009 A1 | 8/2008 | Shklarski |
| 2008/0221418 A1 | 9/2008 | Al-Ali et al. |
| 2008/0242958 A1 | 10/2008 | Al-Ali et al. |
| 2008/0269619 A1 | 10/2008 | Lindberg et al. |
| 2008/0287758 A1 | 11/2008 | Benaron et al. |
| 2009/0018452 A1 | 1/2009 | Sugiura et al. |
| 2009/0036759 A1 | 2/2009 | Ault et al. |
| 2009/0054112 A1 | 2/2009 | Cybart et al. |
| 2009/0054751 A1 | 2/2009 | Babashan et al. |
| 2009/0059730 A1 | 3/2009 | Lyons et al. |
| 2009/0093687 A1 | 4/2009 | Telfort et al. |
| 2009/0095926 A1 | 4/2009 | MacNeish, III |
| 2009/0190198 A1 | 7/2009 | Kwon |
| 2009/0247984 A1 | 10/2009 | Lamego et al. |
| 2009/0275810 A1 | 11/2009 | Ayers et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0113948 A1 | 5/2010 | Yang et al. |
| 2010/0193804 A1 | 8/2010 | Brown et al. |
| 2010/0234718 A1 | 9/2010 | Sampath et al. |
| 2010/0270257 A1 | 10/2010 | Wachman et al. |
| 2010/0324384 A1 | 12/2010 | Moon et al. |
| 2011/0003665 A1 | 1/2011 | Burton et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |

(56) References Cited

U.S. PATENT DOCUMENTS

| | | |
|---|---|---|
| 2011/0172498 A1 | 7/2011 | Olsen et al. |
| 2011/0237969 A1 | 9/2011 | Eckerbom et al. |
| 2011/0288383 A1 | 11/2011 | Diab |
| 2011/0301444 A1 | 12/2011 | Al-Ali |
| 2012/0041316 A1 | 2/2012 | Al-Ali et al. |
| 2012/0046557 A1 | 2/2012 | Kiani |
| 2012/0078069 A1 | 3/2012 | Melker |
| 2012/0078116 A1 | 3/2012 | Yamashita |
| 2012/0088984 A1 | 4/2012 | Al-Ali et al. |
| 2012/0104999 A1 | 5/2012 | Teggatz et al. |
| 2012/0123231 A1 | 5/2012 | O'Reilly |
| 2012/0129495 A1 | 5/2012 | Chae et al. |
| 2012/0150052 A1 | 6/2012 | Buchheim et al. |
| 2012/0165629 A1 | 6/2012 | Merritt et al. |
| 2012/0209084 A1 | 8/2012 | Olsen et al. |
| 2012/0221254 A1 | 8/2012 | Kateraas et al. |
| 2012/0226117 A1 | 9/2012 | Lamego et al. |
| 2012/0283524 A1 | 11/2012 | Kiani et al. |
| 2012/0288230 A1 | 11/2012 | Polonge et al. |
| 2013/0006076 A1 | 1/2013 | McHale |
| 2013/0023775 A1 | 1/2013 | Lamego et al. |
| 2013/0060147 A1 | 3/2013 | Welch et al. |
| 2013/0096405 A1 | 4/2013 | Garfio |
| 2013/0227418 A1 | 8/2013 | Sa et al. |
| 2013/0239058 A1 | 9/2013 | Yao et al. |
| 2013/0262730 A1 | 10/2013 | Al-Ali et al. |
| 2013/0264592 A1 | 10/2013 | Bergmann et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0305351 A1 | 11/2013 | Narendra et al. |
| 2013/0317370 A1 | 11/2013 | Dalvi et al. |
| 2013/0345921 A1 | 12/2013 | Al-Ali et al. |
| 2014/0051943 A1 | 2/2014 | Gillette |
| 2014/0066783 A1 | 3/2014 | Kiani et al. |
| 2014/0101597 A1 | 4/2014 | Bamford et al. |
| 2014/0107493 A1 | 4/2014 | Yuen et al. |
| 2014/0117926 A1 | 5/2014 | Hwu et al. |
| 2014/0135594 A1 | 5/2014 | Yuen et al. |
| 2014/0139486 A1 | 5/2014 | Mistry et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0189577 A1 | 7/2014 | Shuttleworth et al. |
| 2014/0221854 A1 | 8/2014 | Wai |
| 2014/0275852 A1 | 9/2014 | Hong et al. |
| 2014/0275871 A1 | 9/2014 | Lamego et al. |
| 2014/0275872 A1 | 9/2014 | Merritt et al. |
| 2014/0276013 A1 | 9/2014 | Muehlemann et al. |
| 2014/0276115 A1 | 9/2014 | Dalvi et al. |
| 2014/0278229 A1 | 9/2014 | Hong et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2014/0361147 A1 | 12/2014 | Fei |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018647 A1 | 1/2015 | Mandel et al. |
| 2015/0025406 A1 | 1/2015 | Al-Ali |
| 2015/0045637 A1 | 2/2015 | Dalvi |
| 2015/0045685 A1 | 2/2015 | Al-Ali et al. |
| 2015/0051462 A1 | 2/2015 | Olsen |
| 2015/0065889 A1 | 3/2015 | Gandelman et al. |
| 2015/0073241 A1 | 3/2015 | Lamego |
| 2015/0080754 A1 | 3/2015 | Purdon et al. |
| 2015/0095819 A1 | 4/2015 | Hong et al. |
| 2015/0097701 A1 | 4/2015 | Al-Ali et al. |
| 2015/0099324 A1 | 4/2015 | Wojtczuk et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0135310 A1 | 5/2015 | Lee |
| 2015/0140863 A1 | 5/2015 | Al-Ali et al. |
| 2015/0141781 A1 | 5/2015 | Weber et al. |
| 2015/0153843 A1 | 6/2015 | Lee |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0214749 A1 | 7/2015 | Park et al. |
| 2015/0230755 A1 | 8/2015 | Al-Ali et al. |
| 2015/0245773 A1 | 9/2015 | Lamego et al. |
| 2015/0245793 A1 | 9/2015 | Al-Ali et al. |
| 2015/0245794 A1 | 9/2015 | Al-Ali |
| 2015/0250396 A1 | 9/2015 | Ahmed et al. |
| 2015/0255001 A1 | 9/2015 | Haughay et al. |
| 2015/0272514 A1 | 10/2015 | Kiani et al. |
| 2015/0282739 A1 | 10/2015 | Nishida et al. |
| 2015/0346976 A1 | 12/2015 | Karunamuni et al. |
| 2015/0355604 A1 | 12/2015 | Fraser et al. |
| 2016/0019360 A1 | 1/2016 | Pahwa et al. |
| 2016/0041531 A1 | 2/2016 | Mackie et al. |
| 2016/0042162 A1 | 2/2016 | Newell |
| 2016/0051147 A1 | 2/2016 | Cohen et al. |
| 2016/0051158 A1 | 2/2016 | Silva |
| 2016/0058309 A1* | 3/2016 | Han ............... A61B 5/0261 600/479 |
| 2016/0058356 A1 | 3/2016 | Raghuram et al. |
| 2016/0058375 A1 | 3/2016 | Rothkopf |
| 2016/0073914 A1 | 3/2016 | Lapetina et al. |
| 2016/0098137 A1 | 4/2016 | Kim et al. |
| 2016/0103985 A1 | 4/2016 | Shim et al. |
| 2016/0106367 A1 | 4/2016 | Jorov et al. |
| 2016/0157780 A1 | 6/2016 | Rimminen et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0206221 A1 | 7/2016 | Kim et al. |
| 2016/0206251 A1 | 7/2016 | Kwon et al. |
| 2016/0228064 A1 | 8/2016 | Jung et al. |
| 2016/0233632 A1 | 8/2016 | Scruggs et al. |
| 2016/0234944 A1 | 8/2016 | Schmidt et al. |
| 2016/0240721 A1 | 8/2016 | Chu et al. |
| 2016/0256082 A1 | 9/2016 | Ely et al. |
| 2016/0287090 A1 | 10/2016 | Al-Ali et al. |
| 2016/0287107 A1 | 10/2016 | Szabados et al. |
| 2016/0287181 A1 | 10/2016 | Han et al. |
| 2016/0296169 A1 | 10/2016 | McHale et al. |
| 2016/0296173 A1 | 10/2016 | Culbert |
| 2016/0296174 A1 | 10/2016 | Isikman et al. |
| 2016/0310052 A1 | 10/2016 | Al-Ali et al. |
| 2016/0331332 A1 | 11/2016 | Al-Ali |
| 2016/0334332 A1 | 11/2016 | Magnussen et al. |
| 2016/0338598 A1 | 11/2016 | Kegasawa |
| 2016/0367173 A1 | 12/2016 | Dalvi et al. |
| 2017/0007134 A1 | 1/2017 | Al-Ali et al. |
| 2017/0007198 A1 | 1/2017 | Al-Ali et al. |
| 2017/0010858 A1 | 1/2017 | Prest et al. |
| 2017/0011210 A1 | 1/2017 | Cheong et al. |
| 2017/0014084 A1 | 1/2017 | Al-Ali et al. |
| 2017/0024748 A1 | 1/2017 | Haider |
| 2017/0046024 A1 | 2/2017 | Dascola et al. |
| 2017/0055851 A1 | 3/2017 | Al-Ali |
| 2017/0079594 A1 | 3/2017 | Telfort et al. |
| 2017/0086689 A1 | 3/2017 | Shui et al. |
| 2017/0086743 A1 | 3/2017 | Bushnell et al. |
| 2017/0094450 A1 | 3/2017 | Tu et al. |
| 2017/0119262 A1 | 5/2017 | Shim et al. |
| 2017/0164884 A1 | 6/2017 | Culbert et al. |
| 2017/0172476 A1 | 6/2017 | Schilthuizen |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0202505 A1 | 7/2017 | Kirenko et al. |

(56) References Cited

U.S. PATENT DOCUMENTS

| | | |
|---|---|---|
| 2017/0215743 A1 | 8/2017 | Meer et al. |
| 2017/0224262 A1 | 8/2017 | Al-Ali |
| 2017/0251974 A1 | 9/2017 | Shreim et al. |
| 2017/0258403 A1 | 9/2017 | Abdul-Hafiz et al. |
| 2017/0290552 A1 | 10/2017 | Naruse |
| 2017/0293727 A1 | 10/2017 | Klaassen et al. |
| 2017/0311851 A1 | 11/2017 | Schurman et al. |
| 2017/0325728 A1 | 11/2017 | Al-Ali et al. |
| 2017/0325744 A1 | 11/2017 | Allec et al. |
| 2017/0367632 A1 | 12/2017 | Al-Ali et al. |
| 2018/0049656 A1 | 2/2018 | Paulussen et al. |
| 2018/0049694 A1 | 2/2018 | Singh alvarado et al. |
| 2018/0055385 A1 | 3/2018 | Al-Ali |
| 2018/0069776 A1 | 3/2018 | Lamego et al. |
| 2018/0110469 A1 | 4/2018 | Maani et al. |
| 2018/0110478 A1 | 4/2018 | Al-Ali |
| 2018/0116575 A1 | 5/2018 | Perea et al. |
| 2018/0130325 A1 | 5/2018 | Kiani et al. |
| 2018/0132770 A1 | 5/2018 | Lamego |
| 2018/0153418 A1 | 6/2018 | Sullivan et al. |
| 2018/0167806 A1 | 6/2018 | Boyd |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0192955 A1 | 7/2018 | Al-Ali et al. |
| 2018/0235542 A1 | 8/2018 | Yun et al. |
| 2018/0242924 A1 | 8/2018 | Barker et al. |
| 2018/0242926 A1 | 8/2018 | Muhsin et al. |
| 2018/0247712 A1 | 8/2018 | Muhsin et al. |
| 2018/0249933 A1 | 9/2018 | Schurman et al. |
| 2018/0256113 A1 | 9/2018 | Weber et al. |
| 2018/0289337 A1 | 10/2018 | Al-Ali et al. |
| 2018/0360326 A1 | 12/2018 | Lee et al. |
| 2019/0021638 A1 | 1/2019 | Al-Ali et al. |
| 2019/0038143 A1 | 2/2019 | Al-Ali |
| 2019/0059821 A1 | 2/2019 | Pekonen et al. |
| 2019/0090748 A1 | 3/2019 | Al-Ali |
| 2019/0090766 A1* | 3/2019 | Block ............... A61B 5/02433 |
| 2019/0090806 A1 | 3/2019 | Clavelle et al. |
| 2019/0104973 A1 | 4/2019 | Poeze et al. |
| 2019/0110719 A1 | 4/2019 | Poeze et al. |
| 2019/0150800 A1 | 5/2019 | Poeze et al. |
| 2019/0167114 A1 | 6/2019 | Islam |
| 2019/0196411 A1 | 6/2019 | Yuen |
| 2019/0239787 A1 | 8/2019 | Pauley et al. |
| 2019/0320906 A1 | 10/2019 | Olsen |
| 2019/0324593 A1 | 10/2019 | Chung et al. |
| 2019/0357813 A1 | 11/2019 | Poeze et al. |
| 2019/0357823 A1 | 11/2019 | Reichgott et al. |
| 2019/0357824 A1 | 11/2019 | Al-Ali |
| 2019/0358524 A1 | 11/2019 | Kiani |
| 2019/0365294 A1 | 12/2019 | Poeze et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0386908 A1 | 12/2019 | Lamego et al. |
| 2019/0388039 A1 | 12/2019 | Al-Ali |
| 2020/0000338 A1 | 1/2020 | Lamego et al. |
| 2020/0000415 A1 | 1/2020 | Barker et al. |
| 2020/0020493 A1 | 1/2020 | Weaver |
| 2020/0021930 A1 | 1/2020 | Iswanto et al. |
| 2020/0037453 A1 | 1/2020 | Triman et al. |
| 2020/0037891 A1 | 2/2020 | Kiani et al. |
| 2020/0037966 A1 | 2/2020 | Al-Ali |
| 2020/0046257 A1 | 2/2020 | Eckerbom et al. |
| 2020/0054253 A1 | 2/2020 | Al-Ali et al. |
| 2020/0060591 A1 | 2/2020 | Diab et al. |
| 2020/0060628 A1 | 2/2020 | Al-Ali et al. |
| 2020/0060629 A1 | 2/2020 | Muhsin et al. |
| 2020/0060869 A1 | 2/2020 | Telfort et al. |
| 2020/0074819 A1 | 3/2020 | Muhsin et al. |
| 2020/0111552 A1 | 4/2020 | Ahmed |
| 2020/0113435 A1 | 4/2020 | Muhsin |
| 2020/0113496 A1 | 4/2020 | Scruggs et al. |
| 2020/0113520 A1 | 4/2020 | Abdul-Hafiz et al. |
| 2020/0121941 A1 | 4/2020 | Kwon et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0196882 A1 | 6/2020 | Kiani et al. |
| 2020/0221980 A1 | 7/2020 | Poeze et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0358700 A1 | 11/2021 | Weaver |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |

(56) References Cited

U.S. PATENT DOCUMENTS

| | | |
|---|---|---|
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0252046 A1 | 8/2024 | Jansen et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |

FOREIGN PATENT DOCUMENTS

| | | |
|---|---|---|
| CA | 2105681 | 10/1992 |
| CA | 2264029 | 3/1998 |
| CA | 2137878 | 4/2007 |
| CN | 1270793 | 10/2000 |
| CN | 1482448 | 3/2004 |
| CN | 201033073 | 3/2008 |
| CN | 100518630 C | 7/2009 |
| CN | 101564290 | 10/2009 |
| CN | 201481421 | 5/2010 |
| CN | 201542615 | 8/2010 |
| CN | 201578231 | 9/2010 |
| CN | 201585989 | 9/2010 |
| CN | 101484065 | 11/2011 |
| CN | 302687306 S | 12/2013 |
| CN | 103906468 | 7/2014 |
| CN | 203732900 | 7/2014 |
| CN | 302942795 S | 9/2014 |
| CN | 302972990 S | 10/2014 |
| CN | 302864470 | 11/2014 |
| CN | 303285726 | 7/2015 |
| CN | 303285726 S | 7/2015 |
| CN | 303296619 S | 7/2015 |
| CN | 303306604 S | 7/2015 |
| CN | 303327831 S | 8/2015 |
| CN | 303518893 S | 12/2015 |
| CN | 205041396 | 2/2016 |
| CN | 303646405 S | 4/2016 |
| CN | 303737075 S | 7/2016 |
| CN | 106236051 | 12/2016 |
| CN | 104181809 | 1/2017 |
| CN | 304027493 S | 2/2017 |
| CN | 106527106 | 3/2017 |
| CN | 304385323 S | 12/2017 |
| CN | 304481666 S | 1/2018 |
| CN | 105379306 | 2/2020 |
| DE | 202004017631 | 3/2005 |
| DE | 102008002741 | 12/2009 |
| DE | 202007019341 | 1/2012 |
| EM | 001383434-0008 | 9/2013 |
| EM | 001383434-0009 | 9/2013 |
| EM | 002743575-0001 | 7/2015 |
| EM | 004428274-0003 | 10/2017 |
| EM | 005940459-0005 | 12/2018 |
| EM | 005940459-0011 | 12/2018 |
| EM | 005940459-0013 | 12/2018 |
| EM | 005940459-0014 | 12/2018 |
| EM | 005940459-0015 | 12/2018 |
| EM | 006302279-0001 | 3/2019 |
| EM | 006302279-0002 | 3/2019 |
| EM | 007127113-0001 | 10/2019 |
| EP | 0102816 | 3/1984 |
| EP | 0419223 | 3/1991 |
| EP | 0 505 627 | 9/1992 |
| EP | 0630208 | 12/1994 |
| EP | 0724860 | 8/1996 |
| EP | 0665727 | 1/1997 |
| EP | 0760223 | 3/1997 |
| EP | 0770349 | 5/1997 |
| EP | 0781527 | 7/1997 |
| EP | 0 801 938 | 10/1997 |
| EP | 0 872 210 | 10/1998 |
| EP | 0880936 | 12/1998 |
| EP | 0922432 | 6/1999 |
| EP | 0985373 | 3/2000 |
| EP | 1080683 | 3/2001 |
| EP | 1518494 | 3/2005 |
| EP | 1526805 | 5/2005 |
| EP | 1124609 | 8/2006 |
| EP | 1213037 | 11/2006 |
| EP | 1860989 | 12/2007 |
| EP | 1875213 | 1/2008 |
| EP | 1880666 | 1/2008 |
| EP | 2165196 | 3/2010 |
| EP | 2277440 | 1/2011 |
| EP | 14163114.3 | 4/2014 |
| EP | 2194842 | 4/2015 |
| EP | 3015062 | 5/2016 |
| EP | 3316779 | 5/2018 |
| EP | 3430980 | 1/2019 |
| EP | 3 459 447 | 3/2019 |
| EP | 3488776 | 5/2019 |
| EP | 3626159 | 3/2020 |
| EP | 3033992 | 4/2020 |
| GB | 2243691 | 11/1991 |
| GB | 4032616 | 1/2014 |
| JP | S57-037438 | 3/1982 |
| JP | H03-237544 | 10/1991 |
| JP | 05325705 | 12/1993 |
| JP | H06-66633 | 9/1994 |
| JP | H07124138 | 5/1995 |
| JP | 08185864 | 7/1996 |
| JP | H09173322 | 7/1997 |
| JP | H09257508 | 10/1997 |
| JP | H10314133 | 12/1998 |
| JP | H11-70086 | 3/1999 |
| JP | 2919326 | 7/1999 |
| JP | H11-197127 | 7/1999 |
| JP | H11235320 | 8/1999 |
| JP | 3107630 | 11/2000 |
| JP | 3116255 | 12/2000 |
| JP | 2001066990 | 3/2001 |
| JP | 2001087250 | 4/2001 |
| JP | 2002500908 | 1/2002 |
| JP | 2002303576 | 10/2002 |
| JP | 2003024276 | 1/2003 |
| JP | 2003508104 | 3/2003 |
| JP | 2003210438 | 7/2003 |
| JP | 2003265444 | 9/2003 |
| JP | 2004-031485 | 1/2004 |
| JP | 2004-119515 | 4/2004 |
| JP | 2004-298606 | 10/2004 |
| JP | 2004329406 | 11/2004 |
| JP | 2004-337605 | 12/2004 |
| JP | 2004344668 | 12/2004 |
| JP | 2005160641 | 6/2005 |
| JP | 2006061445 | 8/2005 |
| JP | 2005-270543 | 10/2005 |
| JP | 3710570 | 10/2005 |
| JP | 3741147 | 2/2006 |
| JP | 2006-102159 | 4/2006 |
| JP | 2006102164 | 4/2006 |
| JP | 2006177837 | 7/2006 |
| JP | 3803351 | 8/2006 |
| JP | 2006198321 | 8/2006 |
| JP | 2006-288835 | 10/2006 |
| JP | 2006-296564 | 11/2006 |
| JP | 2007-289463 | 11/2007 |
| JP | 2007319232 | 12/2007 |
| JP | 2008099222 | 4/2008 |
| JP | 2008-119026 | 5/2008 |
| JP | 2008-126017 | 6/2008 |
| JP | 2009101057 | 5/2009 |
| JP | 2009106373 | 5/2009 |
| JP | 2010136921 | 6/2010 |

(56) References Cited

FOREIGN PATENT DOCUMENTS

| | | |
|---|---|---|
| JP | D1400735 | 11/2010 |
| JP | 2011-147746 | 8/2011 |
| JP | D1436448 | 3/2012 |
| JP | 5056867 | 10/2012 |
| JP | 2013-009710 | 1/2013 |
| JP | 2013-515528 | 5/2013 |
| JP | 2013118978 | 6/2013 |
| JP | 2013-212315 | 10/2013 |
| JP | 2013541990 | 11/2013 |
| JP | D1489271 | 12/2013 |
| JP | 5756752 | 6/2015 |
| JP | 2015112488 | 6/2015 |
| JP | 2015152601 | 8/2015 |
| JP | 2016054822 | 4/2016 |
| JP | 2016147052 | 8/2016 |
| JP | 2016-154754 | 9/2016 |
| JP | D1568369 | 12/2016 |
| JP | 2018068465 | 5/2018 |
| JP | 2018-524073 | 8/2018 |
| KR | 20-0195400 | 9/2000 |
| KR | 10-2016-0089718 | 11/2003 |
| KR | 10-2006-0083552 | 7/2006 |
| KR | 10-2006-0111159 | 10/2006 |
| KR | 10-2007-0011685 | 1/2007 |
| KR | 10-2007-0058900 | 6/2007 |
| KR | 2007-0061122 | 6/2007 |
| KR | 100755079 | 9/2007 |
| KR | 10-2007-0102089 | 10/2007 |
| KR | 2007-0102089 | 10/2007 |
| KR | 10-2007-0056925 | 4/2008 |
| KR | 10-2008-0048010 | 5/2008 |
| KR | 2010-0091592 | 8/2010 |
| KR | 30-0645410 | 5/2012 |
| KR | 10-2013-0107833 | 10/2013 |
| KR | 30-0740673 | 4/2014 |
| KR | 30-0817671 | 9/2015 |
| KR | 10-2016-0041623 | 4/2016 |
| KR | 10-2016-0044811 | 4/2016 |
| KR | 10-2016-0058476 | 5/2016 |
| KR | 10-2016-0069623 | 8/2016 |
| KR | 10-2016-0096902 | 8/2016 |
| KR | 10-2017-0049279 | 5/2017 |
| KR | 10-2018-0038206 | 4/2018 |
| KR | 10-2019-0115313 | 10/2019 |
| KR | 10-2136836 | 8/2020 |
| KR | 2020-0093247 | 8/2020 |
| WO | WO 82/000088 | 1/1982 |
| WO | WO 93/012712 | 7/1993 |
| WO | WO 94/021173 | 9/1994 |
| WO | WO 94/023643 | 10/1994 |
| WO | WO 95/000070 | 1/1995 |
| WO | WO 96/013208 | 5/1996 |
| WO | WO 96/027325 | 9/1996 |
| WO | WO 96/041566 | 12/1996 |
| WO | WO 97/000923 | 1/1997 |
| WO | WO 97/001985 | 1/1997 |
| WO | WO 97/009923 | 3/1997 |
| WO | WO 99/000053 | 1/1999 |
| WO | WO 99/001704 | 7/1999 |
| WO | WO 99/063883 | 12/1999 |
| WO | WO 00/018290 | 4/2000 |
| WO | WO 00/025112 | 5/2000 |
| WO | WO 00/028892 | 5/2000 |
| WO | WO 01/009589 | 2/2001 |
| WO | WO 01/024700 | 4/2001 |
| WO | WO 01/050433 | 7/2001 |
| WO | WO 01/050955 | 7/2001 |
| WO | WO 02/028274 | 4/2002 |
| WO | WO 02/062213 | 8/2002 |
| WO | WO 02/097324 | 12/2002 |
| WO | WO 03/031961 | 4/2003 |
| WO | WO 03/068060 | 8/2003 |
| WO | WO 2004/082472 | 9/2004 |
| WO | WO 2005/009221 | 2/2005 |
| WO | WO 2005/092182 | 10/2005 |
| WO | WO 2005/094667 | 10/2005 |
| WO | WO 2006/016366 | 2/2006 |
| WO | WO 2006/017117 | 2/2006 |
| WO | WO 2006/060949 | 6/2006 |
| WO | WO 2006/079862 | 8/2006 |
| WO | WO 2006/090371 | 8/2006 |
| WO | WO 2006/110488 | 10/2006 |
| WO | WO 2006/113070 | 10/2006 |
| WO | WO 2007/004083 | 1/2007 |
| WO | WO 2007/017266 | 2/2007 |
| WO | WO 2007/048039 | 4/2007 |
| WO | WO 2007/144817 | 12/2007 |
| WO | WO 2008/002405 | 1/2008 |
| WO | WO 2008/035076 | 3/2008 |
| WO | WO 2008/040736 | 4/2008 |
| WO | WO 2008/107238 | 9/2008 |
| WO | WO 2008/133394 | 11/2008 |
| WO | WO 2008/149081 | 12/2008 |
| WO | WO 2009/001988 | 12/2008 |
| WO | WO 2009/137524 | 11/2009 |
| WO | WO 2010/003134 | 1/2010 |
| WO | WO 2010/107913 | 9/2010 |
| WO | WO 2011/033628 | 3/2011 |
| WO | WO 2011/051888 | 5/2011 |
| WO | WO 2011/069122 | 6/2011 |
| WO | WO 2011/076886 | 6/2011 |
| WO | WO 2012/092221 | 7/2012 |
| WO | WO 2012/140559 | 10/2012 |
| WO | WO 2013/027357 | 2/2013 |
| WO | WO 2013/030744 | 3/2013 |
| WO | WO 2013/066642 | 5/2013 |
| WO | WO 2013/076656 | 5/2013 |
| WO | WO 2013/106607 | 7/2013 |
| WO | WO 2013/124750 | 8/2013 |
| WO | WO 2013/181368 | 12/2013 |
| WO | WO D083678-002 | 6/2014 |
| WO | WO 2014/115075 | 7/2014 |
| WO | WO 2014/149781 | 9/2014 |
| WO | WO 2014/153200 | 9/2014 |
| WO | WO 2014/158820 | 10/2014 |
| WO | WO 2014/178793 | 11/2014 |
| WO | WO 2014/184447 | 11/2014 |
| WO | WO 2015/034149 | 3/2015 |
| WO | WO D086018-0001 | 3/2015 |
| WO | WO D086018-0002 | 3/2015 |
| WO | WO 2015/046624 | 4/2015 |
| WO | WO 2015/049108 | 4/2015 |
| WO | WO D086693-004 | 7/2015 |
| WO | WO 2015/116111 | 8/2015 |
| WO | WO 2015/150199 | 10/2015 |
| WO | WO 2015/187732 | 12/2015 |
| WO | WO 2016/066312 | 5/2016 |
| WO | WO 2017/004260 | 1/2017 |
| WO | WO 2017/165532 | 9/2017 |
| WO | WO 2018/112401 | 6/2018 |
| WO | WO 2019/198991 | 10/2019 |
| WO | WO 2020/006477 | 1/2020 |
| WO | WO 2021/146333 | 7/2021 |
| WO | WO 2023/287789 | 1/2023 |
| WO | WO 2023/034879 | 3/2023 |

OTHER PUBLICATIONS

US 2024/0016391 A1, 01/2024, Lapotko et al. (withdrawn)
International Search Report and Written Opinion received in International Application No. PCT/US2022/036823, dated Oct. 21, 2022, 13 pages.
International Preliminary Report on Patentability and Written Opinion for International Application No. PCT/US2016/040190, dated Jan. 2, 2018, in 7 pages.
International Preliminary Report on Patentability and Written Opinion of the International Searching Authority issued in Application No. PCT US2009/049638, mailed Jan. 5, 2011 in 9 pages.
International Preliminary Report on Patentability and Written Opinion of the International Searching Authority issued in Application No. PCT/US2009/052756, mailed Feb. 8, 2011 in 8 pages.
International Search Report and Written Opinion for PCT/US2009/049638, mailed Jan. 7, 2010.

(56) References Cited

OTHER PUBLICATIONS

International Search Report issued in Application No. PCT/US2009/052756, mailed Feb. 10, 2009 in 14 pages.
International Search Report, App. No. PCT/US2010/047899, Date of Actual Completion of Search: Jan. 26, 2011, 4 pages.
"Introducing Easy Pulse: A DIY Photoplethysmographic Sensor for Measuring Heart Rate", Embedded Lab, 2012.
"PerformTek Precision Biometrics", ValenCell, 2013.
"Universal asynchronous receiver-transmitter", Wikipedia, available at https://en.wikipedia.org/wiki/Universal_asynchronous_receiver-transmitter, accessed Aug. 27, 2020, 10 pages.
"Galaxy S5 Explained: The Heart Rate Sensor and S Health 3.0." Samsung Global Newsroom, 2014.
"Withings Pulse: Activity Tracker—Sleep Analyzer Hear Rate Analyzer; Installation and Operating Instructions", Withings, 2015.
A. C. M. Dassel et al., "Effect of location of the sensor on reflectance pulse oximetry," British Journal of Obstetrics and Gynaecology, vol. 104, Aug. 1997, pp. 910-916.
A. Domingues, "Development of a Stand-Alone Pulse Oximeter," Thesis for Universidade de Coimbra Master of Biomedical Engineering, Sep. 2009, 120 pages.
A. Fontaine et al., "Reflectance-Based Pulse Oximetry for the Chest and Wrist", Worcester Polytechnic Institute Digital WPI, Apr. 2013, 132 pages.
A. Looney, "Respiratory System Monitoring: Basics of Pulse Oximetry and Capnography," Atlantic Coast Veterinary Conference, 2001, retrieved from https://www.vin.com/doc/?id=3844121, 5 pages.
A. Tura et al., "A Wearable Device with Wireless Bluetooth-based Data Transmission," Measurement Science Review, vol. 3, Sec. 2, 2003, pp. 1-4.
A.C. Dassel et al., "Reflectance pulse oximetry at the forehead of newborns: the influence of varying pressure on the probe," Journal of Clinical Monitoring, vol. 12, No. 6, Nov. 1996, pp. 421-428.
Akira Sakane et al., "Estimating Arterial Wall Impedance using a Plethysmogram," IEEE 2003, pp. 580-585.
Anliker et al., "AMON: a wearable multiparameter medical monitoring and alert system," in IEEE Transactions on Information Technology in Biomedicine, vol. 8, No. 4, Dec. 2004.
Asada, et al. "Mobile Monitoring with Wearable Photoplethysmographic Biosensors", IEEE Engineering in Medicine and Biology Magazine, 2003.
B. F. Keogh et al., "Recent findings in the use of reflectance oximetry: a critical review," Current Opinion in Anesthesiology, vol. 18, 2005, pp. 649-654.
B. Landon et al., "Master Visually Windows Mobile 2003", Wiley Publishing, Inc., 2004, 335 pages (uploaded in two parts).
B. McGarry et al., "Reflections on a candidate design of the user-interface for a wireless vital-signs monitor," Proceedings of DARE 2000 on Designing Augmented Reality Environments, Jan. 2000, pp. 33-40.
B.-H. Yang et al., "Development of the ring sensor for healthcare automation," Robotics and Autonomous Systems, 2000, pp. 273-281.
Bagha, et al. "A Real Time Analysis of PPG Signal for Measurement of SpO2 and Pulse Rate", International Journal of Computer Applications (0975-8887), vol. 36, No. 11, Dec. 2011, pp. 45-50.
B-H. Yang et al., "A Twenty-Four Hour Tele-Nursing System Using a Ringer Sensor," Proceedings of 1998 IEEE International Conference on Robotics and Automation, May 16-20, 1998, 6 pages.
Branche, et al. "Measurement Reproducibility and Sensor Placement Considerations in Designing a Wearable Pulse Oximeter for Military Applications", IEEE, 2004.
Branche, et al. "Signal Quality and Power Consumption of a New Prototype Reflectance Pulse Oximeter Sensor", IEEE, 2005.
B-S. Lin et al., "RTWPMS: A Real-Time Wireless Physiological Monitoring System," IEEE Transactions on Information Technology in Biomedicine, vol. 10, No. 4, Oct. 2006, pp. 647-656.
Burritt, Mary F.; Current Analytical Approaches to Measuring Blood Analytes; vol. 36; No. 8(B); 1990.

C. Gutierrez et al, "Non-Invasive Functional Mapping of the Brain Using Cerebral Oximeter," Proceedings of the Second Joint EMBS/BMES Conference, Oct. 2002, pp. 947-948.
C. J. Pujary, "Investigation of Photodetector Optimization in Reducing Power Consumption by a Noninvasive Pulse Oximeter Sensor," Worcester Polytechnic Institute, Jan. 16, 2004, 133 pages.
C. Pujary et al., "Photodetector Size Considerations in the Design of a Noninvasive Reflectance Pulse Oximeter for Telemedicine Applications," Proceedings of IEEE Annual Northeast Bioengineering Conference, 2003, pp. 148-149.
C. W. Mundt et al., "A Multiparameter Wearable Physiologic Monitoring System for Space and Terrestrial Applications," IEEE Transactions on Information Technology in Biomedicine, vol. 9, No. 3, Sep. 2005, pp. 382-391.
Celka, et al. "Motion resistant earphone located infrared based heart rate measurement device", Research Gate, 2004.
Conway, et al. "Wearable computer as a multi-parametric monitor for physiological signals," Proceedings IEEE International Symposium on Bio-Informatics and Biomedical Engineering, pp. 236-242, 2000.
Crilly, et al. "An Integrated Pulse Oximeter System for Telemedicine Applications", IEEE Instrumentation and Measurement Technology Conference, 1997.
D. C. Zheng and Y. T. Zhang, "A ring-type device for the noninvasive measurement of arterial blood pressure," Proceedings of the 25th Annual International Conference of the IEEE Engineering in Medicine and Biology Society (IEEE Cat. No. 03CH37439), Sep. 17-21, 2003, Cancun, pp. 3184-3187 vol. 4.
D. Konstantas et al., "Mobile Patient Monitoring: The MobiHealth System," In Proceedings of International Conference on Medical and Care Compunetics, NCC'04, Feb. 2004, 8 pages.
D. Marculescu et al., "Ready to Ware," IEEE Spectrum, vol. 40, Issue 10, Oct. 2003, pp. 28-32.
D. Thompson et al., "A Small, High-Fidelity Reflectance Pulse Oximeter", American Society for Engineering Education, Jan. 2007, 15 pages.
Definition of "cover", excerpt from Merriam-Webster's Collegiate Dictionary (11th ed.), 2005, 3 pages.
Definition of "gap", excerpt from Merriam-Webster's Collegiate Dictionary (11th ed.), 2005, 3 pages.
Definition of "processor", excerpt from Merriam-Webster's Collegiate Dictionary (10th ed.), 1999, 6 pages.
Design of Pulse Oximeters, J.G. Webster, Institution of Physics Publishing, IOP Publishing Ltd, 1997, 262 pages (uploaded in three parts).
Dresher, et al. "A New Reflectance Pulse Oximeter Housing to Reduce Contact Pressure Effects", IEEE, 2006.
Dresher, et al. "Reflectance Forehead Pulse Oximetry: Effects of Contact Pressure During Walking", IEEE, 2006.
E. Higurashi et al., "An integrated laser blood flowmeter," Journal of Lightwave Technology, vol. 21, No. 3, pp. 591-595, Mar. 2003.
E. Higurashi et al., "Hybrid integration technologies for optical micro-systems", Proc. SPIE 5604, Optomechatronic Micro/Nano Components, Devices, and Systems, Oct. 25, 2004, pp. 67-73.
Eugene Hecht, Excerpts of Optics, Second Edition, Addition-Wesley Publishing Company, 1990, 80 pages (pp. 79-143, 211-220).
Eugene Hecht, Optics, Fourth Edition, Pearson Education, Inc., Addison Wesley, 2002, 355 pages. (uploaded in three parts).
Eugene Hecht, Optics, Second Edition, Addition-Wesley Publishing Company, 1990, 348 pages. (uploaded in two parts).
European Office Action issued in Application No. 09791157.2, dated Jun. 20, 2016.
European Office Action issued in application No. 10763901.5 on Jan. 11, 2013.
European Office Action issued in application No. 10763901.5 on Aug. 6, 2015.
European Office Action issued in application No. 10763901.5 on Aug. 27, 2014.
Fabio Buttussi et al., "Mopet: A context-aware and user-adaptive wearable system for fitness training," Artificial Intelligence in Medicine 42, 2008, pp. 153-163.
Faulkner, "Apple Watch Heart Rate Sensor: Everything You Need to Know." TechRadar India, TechRadar, 2015.

(56) References Cited

OTHER PUBLICATIONS

Fontaine, et al. "Reflectance-Based Pulse Oximetry for the Chest and Wrist," Digitalcommons.wpi.edi/mqp-all/1703.

Frank H. Netter, M.D., Atlas of Human Anatomy Third Edition—Section VI Upper Limb, ICON Learning Systems, LLC, 2003, 81 pages.

G. Comtois et al., "A Noise Reference Input to an Adaptive Filter Algorithm for Signal Processing in a Wearable Pulse Oximeter," IEEE, 2007, pp. 106-107.

G. Comtois, "A Comparative Evaluation of Adaptive Noise Cancellation Algorithms for Minimizing Motion Artifacts in a Forehead-Mounted Wearable Pulse Oximeter," Proceedings of the 29th Annual international Conference of the IEEE EMBS, Aug. 23-26, 2007, pp. 1528-1531.

G. Tamannagari, "Power Efficient Design of Finder-Ring Sensor for Patient Monitoring," Master of Science in Electrical Engineering, the University of Texas at San Antonio, College of Engineering, Department of Electrical Engineering, Dec. 2008, 74 pages.

Geun, et al. "Measurement site and applied pressure consideration in wrist photoplethysmography," The 23rd International Technical Conference on Circuits/Systems, Computers and Communications (ITC-CSCC 2008).

Gibbs, et al. "Active Motion Artifact Cancellation for Wearable Health Monitoring Sensors Using Collocated MEMS Accelerometers," Proceedings of SPIE Smart Structures and Materials: Sensors and Smart Structures Technologies for Civil, Mechanical, and Aerospace Systems, May 17, 2005, pp. 811-819.

H. Ding et al., "Refractive indices of human skin tissues at eight wavelengths and estimated dispersion relations between 300 and 1600 nm", Physics in Medicine & Biology, vol. 51, 2006, pp. 1479-1489.

H. Kisch-Wedel et al., "Does the Estimation of Light Attenuation in Tissue Increase the Accuracy of Reflectance Pulse Oximetry at Low Oxygen Saturations In Vivo?" IEEE Transactions on Biomedical Engineering., vol. 56, No. 9, Sep. 2009, pp. 2271-2279.

Hall, et al., Jeffrey W.; Near-Infrared Spectrophotometry: A New Dimension in Clinical Chemistry; vol. 38; No. 9; 1992.

Hayes, "How the Sensors inside Fitness Tracker Work." Digital Trends, 2014.

Heerlein, et al. "LED-Based Sensor for Wearable Fitness Tracking Products", EDN, 2014.

http://amivital.ugr.es/blog/?tag+spo2; Monitorizacion de la hemoglobina . . . y mucho mas, printed on Aug. 20, 2009.

http://blogderoliveira.blogspot.com/2008_02_01_archive.html; Ricardo Oliveira, as published Feb. 13, 2008 in 6 pages.

http://www.masimo.com/generalFloor/system.htm; Masimo Patient SafetyNet System at a Glance, printed on Aug. 20, 2009.

http://www.masimo.com/partners/GRASEBY.htm; Graseby Medical Limited, printed on Aug. 20, 2009.

http://www.masimo.com/PARTNERS/WELCHALLYN.htm; Welch Allyn Expands Patient Monitor Capabilities with Masimo Pulse Oximetry Technology, printed on Aug. 20, 2009.

http://www.masimo.com/pulseOximeter/PPO.htm; Masimo Personal Pulse Oximeter, printed on Aug. 5, 2009.

http://www.masimo.com/pulseOximeter/Rad5.htm; Signal Extraction Pulse Oximeter, printed on Aug. 20, 2009.

http://www.masimo.com/rad-57/; Noninvasive Measurement of Methemoglobin, Carboxyhemoglobin and Oxyhemoglobin in the blood. Printed on Aug. 20, 2009.

http://www.masimo.com/rainbow/pronto.htm Noninvasive & Immediate Hemoglobin Testing, printed on Aug. 20, 2009.

http://www.masimo.com/spco/; Carboxyhemoglobin Noninvasive > Continuous > Immediate, printed on Aug. 20, 2009.

Humphreys, An Investigation of Remote Non-Contact Photoplethysmography and Pulse Oximetry, National University of Ireland: Department of Electronic Engineering, Aug. 2007.

Interim Procedure for Discretionary Denials in AIA Post-Grant Proceedings with Parallel District Court Litigation, issued Jun. 21, 2022 ("Interim Guidance").

J Kraitl et al., "An optical device to measure blood components by a photoplethysmographic method," Journal of Optics A: Pure and Applied Optics. 7, 2005, pp. S318-S324.

J. A. Tamada et al., "Noninvasive Glucose Monitoring: Comprehensive Clinical Results," JAMA, Nov. 17, 1999, vol. 282, No. 19, pp. 1839-1844.

J. C. D. Conway et al., "Wearable computer as a multi-parametric monitor for physiological signals," Proceedings IEEE International Symposium on Bio-Informatics and Biomedical Engineering, Arlington, VA, USA, 2000, pp. 236-242.

J. Fiala et al., "Implantable optical sensor for continuous monitoring of various hemoglobin derivatives and tissue perfusion," IEEE Sensors Conference, 2009, pp. 1971-1974.

J. Hayano et al., "Assessment of pulse rate variability by the method of pulse frequency demodulation." BioMedical Engineering OnLine vol. 4, No. 62, Nov. 1, 2005, doi:10.1186/1475-925X-4-62, pp. 1-12.

J. Schmitt et al., "An Integrated Circuit-Based Optical Sensor for In Vivo Measurement of Blood Oxygenation," IEEE Transactions on Biomedical Engineering, vol. BME-33, No. 2, Feb. 1986, pp. 98-107.

Japanese Notice of Allowance, re JP Application No. 2011-516895, issued on May 12, 2015, no translation.

Japanese Office Action, re JP Application No. 2011-516895, mailed Sep. 2, 2014, with translation.

Johnston, et al. "Extracting Breathing Rate Information from a Wearable Reflectance Pulse Oximeter Sensor," Proceedings of the 26th Annual International Conference of the IEEE EMBS, Sep. 1-5, 2004, pp. 5388-5391.

Johnston, et al. "Extracting Heart Rate Variability from a Wearable Reflectance Pulse Oximeter," IEEE, 2005, pp. 1-2.

K. Chon et al., "Wearable Wireless Sensor for Multi-Scale Physiological Monitoring," Worcester Polytechnic Institute, Oct. 2015, 142 pages. (Uploaded in 2 parts).

K. Nakajima et al., "Monitoring of heart and respiratory rates by photoplethysmography using digital filtering technique," Med. Eng. Phy. vol. 18, No. 5, pp. 365-372, 1996.

Kanukurthy et al., "Data Acquisition Unit for an Implantable Multi-Channel Optical Glucose Sensor", Electro/Information Technology Conference, Chicago, IL, USA, May 17-20, 2007, pp. 1-6.

Keikhosravi, et al. "Effect of deep breath on the correlation between the wrist and finger photoplethysmograms", pp. 135-138, 2012.

Konig et al., "Reflectance Pulse Oximetry—Principles and Obstetric Application in the Zurich System", Journal of Clinical Monitoring and Computing, vol. 14, No. 6, Aug. 1998, pp. 403-412.

Certified English Translation of Korean Pat. Appl. No. 10-2018-0038206 ("Chung-KR-Application"), as filed Apr. 2, 2018, pp. 64.

Kuenstner, et al., J. Todd; Measurement of Hemoglobin in Unlysed Blood by Near-Infrared Spectroscopy; vol. 48; No. 4, 1994.

Kviesis-Kipge, et al., "Miniature Wireless Photoplethysmography Devices: Integration in Garments and Test Measurements", SPIE vol. 8427 84273H-6, 2012.

L. Grajales et al., "Wearable multisensor heart rate monitor," International Workshop on Wearable and Implantable Body Sensor Networks (BSN'06), Cambridge, MA, 2006, pp. 4-157.

L. Xu et al., "An integrated wrist-worn routine monitoring system for the elderly using BSN," 2008 5th International Summer School and Symposium on Medical Devices and Biosensors, Hong Kong, 2008, pp. 45-48.

Laukkanen RM et al., "Heart Rate Monitors: State of the Art," Journal of Sports Science, Jan. 1998, pp. S3-S7.

Lee, et al. "Development of a Wristwatch-Type PPG Array Sensor Module", IEEE, 2011.

Lee, et al. "Reflectance pulse oximetry: Practical issues and limitations," ICT Express 2 (2016) 195-198.

Lin, et al. "RTWPMS: A Real-Time Wireless Physiological Monitoring System", IEEE Transactions on Information Technology in Biomedicine, vol. 10, No. 4, 2006.

Lingaiah, et al. "Measurement of Pulse rate and SPo2 using Pulse Oximeter developed using LabVIEW", IOSR Journal of Electrical and Electronics Engineering (IOSR-JEEE), e-ISSN: 2278-1676,p-ISSN: 2320-3331, vol. 8, Issue 1, pp. 22-26, 2013.

(56) References Cited

OTHER PUBLICATIONS

Lukowicz, et al. "AMON: A Wearable Medical Computer for High-Risk Patients," Proceedings of the 6th International Symposium on Wearable Computers (ISWC'02), 2002, pp. 1-2.
Lukowicz, et al. "The WearARM Modular, Low-Power Computing Core," IEEE Micro, May-Jun. 2001, pp. 16-28.
M. Savage et al., "Optimizing Power Consumption in the Design of a Wearable Wireless Telesensor: Comparison of Pulse Oximeter Modes," Proceedings of IEEE 29th Annual Nonheust Bioengineering Conference, 2003, pp. 150-151.
M. Yamashita et al., "Development of a Ring-Type Vital Sign Telemeter," Biotelemetry XIII, Mar. 26-31, 1995, pp. 145-150.
Manzke, et al., B., Multi Wavelength Pulse Oximetry in the Measurement of Hemoglobin Fractions; SPIE, vol. 2676, Apr. 24, 1996.
Matthes, K. & W. Hauss, Lichtelektrische Plethysomgramme Klinische Wochenschrift, No. 17 (5):1211-1213, 1938.
McPherson, "How to Do Everything with Windows Mobile", McGraw Hill, 2006, 431 pages (uploaded in three parts).
Mendelson et al. "Noninvasive Pulse Oximetry Utilizing Skin Reflectance Photoplethysmography", IEEE Biomedical Engineering, vol. 35 No. 10, 1988.
Mendelson et al., "A Mobile PDA-Based Wireless Pulse Oximeter," Proceedings of the IASTED International Conference Telehealth, Jul. 19-21, 2005, pp. 1-6.
Mendelson et al., "A Wearable Reflectance Pulse Oximeter for Remote Physiological Monitoring," Proceedings of the 28th IEEE EMBS Annual International Conference, Aug. 30-Sep. 3, 2006, pp. 912-915.
Mendelson et al., "Accelerometery-Based Adaptive Noise Cancellation for Remote Physiological Monitoring by a Wearable Pulse Oximeter," Proceedings of the 3rd IASTED International Conference Telehealth, May 31-Jun. 1, 2007, pp. 28-33.
Mendelson et al., "Measurement Site and Photodetector Size Considerations in Optimizing Power Consumption of a Wearable Reflectance Pulse Oximeter," Proceedings of the 25th Annual International Conference of the IEEE EMBS, Sep. 17-21, 2003, pp. 3016-3019.
Mendelson et al., "Minimization of LED Power Consumption in the Design of a Wearable Pulse Oximeter," Proceedings of the IASTED International Conference Biomedical Engineering, Jun. 25-27, 2003, 6 pages.
Mendelson et al., Skin Reflectance Pulse Oximetry: In Vivo Measurements from the Forearm and Calf, Journal of Clinical Monitoring vol. 7 No. 1, pp. 7-12, dated Jan. 1991.
Mendelson, et al., "Design and Evaluation of a New Reflectance Pulse Oximeter Sensor", Worcester Polytechnic Institute, Biomedical Engineering Program, Worcester, MA 01609, Association for the Advancement of Medical Instrumentation, vol. 22, No. 4, 1988, pp. 167-173, Abstract, 1 page.
Mendelson et al., "The Feasibility of Measuring SpO2 from the Head Using a Reflectance Pulse Oximeter: Effect of Motion Artifacts," Proceeding of the 3rd European Medical & Biological Engineering Conference, 2005, 5 pages.
Mendelson et al., "Wireless Reflectance Pulse Oximetery for Remote Triage Application," Worcester Polytechnic Institute, 1 page. Undated.
Mendelson et al., "A Multiwavelength VIS-NIR Spectrometer for Pulsatile Measurement of Hemoglobin Derivatives in Whole Blood," 18th Annual International Conference of the IEEE Engineering in Medicine and Biology Society, 1996, pp. 134-135.
Mendelson et al., "An In Vitro Tissue Model for Evaluating the Effect of Carboxyhemoglobin Concentration on Pulse Oximetry," IEEE Transactions on Biomedical Engineering, vol. 36, No. 6, Jun. 1989, pp. 625-627.
Mendelson et al., "Blood Glucose Measurement by Multiple Attenuated Total Reflection and Infrared Absorption Spectroscopy," IEEE Transactions on Biomedical Engineering, vol. 37, No. 5, May 1990, pp. 458-465.
Mendelson et al., "Carbon dioxide laser based multiple ATR technique for measuring glucose in aqueous solutions," Applied Optics, vol. 27, No. 24, Dec. 1988, pp. 5077-5081.

Mendelson et al., "Evaluation of the Datascope Accusat Pulse Oximeter in Healthy Adults," Journal of Clinical Monitoring, vol. 4, No. 1, Jan. 1988, pp. 59-63.
Mendelson et al., "Multi-channel pulse oximetry for wearable physiological monitoring," IEEE International Conference on Body Sensor Networks, 2013, pp. 1-6.
Mendelson et al., "Noninvasive Transcutaneous Monitoring of Arterial Blood Gases," IEEE Transactions on Biomedical Engineering, vol. BME-31, No. 12, Dec. 1984, pp. 792-800.
Mendelson et al., Pulse Oximetry: Theory and Applications for Noninvasive Monitoring, Clinical Chemistry, vol. 38, No. 9, 1992, pp. 1601-1607.
Mendelson et al., "Variations in Optical Absorption Spectra of Adult and Fetal Hemoglobins and Its Effect on Pulse Oximetry," IEEE Transactions on Biomedical Engineering, vol. 36, No. 8, Aug. 1989, pp. 844-848.
Mendelson et al., "Wearable Wireless Pulse Oximetry for Physiological Monitoring," Worcester Polytechnic Institute, Precise Personnel Location Workshop, Aug. 4, 2008, pp. 34.
Mendelson et al., A Wireless Wearable Reflectance-Based Forehead Pulse Oximeter, PowerPoint, The Bioengineering Institute, Worcester Polytechnic Institute, 8 pages. Undated.
Mendelson et al., Chapter 9: Biomedical Sensors, Introduction to Biomedical Engineering, Second Edition, Apr. 2005, pp. 505-548.
Mendelson, "Wearable, Wireless, Noninvasive Physiological Sensing," The Bioengineering Institute, Worcester Polytechnic Institute, 2005, 2 pages.
Mendelson, Pulse Oximetry, PowerPoint, UMass Center for Clinical and Translational Science Research Retreat, 2017, 22 pages.
Mio Alpha Complete User Guide, Physical Enterprises, https://www.medisana.com/out/pictures/media/manual/mio_alpha_user_guide_en.pdf (2014).
National Instruments LabVIEW User Manual, National Instruments Corporation, Nov. 2001 Edition, Part No. 320999D-01, 293 pages.
Naumenko, E. K.; Choice of Wavelengths for Stable Determination of Concentrations of Hemoglobin Derivatives from Absorption Spectra of Erythrocytes; vol. 63; No. 1; pp. 60-66 Jan.-Feb. 1996; Original article submitted Nov. 3, 1994.
Netter, Frank H., "Atlas of Human Anatomy", Third Edition, 2003.
Nonin Medical, Inc., "Operator's Manual—Models 8600F0 and 8600F0M Pulse Oximeters," 2005, 25 pages.
Oliver et al., "HealthGear: A Real-time Wearable System for Monitoring and Analyzing Physiological Signals," Proceedings of the International Workshop on Wearable and Implantable Body Sensor Networks, IEEE Computer Society, 2006, pp. 1-4.
P. Branche et al., "Signal Quality and Power Consumption of a New Prototype Reflectance Pulse Oximeter Sensor," Proceeding of the 31th Annual Northeast Bioengineering Conference, Hoboken, NJ, IEEE, 2005, pp. 1-2.
P. C. Branche et al., "Measurement Reproducibility and Sensor Placement Considerations in Designing a Wearable Pulse Oximeter for Military Applications," IEEE, 2004, pp. 216-217.
P. Celka et al., "Motion Resistant Earphone Located Infrared Based Hearth Rate Measurement Device," In Proceeding of the 2nd International Conference on Biomedical Engineering, Innsbruck, Austria, Feb. 16-18, 2004, pp. 582-585.
P. Shaltis et al., "Novel Design for a Wearable, Rapidly Depolyable, Wireless Noninvasive Triage Sensor," Proceedings of the 2005 IEEE, Engineering in Medicine and Biology 27th Annual Conference, Sep. 1-4, 2005, pp. 3567-3570.
Pandian et al., "Smart Vest: Wearable Multi-Parameter Remote Physiological Monitoring System," Medical Engineering & Physics 30, 2008. pp. 466-477.
Perry, T., "Should You Trust Apple's New Blood Oxygen Sensor?" View From the Valley—IEEE Spectrum, Sep. 21, 2020, retrieved from https://spectrum.ieee.org/view-from-the-valley/biomedical/devices/should-you-trust-apples-new-blood-oxygen-sensor, 4 pages.
Phattraprayoon, et al. "Accuracy of Pulse Oximeter Readings From Probe Placementon Newborn Wrist and Ankle", Journal of Perinatology, vol. 32, pp. 276-280, 2012.
Poh et al. "Motion-Tolerant Magnetic Earring Sensor and Wireless Earpiece for Wearable Photoplethysmography", IEEE Transactions on Information Technology in Biomedicine, vol. 14, No. 3, 2010.

(56) References Cited

OTHER PUBLICATIONS

QuickSpecs; HP iPAQ Pocket PC h4150 Series, dated Nov. 20, 2003, in 8 pages.
R. Fensli et al., "A Wireless ECG System for Continuous Event Recording and Communication to a Clinical Alarm Station," Conf Proc IEEE Eng Med Biol Soc, 2004, pp. 1-4.
R. Gupta et al., "Design and Development of Pulse Oximeter," Proceedings RC IEEE-EMBS & 14th BMESI, 1995, pp. 1.13-1.16.
R. Paradiso, "Wearable Health Care System for Vital Signs Monitoring," In Proceedings of IEEE International Conference on Information Technology Applications in Biomedicine, May 2003, pp. 283-286.
R. Yotter et al., "A Review of Photodetectors for Sensing Light-Emitting Reporters in Biological Systems", IEEE Sensors Journal, vol. 3, No. 3, Jun. 2003, pp. 288-303.
Renevey et al., "Wrist-Located Pulse Detection Using IR Signals, Activity and Nonlinear Artifact Cancellation," Proceedings of the 23rd Annual EMBS International Conference, Oct. 25-28, 2001, pp. 3030-3033.
Rhee et al. "Artifact-Resistant, Power Efficient Design of Finger-Ring Plethysmographic Sensors, Part I: Design and Analysis," 22nd Annual International Conference IEEE Engineering in Medicine and Biology Society, Jul. 23-28, 2000, pp. 2792-2795.
Rhee et al., "Design of a Artifact-Free Wearable Plethysmographic Sensor," 21st Annual International Conferemce IEEE Engineering in Medicine and Biology Society, Oct. 13-16, 1999, p. 786.
Rhee et al., "The Ring Sensor: a New Ambulatory Wearable Sensor for Twenty-Four Hour Patient Monitoring," Proceedings of the 20th Annual International Conference of the IEEE Engineering in Medicine and Biology Society, Oct. 29-Nov. 1, 1998, 4 pages.
Dresher, "Wearable Forehead Pulse Oximetry: Minimization of Motion and Pressure Artifacts," May 3, 2006, 93 pages.
S. DeMeulenaere, "Pulse Oximetry: Uses and Limitations," The Journal for Nurse Practitioners—JNP, May 2007, pp. 312-317.
S. Duun et al., "A Novel Ring Shaped Photodiode for Reflectance Pulse Oximetry in Wireless Applications," IEEE Sensors Conference, 2007, pp. 596-599.
S. Salehizadeh et al., "Photoplethysmograph Signal Reconstruction based on a Novel Motion Artifact Detection-Reduction Approach. Part II: Motion and Noise Artifact Removal," Annals of Biomedical Engineering, vol. 42, May 2014, pp. 2251-2263.
S. Mace, "The Fifth Vital Sign: Pulse Oximetetry in Noninvasive Respiratory Monitoring," Relias Media, May 1, 2005, retrieved from https://www.reliasmedia.com/articles/85751-the-fifth-vital-sign-pulse-oximetry-in-noninvasive-respiratory-monitoring, 21 pages.
S. N. Kasarova et al., "Analysis of the dispersion of optical plastic materials", Optical Materials vol. 29, 2007, pp. 1481-1490.
S. Pentland, "Healthwear: Medical Technology Becomes Wearable," IEEE Computer Society, vol. 37, Issue 5, May 2004, pp. 34-41.
Takatani et al., "Experimental and Clinical Evaluation of a Noninvasive Reflectance Pulse Oximeter Sensor," Journal of Clinical Monitoring, vol. 8, No. 4, Oct. 1992, pp. 257-266.
Savage et al., "Optimizing Power Consumption in the Design of a Wearable Wireless Telesensor: Comparison of Pulse Oximeter Modes," Proceedings of IEEE 29th Annual Nonheust Bioengineering Conference, 2003, pp. 150-151.
Schmitt, et al., Joseph M.; Measurement of Blood Hematocrit by Dual-Wavelength near-IR Photoplethysmography; vol. 1641; 1992.
Schmitt, Joseph M.; Simple Photon Diffusion Anaylsis of the Effects of Multiple Scattering on Pulse Oximetry; Mar. 14, 1991; revised Aug. 30, 1991.
Schnapp, et al., L.M.; Pulse Oximetry. Uses and Abuses.; Chest 1990; 98; 1244-1250 DOI 10.1378/Chest.98.5.1244.
Small et al., "Data Handling Issues for Near-Infrared Glucose Measurements", http://www.ieee.org/organizations/pubs/newsletters/leos/apr98/datahandling.htm, accessed Nov. 27, 2007.
Smith, "The Pursuit of Noninvasive Glucose: 'Hunting the Deceitful Turkey'", 2006.

Sonnia Maria López Silva et al., "Near-infrared transmittance pulse oximetry with laser diodes," Journal of Biomedical Optics vol. 8 No. 3, Jul. 2003, pp. 525-533.
Stephen A. Mascaro et al., "Measurement of Finger Posture and Three-Axis Fingertip Touch Force Using Fingernail Sensors," IEEE International Conference on Robotics and Automation, 2002, pp. 1-11.
Stephen A. Mascaro et al., "Photoplethysmograph Fingernail Sensors for Measuring Finger Forces Without Haptic Obstruction," IEEE Transactions on Robotics and Automation, vol. 17, No. 5, Oct. 2001, pp. 698-708.
Stojanovic, et al. "Design of an Oximeter Based on LED-LED Configuration and FPGA Technology", Sensors, 13, 574-586, 2013.
T. Kiyokura et al., "Wearable Laser Blood Flowmeter for Ubiquitous Healthcare Service," 2007 IEEE/LEOS International Conference on Optical MEMS and Nanophotonics, Hualien, 2007, pp. 4-5.
T. Martin et al., "Issues in Wearable Computing for Medical Montioring Applications: A Case Study of a Wearable ECG Monitoring Device," In Proceedings of International Symposium of Wearable Computers (ISWC'00), Feb. 2000, pp. 43-49.
T. Torfs et al., "Body-Heat Powered Autonomous Pulse Oximeter," IEEE Sensors 2006, EXCO, Oct. 22-25, 2006, pp. 427-430.
Takumi Morita et al., "Integrated Blood Flowmeter Using Micromachining Technology," Dec. 2004, pp. 77-80.
Tamura et al. "Wearable Photoplethysmographic Sensors—Past and Present", Electronics, 3, 282-302, 2014.
Team SO-SIG, Final Report, Aug. 22, 2007, 4 pages.
Townsend, et al. "Pulse Oximetry," Medical Electronics, 2001, pp. 32-42.
Tura, et al., "A Medical Wearable Device with Wireless Bluetooth-based Data Transmission", Measurement Science Review, vol. 3, Section 2, 2003.
Vogel et al., "In-Ear Vital Signs Monitoring Using a Novel Microoptic Reflective Sensor," IEEE Transactions on Information Technology in Biomedicine, vol. 13, No. 6, Nov. 2009, pp. 882-889.
W. S. Johnston et al., "Investigation of Signal Processing Algorithms for an Embedded Microcontroller-Based Wearable Pulse Oximeter," Proceedings of the 28th IEEE EMBS Annual International Conference, Aug. 30-Sep. 3, 2006, pp. 5888-5891.
Warren et al., "Designing Smart Health Care Technology into the Home of the Future," Workshops on Future Medical Devices: Home Care Technologies for the 21st Century, Apr. 1999, 19 pages.
Written Opinion received in International Application No. PCT/US2016/040190, dated Jan. 2, 2018.
Yan, et al. "An Efficient Motion-Resistant Method for Wearable Pulse Oximeter," IEEE Transactions on Information Technology in Biomedicine, vol. 12, No. 3, May 2008, pp. 399-405.
Yuan-Hsiang Lin et al., "A wireless PDA-based physiological monitoring system for patient transport," IEEE Transactions on Information Technology in Biomedicine, vol. 8, No. 4, pp. 439-447, Dec. 2004.
Zhai, et al. "A Wireless Sensor Network for Hospital Patient Monitoring," Thesis for University of Calgary Department of Electrical and Computer Engineering, Apr. 2007, 134 pages.
International Search Report and Written Opinion received in International Application No. PCT/US2021/013299, dated Jun. 21, 2021, 23 pages.
U.S. Appl. No. 62/691,822, filed Jun. 29, 2018, Weaver.
International Search Report and Written Opinion received in International Application No. PCT/US2022/075787, dated Dec. 13, 2022, 12 pages.
Jung, Scott, "Medgadget Joins the Verily Baseline Project Study, Part 2: The Tech", MedGadget.com, https://www.medgadget.com/2017/10/medgadget-joins-verily-baseline-project-study-part-2-tech.html, Oct. 27, 2017, pp. 6.
U.S. Appl. No. 61/932,258, filed Jan. 28, 2014, Park et al.
U.S. Appl. No. 61/976,388, filed Apr. 7, 2014, Fei.
Aldinger et al., "Advanced Ceramics and Future Materials: An Introduction to Structure, Properties, Technologies, Methods", Wiley-VCH GmbH & Co., 2010, pp. 17.
Shi, Feng, "Ceramic Materials—Progress in Modern Ceramics", InTech, Apr. 2012, pp. 6.

(56) References Cited

OTHER PUBLICATIONS

Francis, Johnson, "ECG monitoring leads and special leads", Indian Pacing and Electrophysiology Journal, vol. 16, 2016, pp. 92-95.
Shackelford et al., "Ceramic and Glass Materials: Structure, Properties and Processing", Springer, 2008, pp. 33.
Loehman et al., "Characterization of Ceramics", Materials Characterization Series; Surfaces, Interfaces, Thin Films, Butterworth-Heinemann, 1993, pp. 13.
Kingery, W.D., "Introduction to Ceramics", John Wiley & Sons, Inc., 1960, pp. 23.
Ling et al., "The effects of link format and screen location on visual search of web pages," Ergonomics, vol. 47, No. 8, Jun. 22, 2004, pp. 18.
McCarthy et al., "Could I have the Menu Please? An Eye Tracking Study of Design Conventions", People and Computers XVII—Designing for Society, 2003, pp. 20.
Nielsen, Jakob, "Do Interface Standards Stifle Design Creativity?", Alertbox, https://web.archive.org/web/19991128143803/http://www.useit.com/alertbox/990822.html, Aug. 22, 1999, pp. 2.
Nielsen, Jakob, "Enhancing the Explanatory Power of Usability Heuristics", Human Factors in Computing Systems, CHI '94 Conference Proceedings, Aug. 1994, pp. 14.
Norman, Donald A., "The Design of Everyday Things", Double Day, 1988, pp. 37.
Santa-Maria et al., "The effect of violating visual conventions of a website on user performance and disorientation. How bad can it be?," SIGDOC'08, Sep. 22-24, 2008, pp. 8.
Oct. 20, 2022 Complaint for Patent Infringement and Demand for Jury Trial, *Apple Inc.* v. *Masimo Corporation and Sound United, LLC*, Case No. 1:22-cv-01377-UNA, 32 pages.
Oct. 20, 2022 Complaint for Patent Infringement and Demand for Jury Trial, *Apple Inc.* v. *Masimo Corporation and Sound United, LLC*, Case No. 1:22-cv-01378-UNA, 77 pages.
"Agent: The World's Smartest Watch", https://www.kickstarter.com/projects/secretlabs/agent-the-worlds-smartest-watch/faqs, Last updated Apr. 30, 2016, pp. 8.
"An entry-level all-round watch that makes sports unique | Aiwei P1 energy sports watch", https://mp.weixin.qq.com/s/d6ACPZqrRpvqdLHmb7UOsQ, Jun. 10, 2018, pp. 36.
"Android 4.2 Compatibility Definition", Android Compatibility Program, chrome-extension://efaidnbmnnnibpcajpcglclefindmkaj/https://source.android.com/docs/compatibility/4.2/android-4.2-cdd.pdf, Jun. 10, 2013, pp. 36.
"Care for your pillow partner with all your heart, Oranger Snoring Monitor 2.0", https://mp.weixin.qq.com/s/EkQ_fNfotpCMaoDt3xan9Q, Jul. 27, 2015, pp. 10 (21 total pages with Translation).
"Comprehensive functions and excellent cost-effectiveness, Aiwei energy sports watch P1 trial experience", https://mp.weixin.qq.com/s/XvRdKBCYQWqZwBP-Cesz7g, Jun. 27, 2018, pp. 11 (20 total pages with Translation).
"Introducing Verily Study Watch", Verily, https://verily.com/blog/Introducing-Verily-Study-Watch/, Apr. 14, 2017, pp. 6.
"Monitor heart rate and record sports, experience of Avery energy sports watch P1", https://www.sohu.com/a/234524743_115300, Jun. 8, 2018, pp. 9 (26 total pages with Translation).
"Pulse Sensor, Easy to Use Heart Rate Sensor & Kit", PulseSensor.com, World Famous Electronics LLC. NY, USA, pp. 2.
"A New Family of Sensors for Pulse Oximetry," Hewlett-Packard Journal, Feb. 1997 (APL_DEL00637653), in 17 pages. Apple alleges that this reference has a prior art date of 1997.
"A Technology Overview of the Nellcor OxiMax Pulse Oximetry System," Nellcor Technical Staff, 2003 (APL_DEL00031781, APL_DEL00037976), in 8 pages. Apple alleges that this reference has a prior art date of 2003.
"Apple Unveils Apple Watch—Apple's Most Personal Device Ever," https://www.apple.com/newsroom/2014/09/09Apple-Unveils-Apple-Watch-Apples-Most-Personal-Device-Ever/ (last visited Mar. 31, 2023), pp. 4.
"Apple Watch—Technology," archived on Sep. 11, 2014 by the Internet Organization's "Wayback Machine" at https://web.archive.org/web/20140911003437/http://www.apple.com/watch/technology/, pp. 8.
"Apple Watch Magnetic Charging Cable (1 m)," https://www.apple.com/shop/product/MX2E2AM/A/apple-watchmagnetic-charging-cable-1m (last visited Mar. 6, 2023), pp. 4.
"Apple Watch Series 4—Health," archived on Sep. 20, 2018 by the Internet Organization's "Wayback Machine" at https://web.archive.org/web/20180920103403/https:/www.apple.com/apple-watch-series-4/health/, pp. 18.
"Apple Watch Series 4 Teardown," https://www.ifixit.com/Teardown/Apple+Watch+Series+4+Teardown/113044 (last visited Mar. 6, 2023), pp. 14.
"Apple Watch Series 4: Beautifully redesigned with breakthrough communication, fitness and health capabilities," archived on Sep. 12, 2018 by the Internet Organization's Wayback Machine at https://web.archive.org/web/20180912191250/https://www.apple.com/newsroom/2018/09/redesigned-apple-watch-series-4-revolutionizescommunication-fitness-and-health/, pp. 15.
"Apple Watch Teardown—iFixit," https://www.ifixit.com/Teardown/Apple+Watch+Teardown/40655 (last visited Apr. 3, 2023), pp. 18.
"Charge Apple Watch," https://support.apple.com/guide/watch/chargeapple-watch-apd2b717523a/watchos (last visited Mar. 6, 2023), pp. 6.
"Masimo Signal Extraction Technology," Masimo Corp., 2001 (APL_DEL00037764), in 8 pages. Apple alleges that this reference has a prior art date of 2003.
"Masimo Signal Extraction Technology: Technical Bulletin 1," Masimo Corp., 2001 (APL_DEL00037757), in 7 pages. Apple alleges that this reference has a prior art date of 2003.
"Non-Invasive Cardiac Output Monitor Model 7300: User's Manual," Novametrix, 2001 (APL_DEL00031974), in 100 pages. Apple alleges that this reference has a prior art date of 2001.
"NPB-195 Pulse Oximeter: Home Use Guide," Nellcor, 1997 (APL_DEL00032149), in 105 pages. Apple alleges that this reference has a prior art date of 1999.
"NPB-195 Pulse Oximeter: Operator's Manual," Mallinckrodt, 1999 (APL_DEL00032074), in 75 pages. Apple alleges that this reference has a prior art date of 1999.
"OxiMax N-595 Pulse Oximeter Operator's Manual," Nellcor, 2002 (APL_DEL00031597, APL_DEL00037792), in 184 pages. Apple alleges that this reference has a prior art date of 2003.
"Oxinet II Monitoring System Operator's Manual," Nellcor, 2002 (APL_DEL00031789), in 132 pages. Apple alleges that this reference has a prior art date of 2003.
"Oxinet III Central Station and Paging System," Nellcor, 2003 (APL_DEL00031921), in 2 pages. Apple alleges that this reference has a prior art date of 2003.
"Oxinet III Service Manual," Nellcor, 2005 (APL_DEL00031535), in 62 pages. Apple alleges that this reference has a prior art date of 2003.
"Pulse Oximetry Sensors: LNOP & NR," Masimo Set, 2003 (APL_DEL00037755), in 2 pages. Apple alleges that this reference has a prior art date of 2003.
"Radical Signal Extraction Pulse Oximeter: Operator's Manual," Masimo, 2001 (APL_DEL00034347), in 78 pages. Apple alleges that this reference has a prior art date of 2001.
"Sotera Wireless," Tuck School of Business at Dartmouth: Center for Digital Strategies Case Series, Sep. 4, 2012 (APL_DEL00037109), in 20 pages. Apple alleges that this reference has a prior art date of 2011.
"Your heart rate. What it means, and where on Apple Watch you'll find it," archived on Jan. 23, 2019 by the Internet Organization's "Wayback Machine" at https://web.archive.org/web/20190123031906/https://support.apple.com/en-us/HT204666, pp. 4.
2012 LG Nexus 4 https://www.gsmarena.com/lg_nexus_4_e960-5048.php, pp. 4.
2013 Adidas MiCoach Smart Run, https://www.cnet.com/reviews/adidas-micoach-smart-run-preview/, pp. 7.
2013 LG G Flex https://www.gsmarena.com/lg_g_flex-5806.php, pp. 4.
2013 LG G2 https://www.gsmarena.com/lg_g2-5543.php, pp. 4.

(56) References Cited

OTHER PUBLICATIONS

2013 Samsung Galaxy S4 https://www.gsmarena.com/samsung_i9500_galaxy_s4-5125.php, pp. 4.
2014 LG G Watch W100 https://www.gsmarena.com/lg_g_watch_w100-7718.php, pp. 2.
A Decision Support Service Platform for Neurodegenerative Disease Patients, Sixth International Conference on Networking and Services, 2010 (APL_DEL00034343), in 4 pages. Apple alleges that this reference has a prior art date of 2010.
Adecro Plastics, ABS Plastic Properties, (last visited Mar. 13, 2023), www.adrecoplastics.co.uk/abs-plasticproperties/#:~:text=Finally%2C%20ABS%20has%20low%20heat,absorb%20shock%20effectively%20and%20reliably, pp. 7.
Android Device List Page https://www.androidheadlines.com/android-device-list-page, Sep. 13, 2023, pp. 8.
Android-based Healthcare Smartphone Packed with Medical Sensors, Jul. 5, 2012 (APL_DEL00038072), in 3 pages. Apple alleges that this reference has a prior art date of 2012.
Apr. 2017 Samsung Galaxy S8, https://www.gsmarena.com/samsung_galaxy_s8-8161.php, pp. 3.
Ashley et al., "Cardiology Explained", Remedica, 2004, pp. 257. [Uploaded in 2 parts].
Bacchillone, et al. "A flexible home gateway system for telecare of patients affected by chronic heart failure," APL_DEL00032311, 2011, in 4 pages.
Bailey, et al. "Development of a Remote Pulse Oximeter," APL_DEL00032315, 2010, in 91 pages.
Bennett, Brian, "LG's WCP-300 easily charges sans wires (hands-on)", https://www.cnet.com/reviews/lg-wcp-300-wireless-charger-preview/, Feb. 26, 2013, pp. 3.
Berbari, Edward J., "Principles of Electrocardiography", Biomedical Engineering Fundamentals, The Biomedical Engineering Handbook, 4th Ed., 2015, pp. 5.
Canfield, Douglas, "Drying and Curing Inks and Coatings on Glass", Mar. 26, 2013, pp. 5. https://www.glassmagazine.com/article/drying-and-curing-inks-and-coatings-glass.
Carl R. Nave, Conductors and Insulators, Hyperphysics (last visited Mar. 13, 2023), http://hyperphysics.phyastr.gsu.edu/hbase/electric/conins.html#c1, pp. 3.
Chad, "Widget Tutorial Part 2—How to add lockscreen widgets on your device", https://digibites.zendesk.com/hc/en-us/articles/200351831-Widget-tutorial-part-2-How-to-add-lockscreen-widgets-on-your-device, Jan. 25, 2016, pp. 11.
Chang, et al. "Microlens array diffuser for a light-emitting diode backlight system," APL_DEL00030110, 2+B256006, in 4 pages.
Chang-Wook, Kim, "Mobile 11th Street, Mobile Phone Wireless Charger Unlimited Sale", etnews, Mar. 11, 2013, pp. 2.
Chiu et al., "Discrete Wavelet Transform Applied on Personal Identity Verification with ECG Signal", Research Gate, Conference Paper, May 2008, pp. 20.
CMS50K Wearable SpO2/ECG Monitor from Contec Medical Systems Co., Ltd. ("CMS50K Watch"), Per Apple: Date of Public Knowledge, Use, and/or Sale is No later than Apr. 2016, 1 page.
CODE-STAT 10 Basic Annotation Guide, 2015 (APL_DEL00032565), in 62 pages. Apple alleges that this reference has a prior art date of 2011.
CODE-STAT data review software and service, Jun. 5, 2023 (APL_DEL00032627), in 4 pages. Apple alleges that this reference has a prior art date of 2011.
DC Rainmaker, "Garmin Vivoactive 3 In-Depth Review", https://www.dcrainmaker.com/2017/10/garmin-vivoactive-3-in-depth-review.html, Oct. 18, 2017, pp. 119.
DC Rainmaker, "Garmin's Vivomove HR: Everything you need to know", https://www.dcrainmaker.com/2017/09/garmins-vivomove-hr-everything.html, Sep. 6, 2017, pp. 27.
DC Rainmaker, Fitbit Surge In-Depth Review, Jan. 20, 2015 ("Surge Review") (APL_DEL00030150), in 109 pages. Apple alleges that this reference has a prior art date of May 2015.
Dictionary.com, Definition of "enclosure", printed Jun. 14, 2024, https://www.dictionary.com/browse/enclosure, pp. 5.
Donati, et al. "A flexible home monitoring platform for patients affected by chronic heart failure directly integrated with the remote Hospital Information System," APL_DEL00032456, 2011, in 8 pages.
Dynamic Adaptive Remote Health Monitoring for Patients with Chronic Disease, University of California, Los Angeles, 2012 (APL_DEL00038075), in 127 pages. Apple alleges that this reference has a prior art date of 2012.
Ertin et al., "AutoSense: Unobtrusively Wearable Sensor Suite for Inferring the Onset, Causality, and Consequences of Stress in the Field", SenSys'11, Nov. 1-4, 2011, pp. 14.
Fantini, et al. "Frequency-domain multichannel optical detector for noninvasive tissue spectroscopy and oximetry," APL_DEL00037609, 1995, in 12 pages.
Feb. 2017 LG Watch Style, https://www.gsmarena.com/lg_watch_style-8551.php, pp. 2.
Fitbit, Fitbit Surge Fitness Super Watch User Manual Version 1.0 ("Surge Manual") (APL_DEL00030259), in 49 pages. Apple alleges that this reference has a prior art date of May 2015.
Fitbit's New Fitness Watch Can Display Your Calls and Track Your Location While You Run, Oct. 27, 2014 ("Fitbit's New Fitness Watch") (APL_DEL00030308), in 5 pages. Apple alleges that this reference has a prior art date of May 2015.
gov.uk Designs Journal Entry for Lee-616, https://www.registereddesign.service.gov.uk/view/2013/11/215 (last visited Mar. 28, 2023), pp. 12.
Hamamatsu, "Lens for Side-on Type Photomultiplier Tubes" (Mar. 1999) (APL_DEL00037641), in 4 pages. Apple alleges that this reference has a prior art date of Mar. 1999.
Hanselman, Scott, "Exclusive Sneak Peek: The AGENT Smart Watch Emulator and managed .NET code on my wrist!", https://www.hanselman.com/blog/exclusive-sneak-peek-the-agent-smart-watch-emulator-and-managed-net-code-on-my-wrist, Jun. 18, 2013, pp. 2.
How ViSi Mobile Can Help With Infectious Disease / Sotera ViSi Mobile Brochures (APL_DEL00036979), in 1 page. Apple alleges that this reference has a prior art date of 2011.
https://www.stryker.com/us/en/emergencycare/products/lifepak-15.html (APL_DEL00033792), in 6 pages. Apple alleges that this reference has a prior art date of 2011.
Human-Centered Phone Oximeter Interface Design for the Operating Room, Proceedings of the International Conference on Health Informatics, SciTePress (APL_DEL00032489), in 6 pages. Apple alleges that this reference has a prior art date of 2011.
Ideal Life SpO2 Manager, 2011 (APL_DEL00038204), in 2 pages. Apple alleges that this reference has a prior art date of 2012.
IntelliVue MX40 Brochures (APL_DEL00036821), in 3 pages. Apple alleges that this reference has a prior art date of Feb. 2012.
IntelliVue MX40 Brochures (APL_DEL00036878), in 8 pages. Apple alleges that this reference has a prior art date of Feb. 2012.
IntelliVue MX40 Brochures, Jan. 2020 (APL_DEL00036861), in 17 pages. Apple alleges that this reference has a prior art date of Feb. 2012.
IntelliVue MX40 Brochures, Mar. 2016 (APL_DEL00036603), in 8 pages. Apple alleges that this reference has a prior art date of Feb. 2012.
IntelliVue MX40 Installation and Service, Jun. 2012 (APL_DEL00035983), in 158 pages. Apple alleges that this reference has a prior art date of Feb. 2012.
IntelliVue MX40 Instructions for Use, Feb. 2012 (APL_DEL00036141), in 246 pages. Apple alleges that this reference has a prior art date of Feb. 2012. [Uploaded in 2 parts].
IntelliVue MX40 Instructions for Use, Jun. 2011 (APL_DEL00036611), in 210 pages. Apple alleges that this reference has a prior art date of Feb. 2012.
IntelliVue MX40 with Masimo SET Reusable Adapter and Patient Cables Instructions for Use, 2020 (APL_DEL00036387), in 206 pages. Apple alleges that this reference has a prior art date of Feb. 2012.
Ion et al., "Hands-on: Multiple users, lock screen widgets round out Android 4.2", ARSTechnica, https://arstechnica.com/gadgets/2012/11/hands-on-multiple-users-lock-screen-widgets-round-out-android-4-2/, Nov. 14, 2012, pp. 12.

(56) References Cited

OTHER PUBLICATIONS

Johns et al., "Adapting Qi-compliant wireless-power solutions to low-power wearable products", Texas Instruments, Analog Applications Journal, 2Q, 2014, pp. 7.
Kyoso et al., "Development of an ECG Indentification System", 2001 Proceedings of the 23rd Annual EMBS Internation Conference, Oct. 25-28, 2001, Istanbul, Turkey, pp. 3721-3723.
Leslie Cromwell et al., Biomedical Instrumentation and Measurements (1973), pp. 31-32.
Letter from Jennifer Shih to Verily Life Sciences LLC re 510(k) No. K192415, U.S. Food & Drug Administration, dated Jan. 17, 2020 in 7 pages. https://www.accessdata.fda.gov/cdrh_docs/pdf19/K192415.pdf.
LifePak 15 Monitor Defibrillator Operating Instructions, Jun. 2015 (APL_DEL00032631), in 284 pages. Apple alleges that this reference has a prior art date of 2011. [Uploaded in 2 parts].
LifePak 15 Monitor Defibrillator Power Module Upgrade (APL_DEL00032915), in 52 pages. Apple alleges that this reference has a prior art date of 2011.
LifePak 15 Monitor Defibrillator Service Manuals, Jun. 2015 (APL_DEL00033798), in 527 pages. Apple alleges that this reference has a prior art date of 2011. [Uploaded in 2 parts].
LifePak 15 Monitor Defibrillator Service Manuals, Mar. 2019 (APL_DEL00032967), in 507 pages. Apple alleges that this reference has a prior art date of 2011. [Uploaded in 2 parts].
LifePak 15 Operating Instructions, Jan. 2019 (APL_DEL00033474), in 318 pages. Apple alleges that this reference has a prior art date of 2011. [Uploaded in 3 parts].
LifeWatch V User Manual, 2012 (APL_DEL00038208), in 136 pages. Apple alleges that this reference has a prior art date of 2012.
LifeWatch V, A smartphone that connects to you, Jul. 7, 2012 (APL_DEL00038344), in 1 page. Apple alleges that this reference has a prior art date of 2012.
Lin, et al. "Wireless PDA-Based Physiological Monitoring System for Patient Transport," APL_DEL00031220, Dec. 2004, in 9 pages.
Lucas 3 Quick User Guide (APL_DEL00034325), 2020, in 5 pages. Apple alleges that this reference has a prior art date of 2011.
Luke, Jack, "Garmin VivoActive 3 brings new design, interface and features", https://www.bikeradar.com/news/garmin-vivoactive-3-brings-new-design-interface-and-features, Sep. 1, 2017, pp. 6.
Mendelson et al., "A Wearable Reflectance Pulse Oximeter for Remote Physiological Monitoring", Proceedings of the 28th IEEE EMBS Annual International Conference, New York City, 2006, pp. 912-915. (APL_DEL00030452).
Mendelson, Yitzhak, "Invasive and Noninvasive Blood Gas Monitoring", Bioinstrumentation and Biosensors, 1991, pp. 249-279.
Merriam-Webster, Definition of "enclosure", printed Jun. 14, 2024, https://www.merriam-webster.com/dictionary/enclosure#:~:text=1,%3A%20something%20that%20encloses, pp. 10.
Merriam-Webster's Collegiate Dictionary, 11th ed. 2004, Definition of "embedded" and "Pad", pp. 406 & 890 (5 pgs. Total).
Meziane et al., Dry Electrodes for Electrocardiograma, IOP Publishing, Physiological Measurement, 34 (2013) R47-R69.
Microsoft HealthVault Drivers—Installation Quick Start Guide (APL_DEL00034971), in 4 pages. Apple alleges that this reference has a prior art date of 2008.
Microsoft HealthVault Service Specification, Mar. 27, 2009 (APL_DEL00034580), in 391 pages. Apple alleges that this reference has a prior art date of 2008.
Model 3150 WristOx2 Operator's Manual and 3150SC USB Cable Driver Software (APL_DEL00035230), in 699 pages. Apple alleges that this reference has a prior art date of 2011. [Uploaded in 6 parts].
Motorola, LG announce upcoming Android Wear smartwatches (Mar. 18, 2014), available at https://www.theverge.com/2014/3/18/5522340/motorola-lg-announce-upcoming-android-wear-smartwatches, pp. 3.
Moyle, "Pulse Oximetry," APL_DEL00031253, 2002, in 192 pages.
Nellcor N-3000 Pulse Oximeter Service Manual, 1996 (APL_DEL00034470), in 110 pages. Apple alleges that this reference has a prior art date of 1996.
Nogawa, et al. "New hybrid reflectance optical pulse oximetry sensor for lower oxygen saturation measurement and for broader clinical application," APL_DEL00037781, 1997, in 11 pages.
Nonin Comparative Accuracy Testing of Nonin PureSAT, Nov. 8, 2004 (APL_DEL00034975), in 6 pages. Apple alleges that this reference has a prior art date of 2008.
Nonin nVision Operator's Manual (APL_DEL00035127), 2017, in 54 pages. Apple alleges that this reference has a prior art date of 2008.
Nonin nVision SpO2 Data Management Software (APL_DEL00035111), 2009, in 4 pages. Apple alleges that this reference has a prior art date of 2008.
Nonin nVision User Guide (APL_DEL00035018), 2014, in 89 pages. Apple alleges that this reference has a prior art date of 2008.
Nonin OEM Family Brochure (APL_DEL00035115), 2005, in 12 pages. Apple alleges that this reference has a prior art date of 2008.
Nonin Onyx II 9560 User Manual (APL_DEL00035014), 2008, in 4 pages. Apple alleges that this reference has a prior art date of 2008.
Nonin Onyx II Model 9560 Finger Pulse Oximeter Instructions for Use—English (APL_DEL00034981), 2012, in 9 pages. Apple alleges that this reference has a prior art date of 2008.
Nonin Pulse Oximeter Avant 4100 Service Manual (APL_DEL00035929), 2005, in 44 pages. Apple alleges that this reference has a prior art date of 2008.
Nonin Sample nVision Report (APL_DEL00035107), in 4 pages. Apple alleges that this reference has a prior art date of 2008.
Nonin WristOx 3100 Operator's Manual (APL_DEL00035187), 2005, in 43 pages. Apple alleges that this reference has a prior art date of 2011.
Nonin WristOx2 3150 Bluetooth Connection Tutorial (APL_DEL00034990), in 20 pages. Apple alleges that this reference has a prior art date of 2011.
Oranger Watch 2.0 from Oranger (Cheng Yi Family) Technology Co. Ltd.; May 31, 2015, pp. 5.
OxiMax N-595 Pulse Oximeter Home Use Guide APL_DEL00031445), in 90 pages. Apple alleges that this reference has a prior art date of 2003.
PAS: A Wireless-Enabled, Cell-Phone-Incorporated Personal Assistance System for Independent and Assisted Living, 28th International Conference on Distributed Computing Systems, 2008 (APL_DEL00035973), in 10 pages. Apple alleges that this reference has a prior art date of 2008.
Patancheru, Govardhan Reddy, "Wearable Heart Rate Measuring Unit", Master's Thesis in Electronics Design, 30HP, Mid Sweden University, Nov. 5, 2014, pp. 75.
Philips IntelliVue Information Center iX Brochures (APL_DEL00036593), 2014, in 2 pages. Apple alleges that this reference has a prior art date of Feb. 2012.
Philips IntelliVue Information Center iX Brochures (APL_DEL00036595), Nov. 2015, in 8 pages. Apple alleges that this reference has a prior art date of Feb. 2012.
Philips IntelliVue Information Center iX Brochures (APL_DEL00036824), Sep. 2019, in 16 pages. Apple alleges that this reference has a prior art date of Feb. 2012.
Philips IntelliVue Information Center iX Brochures, Apr. 2015 (APL_DEL00036846), in 4 pages. Apple alleges that this reference has a prior art date of Feb. 2012.
Philips IntelliVue Information Center iX Brochures, Jun. 2015 (APL_DEL00036842), in 4 pages. Apple alleges that this reference has a prior art date of Feb. 2012.
Philips IntelliVue Information Center iX Brochures, Jun. 2015 (APL_DEL00036850), in 4 pages. Apple alleges that this reference has a prior art date of Feb. 2012.
Philips IntelliVue Information Center iX Brochures, Jun. 2022 (APL_DEL00036854), in 7 pages. Apple alleges that this reference has a prior art date of Feb. 2012.
Philips IntelliVue Smart-Hopping Network Product Website (APL_DEL00036840), in 2 pages. Apple alleges that this reference has a prior art date of Feb. 2012.
Physio-Control CODE-STAT 10.0 Data Review Software (APL_DEL00034330), in 2 pages. Apple alleges that this reference has a prior art date of 2011.

(56) References Cited

OTHER PUBLICATIONS

Prior Use of Android Devices ("Android Prior Use"), Android versions: A living history from 1.0 to 14, available at https://www.computerworld.com/article/3235946/android-versions-a-living-history-from-1-0-to-today.html, pp. 18.
Random House Unabridged Dictionary (2nd ed. 1993), Definition of "embedded" pp. 635.
Rodrigues, et al. "Using Discovery and Monitoring Services to Support Context-Aware Remote Assisted Living Applications," APL_DEL00036886, 2009, in 6 pages.
Samsung Galaxy S4, 4G LTE Smartphone, User Manual, 2013, pp. 260. [Uploaded in 3 parts].
Samsung GT-19500, User Manual, 2013, pp. 147.
Sanofi-aventis and AgaMatrix Unveil iBGStar Plug-In Glucose Meter for the iPhone, Medgadget, Sep. 21, 2010 (APL_DEL00038345), in 4 pages. Apple alleges that this reference has a prior art date of 2010.
Sanofi-aventis to launch blood glucose monitoring devices, PharmaBiz.com, Sep. 22, 2010 (APL_DEL00038349), in 2 pages. Apple alleges that this reference has a prior art date of 2010.
Santa Barbara Cottage Hospital, Nonin's Onyx II Fingertip Pulse Oximeter, 2007 (APL_DEL00035181), in 4 pages. Apple alleges that this reference has a prior art date of 2008.
Screen captures from YouTube video clip entitled "iBGStar bloedglucosemeter instructievideo," in 5 pages, uploaded on Mar. 9, 2011 by user "gezondheidbovenalles". Retrieved from Internet: <https://www.youtube.com/watch?v=ZIS-tTFfoUY>. Corresponds to "Sanofi-aventis and AgaMatrix Unveil iBGStar Plug-In Glucose Meter for the iPhone, Medgadget" (APL_DEL00038202). Apple alleges that this reference has a prior art date of 2010.
Screen captures from YouTube video clip entitled "iBGStar Review," in 1 page, uploaded on Mar. 27, 2012 by user "Valerie Anne C". Retrieved from Internet: <https://www.youtube.com/watch?v=0uGbNsh-pUc>. Corresponds to "Sanofi-aventis and AgaMatrix Unveil iBGStar Plug-In Glucose Meter for the iPhone, Medgadget" (APL_DEL00038203). Apple alleges that this reference has a prior art date of 2010.
Screen captures from YouTube video clip entitled "LifeWatch V—A Smartphone that Connects to You," in 9 pages, uploaded on Jul. 4, 2012 by user "LifeWatchTech". Retrieved from Internet: <https://www.youtube.com/watch?v=A75GggZSWgc>. Corresponds to "LifeWatch V, a smartphone that connects to you" (APL_DEL00038206). Apple alleges that this reference has a prior art date of 2012.
Screen captures from YouTube video clip entitled "LifeWatch V—Blood Oxygen Saturation Level Test Tutorial," in 3 pages, uploaded on Jul. 8, 2013 by user "LifeWatchTech". Retrieved from Internet: <https://www.youtube.com/watch?v=68UHtoo1KIY>. Corresponds to "LifeWatch V, Blood Oxygen Saturation Level Test Tutorial" (APL_DEL00038207). Apple alleges that this reference has a prior art date of 2012.
Screen captures from YouTube video clip entitled "Visi Mobile System for Vital Signs | Sotera Wireless," in 5 pages, uploaded on Aug. 29, 2012 by user "Eastman". Retrieved from Internet: <https://www.youtube.com/watch?v=ug9U43bsn6g>. Corresponds to "ViSi Mobile Patient Monitoring System Promotional Video" (APL_DEL00037306). Apple alleges that this reference has a prior art date of 2011.
Singh et al., "ECG to Individual Identification", Research Gate, Conference Paper, Nov. 2008, pp. 9.
Sotera ViSi Mobile Brochures (APL_DEL00037129), in 6 pages. Apple alleges that this reference has a prior art date of 2011.
Sotera ViSi Mobile Brochures (APL_DEL00037305), Aug. 21, 2012, in 1 page. B258.
Sotera ViSi Mobile Brochures, 2018 (APL_DEL00037313), in 2 pages. Apple alleges that this reference has a prior art date of 2011.
Sotera ViSi Mobile Brochures, Oct. 9, 2013 (APL_DEL00036984), in 2 pages. Apple alleges that this reference has a prior art date of 2011.
Sotera ViSi Mobile Monitoring System Technical Reference Manual, Jul. 2015 (APL_DEL00036993), in 116 pages. Apple alleges that this reference has a prior art date of 2011.
Sotera ViSi Mobile Monitoring System User Manual, Aug. 2012 (APL_DEL00037135), in 170 pages. Apple alleges that this reference has a prior art date of 2011.
Sotera ViSi Mobile Technical Specifications, Oct. 9, 2013 (APL_DEL00036986), in 7 pages. Apple alleges that this reference has a prior art date of 2011.
SpO2 Accuracy of PureSAT Signal Processing Technology—The Onyx II, Aug. 8, 2006 (APL_DEL00035185), in 2 pages. Apple alleges that this reference has a prior art date of 2008.
Stedman's Medical Dictionary (28th ed. 2006) Definition of "lead" pp. 1062.
Stein, Scott, "Garmin Vivomove HR review: The best fitness tracker in disguise", https://www.cnet.com/reviews/garmin-vivomove-hr-review/, Nov. 22, 2017, pp. 5.
Steven M. Kaplan, Wiley Electrical and Electronics Engineering Dictionary (2004) Definition of "lead", pp. 414-415 [Total pages 4].
Sumra, Husain, "Garmin Vivomove HR: Essential guide to the stylish hybrid fitness watch", https://www.wareable.com/garmin/garmin-vivomove-hr-release-date-price-specs-4983, Sep. 5, 2017, pp. 5.
Tablado, et al. "A Flexible Data Processing Technique for a Tele-assistance System of Elderly People," APL_DEL00032254, 2004, in 24 pages.
The American Heritage Dictionary of the English Language (4th ed. 2000) Definition of "embedded" pp. 583.
The American Heritage Dictionary of the English Language, Definition of "enclosure", printed Jun. 14, 2024, https://ahdictionary.com/word/search.html?q=enclosure, pp. 3.
U.S. Appl. No. 61/886,930 ("Lee Provisional"), filed Oct. 4, 2013 in 22 pages.
ViSi Mobile Monitoring System 510(k) Summary, 2013 (APL_DEL00036980), in 4 pages. Apple alleges that this reference has a prior art date of 2011.
ViSi Mobile System General Information (APL_DEL00037307), in 6 pages. Apple alleges that this reference has a prior art date of 2011.
Wanda B.: Weight and Activity with Blood Pressure Monitoring System for Heart Failure Patients, 2010 (APL_DEL00038351), in 7 pages. Apple alleges that this reference has a prior art date of 2012.
Wayback Machine, Fitbit Surge Fitness Super Watch User Manual Version 1.0, May 2015 ("Wayback Machine: Fitbit Surge") (APL_DEL00030689), in 1 page. Apple alleges that this reference has a prior art date of May 2015.
Webster, J G, "Design of Pulse Oximeters", Medical Science Series, 1997, pp. 262. (APL_DEL00030690).
WristOx2, Model 3150 Wrist-worn Pulse Oximeter, 2011 (APL_DEL00035010), in 2 pages. Apple alleges that this reference has a prior art date of 2011.
WristOx2, Model 3150 Wrist-worn Pulse Oximeter, 2011 (APL_DEL00035012), in 2 pages. Apple alleges that this reference has a prior art date of 2011.
Wübbeler et al., "Verification of humans using the electrocardiogram", Science Direct, Pattern Recognition Letters, vol. 28, 2007, pp. 1172-1175.
Y. Mendelson, "Wearable Wireless Pulse Oximetry for Physiological Monitoring," PPL Workshop (2008), PPT Presentation, pp. 18.
YouTube, "Adidas MiCoach Smart Run review | Engadget", https://www.youtube.com/watch?v=k5LpMY0okVo, Nov. 20, 2013, pp. 4.
YouTube, "Agent Smartwatch", https://www.youtube.com/watch?v=IsIE0ILBuKM, Jun. 27, 2013, pp. 3.
YouTube, "Android 4.2 Lock Screen Widgets", https://www.youtube.com/watch?v=ZpN8Wyu_z6Y, Nov. 12, 2012, pp. 6.
YouTube, "Galaxy S8 review, how does the home button feel? [4K]", https://www.youtube.com/watch?v=_DIHga3ByoE, Apr. 5, 2017, pp. 5.
YouTube, "GMYLE(R) Qi Wireless Charger Review (Nexus 5)", https://www.youtube.com/watch?v=EvJ4Jkvj_R8, Nov. 28, 2013, pp. 10.
YouTube, "LG G Flex—How to reorganize page, app and widget". https://www.youtube.com/watch?v=J_12W-MrkVM, Dec. 6, 2013, pp. 3.

(56) References Cited

OTHER PUBLICATIONS

YouTube, "LG G2 Quick Tips—Adding Widgets to the Home Screen", https://www.youtube.com/watch?v=9xEwmiNoKok, Oct. 15, 2013, pp. 3.
YouTube, "Magconn, Wireless Charger", https://www.youtube.com/watch?v=qxEXCOChLNA, Aug. 22, 2012, 1 page.
YouTube, "Samsung Galaxy S4 Lock Screen Widget Tutorial", https://www.youtube.com/watch?v=oaWa905892s, Apr. 25, 2013, pp. 8.
YouTube, "Small, thin, and light LG Watch Style unboxing & review! (LG Watch Style Unboxing&Review)", https://www.youtube.com/watch?v=IJYtazmdMI0, Mar. 24, 2017, pp. 5.
YouTube, "VivoActive 3 Review—Final Verdict after 30 days of use (EP4)", https://www.youtube.com/watch?v=IDcakqddUCU, Oct. 15, 2017, pp. 5.
12 pages of images, identified by bates Nos. "APL_MAS_ITC_00383288" to "APL_MAS_ITC_00383299". Undated.
137 pages of images, identified by bates Nos. "APL_MAS_ITC_00378839" to "APL_MAS_ITC_00378975". Undated. [uploaded in 3 parts].
Jun. 30, 2021 Complaint under Section 337 of the Tariff Act of 1930, as Amended, and including Exhibits 11-40 (Exhibits 1-10 comprise copies of publicly available U.S. patents, and are not included herein for ease of transmission), *Masimo Corporation and Cercacor Laboratories, Inc. v. Apple Inc.*, United States International Trade Commission, Investigation No. 337-TA-1276, 736 pages. [uploaded in 13 parts].
Jul. 7, 2021 First Amended Complaint under Section 337 of the Tariff Act of 1930, as Amended, *Masimo Corporation and Cercacor Laboratories, Inc. v. Apple Inc.*, United States International Trade Commission, Investigation No. 337-TA-1276, 44 pages.
Sep. 23, 2021 Response of Apple Inc. to First Amended Complaint and Notice of Investigation, and including Exhibit A and Appendix A, *Masimo Corporation and Cercacor Laboratories, Inc. v. Apple Inc.*, United States International Trade Commission, Investigation No. 337-TA-1276, 664 pages.
Dec. 3, 2021 Respondent Apple Inc.'s Preliminary Invalidity Contentions for U.S. Pat. No. 10,912,501, U.S. Pat. No. 10,912,502, U.S. Pat. No. 10,945,648, U.S. Pat. No. 10,687,745, and U.S. Pat. No. 7,761,127, and including Exhibits A1-A6, B1-B6, and C1-C6 related to U.S. Pat. No. 10,912,501, U.S. Pat. No. 10,912,502, U.S. Pat. No. 10,945,648 (Exhibits D1-D16 and E1-E13 relate to U.S. Pat. No. 10,687,745, and U.S. Pat. No. 7,761,127, and are not included herein but are available upon request), *Masimo Corporation and Cercacor Laboratories, Inc. v. Apple Inc.*, United States International Trade Commission, Investigation No. 337-TA-1276, 443 pages.
Dec. 3, 2021 Respondent Apple Inc.'s Preliminary Invalidity Contentions for U.S. Pat. No. 10,912,501, U.S. Pat. No. 10,912,502, U.S. Pat. No. 10,945,648, U.S. Pat. No. 10,687,745, and U.S. Pat. No. 7,761,127, and including Exhibits D1-D16 related to U.S. Pat. No. 10,687,745 (Exhibits A1-A6, B1-B6, C1-C6, and E1-E13 relate to U.S. Pat. No. 10,912,501, U.S. Pat. No. 10,912,502, U.S. Pat. No. 10,945,648, and U.S. Pat. No. 7,761,127, and are not included herein but are available upon request), *Masimo Corporation and Cercacor Laboratories, Inc. v. Apple Inc.*, United States International Trade Commission, Investigation No. 337-TA-1276, 443 pages.
Dec. 3, 2021 Respondent Apple Inc.'s Preliminary Invalidity Contentions for U.S. Pat. No. 10,912,501, U.S. Pat. No. U.S. Pat. No. 10,912,502, U.S. Pat. No. 10,945,648, U.S. Pat. No. 10,687,745, and U.S. Pat. No. 7,761,127, Exhibits A-1 to A-6, *Masimo Corporation and Cercacor Laboratories, Inc. v. Apple Inc.*, United States International Trade Commission, Investigation No. 337-TA-1276, 1230 pages. [uploaded in 2 parts].
Dec. 3, 2021 Respondent Apple Inc.'s Preliminary Invalidity Contentions for U.S. Pat. No. 10,912,501, U.S. Pat. No. U.S. Pat. No. 10,912,502, U.S. Pat. No. 10,945,648, U.S. Pat. No. 10,687,745, and U.S. Pat. No. 7,761,127, Exhibits B-1 to B-6, *Masimo Corporation and Cercacor Laboratories, Inc. v. Apple Inc.*, United States International Trade Commission, Investigation No. 337-TA-1276, 1343 pages. [uploaded in 2 parts].
Dec. 3, 2021 Respondent Apple Inc.'s Preliminary Invalidity Contentions for U.S. Pat. No. 10,912,501, U.S. Pat. No. U.S. Pat. No. 10,912,502, U.S. Pat. No. 10,945,648, U.S. Pat. No. 10,687,745, and U.S. Pat. No. 7,761,127, Exhibits C-1 to C-6, *Masimo Corporation and Cercacor Laboratories, Inc. v. Apple Inc.*, United States International Trade Commission, Investigation No. 337-TA-1276, 1222 pages. [uploaded in 2 parts].
Jan. 13, 2022 Joint Proposed Claim Construction Chart, *Masimo Corporation and Cercacor Laboratories, Inc. v. Apple Inc.*, United States International Trade Commission, Investigation No. 337-TA-1276, 8 pages.
Jan. 27, 2022 Complainant's Opening Claim Construction Brief, and including Exhibits 1-16, *Masimo Corporation and Cercacor Laboratories, Inc. v. Apple Inc.*, United States International Trade Commission, Investigation No. 337-TA-1276, 1019 pages. [uploaded in 9 parts].
Jan. 27, 2022 Respondent Apple Inc.'s Opening Markman Brief, and including Exhibits 1-7, *Masimo Corporation and Cercacor Laboratories, Inc. v. Apple Inc.*, United States International Trade Commission, Investigation No. 337-TA-1276, 144 pages.
Feb. 9, 2022 Memorandum in support of Respondent Apple Inc.'s Motion for Leave to File Amended Response to the First Amended Complaint, and including Exhibits 1 (with Exhibits A-J) and 2, *Masimo Corporation and Cercacor Laboratories, Inc. v. Apple Inc.*, United States International Trade Commission, Investigation No. 337-TA-1276, 1477 pages. [uploaded in 2 parts].
Feb. 9, 2022 Respondent Apple Inc.'s Motion for Leave to File Amended Response to the First Amended Complaint, *Masimo Corporation and Cercacor Laboratories, Inc. v. Apple Inc.*, United States International Trade Commission, Investigation No. 337-TA-1276, 4 pages.
Feb. 10, 2022 Complainants' Rebuttal Claim Construction Brief, and including Exhibits 17-21, *Masimo Corporation and Cercacor Laboratories, Inc. v. Apple Inc.*, United States International Trade Commission, Investigation No. 337-TA-1276, 59 pages.
Feb. 10, 2022 Respondent Apple Inc.'s Rebuttal Markman Brief, and including Exhibit 8, *Masimo Corporation and Cercacor Laboratories, Inc. v. Apple Inc.*, United States International Trade Commission, Investigation No. 337-TA-1276, 21 pages.
Feb. 15, 2022 Respondent Apple Inc.'s Notice of Prior Art, *Masimo Corporation and Cercacor Laboratories, Inc. v. Apple Inc.*, United States International Trade Commission, Investigation No. 337-TA-1276, 15 pages.
Feb. 17, 2022 Hearing Transcript, *Masimo Corporation and Cercacor Laboratories, Inc. v. Apple Inc.*, United States International Trade Commission, Investigation No. 337-TA-1276, 106 pages.
Feb. 18, 2022 Complainants' Opposition to Respondent's Motion for Leave to File Amended Response to the First Amended Complaint, and including Exhibits A-J, *Masimo Corporation and Cercacor Laboratories, Inc. v. Apple Inc.*, United States International Trade Commission, Investigation No. 337-TA-1276, 691 pages. [uploaded in 5 parts].
Feb. 18, 2022 Respondent Apple Inc.'s Rebuttal Claim Construction Evidence, and including Exhibit 9, *Masimo Corporation and Cercacor Laboratories, Inc. v. Apple Inc.*, United States International Trade Commission, Investigation No. 337-TA-1276, 12 pages.
Feb. 22, 2022 Deposition Transcript of Robert Rowe, Ph.D., *Masimo Corp. et al. v. Apple Inc.*, ITC Inv. No. 337-TA-1276, pp. 213.
Feb. 23, 2022 Respondent Apple Inc.'s Reply in support of its Motion for Leave to File Amended Response to First Amended Complaint (Motion No. 1276-018), and including Exhibit 3, *Masimo Corporation and Cercacor Laboratories, Inc. v. Apple Inc.*, United States International Trade Commission, Investigation No. 337-TA-1276, 65 pages.
Feb.23, 2022 Updated Joint Proposed Claim Construction Chart, *Masimo Corporation and Cercacor Laboratories, Inc. v. Apple Inc.*, United States International Trade Commission, Investigation No. 337-TA-1276, 6 pages.
Apr. 11, 2022 Order No. 24 Granting-in-Part and Denying-in-Part Respondent's Motion for Leave to File Amended Response to the Complaint to Add Affirmative Defenses, *Masimo Corporation and*

(56) References Cited

OTHER PUBLICATIONS

*Cercacor Laboratories, Inc. v. Apple Inc.*, United States International Trade Commission, Investigation No. 337-TA-1276, 10 pages.
May 13, 2022 Complainants' Pre-Hearing Brief, *Masimo Corporation and Cercacor Laboratories, Inc. v. Apple Inc.*, United States International Trade Commission, Investigation No. 337-TA-1276, 274 pages.
May 16, 2022 Respondent Apple Inc.'s Corrected Pre-Hearing Brief, *Masimo Corporation and Cercacor Laboratories, Inc. v. Apple Inc.*, United States International Trade Commission, Investigation No. 337-TA-1276, 264 pages.
Jun. 6, 2022 through Jun. 10, 2022 *Masimo Corp et al. v. Apple Inc.*, Public Hearing Transcript, ITC Inv. No. 337-TA-1276, pp. 670.
Jun. 27, 2022 Complainants' Initial Post-Hearing Brief and including Complainants' Final Exhibit Lists, *Masimo Corporation and Cercacor Laboratories, Inc. v. Apple Inc.*, United States International Trade Commission, Investigation No. 337-TA-1276, 434 pages. [uploaded in 3 parts].
Jun. 27, 2022 Respondent Apple Inc.'s Post-Hearing Brief and including Respondent's Final Exhibit Lists and Respondent's Corrected Final Exhibit Lists, *Masimo Corporation and Cercacor Laboratories, Inc. v. Apple Inc.*, United States International Trade Commission, Investigation No. 337-TA-1276, 338 pages.
Jul. 11, 2022 Complainants' Reply Post-Hearing Brief, *Masimo Corporation and Cercacor Laboratories, Inc. v. Apple Inc.*, United States International Trade Commission, Investigation No. 337-TA-1276, 217 pages. [uploaded in 2 parts].
Jul. 11, 2022 Respondent Apple Inc.'s Reply Post-Hearing Brief, *Masimo Corporation and Cercacor Laboratories, Inc. v. Apple Inc.*, United States International Trade Commission, Investigation No. 337-TA-1276, 191 pages.
Aug. 19, 2022 Complainant's Corrected Initial Post-Hearing Brief, *Masimo Corporation and Cercacor Laboratories, Inc. v. Apple Inc.*, United States International Trade Commission, Investigation No. 337-TA-1276, 380 pages. [uploaded in 9 parts].
Sep. 2, 2022 Respondent's Corrected Reply Post-Hearing Brief, *Masimo Corporation and Cercacor Laboratories, Inc. v. Apple Inc.*, United States International Trade Commission, Investigation No. 337-TA-1276, 191 pages.
Sep. 14, 2022 Respondent's Second Corrected Reply Post-Hearing Brief, *Masimo Corporation and Cercacor Laboratories, Inc. v. Apple Inc.*, United States International Trade Commission, Investigation No. 337-TA-1276, 312 pages.
Jan. 10, 2023 Final Initial Determination on Violation of Section 337, Inv. No. 337-TA-1276, pp. 342. [Submitted in 10 parts].
Jan. 10, 2023 Notice of Final Initial Determination on Violation of Section 337, Inv. No. 337-TA-1276, pp. 2.
Jan. 23, 2023 Respondent Apple Inc.'s Summary of Petition for Review of the Initial Determination of Violation of Section 337, Inv. No. 337-TA-1276, pp. 25.
Jan. 24, 2023 Recommended Determination in Remedy and Bonding, Inv. No. 337-TA-1276, pp. 7.
Jan. 31, 2023 Respondent Apple Inc.'s Response to Complainants' Petition for Review, Inv. No. 337-TA-1276, pp. 105.
Jan. 31, 2023 Respondent Apple Inc.'s Summary of its Response to Complainants' Petition for Review, Inv. No. 337-TA-1276, pp. 25.
Feb. 2, 2023 Complainants' Petition for Review of the Final Initial Determination on Violation of Section 337, Inv. No. 337-TA-1276, pp. 104.
Feb. 2, 2023 Complainants' Summary of Petition for Review of the Final Initial Determination on Violation of Section 337, Inv. No. 337-TA-1276, pp. 13.
Feb. 2, 2023 Respondent Apple Inc.'s Petition for Review of the Initial Determination of Violation of Section 337, Inv. No. 337-TA-1276, pp. 120.
Feb. 10, 2023 Complainants' Response to Apple Inc.'s Petition for Review of the Final Initial Determination on Violation of Section 337, Inv. No. 337-TA-1276, pp. 297.
Feb. 10, 2023 Complainants' Summary of Response to Apple's Petition for Review of the Final Initial Determination on Violation of Section 337, Inv. No. 337-TA-1276, pp. 13.
May 15, 2023 Notice of a Commission Determination to Review in Part a Final Initial Determination; Request for Written Submissions on the Issues Under Review and on Remedy, The Public Interest, and Bonding, Inv. No. 337-TA-1276, pp. 7.
Jun. 12, 2023 Complainants' Reply to Apple Inc.'s Response to the Commission's Notice to Review in Part a Final Initial Determination and Request for Written Submissions, Inv. No. 337-TA-1276, pp. 65.
Jun. 12, 2023 Exhibits 54-93 for Complainants' Reply to Apple Inc.'s Response to the Commission's Notice to Review in Part a Final Initial Determination and Request for Written Submissions, Inv. No. 337-TA-1276, pp. 590.
Jun. 15, 2023 Complainants' Submission in Response to the Commission's May 15, 2023 Notice of Commission Determination to Review in Part, Inv. No. 337-TA-1276, pp. 130.
Jun. 15, 2023 Exhibits 1-53 of Complainants' Submission in Response to the Commission's May 15, 2023 Notice of Commission Determination to Review in Part, Inv. No. 337-TA-1276, pp. 781. [uploaded in 2 parts].
Jun. 15, 2023 Respondent Apple Inc.'s Response to the Commissions' Notice to Review in Part a Final Initial Determination and Request for Written Submissions, Inv. No. 337-TA-1276, pp. 263.
Jun. 22, 2023 Respondent Apple Inc.'s Reply to Complainants' Response to the Commission's Notice to Review in Part a Final Initial Determination and Request for Written Submissions, Inv. No. 337-TA-1276, pp. 60.
Jun. 23, 2023 Exhibits A & B for Notice of Denial of Respondent Apple Inc.'s Request for Rehearing of Decisions Denying Institution of Inter Partes Review for U.S. Pat. No. 10,945,648, Inv. No. 337-TA-1276, pp. 19.
Jun. 23, 2023 Notice of Denial of Respondent Apple Inc.'s Request for Rehearing of Decisions Denying Institution of Inter Partes Review for U.S. Pat. No. 10,945,648, Inv. No. 337-TA-1276, pp. 5.
Oct. 26, 2023 Limited Exclusion Order, Inv. No. 337-TA-1276, pp. 4.
Oct. 26, 2023 Notice of the Commission's Final Determination Finding a Violation of Section 337; Issuance of a Limited Exclusion Order and a Cease and Desist Order; Termination of the Investigation, Inv. No. 337-TA-1276, pp. 4.
Oct. 30, 2023 Respondent Apple Inc.'s Motion to Stay Exclusion and Cease and Desist Orders Pending Appeal and/or in light of the Potential Government Shutdown, Inv. No. 337-TA-1276, pp. 36.
Nov. 9, 2023 Complainants' Opposition to Respondent Apple Inc.'s Motion to Stay Exclusion and Cease and Desist Orders Pending Appeal and/or in light of the Potential Government Shutdown, Inv. No. 337-TA-1276, pp. 124.
Nov. 14, 2023 Commission Opinion [Public Version], Inv. No. 337-TA-1276, pp. 124.
Dec. 26, 2023 Appellant Apple Inc.'s Non-Confidential Emergency Motion for an Immediate Interim Stay Pending Disposition of Motion for Stay Pending Appeal, Inv. No. 337-TA-1276, pp. 15.
Dec. 26, 2023 Appellant Apple Inc.'s Non-Confidential Emergency Motion to Stay Enforcement of ITC's Orders Pending Review in Inter Partes Review, Inv. No. 337-TA-1276, pp. 939. [Uploaded in 4 parts].
Dec. 26, 2023 Apple Inc.'s Petition for Review and Notice of Appeal Regarding U.S. Pat. No. 10,912,502 and U.S. Pat. No. 10,945,648, Inv. No. 337-TA-1276, pp. 492. [Uploaded in 3 parts].
Jan. 3, 2024 Commission Opinion Denying Respondent's Motion to Stay the Remedial Orders [Public Version], Inv. No. 337-TA-1276, pp. 14.
Jan. 10, 2024 Addendum, Declaration of Joe Kiani in Support of Masimo Corporation and Cercacor Laboratories, Inc.'s Opposition to Apple's Emergency Motion to Stay Enforcement of ITC's Order Pending Review, Inv. No. 337-TA-1276, pp. 67.
Jan. 10, 2024 Appellee International Trade Commission's Nonconfidential Response in Opposition to Appellant's Motion for a Stay Pending Appeal, Inv. No. 337-TA-1276, pp. 137.

(56) References Cited

OTHER PUBLICATIONS

Jan. 10, 2024 Masimo Corporation and Cercacor Laboratories, Inc.'s Nonconfidential Opposition to Apple Inc.'s Emergency Motion to Stay Enforcement of ITC's Orders Pending Review, Inv. No. 337-TA-1276, pp. 34.
Jan. 10, 2024 Masimo Exhibits: Part 1 in Support of Opposition, Inv. No. 337-TA-1276, pp. 468.
Jan. 10, 2024 Masimo Exhibits: Part 2 in Support of Opposition, Inv. No. 337-TA-1276, pp. 138.
Jan. 12, 2024 Ruling; U.S. Customs and Border Protection; U.S. International Trade Commission; Limited Exclusion Order; HQ H335304, Inv. No. 337-TA-1276; pp. 31.
Jan. 15, 2024 Non-Confidential Reply in Support of Appellant Apple Inc.'s Emergency Motion to Stay Enforcement of ITC's Orders Pending Review, Inv. No. 337-TA-1276, pp. 123.
Apr. 5, 2024 Non-Confidential Brief for Appellant Apple Inc., vol. I of II (Brief pp. 1-68 and Addendum pp. Appx1-484), Federal Circuit appeal of ITC Inv. No. 337-TA-1276, pp. 578.
Apr. 5, 2024 Non-Confidential Brief for Appellant Apple Inc., vol. II of II (Addendum pp. Appx485-817), Federal Circuit appeal of ITC Inv. No. 337-TA-1276, pp. 338.
54 pages of images, identified by bates Nos. "APL_MAS_ITC_00383217" to "APL_MAS_ITC_00383270". Undated. [uploaded in 3 parts].
7 pages of images, identified by bates Nos. "APL_MAS_ITC_00383308" to "APL_MAS_ITC_00383314". Undated.
A. Keikhosravi et al., "Effect of deep breath on the correlation between the wrist and finger photoplethysmograms," Proceedings of the 19th Iranian conference on Biomedical Engineering (ICBME 2012), Dec. 21-22, 2012, pp. 135-138.
B. Mapar, "Wearable Sensor for Continuously Vigilant Blood Perfusion and Oxygenation Monitoring," UCLA Electronic Theses and Dissertations, 2012, 112 pages.
Bagha et al., "A Real Time Analysis of PPG Signal for Measurement of SpO2 and Pulse Rate," International Journal of Computer Applications, vol. 36, No. 11, Dec. 2011, pp. 45-50.
C. Faulkner, "Apple Watch heart rate sensor: everything you need to know," Apr. 24, 2015, 5 pages.
Cahill, Laser-Based Fibre-Optic Sensor for Measurement of Surface Properties, Thesis for Dublin City University Faculty of Engineering and Design, May 1998, 208 pages. [uploaded in 5 parts].
Chang et al., "Microlens array diffuser for a light-emitting diode backlight system", Optics Letters, vol. 31, No. 20, Oct. 15, 2006, pp. 3016-3018.
D. Yang et al., "SpO2 and Heart Rate Measurement with Wearable Watch Based on PPG," 2015 IET International Conference on Biomedical Image and Signal Processing (ICBISP 2015), Nov. 2015, pp. 1-5.
DC Rainmaker, 'Mio Alpha Optical Heart Rate Monitor in-Depth Review (Bluetooth Smart/ANT+)', published Feb. 12, 2013, retrieved from https://www.dcrainmaker.com/2013/02/monitor-bluetooth-smartant.html, 108 pages. [uploaded in 5 parts].
E. Kviesis-Kipge et al., "Miniature wireless photoplethysmography devices: integration in garments and test measurements," Proc. SPIE vol. 8427, Biophotonics: Photonic Solutions for Better Health Care III, May 2012, 7 pages.
Excerpts of Design of Pulse Oximeters, J.G. Webster, Institution of Physics Publishing, IOP Publishing Ltd, 1997, 150 pages. [uploaded in 3 parts].
Feather et al., "A portable reflectometer for the rapid quantification of cutaneous haemoglobin and melanin," Phys. Med. Biol., vol. 33, No. 6, 1988, pp. 711-722.
Graaff et al., "Optical Properties of Human Dermis In Vitro and In Vivo," Applied Optics, vol. 32, No. 4, Feb. 1, 1993, pp. 435-447.
Harsanyi, Sensors in Biomedical Applications, Fundamentals, Technology and Applications, CRC Press LLC, 2000, 368 pages. [uploaded in 2 parts].
Heart Rate Measurement Technology, Seiko Epson Corporation, retrieved from https://global.epson.com/innovation/core_technology/wearable/vital_sensing.html, accessed Dec. 2, 2019, 6 pages.
International Trade Commission, Determination to Review, Federal Register, vol. 88, No. 210, Nov. 1, 2023, Investigation No. 337-TA-1276, pp. 75032-75033.
International Trade Commission, Determination to Review, Federal Register, vol. 88, No. 97, May 19, 2023, Investigation No. 337-TA-1276, pp. 32243-32246.
J. Heerlein et al., 'LED-based sensors for wearable fitness tracking products,' published Dec. 16, 2014, retrieved from https://www.edn.com/design/led/4437996/1/LED-based-sensors-for-fitness-tracking-wearables, accessed Nov. 25, 2019, 6 pages.
K. Kilbane, "Design Considerations for Wrist-Wearable Heart Rate Monitors," GSA, Copyright 2021, 5 pages.
K. Kuboyama, "Motion Artifact Cancellation for Wearable Photoplethysmographic Sensor," Massachusetts Institute of Technology, 2010, 66 pages.
K. Shin et al., "A Novel Headset with a Transmissive PPG Sensor for Heart Rate Measurement," ICBME 2008 Proceedings vol. 23, 2009, 519-522 Pages.
Lam et al., "A Smartphone-Centric Platform for Personal Health Monitoring using Wireless Wearable Biosensors", IEEE, ICICS 2009, 7 pages.
Love et al., Personal Status Monitor, Sandia National Laboratories, Feb. 1997, 211 pages. [uploaded in 2 parts].
M. Poh et al., "Motion-Tolerant Magnetic Earring Sensor and Wireless Earpiece for Wearable Photoplethysmography," IEEE Transactions on Information Technology in Biomedicine, vol. 14, No. 3, May 2010, pp. 786-794.
Matthes, K. & W. Hauss, Lichtelektrische Plethysomgramme Klinische Wochenschrift No. 17 (5):1211-1213, 1938.
McGraw-Hill Dictionary of Scientific and Technical Terms, Sixth Edition, 2003. p. 2133.
Mendelson, "Invasive and Noninvasive Blood Gas Monitoring," Bioinstrumentation and biosensors, 1991, pp. 249-279.
Mendelson, Theory and Development of a Transcutaneous Reflectance Oximeter System for Noninvasive Measurements of Arterial Oxygen Saturation, Thesis for Case Western Reserve University Department of Biomedical Engineering, May 25, 1983, 284 pages. [uploaded in 2 parts].
N. Phattraprayoon et al., "Accuracy of pulse oximeter readings from probe placement on newborn wrist and ankle," Journal of Perinatology, vol. 32, 2012, pp. 276-280.
N. Stuban et al., "Optimal filter bandwidth for pulse oximetry," Review of Scientific Instruments vol. 83, 2012, 6 pages.
Nixon et al., "Novel Spectroscopy-Based Technology for Biometric and Liveness Verification," Proceedings of SPIE vol. 5404, Biometric Technology for Human Identification, Aug. 25, 2004, pp. 287-295.
P. Shyamkumar et al., "Wearable Wireless Cardiovascular Monitoring Using Textile-Based Nanosensor and Nanomaterial Systems," Electronics vol. 3, 2014, pp. 504-520.
P.B. Crilly et al., "An Integrated Pulse Oximeter System for Telemedicine Applications," IEEE Instrumentation and Measurement Technology Conference Sensing, Processing, Networking, IMTC Proceedings, 1997, pp. 102-104.
PerformTek Precision Biometrics White Paper, ValenCell, Jan. 4, 2013, 13 pages.
Physical Enterprises Inc., Mio Alpha Complete User Guide, Copyright 2012, 15 pages.
R. Stojanovic et al., "Design of an Oximeter Based on LED-LED Configuration and FPGA Technology," Sensors vol. 13, 2013, pp. 574-586.
S. Vogel et al., "In-Ear Vital Signs Monitoring Using a Novel Microoptic Reflective Sensor," IEEE Transactions on Information Technology in Biomedicine, vol. 13, No. 6, Nov. 2009, pp. 882-889.
Scarlett, The Multilayer Printed Circuit Board Handbook, Electrochemical Publications Limited, 1985, 130 pages.
Severinghaus, "Pulse Oximetry," Computing and Monitoring in Anesthesia and Intensive Care, 1992, pp. 391-403.
Silicon Planar Epitaxial Phototransistor, pp. 5-5-5-6, 1972.
T. Hayes, 'What's inside a fitness tracker, anyway?' published Nov. 29, 2014, retrieved from https://www.digitaltrends.com/wearables/whats-inside-fitness-tracker-anyway/, 24 Pages.

(56) References Cited

OTHER PUBLICATIONS

T. Tamura et al., "Wearable Photoplethysmographic Sensors—Past and Present," Electronics vol. 3, 2014, pp. 282-302.
Takatani et al., "Optical Oximetry Sensors for Whole Blood and Tissue," IEEE Engineering in Medicine and Biology, 1994, pp. 347-357.
Vashist et al., "Commercial Smartphone-Based Devices and Smart Applications for Personalized Healthcare Monitoring and Management", Diagnostics, 2014, vol. 4, pp. 104-128.
Wang et al., "Multichannel Reflective PPG Earpiece Sensor with Passive Motion Cancelation," IEEE Transactions on Biomedical Circuits and Systems, vol. 1, No. 4, Dec. 2007, pp. 235-241.
Wareing, Optimization of Reflectance-Mode Pulse Oximeter Sensors, National Science Foundation Research Experiences, 1 page. Undated.
Wareing, Previous Research Experience, 2 pages. Undated.
Warren et al., "Wearable Sensors and Component-Based Design for Home Health Care," Proceedings of the Second Joint EMBS/BMES Conference, Oct. 23-26, 2002, pp. 1871-1872.
Warren et al., "Wearable Telemonitoring Systems Designed with Interoperability in Mind," Proceedings of the 25th Annual International Conference of the IEEE Engineering in Medicine and Biology Society, vol. 4, 2003, 4 pages.
Warren, Pulse Oximetry Laboratory, 8 pages. Undated.
Withings, Withings Pulse: Activity Tracker—Sleep Analyzer Heart Rate Analyzer—Installation and Operating Instructions (iOS users), Apr. 2015, 43 pages.
Y. Lee et al., "Development of a Wristwatch-Type PPG Array Sensor Module," 2011 IEEE International Conference on Consumer Electronics (ICCE-Berlin), 2011, pp. 168-171.
Y. Mendelson, et al., "Design and Evaluation of a New Reflectance Pulse Oximeter Sensor", Worcester Polytechnic Institute, Biomedical Engineering Program, Worcester, MA 01609, Association for the Advancement of Medical Instrumentation, vol. 22, No. 4, 1988, pp. 167-173, Abstract, 1 page.
Y. Zhai, "A Wireless Sensor Network for Hospital Patient Monitoring," Thesis for University of Calgary Department of Eletrical and Computer Engineering, Apr. 2007, 134 pages.
Yao et al., "A Novel Algorithm to Separate Motion Artifacts from Photoplethysmographic Signals Obtained with a Reflectance Pulse Oximeter", Conf Proc IEEE Eng Med Biol Soc., 2004, 4 pages.
Yao et al., "A Wearable Point-of-Care System for Home Use That Incorporates Plug-and-Play and Wireless Standards", IEEE Transactions on Information Technology in Biomedicine, vol. 9, No. 3, Sep. 2005, pp. 363-371.
Yao et al., "A Wearable Standards-Based Point-of-Care System for Home Use," Proceedings of the 25th Annual International Conference of the IEEE, vol. 4, 2003, 4 pages.
Yao et al., "Applying the ISO/IEEE 11073 Standards to Wearable Home Health Monitoring Systems," Journal of Clinical Monitoring and Computing, vol. 19, No. 6, 2005, pp. 427-436.
Yao et al., "Design of a Plug-and-Play Pulse Oximeter," Proceedings of the Second Joint EMBS/BMES Conference, Oct. 23-26, 2002, pp. 1752-1753.
Yao, Design of Standards-Based Medical Components and a Plug-and-Play Home Health Monitoring System, a Dissertation for Kansas State University Department of Electrical & Computer Engineering, 2005, 155 pages. [uploaded in 2 parts].
2 pages of images, identified by bates Nos. "APL-MAS_00057598" and "APL-MAS_00057599". Undated.
Jan. 9, 2020 Complaint for (1) Patent Infringement (2) Trade Secret Misappropriation and (3) Ownership of Patents and Demand for Jury Trial, *Masimo Corporation and Cercacor Laboratories, Inc. v. Apple Inc.*, Case No. 8:20-cv-00048, 64 pages.
Mar. 25, 2020 First Amended Complaint for (1) Patent Infringement (2) Trade Secret Misappropriation (3) Correction of Inventorship and (4) Ownership of Patents and Demand for Jury Trial, and including Exhibits 13-24 (Exhibits 1-12 and 25-31 comprise publicly available U.S. patents and U.S. patent application publications, and are not included herein for ease of transmission), *Masimo Corporation and Cercacor Laboratories, Inc. v. Apple Inc.*, Case No. 8:20-cv-00048, pp. 1-94, 983-1043 (total of 156 pages).
Jul. 24, 2020 Second Amended Complaint for (1) Patent Infringement (2) Trade Secret Misappropriation (3) Correction of Inventorship and (4) Ownership of Patents and Demand for Jury Trial, and including Exhibit 1, *Masimo Corporation and Cercacor Laboratories, Inc. v. Apple Inc.*, Case No. 8:20-cv-00048, 182 pages.
Jul. 27, 2020 Plaintiffs' Infringement Contentions, and including Exhibit 1 and Appendices A-P, *Masimo Corporation and Cercacor Laboratories, Inc. v. Apple Inc.*, Case No. 8:20-cv-00048, 305 pages.
Sep. 8, 2020 Apple's Preliminary Invalidity Contentions, and including Exhibits A-G, *Masimo Corporation and Cercacor Laboratories, Inc. v. Apple Inc.*, Case No. 8:20-cv-00048, 3960 pages. [uploaded in 15 parts].
Sep. 16, 2020 Public Order Regarding Masimo's Motion for Preliminary Injunction, *Masimo Corporation and Cercacor Laboratories, Inc. v. Apple Inc.*, Case No. SACV 20-00048, 14 pages.
Oct. 20, 2020 Letter from B. K. Andrea to J. Re et al., Re: *Masimo Corp, et al. v. Apple, Inc.*, C.A. 8:20-cv-00048 (C.D. Cal.), 19 pages.
Nov. 12, 2020 Third Amended Complaint for (1) Patent Infringement (2) Trade Secret Misappropriation (3) Correction of Inventorship and (4) Ownership of Patents and Demand for Jury Trial, and including Exhibit 1, *Masimo Corporation and Cercacor Laboratories, Inc. v. Apple Inc.*, Case No. 8:20-cv-00048, 196 pages. [uploaded in 2 parts].
Feb. 3, 2021 Defendant Apple Inc.'s Answer to Plaintiffs' Third Amended Complaint and Demand for Jury Trial, *Masimo Corporation and Cercacor Laboratories, Inc. v. Apple Inc.*, Case No. 8:20-cv-00048, 72 pages.
Feb. 5, 2021 Fourth Amended Complaint for (1) Patent Infringement (2) Trade Secret Misappropriation (3) Correction of Inventorship and (4) Ownership of Patents and Demand for Jury Trial, and including Exhibit 1, *Masimo Corporation and Cercacor Laboratories, Inc. v. Apple Inc.*, Case No. 8:20-cv-00048, 207 pages.
Feb. 24, 2021 Defendant Apple Inc.'s Amended Answer to Plaintiffs' Third Amended Complaint and Demand for Jury Trial, *Masimo Corporation and Cercacor Laboratories, Inc. v. Apple Inc.*, Case No. 8:20-cv-00048, 85 pages.
May 5, 2021 Defendant Apple Inc.'s Amended Answer to Plaintiffs' Fourth Amended Complaint and Demand for Jury Trial, *Masimo Corporation and Cercacor Laboratories, Inc. v. Apple Inc.*, Case No. 8:20-cv-00048, 90 pages.
Jun. 6, 2022 First Supplement to the Fourth Amended Complaint and Demand for Jury Trial, *Masimo Corporation and Cercacor Laboratories, Inc. v. Apple Inc.*, Case No. 8:20-cv-00048, 7 pages.
Jun. 27, 2022 Defendant Apple Inc.'s Answer to Plaintiffs' First Supplement to the Fourth Amended Complaint and Demand for Jury Trial, *Masimo Corporation and Cercacor Laboratories, Inc. v. Apple Inc.*, Case No. 8:20-cv-00048, 7 pages.
Jan. 29, 2024 Plaintiff's Memorandum in Support of Motion to Lift Patent Stay, *Masimo Corporation and Cercacor Laboratories, Inc. v. Apple Inc.*, Case No. 8:20-cv-00048, 10 pages.
Feb. 5, 2024 Defendant Apple Inc.'s Opposition to Plaintiffs' Motion to Lift the Patent Stay, *Masimo Corporation and Cercacor Laboratories, Inc. v. Apple Inc.*, Case No. 8:20-cv-00048, 23 pages.
Feb. 12, 2024 Plaintiff's Reply Memorandum in Support of Motion to Lift Patent Stay, *Masimo Corporation and Cercacor Laboratories, Inc. v. Apple Inc.*, Case No. 8:20-cv-00048, 18 pages.
3 pages of images, identified by bates Nos. "APL-MAS_00057600", "APL-MAS_00057601", and "APL-MAS_00057602". Undated.
A Wireless Wearable Reflectance Pulse Oximeter Printout, The Bioengineering Institute, Worcester Polytechnic Institute, 1 page. Undated.
A. C. M. Dassel et al., "Effect of location of the sensor on reflectance pulse oximetry," British Journal of Obstetrics and Gynecology, vol. 104, Aug. 1997, pp. 910-916.
A. C. M. Dassel et al., "Reflectance Pulse Oximetry at the Forehead Improves by Pressure on the Probe," Journal of Clinical Monitoring, vol. 11, No. 4, Jul. 1995, pp. 237-244.

(56) References Cited

OTHER PUBLICATIONS

A. Gendler et al., "A PAB-Based Multi-Prefetcher Mechanism," International Journal of Parallel Programming, vol. 34, No. 2, Apr. 2006, pp. 171-188.

A. Lader et al., "An Investigative Study of Membrane-Based Biosensors," Proceedings of the IEEE 17th Annual Northeast Bioengineering Conference, 1991, pp. 253-254.

A. Nagre et al., "Effects of Motion Artifacts on Pulse Oximeter Readings from Different Facial Regions," Proceedings of the IEEE 31st Annual Northeast Bioengineering Conference, 2005, pp. 1-3.

B. F. Koegh et al., "Recent findings in the use of reflectance oximetry: a critical review," Current Opinion in Anesthesiology, vol. 18, 2005, pp. 649-654.

B. Odegard et al., "An Analysis of Racewalking Styles Using a 2-Dimensional Mathematical Knee Model," Proceedings of the IEEE 23rd Northeast Bioengineering Conference, 1997, pp. 73-74.

B. Yocum et al., "Design of a Reflectance Pulse Oximeter Sensor and its Evaluation in Swine," Proceedings of the 15th Annual Northeast Bioengineering Conference, IEEE, 1989, pp. 239-240.

C. E. Darling et al., "Detecting Blood Loss With a Wearable Photoplethysmography Device," Annals of Emergency Medicine, vol. 68, No. 45, Oct. 2016, p. S116.

C. G. Scully et al., "Physiological Parameter Monitoring from Optical Recordings With a Mobile Phone," IEEE Transactions on Biomedical Engineering, vol. 59, No. 2, Feb. 2012, pp. 303-306.

C. J. Pujary, "Investigation of Photodetector Optimization in Reducing Power Consumption by a Noninvasive Pulse Oximeter Sensor," Master thesis, Worcester Polytechnic Institute, Jan. 2004, 133 pages.

C. Pujary et al., "Photodetector Size Considerations in the Design of a Noninvasive Reflectance Pulse Oximeter for Telemedicine Applications," Proceedings of the IEEE 29th Annual Bioengineering Conference, 2003, pp. 148-149.

C. Tamanaha et al., "An Inorganic Membrane Filter to Support Biomembrane-Mimetic Structures," Proceedings of 17th International Conference of the Engineering in Medicine and Biology Society, Sep. 1995, pp. 1559-1560.

C. Tamanaha et al., "Feasibility Study of an Inorganic Membrane Filter as a Support for Biomembrane-Mimetic Structures," Proceedings of the IEEE 21st Annual Northeast Bioengineering Conference, 1995, pp. 99-101.

C. Tamanaha et al., "Humidity and Cation Dependency of Purple Membrane Based Biosensors," Proceedings of the 18th IEEE Annual Northeast Bioengineering Conference, Mar. 1992, pp. 107-108.

C. Tamanaha et al., "Surface Modification of y-$Al_2O_3$ Filters by Chemisorption of Alkyltrichlorosilane Molecules," 18th Annual International Conference of the IEEE Engineering in Medicine and Biology Society, 1996, pp. 2069-2070.

D. Dao et al., "A Robust Motion Artifact Detection Algorithm for Accurate Detection of Heart Rates from Photoplethysmographic Signals Using Time-Frequency Spectral Features," IEEE Journal of Biomedical and Health Informatics, vol. 21, No. 5, Sep. 2017, pp. 1242-1253.

D. Sen et al., "A New Vision for Preventing Pressure Ulcers: Wearable Wireless Devices Could Help Solve a Common-and Serious-Problem," IEEE Pulse, vol. 9, No. 6, Nov. 2018, pp. 28-31.

D. Sen et al., "Pressure Ulcer Prevention System: Validation in a Clinical Setting," IEEE Life Sciences Conference (LSC), 2018, pp. 105-108.

D. Sen et al., "Time-Domain-Based Measurement Technique for Pressure Measurement in a Wearable Wireless Sensor Patch," IEEE International Symposium on Circuits and Systems (ISCAS), 2018, pp. 1-5.

D. Sen et al., "Wireless Sensor Patch Suitable for Continuous Monitoring of Contact Pressure in a Clinical Setting," 16th IEEE International New Circuits and Systems Conference (NEWCAS), 2018, pp. 91-95.

D. Thompson et al., "A Small, High-Fidelity Reflectance Pulse Oximeter," American Society for Engineering Education, 2007, 14 pages.

D. Thompson et al., "Pulse Oximeter Improvement with an ADC-DAC Feedback Loop and a Radical Reflectance Sensor," Proceedings of the 28th IEEE EMBS Annual International Conference, 2006, pp. 815-818.

D. Traviglia et al., "A Portable Setup for Comparing Transmittance and Reflectance Pulse Oximeters for Field Testing Applications," Proceedings of the IEEE 30th Annual Northeast Bioengineering Conference, 2004, pp. 212-213.

E. Morillo et al., "Multiwavelength Transmission Spectrophotometry in the Pulsatile Measurement of Hemoglobin Derivatives in Whole Blood," Proceedings of the IEEE 23rd Northeast Bioengineering Conference, 1997, pp. 5-6.

E. Stohr et al., "Quantitative FT-IR Spectrometry of Blood Constituents," 14th Annual International Conference of the IEEE Engineering in Medicine and Biology Society, 1992, pp. 173-174.

E. Stohr et al., "Quantitative FTIR Spectrophotometry of Cholesterol and Other Blood Constituents and their Interference with the In-Vitro Measurement of Blood Glucose," Proceedings of the 18th IEEE Annual Northeast Bioengineering Conference, 1992, pp. 105-106.

E. Tuite et al., "Design of Individual Balance Control Device Utilized during the Sit-to-Stand Task," ISB 2011 Brussels, 2011, pp. 1-2.

G. Comtois et al., "A Comparative Evaluation of Adaptive Noise Cancellation Algorithms for Minimizing Motion Artifacts in a Forehead-Mounted Wearable Pulse Oximeter," Proceedings of the 29th Annual International Conference of the IEEE EMBS, Aug. 2007, pp. 1528-1531.

G. Comtois et al., "A Noise Reference Input to an Adaptive Filter Algorithm for Signal Processing in a Wearable Pulse Oximeter," IEEE 33rd Annual Northeast Bioengineering Conference, 2007, pp. 106-107.

G. Comtois et al., "A Wearable Wireless Reflectance Pulse Oximeter for Remote Triage Applications," Proceedings of the IEEE 32nd Annual Northeast Bioengineering Conference, 2006, pp. 53-54.

H. DiSpirito et al., "A Neural Stimulation System Model to Enhance Neural Integrated Circuit Design," 29th Southern Biomedical Engineering Conference, 2013, pp. 9-10.

Home Use Guide: Nellcor Symphony N-3000 Pulse Oximeter, Nellcor Puritan Bennett, Inc., Copyright 1996, 50 pages.

J. A. Pologe, "Pulse Oximetry: Technical Aspects of Machine Design," International Anesthesiology Clinics, vol. 25, No. 3, 1987, pp. 137-153.

J. Bronzino et al., Medical Devices and Systems, The Biomedical Engineering Handbook, Third Edition, Taylor & Francis Group, LLC, Apr. 2006, 20 pages.

J. Bronzino et al., The Biomedical Engineering Handbook, Second Edition, CRC Press LLC, 2000, 21 pages.

J. Chong et al., "Photoplethysmograph Signal Reconstruction Based on a Novel Hybrid Motion Artifact Detection-Reduction Approach. Part I: Motion and Noise Artifact Detection," Annals of Biomedical Engineering, vol. 42, No. 11, Nov. 2014, pp. 2238-2250.

J. Harvey et al., "A Portable Sensor for Skin Bioimpedance Measurements," International Journal of Sensors and Sensor Networks, vol. 7, No. 1, Aug. 2019, pp. 1-8.

J. Harvey et al., "Correlation of bioimpedance changes after compressive loading of murine tissues in vivo," Physiological Measurement, vol. 40, No. 10, Oct. 2019, pp. 1-13.

J. Harvey et al., "OxiMA: A Frequency-Domain Approach to Address Motion Artifacts in Photoplethysmograms for Improved Estimation of Arterial Oxygen Saturation and Pulse Rate," IEEE Transactions on Biomedical Engineering, vol. 66, No. 2, Feb. 2019, pp. 311-318.

J. Hodby, "A ratio-measuring detection system for use in pulsed spectroscopic measurements," Journal of Physics E: Scientific Instruments, vol. 3, 1970, pp. 229-233.

J. McNeill et al., "Flexible Sensor for Measurement of Skin Pressure and Temperature in a Clinical Setting," 2016 IEEE Sensors, Nov. 2016, pp. 1-3.

J. McNeill et al., "Wearable Wireless Sensor Patch for Continuous Monitoring of Skin Temperature, Pressure, and Relative Humidity," IEEE International Symposium on Circuits and Systems (ISCAS), 2017, pp. 1-4.

(56) References Cited

OTHER PUBLICATIONS

J. Webster et al., Nanoparticles—Radiotherapy Accessories, Encyclopedia of Medical Devices and Instrumentation, Second Edition, vol. 5, Wiley-Interscience, 2006, 42 pages.
J. Yao, et al., "Stimulating Student Learning with a Novel 'In-House' Pulse Oximeter Design", Proceedings of the 2005 American Society for Engineering Education Annual Conference & Exposition, 2005, 14 pages.
K. Chon et al., "Wearable Wireless Sensor for Multi-Scale Physiological Monitoring," Worcester Polytechnic Institute, Oct. 2014, 82 pages.
K. Chon et al., "Wearable Wireless Sensor for Multi-Scale Physiological Monitoring," Worcester Polytechnic Institute, Oct. 2015, 142 pages.
K. Faisst et al., "Reflectance pulse oximetry in neonates," European Journal of Obstetrics & Gynecology and Reproductive Biology, vol. 61, No. 2, Aug. 1995, pp. 117-122.
K. Hickle et al., "Wireless Pressure Ulcer Sensor," Annals of Plastic Surgery, vol. 82, Supplement 3, Apr. 2019, pp. S215-S221.
K. Li et al., "A High-Performance Wireless Reflectance Pulse Oximeter for Photo-Plethysmogram Acquisition and Analysis in the Classroom," American Society for Engineering Education, 2010, 12 pages.
K. Li et al., "A Wireless Reflectance Pulse Oximeter with Digital Baseline Control for Unfiltered Photoplethysmograms," IEEE Transactions on Biomedical Circuits and Systems, Nov. 2011, pp. 1-11.
K. M. Warren et al., "Improving Pulse Rate Measurements during Random Motion Using a Wearable Multichannel Reflectance Photoplethysmograph," Sensors (Basel), vol. 16, No. 3, Mar. 2016, p. 1-18.
K. Ono et al., "Fiber optic reflectance spectrophotometry system for in vivo tissue diagnosis," Applied Optics, vol. 30, No. 1, Jan. 1991, pp. 98-105.
K. Self, Application Note 78—Using Power Management with High-Speed Microcontrollers, Maxim Integrated Products, Inc., Mar. 29, 2001, 25 pages.
M. Barr, "Introduction to Pulse Width Modulation (PWM)," Barr Group, Embedded Systems Programming, Sep. 2001, pp. 1-3.
M. Corcoran et al., "A Humidifier for Olfaction Studies During Functional Magnetic Resonance Imaging," Proceedings of the IEEE 31st Annual Northeast Bioengineering Conference, 2005, pp. 1-2.
M. J. Hayes, "Artefact Reduction in Photoplethysmography," Doctoral thesis, Department of Electronic and Electrical Engineering, Loughborough University, Nov. 1998, 195 pages. (uploaded in 2 parts).
M. Last et al., Chapter 14: Early Warning from Car Warranty Data using a Fuzzy Logic Technique, Scalable Fuzzy Algorithms for Data Management and Analysis: Methods and Design, 2010, pp. 347-364.
M. Nogawa et al., "A Novel Hybrid Reflectance Pulse Oximeter Sensor with Improved Linearity and General Applicability to Various Portions of the Body," Proceedings of the 20th Annual International Conference of the IEEE Engineering in Medicine and Biology Society, vol. 20, No. 4, 1998, pp. 1858-1861.
M. Savage et al., "Optimizing Power Consumption in the Design of a Wearable Wireless Telesensor: Comparison of Pulse Oximeter Modes," IEEE 29th Annual Proceedings of Bioengineering Conference, 2003, pp. 150-151.
N. Reljin et al., "Automatic Detection of Dehydration using Support Vector Machines," 14th Symposium on Neural Networks and Applications (Neurel), Nov. 2018, pp. 1-6.
N. Reljin et al., "Detection of Blood Loss in Trauma Patients using Time-Frequency Analysis of Photoplethysmographic Signal," IEEE-EMBS International Conference on Biomedical and Health Informatics (BHI), 2016, pp. 118-121.
N. Reljin et al., "Using support vector machines on photoplethysmographic signals to discriminate between hypovolemia and euvolemia," PLoS One, vol. 13, No. 3, Mar. 2018, pp. 1-14.
N. Selvaraj et al., "A Novel Approach Using Time-Frequency Analysis of Pulse-Oximeter Data to Detect Progressive Hypovolemia in Spontaneously Breathing Healthy Subjects," IEEE Transactions on Biomedical Engineering, vol. 58, No. 8, Aug. 2011, pp. 2272-2279.
N. Selvaraj et al., "Statistical Approach for the Detection of Motion/Noise Artifacts in Photoplethysmogram," 33rd Annual International Conference of the IEEE EMBS, Sep. 2011, pp. 4972-4975.
Operator's Manual: Nellcor N-200 Pulse Oximeter, Nellcor Incorporated, Copyright 2003, 96 pages.
Optoelectronics, Data Book 1990, Siemens Components, Inc., 770 pages. (uploaded in 7 parts).
OxiplexTS Near Infrared, Non-Invasive, Tissue Spectrometer Brochure, ISS, Inc., Copyright 2001, 6 pages.
P. Bhandare et al. "Glucose Determination in Simulated Plasma Solutions Using Infrared Spectrophotometry," 14th Annual International Conference of the IEEE Engineering in Medicine and Biology Society, Nov. 1992, pp. 163-164.
P. Bhandare et al., "Glucose determination in simulated blood serum solutions by Fourier transforms infrared spectroscopy: investigation of spectral interferences," Vibrational Spectroscopy, vol. 6, No. 3, Mar. 1994, pp. 363-378.
P. Bhandare et al., "IR Spectrophotometric Measurement of Glucose in Phosphate Buffered Saline Solutions: Effects of Temperature and pH," Proceedings of the 18th IEEE Annual Northeast Bioengineering Conference, 1992, pp. 103-104.
P. Bhandare et al., "Multivariate Determination of Glucose in Whole Blood Using Partial Least-Squares and Artificial Neural Networks Based on Mid-Infrared Spectroscopy," Society for Applied Spectroscopy, vol. 47, No. 8, 1993, pp. 1214-1221.
P. Bhandare et al., "Neural Network Based Spectral Analysis of Multicomponent Mixtures for Glucose Determination," Proceedings of the IEEE, 17th Annual Northeast Bioengineering Conference, 1991, pp. 249-250.
P. Branche et al., "Signal Quality and Power Consumption of a New Prototype Reflectance Pulse Oximeter Sensor," Proceedings of the IEEE 31st Annual Northeast Bioengineering Conference, 2005, pp. 1-2.
P. C. Branche et al., "A Wearable Wireless Reflectance Pulse Oximeter with Automatic and Remote On-Demand Activation," Annual Fall Meeting of the BMES, 2004, p. 1.
P. C. Branche et al., "Measurement Reproducibility and Sensor Placement Considerations in Designing a Wearable Pulse Oximeter for Military Applications," Proceedings of the IEEE 30th Annual Northeast Bioengineering Conference, 2004, pp. 216-217.
P. Muller et al., "A Preliminary In-Vitro Evaluation and Comparative Study of Various Tissue pH Sensors," Proceedings of the 18th IEEE Annual Northeast Bioengineering Conference, 1992, pp. 158-159.
P. P. Vaidyanathan, "Multirate Digital Filters, Filter Banks, Polyphase Networks, and Applications: A Tutorial," Proceedings of the IEEE, vol. 78, No. 1, Jan. 1990, pp. 56-93.
R. Dresher, "Wearable Forehead Pulse Oximetry: Minimization of Motion and Pressure Artifacts," Master thesis, Worcester Polytechnic Institute, May 2006, 93 pages.
R. J. Duckworth et al., Field Testing of a Wireless Wearable Reflectance Pulse Oximeter Printout, Department of Electrical and Computer Engineering and Department of Biomedical Engineering, Worcester Polytechnic Institute, 1 page. Undated.
R. Kasbekar et al., "Evaluation of key design parameters for mitigating motion artefact in the mobile reflectance PPG signal to improve estimation of arterial oxygenation," Physiological Measurement, vol. 39, No. 7, Jul. 2018, pp. 1-12.
R. P. Dresher et al., "A New Reflectance Pulse Oximeter Housing to Reduce Contact Pressure Effects," Proceedings of the IEEE 32nd Annual Northeast Bioengineering Conference, 2006, pp. 49-50.
R. P. Dresher et al., "Reflectance Forehead Pulse Oximetry: Effects of Contact Pressure During Walking," Proceedings of the 28th IEEE EMBS Annual International Conference, Sep. 2006, pp. 3529-3532.
R. Peura et al, "Biotechnology for Biomedical Engineers," IEEE Engineering in Medicine and Biology, vol. 14, No. 2, Apr. 1995, pp. 199-200.

(56) References Cited

OTHER PUBLICATIONS

RF Cafe, Electronic Warfare and Radar Systems Engineering Handbook, Duty Cycle, available at https://www.rfcafe.com/references/electrical/ew-radar-handbook/duty-cycle.htm, retrieved Jul. 11, 2020, 3 pages.
S. Djamasbi et al., "Affect Feedback during Crisis and Its Role in Improving IS Utilization," Proceedings of the 7th International Conference on Information Systems for Crisis Response and Management (ISCRAM), 2010, pp. 1-4.
S. Kastle et al., "A New Family of Sensors for Pulse Oximetry," Hewlett-Packard Journal, Article 7, Feb. 1997, pp. 1-17.
S. LeGare et al., "A Device to Assess the Severity of Peripheral Edema," IEEE 33rd Annual Northeast Bioengineering Conference, 2007, pp. 257-258.
S. M. A. Salehizadeh et al., "Photoplethysmograph Signal Reconstruction based on a Novel Motion Artifact Detection-Reduction Approach. Part II: Motion and Noise Artifact Removal," Annals of Biomedical Engineering, vol. 42, May 2014, pp. 2251-2263.
S. Oshima et al., "Optical Measurement of Blood Hematocrit on Medical Tubing with Dual Wavelength and Detector Model," 31st Annual International Conference of the IEEE EMBS, Sep. 2009, pp. 5891-5896.
S. Patrick et al., "An Electromyogram Simulator for Myoelectric Prosthesis Testing," Proceedings of the IEEE 36th Annual Northeast Bioengineering Conference (NEBEC), 2010, pp. 1-2.
S. Salehizadeh et al., "A Novel Time-Varying Spectral Filtering Algorithm for Reconstruction of Motion Artifact Corrupted Heart Rate Signals During Intense Physical Activities Using a Wearable Photoplethysmogram Sensor," Sensors 2016, vol. 16, No. 1, Dec. 2015, pp. 1-20.
S. Takatani et al., "Experimental and Clinical Evaluation of a Noninvasive Reflectance Pulse Oximeter Sensor," Journal of Clinical Monitoring, vol. 8, No. 4, Oct. 1992, pp. 257-266.
S. Xie et al., "A Predictive Model for Force-Sensing Resistor Nonlinearity for Pressure Measurement in a Wearable Wireless Sensor Patch," IEEE 61st International Midwest Symposium on Circuits and Systems, 2018, pp. 476-479.
Service Manual: Nellcor Symphony N-3000 Pulse Oximeter, Nellcor Puritan Bennett, Inc., Copyright 1996, 110 pages.
Service Manual: NPB-40 Handheld Pulse Oximeter, Nellcor Puritan Bennett, Inc., Copyright 2001, 55 pages.
V. Floroff, "PDA Interface for the WPI Wireless Physiological Monitor," Directed research, Department of Biomedical Engineering, Worcester Polytechnic Institute, Mar. 2006, 42 pages.
V. Floroff, "Remote Pulse Oximetry: The wireless side of the TATRC project." Thesis, Worcester Polytechnic Institute, Feb. 2005, pp. 1-20.
V. Konig et al., "Reflectance Pulse Oximetry—Principles and Obstetric Application in the Zurich System," Journal of Clinical Monitoring and Computing, vol. 14, No. 6, Aug. 1998, pp. 403-412.
V. Konig et al., "Reflexions-Pulsoximetrie—Untersuchungen mit eigenem Mess-System," Biomedical Engineering, Biomedizinische Technik, vol. 37. No. s2, 1992, pp. 39-40.
W. Johnston et al., "Effects of Motion Artifacts on Helmet-Mounted Pulse Oximeter Sensors," Proceedings of the IEEE 30th Annual Northeast Bioengineering Conference, 2014, pp. 214-215.
W. Johnston et al., "Extracting Heart Rate Variability from a Wearable Reflectance Pulse Oximeter," Proceedings of the IEEE 31st Annual Northeast Bioengineering Conference, 2005, pp. 1-2.
W. S. Johnston et al., "Extracting Breathing Rate Information from a Wearable Reflectance Pulse Oximeter Sensor," Proceedings of the 26th Annual International Conference of the IEEE EMBS, Sep. 2004, pp. 5388-5391.
W. S. Johnston et al., "Investigation of Signal Processing Algorithms for an Embedded Microcontroller-Based Wearable Pulse Oximeter," Proceedings of the 28th IEEE EMBS Annual International Conference, Sep. 2006, pp. 5888-5891.
Wireless Wearable Reflectance Pulse Oximeter, PowerPoint, The Bioengineering Institute, Worcester Polytechnic Institute, TATRC, 10 pages. Undated.
Y. Mendelson et al., "A Mobile PDA-Based Wireless Pulse Oximeter," Proceedings of the IASTED International Conference, Jul. 2005, pp. 1-6.
Y. Mendelson et al., "Accelerometery-Based Adaptive Noise Cancellation for Remote Physiological Monitoring by a Wearable Pulse Oximeter," Proceedings of the 3rd IASTED International Conference on Telehealth, May 2007, pp. 28-33.
Y. Mendelson et al., "Minimization of LED Power Consumption in the Design of a Wearable Pulse Oximeter," Proceedings of the IASTED International Conference Biomedical Engineering, Jun. 2003, pp. 249-254.
Y. Mendelson et al., "The Feasibility of Measuring $SpO_2$ from the Head Using a Reflectance Pulse Oximeter: Effect of Motion Artifacts," Proceeding of the 3rd European Medical & Biological Engineering Conference, 2005, 5 pages.
Y. Mendelson et al., "Wireless Reflectance Pulse Oximetery for Remote Triage Application," Worcester Polytechnic Institute, 1 page. Undated.
Y. Mendelson et al., "A Multiwavelength VIS-NIR Spectrometer for Pulsatile Measurement of Hemoglobin Derivatives in Whole Blood," 18th Annual International Conference of the IEEE Engineering in Medicine and Biology Society, 1996, pp. 134-135.
Y. Mendelson et al., "An In Vitro Tissue Model for Evaluating the Effect of Carboxyhemoglobin Concentration on Pulse Oximetry," IEEE Transactions on Biomedical Engineering, vol. 36, No. 6, Jun. 1989, pp. 625-627.
Y. Mendelson et al., "Blood Glucose Measurement by Multiple Attenuated Total Reflection and Infrared Absorption Spectroscopy," IEEE Transactions on Biomedical Engineering, vol. 37, No. 5, May 1990, pp. 458-465.
Y. Mendelson et al., "Carbon dioxide laser based multiple ATR technique for measuring glucose in aqueous solutions," Applied Optics, vol. 27, No. 24, Dec. 1988, pp. 5077-5081.
Y. Mendelson et al., "Evaluation of the Datascope ACCUSAT Pulse Oximeter in Healthy Adults," Journal of Clinical Monitoring, vol. 4, No. 1, Jan. 1988, pp. 59-63.
Y. Mendelson et al., "Multi-channel pulse oximetry for wearable physiological monitoring," IEEE International Conference on Body Sensor Networks, 2013, pp. 1-6.
Y. Mendelson et al., "Noninvasive Pulse Oximetry Utilizing Skin Reflectance Photoplethysmography," IEEE Transactions on Biomedical Engineering, vol. 35, No. 10, Oct. 1988, pp. 798-805.
Y. Mendelson et al., "Noninvasive Transcutaneous Monitoring of Arterial Blood Gases," IEEE Transactions on Biomedical Engineering, vol. BME-31, No. 12, Dec. 1984, pp. 792-800.
Y. Mendelson et al., Pulse Oximetry: Theory and Applications for Noninvasive Monitoring, Clinical Chemistry, vol. 38, No. 9, 1992, pp. 1601-1607.
Y. Mendelson et al., "Variations in Optical Absorption Spectra of Adult and Fetal Hemoglobins and Its Effect on Pulse Oximetry," IEEE Transactions on Biomedical Engineering, vol. 36, No. 8, Aug. 1989, pp. 844-848.
Y. Mendelson et al., A Wearable Reflectance Pulse Oximeter for Remote Physiological Monitoring, PowerPoint, The Bioengineering Institute, Worcester Polytechnic Institute, 18 pages. Undated.
Y. Mendelson et al., A Wireless Wearable Reflectance-Based Forehead Pulse Oximeter, PowerPoint, The Bioengineering Institute, Worcester Polytechnic Institute, 8 pages. Undated.
Y. Mendelson et al., Chapter 9: Biomedical Sensors, Introduction to Biomedical Engineering, Second Edition, Apr. 2005, pp. 505-548.
Y. Mendelson, "Wearable, Wireless, Noninvasive Physiological Sensing," The Bioengineering Institute, Worcester Polytechnic Institute, 2005, 2 pages.
Y. Mendelson, et al., "A Wearable Reflectance Pulse Oximeter for Remote Physiological Monitoring", Proceedings of the 28th IEEE EMBS Annual International Conference, 2006, pp. 912-915.
Y. Mendelson, et al., "Design and Evaluation of a New Reflectance Pulse Oximeter Sensor", Worcester Polytechnic Institute, Biomedical Engineering Program, Worcester, MA 01609, Association for the Advancement of Medical Instrumentation, vol. 22, No. 4, 1988, pp. 167-173.
Y. Mendelson, et al., "Measurement Site and Photodetector Size Considerations in Optimizing Power Consumption of a Wearable

(56) References Cited

OTHER PUBLICATIONS

Reflectance Pulse Oximeter", Proceedings of the 25th IEEE EMBS Annual International Conference, 2003, pp. 3016-3019.

Y. Mendelson, et al., "Skin Reflectance Pulse Oximetry: In Vivo Measurements from the Forearm and Calf", Journal of Clinical Monitoring, vol. 7, No. 1, Jan. 1991, pp. 7-12.

Y. Mendelson, Pulse Oximetry, PowerPoint, UMass Center for Clinical and Translational Science Research Retreat, 2017, 22 pages.

Y. Shimada et al., "Evaluation of a new reflectance pulse oximeter for clinical applications," Medical & Biological Engineering & Computing, vol. 29, No. 5, Sep. 1991, pp. 557-561.

Y. Xu et al., "Drowsiness Control Center by Photoplethysmogram," 38th Annual Northeast Bioengineering Conference (NECBEC), IEEE, 2012, pp. 430-431.

Letter from Jennifer Shih to Masimo Corporation re 510(k) No. K232512, U.S. Food & Drug Administration, dated Nov. 17, 2023, in 14 pages.

Feb. 10, 2023 Plaintiff Apple Inc.'s Opening Brief in Support of its Motion for an Expedited Trial, *Apple Inc. v. Masimo Corporation and Sound United, LLC, Masimo Corporation and Cercacor Laboratories, Inc. v. Apple Inc.*, Case No. 1:22-cv-01377-MN, 29 pages.

Sep. 14, 2023 Transcript of Markman Hearing, *Apple Inc. v. Masimo Corporation and Sound United, LLC, Masimo Corporation v. Apple Inc.*, Case No. 1:22-cv-01377-MN & *Apple Inc. v. Masimo Corporation and Sound United, LLC, Masimo Corporation and Cercacor Laboratories, Inc. v. Apple Inc.*, Case No. 1:22-cv-01378-MN, 64 pages.

Jan. 10, 2024 Plaintiff Apple Inc.'s Opposition to Defendants' Motion for Stay Pending Inter Partes Review, *Apple Inc. v. Masimo Corporation and Sound United, LLC, Masimo Corporation and Cercacor Laboratories, Inc. v. Apple Inc.*, Case No. 1:22-cv-01378-MN, 20 pages.

Mar. 13, 2024 Counter-Defendant Apple Inc.'s Final Invalidity Contentions, *Apple Inc. v. Masimo Corporation and Sound United, LLC, Masimo Corporation and Cercacor Laboratories, Inc. v. Apple Inc.*, Case No. 1:22-cv-01378-MN, 33 pages.

Mar. 16, 2024 Joint Letter for Mar. 20, 2024 Case Management Conference, *Apple Inc. v. Masimo Corporation and Sound United, LLC, Masimo Corporation and Cercacor Laboratories, Inc. v. Apple Inc.*, Case No. 1:22-cv-01378-MN, 52 pages.

Jul. 19, 2024 Non-Confidential Rely Brief for Appellant Apple Inc., Federal Circuit appeal of ITC Inv. No. 337-TA-1276, pp. 42.

Apple MessagePad Handbook, Newton, Apple, 1995, pp. 196.

Arbetter et al., "Control Method for Low-Voltage DC Power Supply in Battery-Powered Systems with Power Management", Record 28th Annual IEEE Power Electronics Specialists Conference, 1997, pp. 1198-1204.

Exhibit 12, Markman Hearing Certified Deposition Transcript, *Masimo Corporation, et al., v. Apple Inc.*, Case No. 8:20-cv-00048 as filed Jul. 26, 2024, in 28 pages.

Greatbatch et al., "History of Implantable Devices", IEEE Engineering in Medicine and Biology Magazine, Sep. 1991, vol. 10, No. 3, pp. 5.

Martin et al., "Non-Ideal Battery Properties and Low Power Operation in Wearable Computing", IEEE Third International Symposium on Wearable Computers, San Francisco, CA, 1999, pp. 8.

Melear, Charles, Hardware and Software Techniques for Power Conservation in Portable Devices, Proceedings of WESCON '94, pp. 453-461.

MIT Ring Monitors Patients' Vital Signs, MIT News, https://news.mit.edu/1997/vitalsigns, Apr. 7, 1997, pp. 2.

"Mobile Station-Base Station Compatibility Standard for Dual-Mode Spread Spectrum Systems", TIA/EIA-95-B, 1999, pp. 1205.

Nordman et al., "User Guide to Power Management for PCs and Monitors", UC Berkeley, Jan. 1997, pp. 72.

Polar Accurex Plus, Heart Rate Monitor—User's Manual, 1996, pp. 27.

Rhee et al., "Artifact-Resistant Power-Efficient Design of Finger-Ring Plethysmographic Sensors", IEEE Transactions on Biomedical Engineering, vol. 48, No. 7, Jul. 2001, pp. 795-805.

Rhee et al., "Artifact-Resistant, Power-Efficient Design of Finger-Ring Plethysmographic Sensors Part I: Design and Analysis", Proceedings of the 22nd Annual EMBS International Conference, Jul. 23-28, 2000, Chicago, IL, pp. 2792-2795.

Rhee et al., "Artifact-Resistant, Power-Efficient Design of Finger-Ring Plethysmographic Sensors Part II: Prototyping and Benchmarking", Proceedings of the 22nd Annual EMBS International Conference, Jul. 23-28, 2000, Chicago, IL, pp. 2796-2799.

Rhee et al., "The Ring Sensor: a New Ambulatory Wearable Sensor for Twenty-Four Hour Patient Monitoring", Proceedings of the 20th Annual International Conference of the IEEE Engineering in Medicine and Biology Society, Hong Kong, Oct. 29-Nov. 1, 1998, pp. 4.

Rhee, Sokwoo, "Design and Analysis of Artifact-Resistive Finger Photoplethysmographic Sensors for Vital Sign Monitoring", Doctor of Philosophy, Massachusetts Institute of Technology, Jun. 2000, pp. 101.

Shults et al., "A Telemetry-Instrumentation System for Monitoring Multiple Subcutaneously Implanted Glucose Sensors", IEEE Transactions on Biomedical Engineering, vol. 41, No. 10, Oct. 1994, pp. 6.

Tamura et al., "An Ambulatory Fall Monitor for the Elderly", EMBS International Conference, 2000, pp. 3.

TS 101 350 V8.5.0 (Jul. 2000), Technical Specification, Digital cellular telecommunications system (Phase 2+); General Packet Radio Service (GPRS); Overall description of the GPRS radio interface; Stage 2 (GSM 03.64 version 8.5.0 Release 1999), ETSI, 1999, pp. 58.

Yang et al., "A Twenty-Four Hour Tele-Nursing System Using a Ring Sensor", Proc. of 1998 Int. Conf. on Robotics and Automation Leuven, Belgium, May 16-20, 1998, pp. 6.

Yang et al., "Development of the Ring Sensor for Healthcare Automation", Robotics and Autonomous Systems, vol. 30, 2000, pp. 273-281.

May 6, 2024 Defendant Apple Inc.'s Amended Preliminary Invalidity Contentions (Patent L.R. 3-3 and 3-4), and including Exhibits A1-A7 and B1-B7, *Masimo Corporation and Cercacor Laboratories, Inc. v. Apple Inc.*, Case No. 8:20-cv-00048, 2227 pages.

Jul. 26, 2024 Apple Inc.'s Supplemental Markman Brief on Indefiniteness, *Masimo Corporation and Cercacor Laboratories, Inc. v. Apple Inc.*, Case No. 8:20-cv-00048, 8 pages.

Aug. 2, 2024 Masimo's Supplemental Claim Construction Brief, *Masimo Corporation and Cercacor Laboratories, Inc. v. Apple Inc.*, Case No. 8:20-cv-00048, 7 pages.

Polar Protrainer XT, Heart Rate Monitor—User's Manual, 2001, pp. 29.

Polar S610, Heart Rate Monitor, User's Manual, 2000, pp. 51.

Asada, Haruhiko H., Ph.D., "Ch. 4 Miniaturization of the Ring Sensor", Massachusetts Institute of Technology Consortium Agreement, Prepared for: U.S. Army Medical Research and Materiel Command Fort Detrick, Maryland 21702-5012, Award No. AMD17-98-2-8003, Type of Report: Final I of Phase 2, Mar. 1999, pp. 333. [Uploaded in 3 Parts].

Asada et al., "Mobile Monitoring with Wearable Photoplethysmographic Biosensors", IEEE Engineering in Medicine and Biology Magazine, May/Jun. 2003, pp. 28-40.

Culbert, Michael, "Low Power Hardware for a High Performance PDA", Proceedings of the 1994 IEEE Computer Conference, San Francisco, CA, 1994, pp. 4.

"You Surely Won't Grouse if you Switch to this Mouse", The Houston Chronicle, Apr. 19, 2001, pp. 2.

"Agilent Technologies' Sensor Powers New Logitech Cordless Mouseman Optical Mouse; Breakthrough Cordless Optical Mouse Features Higher Pointing Accuracy and Three-Month Battery Life", Business Wire, Mar. 21, 2001, pp. 2.

Dan's Data, "Logitech Cordless MouseMan Optical", www.dansdata.com/Itcmmo.htm, 2001, pp. 14.

Logitech, "Cordless MouseMan Optical", 2001, pp. 2.

Letter from Thomas J. Callahan to Masimo Corporation re 510(k) No. K992238, U.S. Food & Drug Administration, dated Oct. 8, 1999 in 10 pages.

(56) References Cited

OTHER PUBLICATIONS

Masimo, News & Media, https://professional.masimo.com/company/news/news-media/2000/, pp. 46.
MasimoSET, https://web.archive.org/web/20000302022748/http://www.masimo.com/radical.htm, as archived Mar. 2, 2000, pp. 4.
Newton MessagePad 2000, Tech Article, Worlwide Apple Assist, Apple Computer, Inc., Jan. 1997, pp. 45.
Newton MessagePad 2100: Description, Article 28047, Nov. 14, 1997, pp. 2.
Nonin, Instruction and Service Manual, Models 8500 & 8500M, Hand Held Pulse Oximeters, Dec. 12, 1995, pp. 306.
Nonin Medical, Inc., Home Page, https://web.archive.org/web/19991009002411/http://www.nonin.com:80/, as archived Oct. 9, 1999, pp. 2.
Nonin Medical, Inc., Model 8500 Hand-held Pulse Oximeter, https://web.archive.org/web/20000711024143/http://www.nonin.com/m8500_1.html, as archived Jan. 19, 1997, pp. 2.
Nonin Medical, Inc., Model 8500 Hand-held Pulse Oximeter, https://web.archive.org/web/20000711024143/http://www.nonin.com/m8500_1.html, as archived Jul. 11, 2000, pp. 2.
Nonin Medical, Inc., Onyx® Finger Pulse Oximeter, https://web.archive.org/web/19990508064315/http://www.nonin.com/onyx1.html, as archived May 8, 1999, pp. 2.
Nellcor, N-20 Series, Handheld Pulse Oximeters, 1998, pp. 2.
Nellcor, Service Manual, NPB-40, Handheld Pulse Oximeter, 1998, pp. 51.
Nellcor, Operator's Manual, Nellcor N-20/N-20P, Portable Pulse Oximeter, 1993, pp. 228.
Nellcor, Operator's Manual, NPB-40, Handheld Pulse Oximeter, 2001, pp. 47.
Nellcor, Service Manual, N-20PA, Portable Pulse Oximeter, 2000, pp. 92.
Nellcor, Service Manual, N-20/N-20PA, Portable Pulse Oximeter, 2000, pp. 82.
Wood et al., "Measurement of Pressures in Man by Cardiac Catheters", Circulation Research, vol. II, Jul. 1954, pp. 294-303.
Ohmeda, Ohmeda Biox 3740 Pulse Oximeter Operating/Maintenance Manual, BOC Health Care Inc., 1990, pp. 60.
De Kock et al., "The Effect of Varying LED Intensity on Pulse Oximeter Accuracy", Journal of Medical Engineering & Technology, May-Jun. 1991, vol. 15, No. 3, pp. 111-116.
Swanagin, Stephen, "The Effect of Inspired Oxygen Concentration and Transportation Time on Arterial Hemoglobin Oxygen Saturation During Transport From the Operating Room to the Postanesthesia Care Unit", UMI Microform 1385143, 1996, pp. 48.
Guinta, Steve, "Considerations in Designing Single Supply, Low-Power Systems Part II: Battery Powered Systems", Analog Dialogue 30-1, 1996, pp. 9-11.
Wang, Lei, "Surface Micromachined PZT Accelerometers and Low-Power CMOS Sensor Circuits", Thesis, University of Minnesota, Aug. 1997, pp. 143.
Kästle et al., "A New Family of Sensors for Pulse Oximetry", Hewlett-Packard Journal, Feb. 1997, pp. 17.
Aritomo et al., "A Wrist-Mounted Activity and Pulse Recording System", Proceedings of the First Joint BMES/EMBS Conference, Oct. 1999, p. 693.
Chandrakasan et al., "Design Considerations for Distributed Microsensor Systems", IEEE Proceedings of the IEEE 1999 Custom Integrated Circuits Conference, 1999, pp. 8.
Lee et al., "Coil Design with Frequency-Insensitive Characteristics for Wireless Power Transfer", IEICE Proceedings Series, 2011, pp. 4.
Girod et al., "Instrumenting the World with Wireless Sensor Networks", IEEE Conference on Acoustics, Speech, and Signal Processing, 2001, pp. 4.
Marquette, Responder 3000, Operator's Manual, Version 2, Revision C, 2000, pp. 90.
Biotronik, ACTROS—The New Pacemaker Family, https://web.archive.org/web/19990505175806/http://www.biotronik.de/products/brady/actros/actros.html, as archived May 5, 1999, pp. 137.
Hertzman, Alrick, "Photoelectric Plethysmography of the Fingers and Toes in Man", Society for Experimental Biology and Medicine, 1937, pp. 529-534.
Millikan, G.A., "The Oximeter, an Instrument for Measuring Continuously the Oxygen Saturation of Arterial Blood in Man", Review of Scientific Instruments, Oct. 1942, vol. 13, pp. 434-444.
Öberg et al., "Sensors in Medicine and Health Care", Sensors Applications vol. 3, Wiley-VCH Verlag GmbH & Co., 2004, pp. 30.
Severinghaus et al., "History of Blood Gas Analysis: VII. Pulse Oximetry", Journal of Clinical Monitoring, vol. 3, No. 2, Apr. 1987, pp. 135-138.
Matthes, K., "Investigations Into the Oxygen Saturation of Human Arterial Blood", From the Medical University Clinic in Leipzig, Aug. 6, 1935, pp. 698-711.
May 24, 2024 Joint Claim Construction Prehearing Statement, *Masimo Corporation and Cercacor Laboratories, Inc. v. Apple Inc.*, Case No. 8:20-cv-00048, 49 pages.
Jun. 3, 2024 Defendant Apple Inc.'s Opening Claim Construction Brief, *Masimo Corporation and Cercacor Laboratories, Inc. v. Apple Inc.*, Case No. 8:20-cv-00048, 23 pages.
Jun. 3, 2024 Masimo's Opening Claim Construction Brief, *Masimo Corporation and Cercacor Laboratories, Inc. v. Apple Inc.*, Case No. 8:20-cv-00048, 25 pages.
Jun. 3, 2024 Declaration of Mark D. Selwyn in Support of Apple Inc.'s Opening Claim Construction Brief, Including Exhibits 1-11, *Masimo Corporation and Cercacor Laboratories, Inc. v. Apple Inc.*, Case No. 8:20-cv-00048, 408 pages.
Jun. 3, 2024 Declaration of Daniel P. Hughes in Support of Masimo's Opening Claim Construction Brief, Including Exhibits 1-15, *Masimo Corporation and Cercacor Laboratories, Inc. v. Apple Inc.*, Case No. 8:20-cv-00048, 802 pages.
Jun. 3, 2024 Declaration of Vijay K. Madisetti, Ph.D. in Support of Plaintiffs' Claim Construction Brief, *Masimo Corporation and Cercacor Laboratories, Inc. v. Apple Inc.*, Case No. 8:20-cv-00048, 70 pages.
Jun. 17, 2024 Defendant Apple Inc.'s Claim Construction Response Brief, *Masimo Corporation and Cercacor Laboratories, Inc. v. Apple Inc.*, Case No. 8:20-cv-00048, 29 pages.
Jun. 17, 2024 Masimo's Responding Claim Construction Brief, *Masimo Corporation and Cercacor Laboratories, Inc. v. Apple Inc.*, Case No. 8:20-cv-00048, 27+B423 pages.
Jun. 17, 2024 Response Declaration of Majid Sarrafzadeh, Ph.D. Regarding Claim Construction, *Masimo Corporation and Cercacor Laboratories, Inc. v. Apple Inc.*, Case No. 8:20-cv-00048, 10 pages.
Jul. 11, 2024 Apple's Report Regarding Plaintiffs' Jul. 5 Infringement Contentions, *Masimo Corporation and Cercacor Laboratories, Inc. v. Apple Inc.*, Case No. 8:20-cv-00048, 16 pages.
Jul. 11, 2024 Declaration of Adam B. Powell in Support of Plaintiffs' Status Report Regarding Supplemental Infrigement Contentions, Including Exhibit B, *Masimo Corporation and Cercacor Laboratories, Inc. v. Apple Inc.*, Case No. 8:20-cv-00048, 5 pages.
Jul. 11, 2024 Masimo's Status Report in Advance of Jul. 12 Hearing, *Masimo Corporation and Cercacor Laboratories, Inc. v. Apple Inc.*, Case No. 8:20-cv-00048, 14 pages.
Jul. 15, 2024 Masimo's Notice of Mooted Issue in Claim Construction Briefing, *Masimo Corporation and Cercacor Laboratories, Inc. v. Apple Inc.*, Case No. 8:20-cv-00048, 2 pages.
Jul. 16, 2024 Defendant Apple Inc.'s Notice of Narrowing of Proposed Terms for Claim Construction, *Masimo Corporation and Cercacor Laboratories, Inc. v. Apple Inc.*, Case No. 8:20-cv-00048, 4 pages.
Nov. 22, 2024 Apple's Memorandum in Support of its Motion for Review of and Objections to Magistrate Judge Early's Nov. 8, 2024 Report and Recommendation Regarding Plaintiffs' Infringement Contentions, *Masimo Corporation and Cercacor Laboratories, Inc. v. Apple Inc.*, Case No. 8:20-cv-00048, 28 pages.
Nov. 26, 2024 Report and Recommendation of United States Magistrate Judge [Redacted], *Masimo Corporation and Cercacor Laboratories, Inc. v. Apple Inc.*, Case No. 8:20-cv-00048, 25 pages.
Nov. 27, 2024 Order Regarding Claim Construction, *Masimo Corporation and Cercacor Laboratories, Inc. v. Apple Inc.*, Case No. 8:20-cv-00048, 16 pages.

(56) References Cited

OTHER PUBLICATIONS

Dec. 6, 2024 Masimo's Opposition to Apple's Motion for Review of and Objections to Magistrate Judge Early's Nov. 8, 2024 Report and Recommendation Regarding Plaintiffs' Infringement Contentions, *Masimo Corporation and Cercacor Laboratories, Inc.* v. *Apple Inc.*, Case No. 8:20-cv-00048, 25 pages.
Dec. 23, 2024 Apple's Reply in Support of its Motion for Review of and Objections to Magistrate Judge Early's Nov. 8, 2024 Report and Recommendation Regarding Plaintiffs' Infringement Contentions, *Masimo Corporation and Cercacor Laboratories, Inc.* v. *Apple Inc.*, Case No. 8:20-cv-00048, 19 pages.
Dec. 23, 2024 Declaration of Adam B. Powell in Support of Plaintiffs' Motion to Amend Infringement Contentions, Including Exhibit 1, *Masimo Corporation and Cercacor Laboratories, Inc.* v. *Apple Inc.*, Case No. 8:20-cv-00048, 7 pages.
Dec. 23, 2024 Memorandum in Support of Masimo's Motion to Attend Infringement Contentions, *Masimo Corporation and Cercacor Laboratories, Inc.* v. *Apple Inc.*, Case No. 8:20-cv-00048, 5 pages.
Jan. 8, 2025 Apple's Post-Trial Brief, Redacted Version, *Masimo Corporation and Cercacor Laboratories, Inc.* v. *Apple Inc.*, Case No. 8:20-cv-00048, 58 pages.
Jan. 8, 2025 Apple's [Proposed] Post-Trial Findings of Fact and Conclusions of Law, Redacted Version, *Masimo Corporation and Cercacor Laboratories, Inc.* v. *Apple Inc.*, Case No. 8:20-cv-00048, 109 pages.
Jan. 10, 2025 Opening Post-Trial Brief of Masimo Corporation and Cercacor Laboratories, Inc., Redacted Version, *Masimo Corporation and Cercacor Laboratories, Inc.* v. *Apple Inc.*, Case No. 8:20-cv-00048, 60 pages.
Jan. 10, 2025 Plaintiffs Masimo Corporation and Cercacor Laboratories, Inc.'s Post-Trial [Proposed] Findings of Fact and Conclusions of Law, Redacted Version, *Masimo Corporation and Cercacor Laboratories, Inc.* v. *Apple Inc.*, Case No. 8:20-cv-00048, 113 pages.
Jan. 24, 2025 Apple's Post-Trial Reply Brief, Redacted Version, *Masimo Corporation and Cercacor Laboratories, Inc.* v. *Apple Inc.*, Case No. 8:20-cv-00048, 32 pages.
Jan. 29, 2025 Responsive Post-Trial Brief of Masimo Corporation and Cercacor Laboratories, Inc., Redacted Version, *Masimo Corporation and Cercacor Laboratories, Inc.* v. *Apple Inc.*, Case No. 8:20-cv-00048, 33 pages.
Sep. 24, 2024 Declaration of Edward M. Cannon in Support of Masimo's Motion to Supplement the Claim Construction Record, Including Exhibits 52-55 and 57-62, *Apple Inc.* v. *Masimo Corporation and Sound United, LLC*, Case Nos. 1:22-cv-01377-JLH and 1:22-cv-01378-JLH, 681 pages.
Sep. 26, 2024 [Proposed] Final Jury Instructions, *Apple Inc.* v. *Masimo Corporation and Sound United, LLC*, Case Nos. 1:22-cv-01377-JLH and 1:22-cv-01378-JLH, 97 pages.
Oct. 17, 2024 Masimo's Notice of Masimo Defenses no Longer Asserted, *Apple Inc.* v. *Masimo Corporation and Sound United, LLC*, Case Nos. 1:22-cv-01377-JLH and 1:22-cv-01378-JLH, 2 pages.
Oct. 22, 2024 Letter to the Honorable Jennifer L. Hall from David E. Moore, *Apple Inc.* v. *Masimo Corporation and Sound United, LLC*, Case Nos. 1:22-cv-01377-JLH and 1:22-cv-01378-JLH, 5 pages.
Oct. 22, 2024 Letter to the Honorable Jennifer L. Hall from John C. Phillips, Jr., *Apple Inc.* v. *Masimo Corporation and Sound United, LLC*, Case Nos. 1:22-cv-01377-JLH and 1:22-cv-B60801378-JLH, 3 pages.
Dec. 11, 2024 Plaintiff and Counterclaim-Defendant Apple Inc.'s Motion for Injunctive Relief, *Apple Inc.* v. *Masimo Corporation and Sound United, LLC*, Case No. 1:22-cv-01377-JLH, 2 pages.
Dec. 11, 2024 Plaintiff and Counterclaim-Defendant Apple Inc.'s Motion to Correct Clerical Mistakes or, in the Alternative, to Alter or Amend the Judgement, *Apple Inc.* v. *Masimo Corporation and Sound United, LLC*, Case No. 1:22-cv-01377-JLH, 3 pages.

Dec. 11, 2024 Corrected Judgement Following Jury Verdict, *Apple Inc.* v. *Masimo Corporation and Sound United, LLC*, Case No. 1:22-cv-01377-JLH, 4 pages.
Dec. 11, 2024 Masimo's Motion for Judgement as a Matter of Law, *Apple Inc.* v. *Masimo Corporation and Sound United, LLC*, Case No. 1:22-cv-01377-JLH, 7 pages.
Dec. 13, 2024 Defendants' Opening Brief in Support of Motion for Judgment as a Matter of Law, *Apple Inc.* v. *Masimo Corporation and Sound United, LLC*, Case No. 1:22-cv-01377-JLH, 21 pages.
Jan. 10, 2025 Apple's Opening Brief in Support of: (I) Its Motion for a Permanent Injunction (35 U.S.C. § 283) [-1377 Case], (II) Its Motions to Amend and/or Correct the Judgments (Fed. R. Civ.P. 52(b), 59(e), 60) [-1377 Case], (III) Its Motion for Judgment as a Matter of Law (Fed. R. Civ. P. 50(b)) [-1378 Case], (IV) Its Motion in the Alternative for a New Trial (Fed. R Civ. P. 59(a)) [-1378 Case], Public Version, *Apple Inc.* v. *Masimo Corporation and Sound United, LLC*, Case No. 1:22-cv-01377-JLH, 33 pages.
Jan. 10, 2025 Declaration of Lee J. Matalon in Support of Apple's Post-Trial Motions, Including Exhibits 76-94, Public Version, *Apple Inc.* v. *Masimo Corporation and Sound United, LLC*, Case No. 1:22-cv-01377-JLH, 147 pages.
Jan. 10, 2025 Letter to the Honorable Jennifer L. Hall from David E. Moore, Public Version, *Apple Inc.* v. *Masimo Corporation and Sound United*, LLC, Case No. 1:22-cv-01377-JLH, 11 pages.
Jan. 10, 2025 Letter to the Honorable Jennifer L. Hall from John C. Phillips, Jr., Redacted—Public Version, *Apple Inc.* v. *Masimo Corporation and Sound United, LLC*, Case No. 1:22-cv-01377-JLH, 90 pages.
Jan. 31, 2025 Apple's Brief Opposing Defendant's Motion for Judgment as a Matter of Law, Public Version, *Apple Inc.* v. *Masimo Corporation and Sound United, LLC*, Case No. 1:22-cv-01377-JLH, 32 pages.
Jan. 31, 2025 Declaration of Kendall M. Loebbaka in Support of Masimo's Answering Brief in Opposition to (I) Apple's Motion for a Permanent Injunction, and (II) Apple's Motion to Amend and/or Correct the Judgment, Including Exhibit A, Redacted-Public Version, *Apple Inc.* v. *Masimo Corporation and Sound United, LLC*, Case No. 1:22-cv-01377-JLH, 18 pages.
Jan. 31, 2025 Masimo's Answering Brief in Opposition to (I) Apple's Motion for a Permanent Injunction, and (II) Apple's Motion to Amend and/or Correct the Judgment, Redacted-Public Version, *Apple Inc.* v. *Masimo Corporation and Sound United, LLC*, Case No. 1:22-cv-01377-JLH, 18 pages.
Jan. 31, 2025 Declaration of Bilal Muhsin, Redacted-Public Version, *Apple Inc.* v. *Masimo Corporation and Sound United, LLC*, Case No. 1:22-cv-01377-JLH, 2 pages.
Sep. 24, 2024 Masimo's Brief in Support of Motion to Supplement the Claim Construction Record, *Apple Inc.* v. *Masimo Corporation and Sound United, LLC*, Case Nos. 1:22-cv-01377-JLH and 1:22-cv-01378-JLH, 8 pages.
Oct. 7, 2024 Memorandum Order, *Apple Inc.* v. *Masimo Corporation and Sound United, LLC*, Case Nos. 1:22-cv-01377-JLH and 1:22-cv-01378-JLH, 16 pages.
Oct. 8, 2024 Apple Inc.'s Opposition to Masimo's Motion to Supplement the Claim Construction Record, *Apple Inc.* v. *Masimo Corporation and Sound United, LLC*, Case Nos. 1:22-cv-01377-JLH and 1:22-cv-01378-JLH, 3 pages.
Oct. 8, 2024 Markman Opinion, *Apple Inc.* v. *Masimo Corporation and Sound United, LLC*, Case Nos. 1:22-CV-01377-JLH and 1:22-cv-01378-JLH, 15 pages.
Oct. 8, 2024 Memorandum Order, *Apple Inc.* v. *Masimo Corporation and Sound United, LLC*, Case Nos. 1:22-cv-01377-JLH and 1:22-cv-01378-JLH, 4 pages.
Oct. 9, 2024 Masimo's Reply Brief in Support of Motion to Supplement the Claim Construction Record, *Apple Inc.* v. *Masimo Corporation and Sound United, LLC*, Case Nos. 1:22-cv-01377-JLH and 1:22-cv-01378-JLH, 6 pages.
Oct. 9, 2024 Memorandum Order, *Apple Inc.* v. *Masimo Corporation and Sound United, LLC*, Case Nos. 1:22-cv-01377-JLH and 1:22-cv-01378-JLH, 7 pages.
Oct. 10, 2024 Markman Opinion and Order, *Apple Inc.* v. *Masimo Corporation and Sound United, LLC*, Case Nos. 1:22-cv-01377-JLH and 1:22-cv-01378-JLH, 11 pages.

(56) References Cited

OTHER PUBLICATIONS

Oct. 10, 2024 Memorandum Order, *Apple Inc. v. Masimo Corporation and Sound United, LLC*, Case Nos. 1:22-cv-01377-JLH and 1:22-cv-01378-JLH, 4 pages.

Oct. 25, 2024 Final Jury Instructions, *Apple Inc. v. Masimo Corporation and Sound United, LLC*, Case Nos. 1:22-cv-01377-JLH and 1:22-cv-01378-JLH, 54 pages.

Oct. 25, 2024 Verdict Form, *Apple Inc. v. Masimo Corporation and Sound United, LLC*, Case Nos. 1:22-cv-01377-JLH and 1:22-cv-01378-JLH, 7 pages.

Nov. 13, 2024 Judgement Following Jury Verdict, *Apple Inc. v. Masimo Corporation and Sound United, LLC, Masimo Corporation and Sound United. LLC. v. Apple Inc.*, Case No. 1:22-cv-01378-JLH, 4 pages.

Dec. 2, 2024 Joint Notice Regarding Judgements Following Jury Verdict, Including Exhibits 1 & 2, *Apple Inc. v. Masimo Corporation and Sound United, LLC, Masimo Corporation and Sound United. LLC. v. Apple Inc.*, Case No. 1:22-cv-01378-JLH, 12 pages.

Dec. 11, 2024 Plaintiff and Counterclaim-Defendant Apple Inc.'s Motion for Judgment as a Matter of Law or, in the Alternative, for a New Trial, *Apple Inc. v. Masimo Corporation and Sound United, LLC, Masimo Corporation and Sound United. LLC. v. Apple Inc.*, Case No. 1:22-cv-01378-JLH, 2 pages.

Dec. 11, 2024 Corrected Judgement Following Jury Verdict, *Apple Inc. v. Masimo Corporation and Sound United, LLC, Masimo Corporation and Sound United. LLC. v. Apple Inc.*, Case No. 1:22-cv-01378-JLH, 4 pages.

Jan. 31, 2025 Declaration of Kendall M. Loebbaka in Support of Masimo's Answering Brief in Opposition to Apple Inc.'s Motion for Judgment as a Matter of Law or, in the Alternative, for a New Trial, Including Exhibit B & C, Redacted-Public Version, *Apple Inc. v. Masimo Corporation and Sound United, LLC*, Case No. 1:22-cv-01378-JLH, 20 pages.

Jan. 31, 2025 Masimo's Answering Brief in Opposition to (III) Apple's Motion for Judgment as a Matter of Law and (IV) Apple's Motion in the Alternative for a New Trial, Redacted-Public Version, *Apple Inc. v. Masimo Corporation and Sound United, LLC*, Case No. 1:22-cv-01378-JLH, 26 pages.

Letter from Jennifer Shih to Masimo Corporation re 510(k) No. K240229, U.S. Food & Drug Administration, dated Aug. 8, 2024 in 13 pages.

Feb. 19, 2025 Civil Minutes—General, Order Regarding Apple's Motion for Review of and Objections to Report and Recommendation Regarding Masimo's Infringement Contentions, Redacted, *Masimo Corporation and Cercacor Laboratories, Inc. v. Apple Inc.*, Case No. 8:20-cv-00048, 6 pages.

Jun. 3, 2024 Corrected Non-Confidential Brief for Appellant Apple Inc., vol. 1, Federal Circuit appeal of ITC Inv. No 337-TA-1276, p. 576. [Uploaded in 11 parts].

Jun. 3, 2024 Corrected Non-Confidential Brief for Appellant Apple Inc., vol. 2, Federal Circuit appeal of ITC Inv. No. 337-TA-1276, pp. 338. [Uploaded in 4 parts].

Jun. 28, 2024 Nonconfidential Brief of Appellee International Trade Commission, Federal Circuit appeal of ITC Inv. No. 337-TA-1276, pp. 84.

Jun. 28, 2024 Nonconfidential Brief of Intervenors Masimo Corporation and Cercacor Laboratories, Inc., Federal Circuit appeal of ITC Inv. No. 337-TA-1276, pp. 87.

Jul. 10, 2024 Corrected Nonconfidential Brief of Intervenors Masimo Corporation and Cercacor Laboratories, Inc., Federal Circuit appeal of ITC Inv. No. 337-TA-1276, pp. 87.

Jul. 19, 2024 Non-Confidential Reply Brief for Appellant Apple Inc., Federal Circuit appeal of ITC Inv. No. 337-TA-1276, pp. 42.

Aug. 7, 2024 Non-Confidential Joint Appendix vols. 1-9, Federal Circuit appeal of ITC Inv. No. 337-TA-1276, pp. 5349. [Uploaded in 15 parts].

Letter to Chief Terrill from Secretary to the Commission, Lisa R. Barton Re: Certain Light-Based Physiological Measurement Devices and Components Thereof, Investigation No. 337-TA-1276, Dated Oct. 2, 2024, 3 pages.

\* cited by examiner

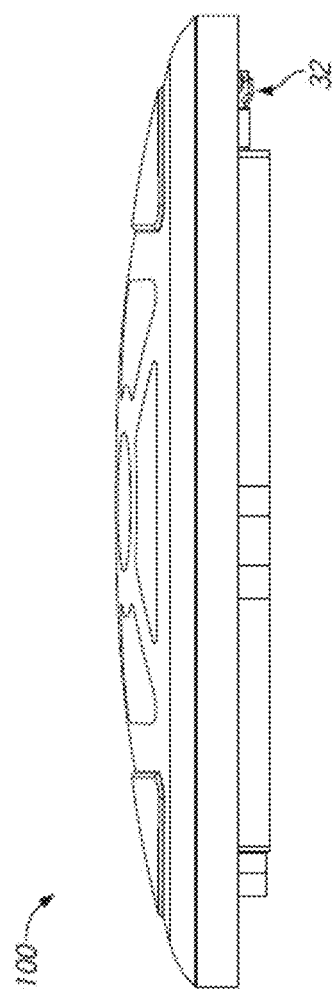

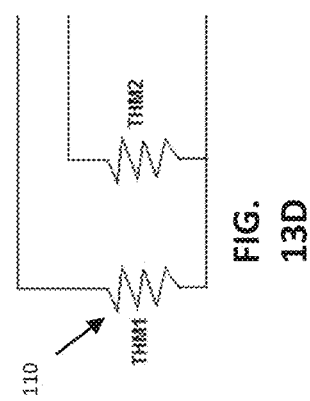
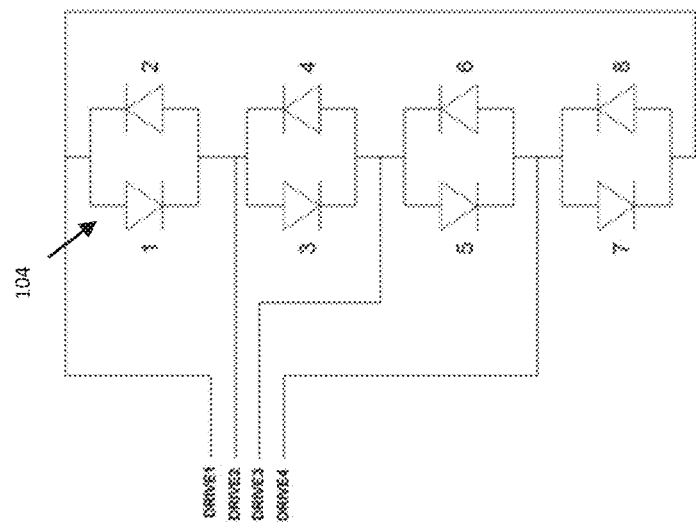
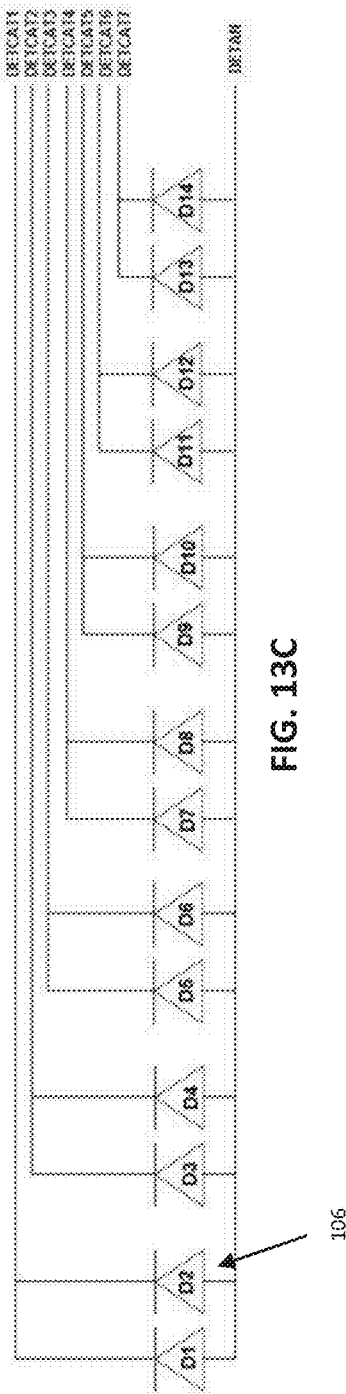

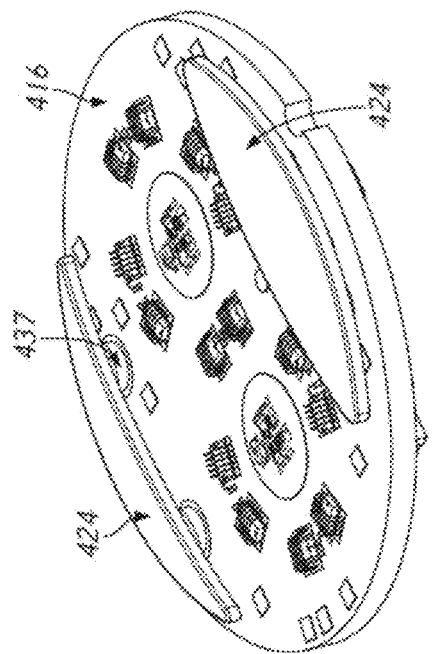
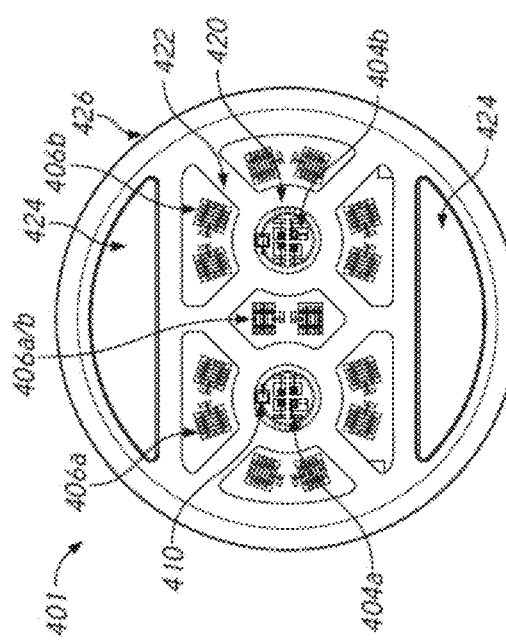
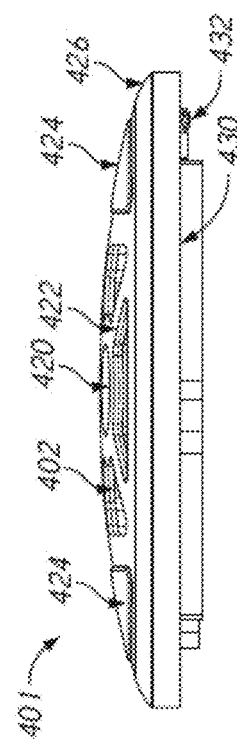
FIG. 16E
FIG. 16F
FIG. 16G

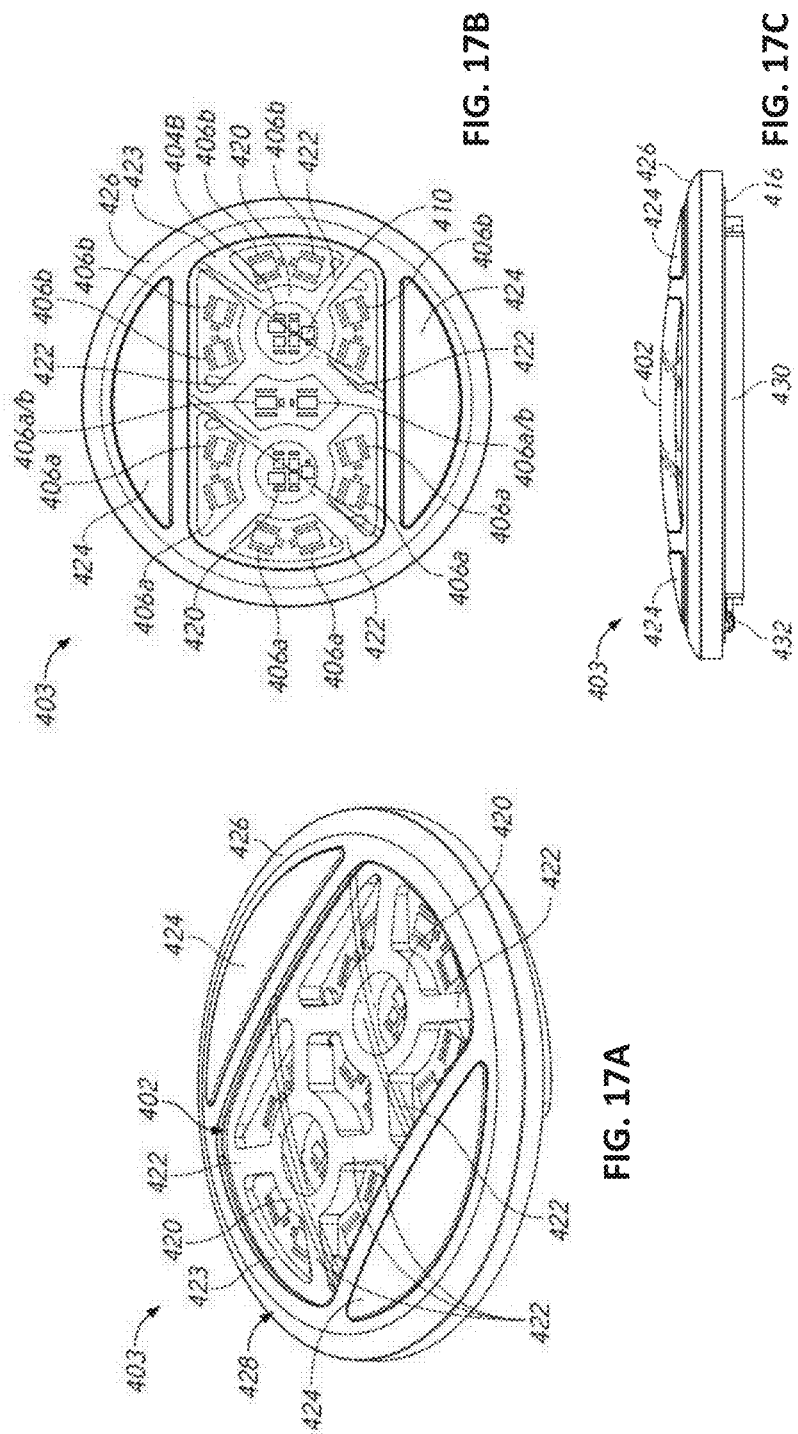

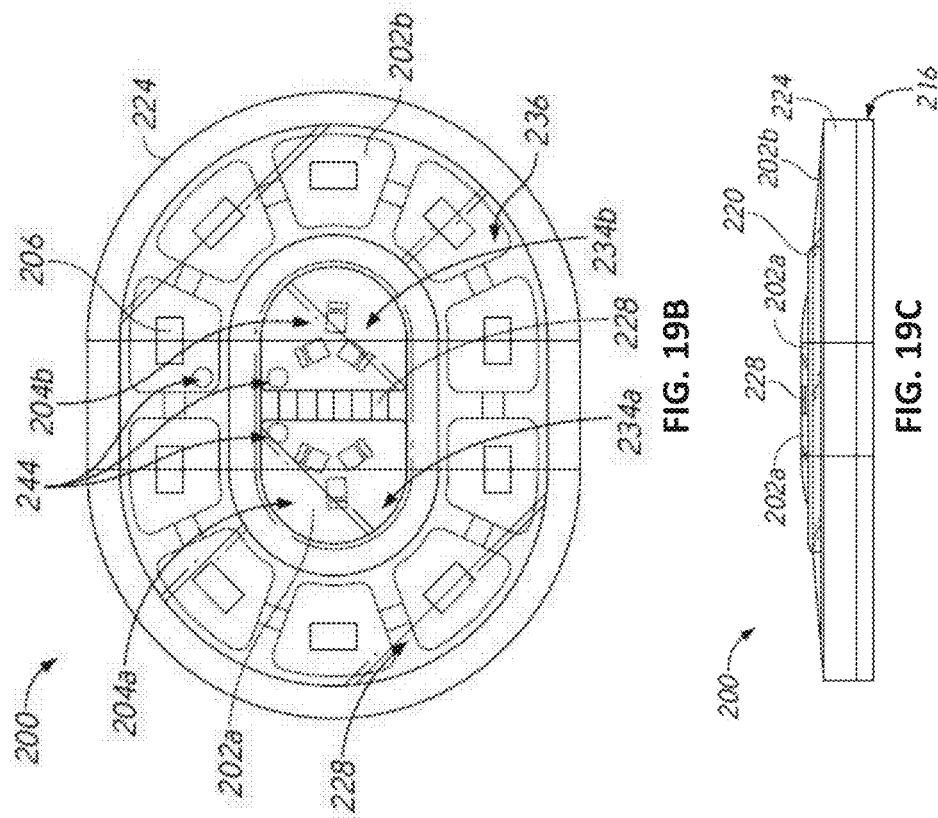
FIG. 19B
FIG. 19C
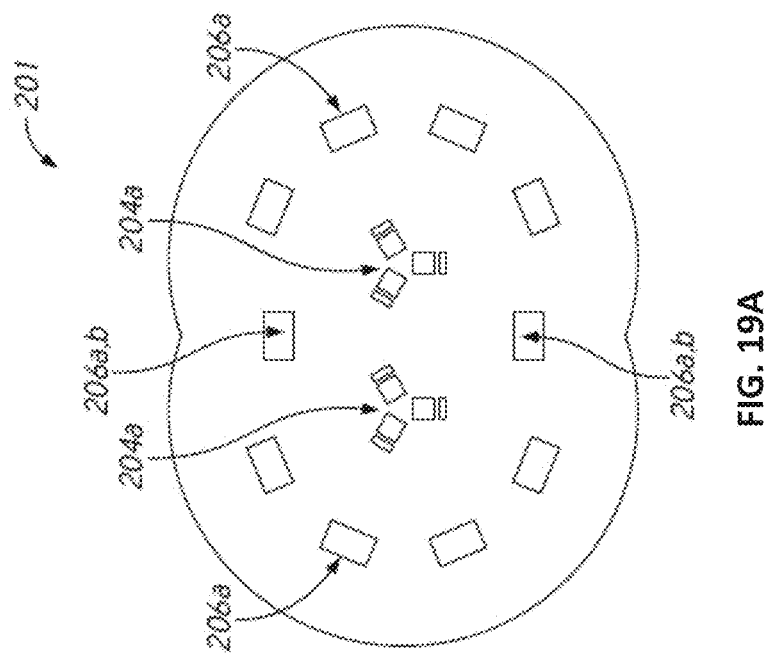
FIG. 19A

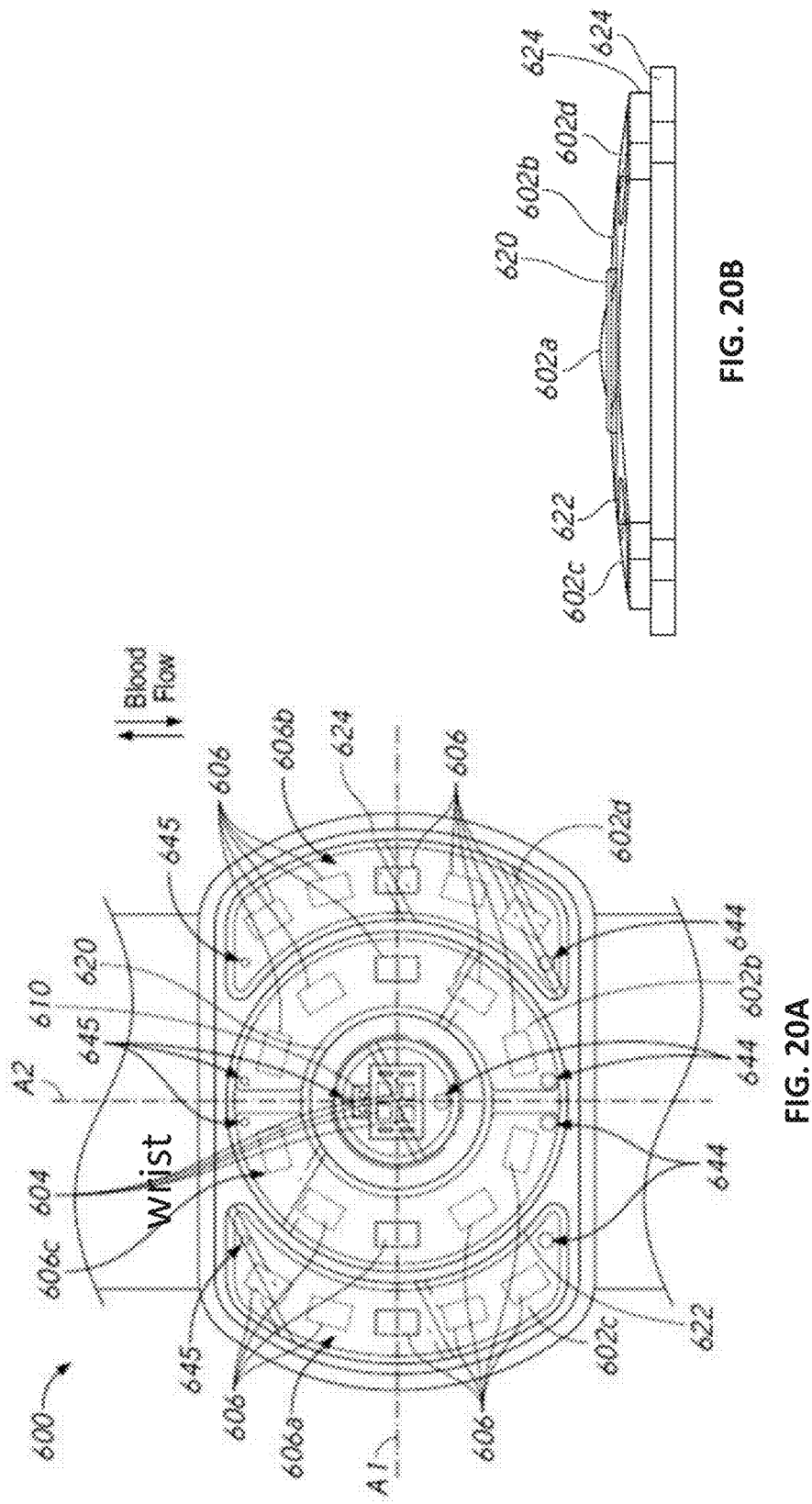

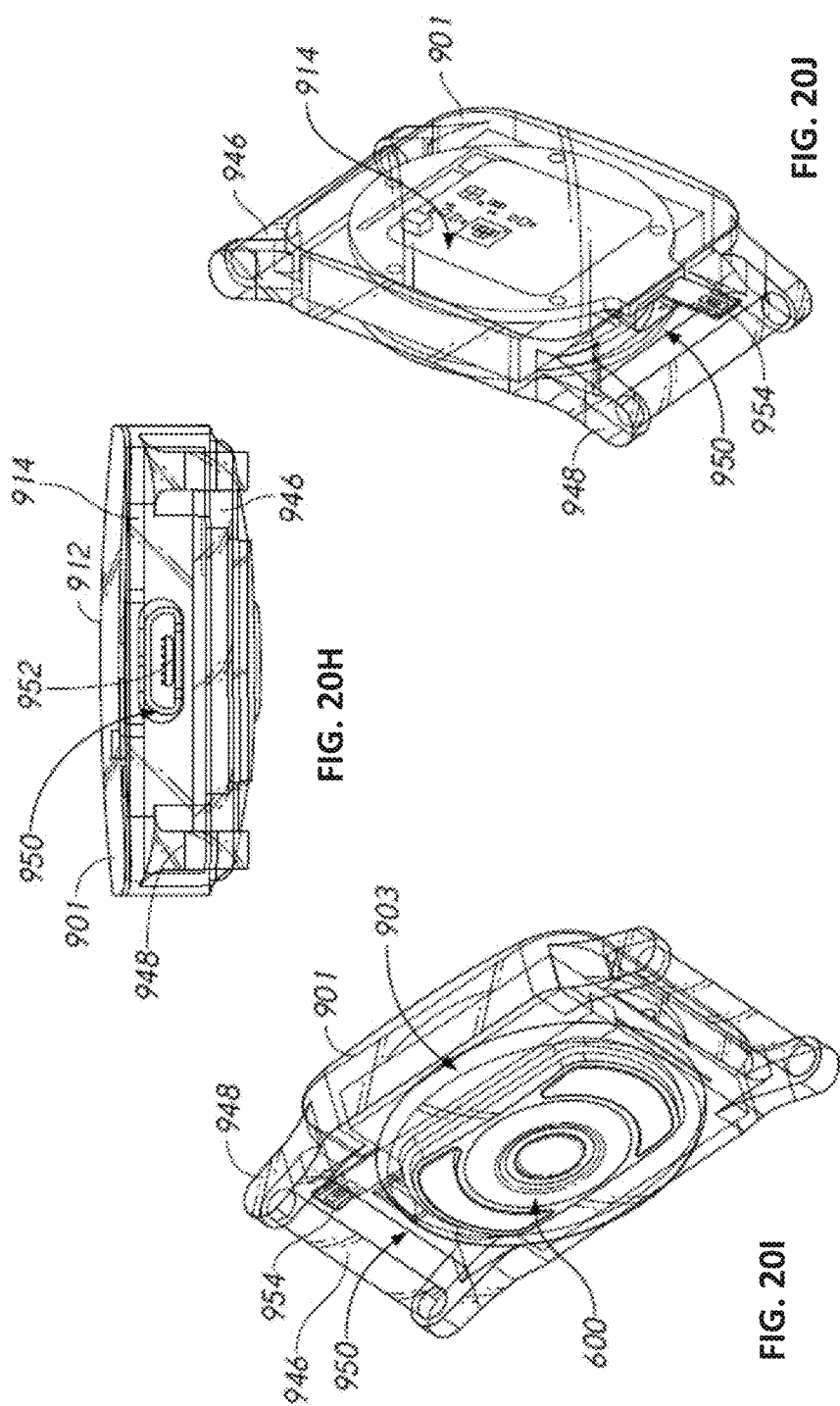

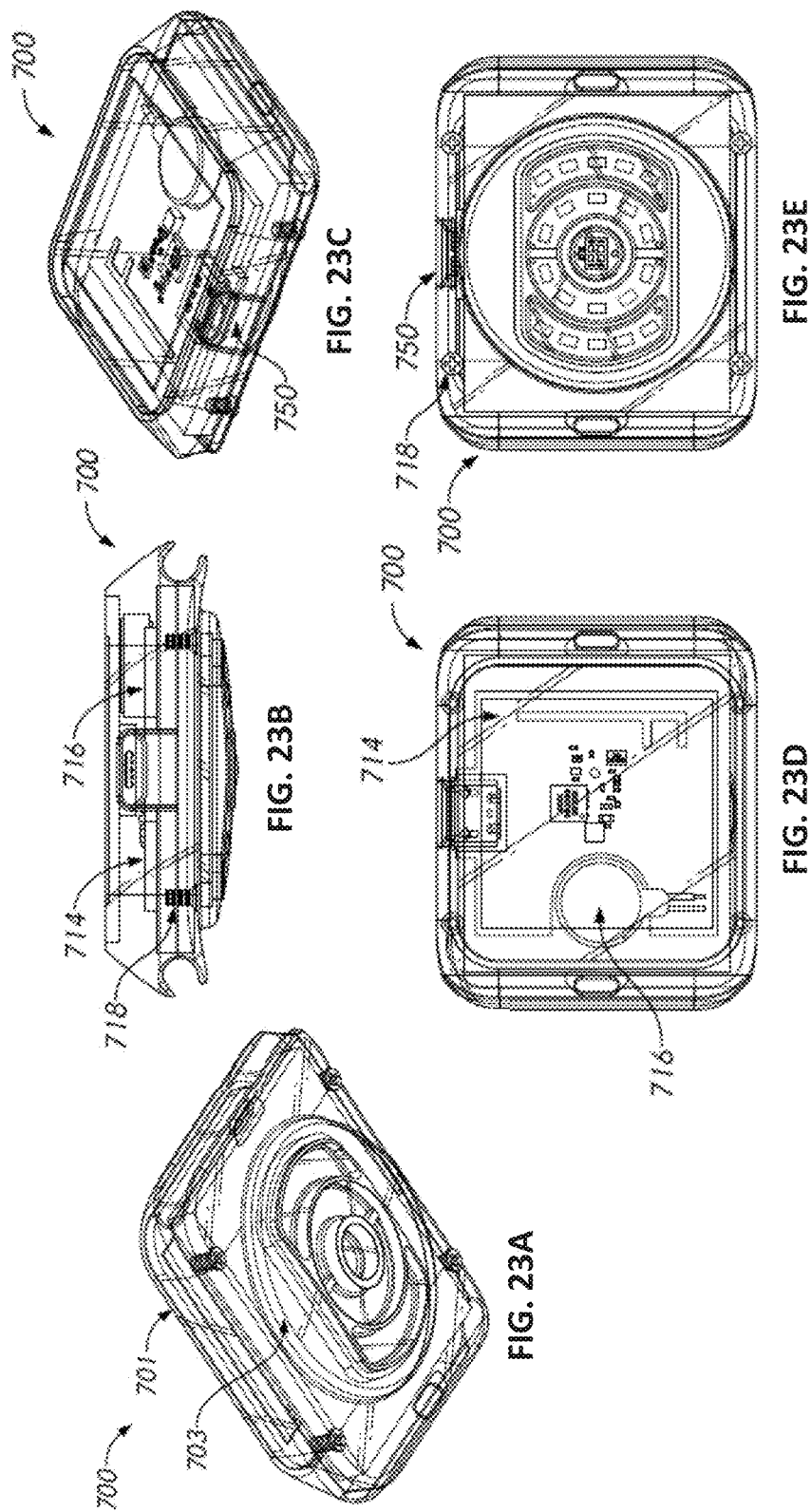

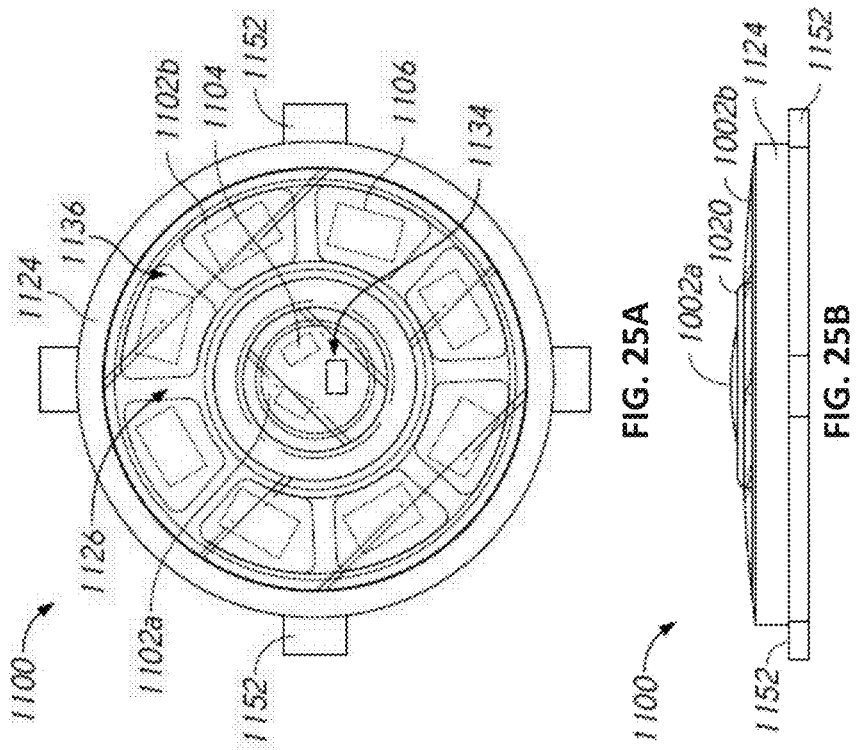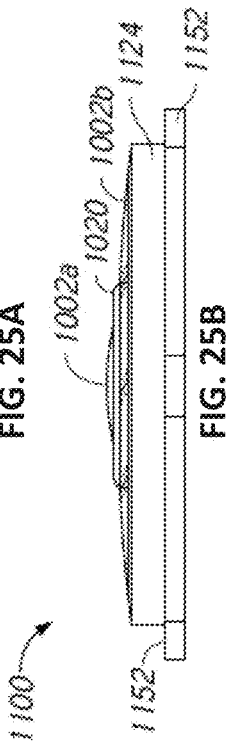
FIG. 25A  FIG. 25B
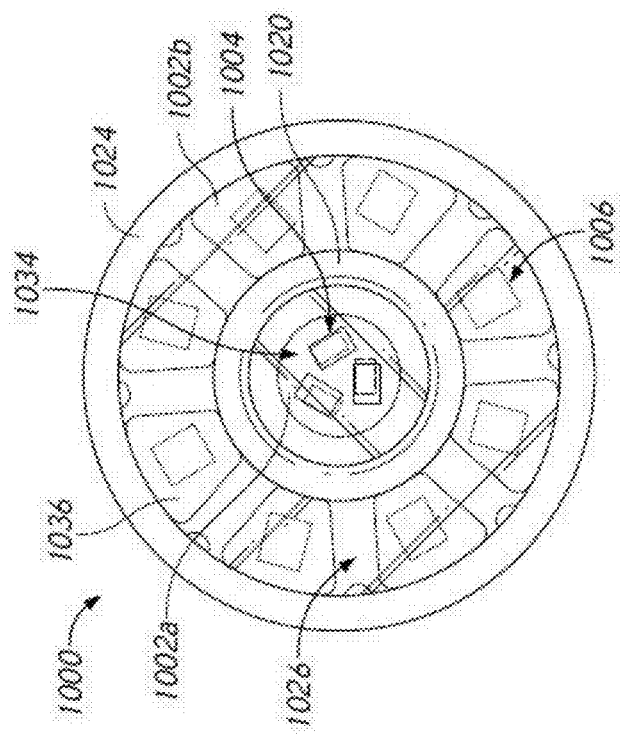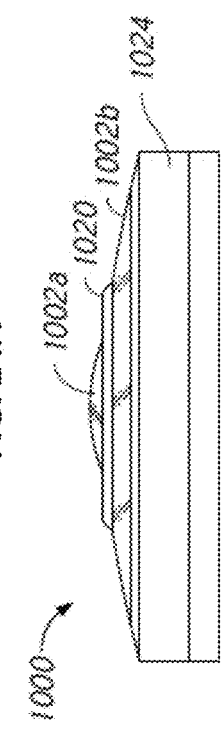
FIG. 24A  FIG. 24B

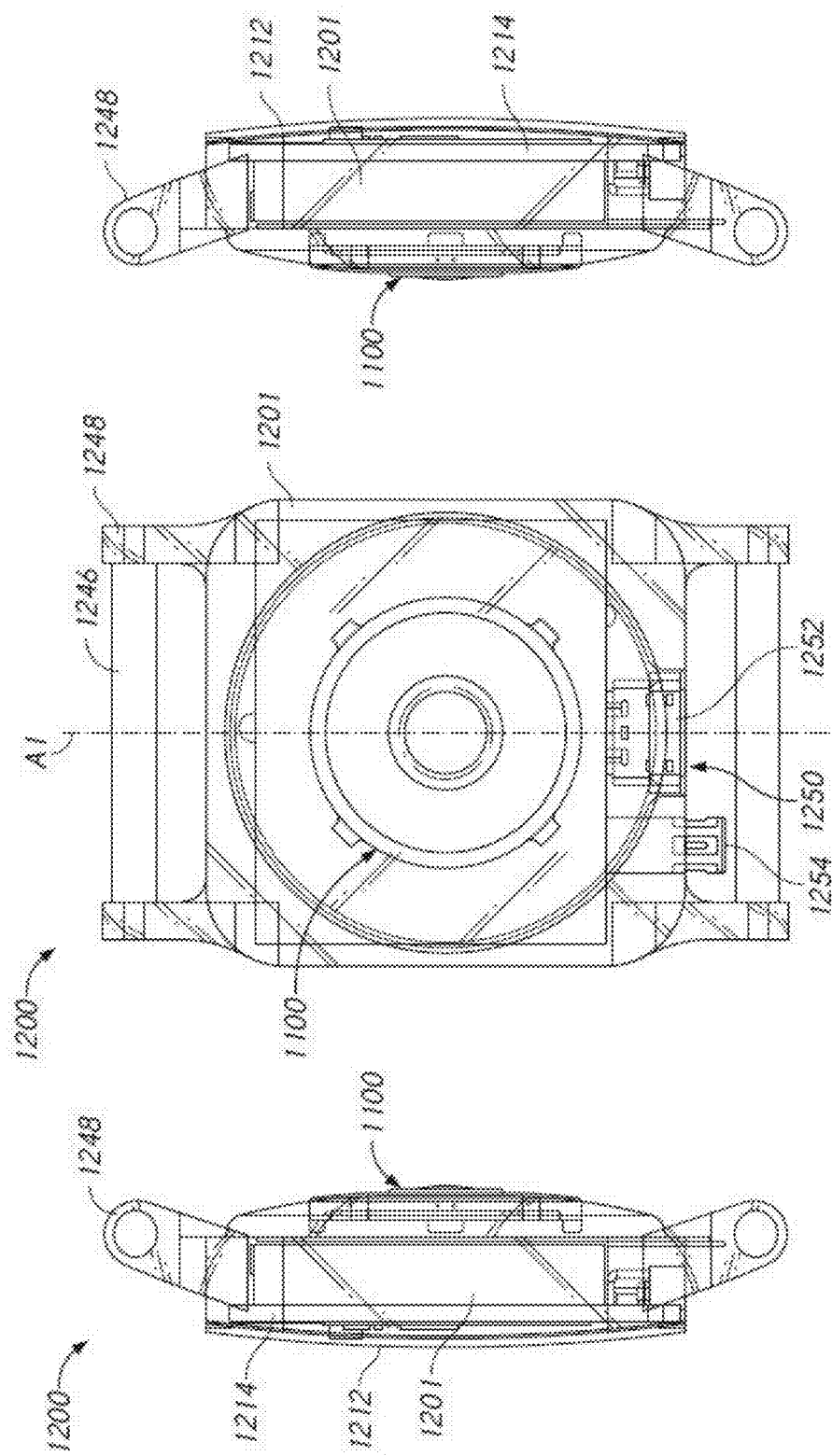

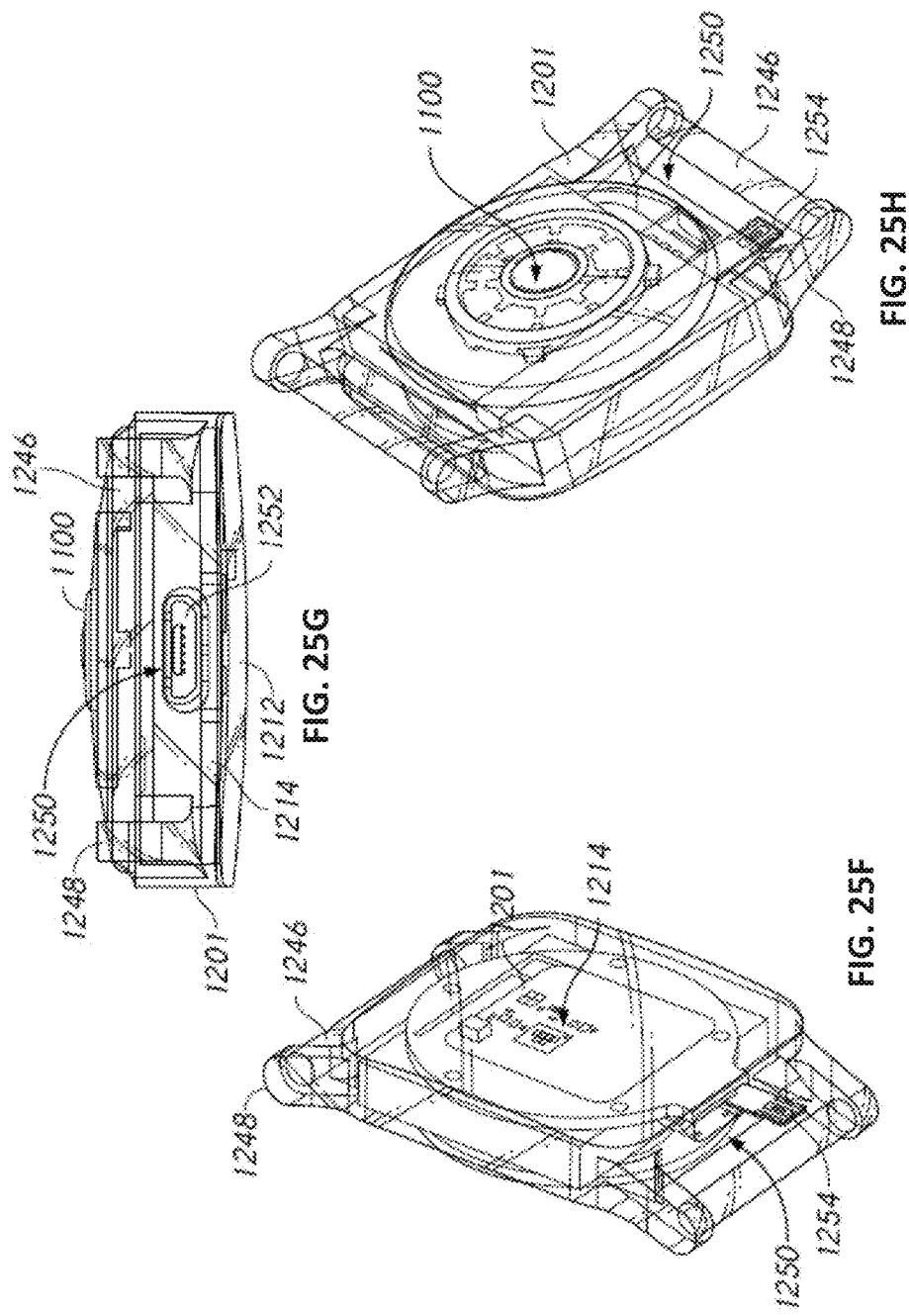

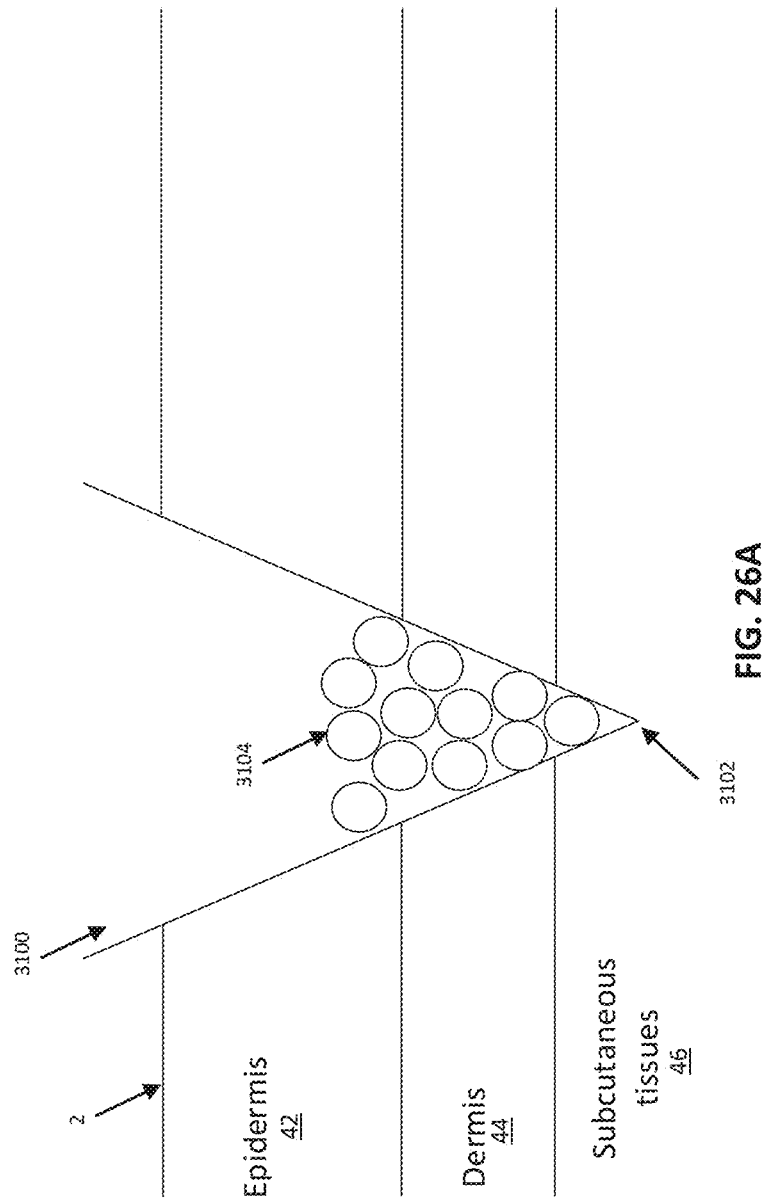

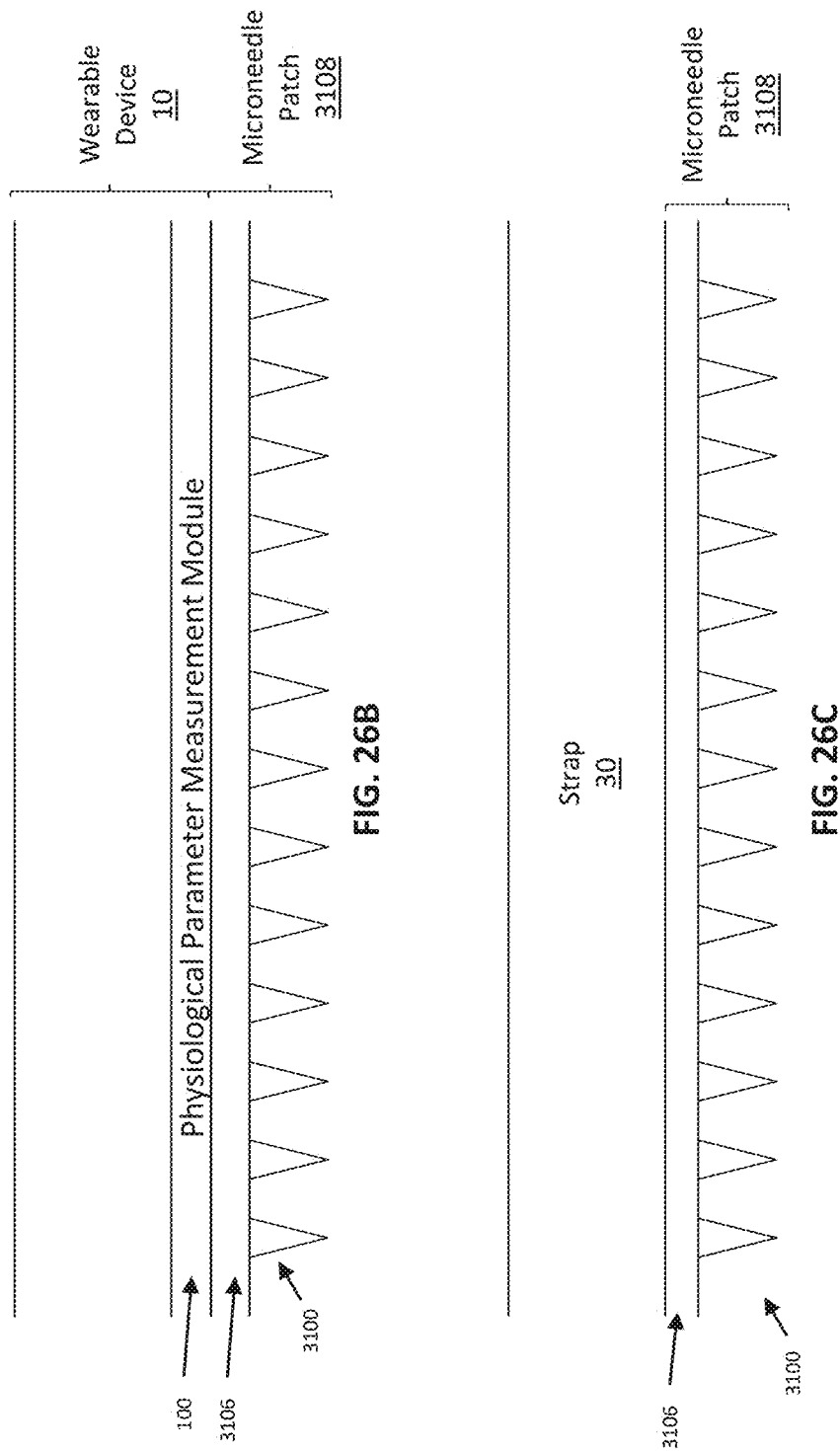

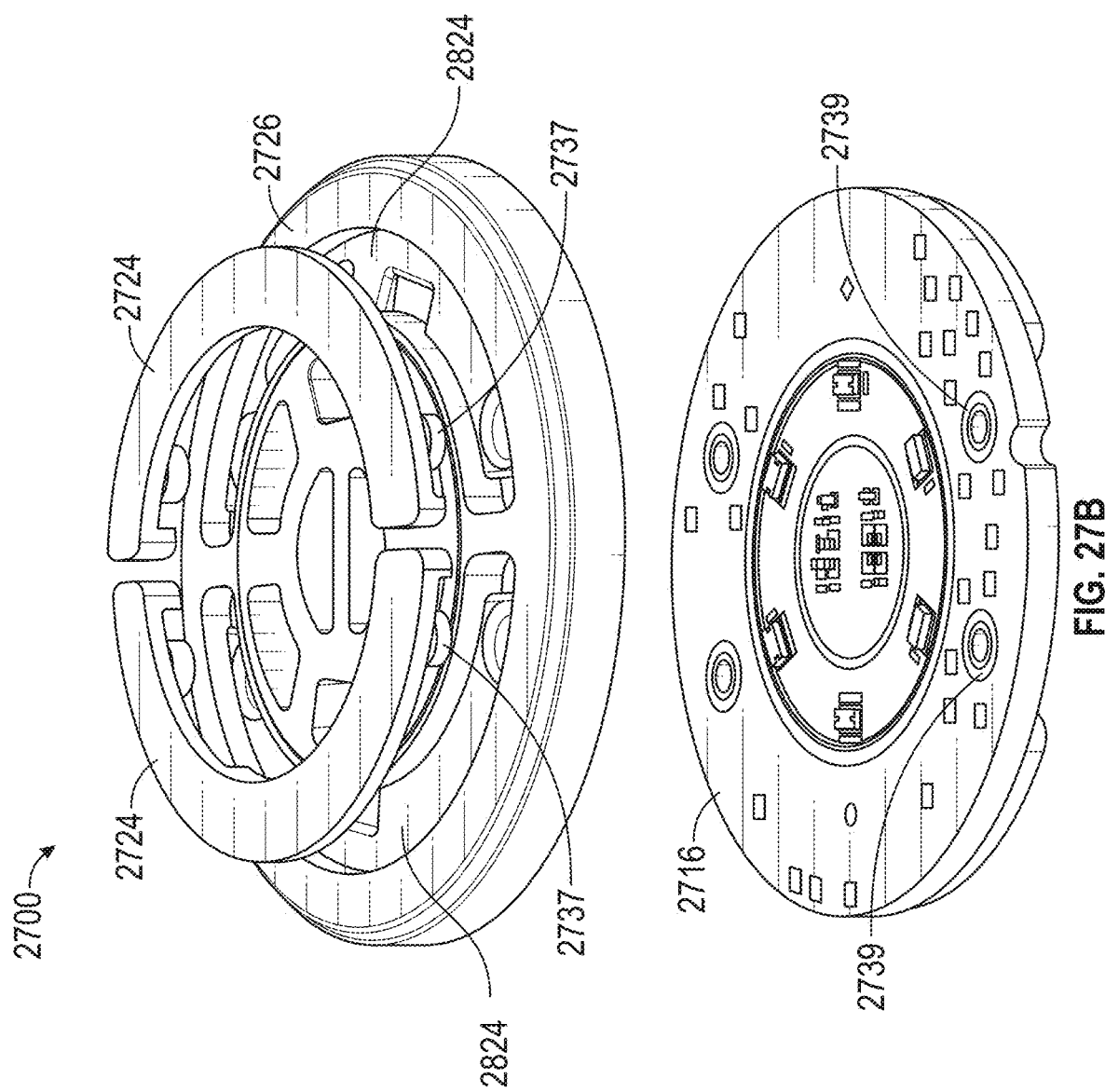

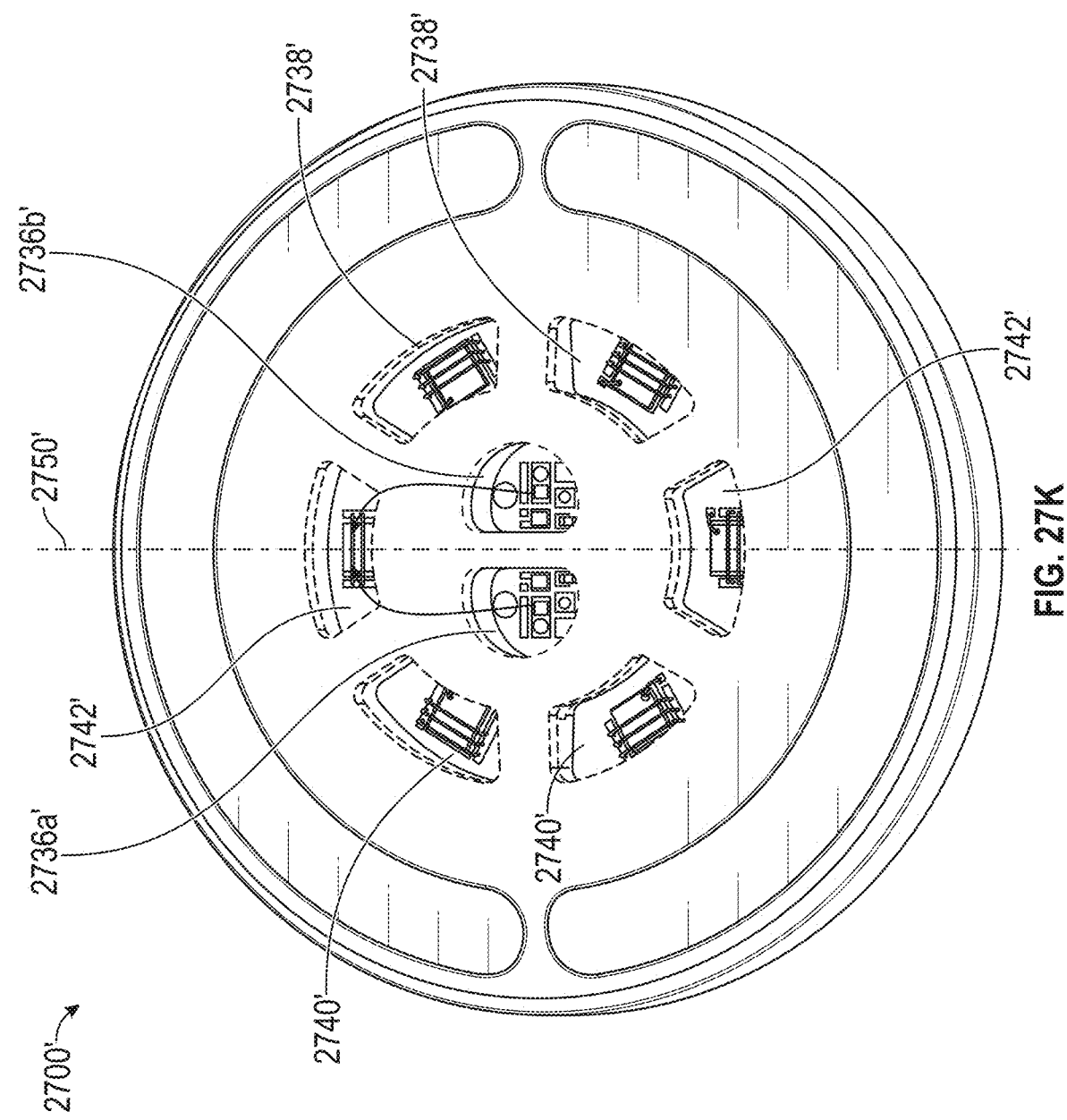

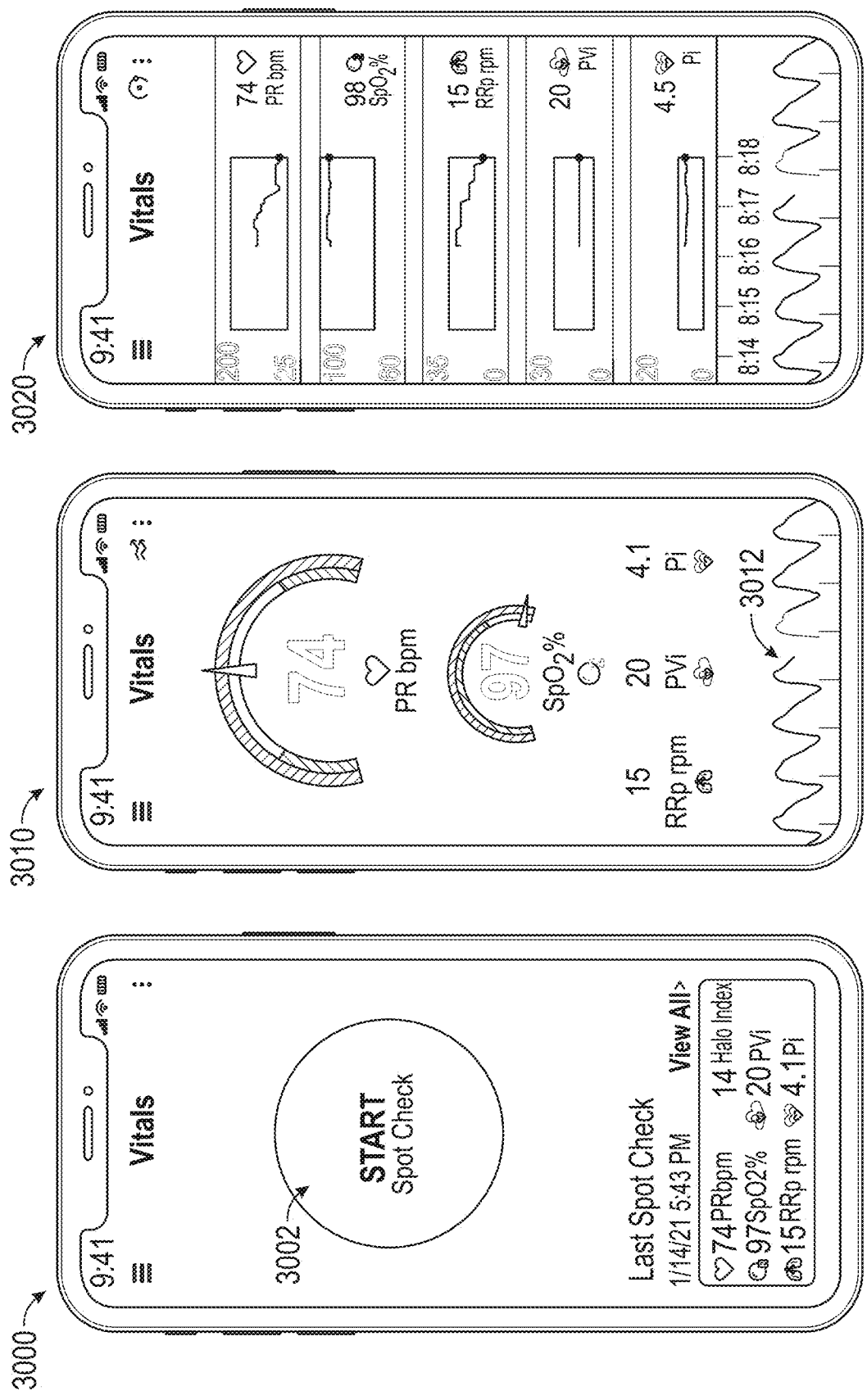

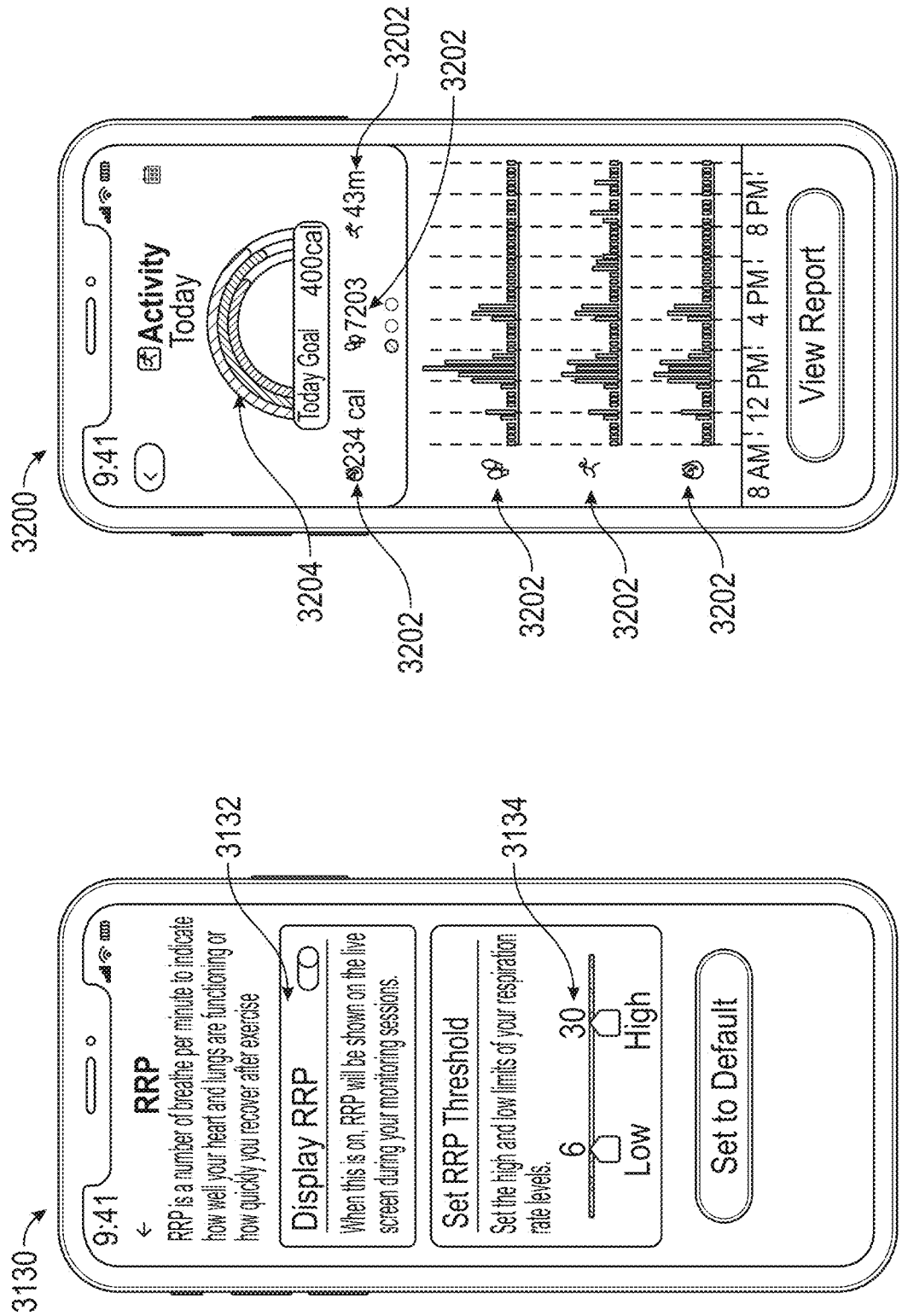

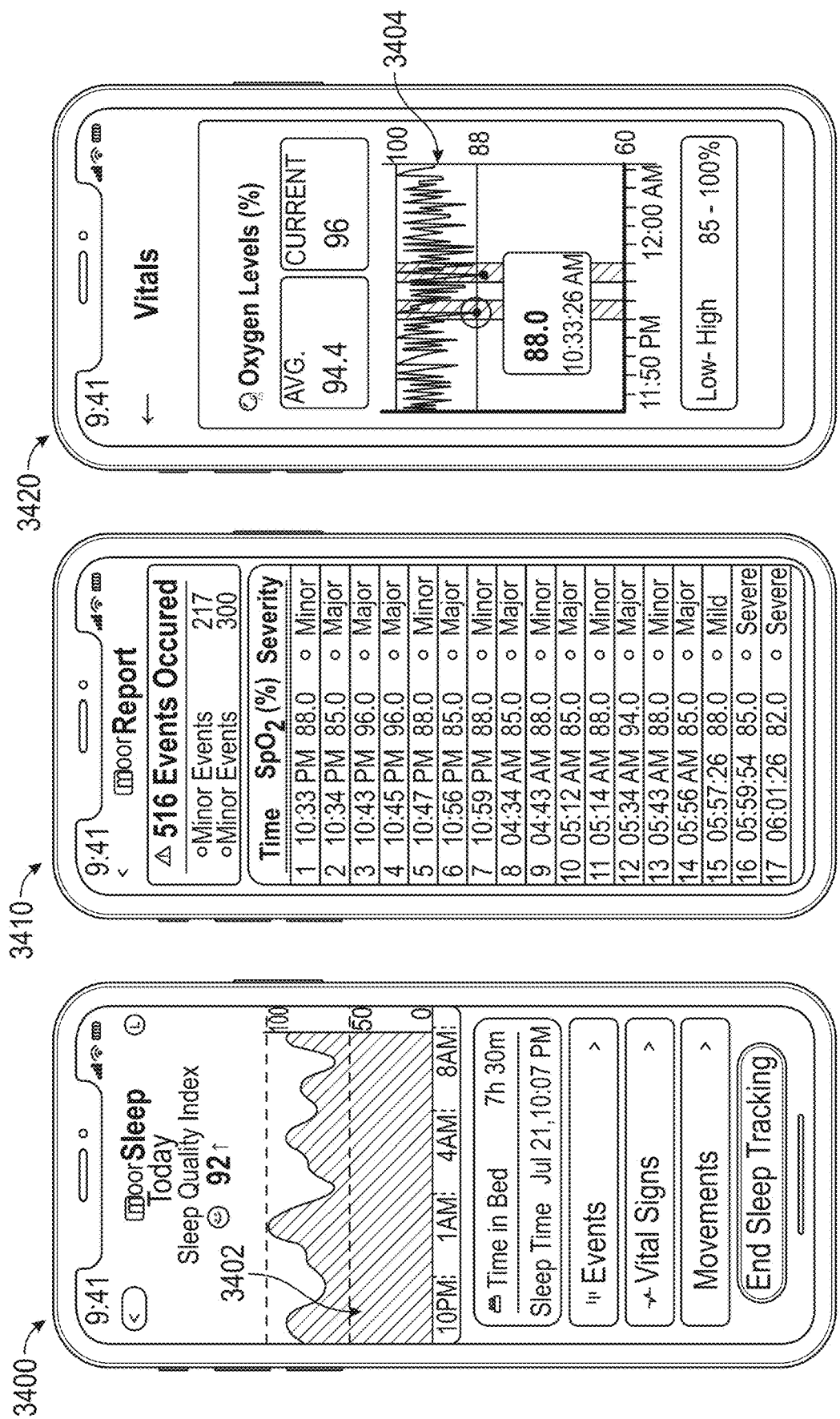

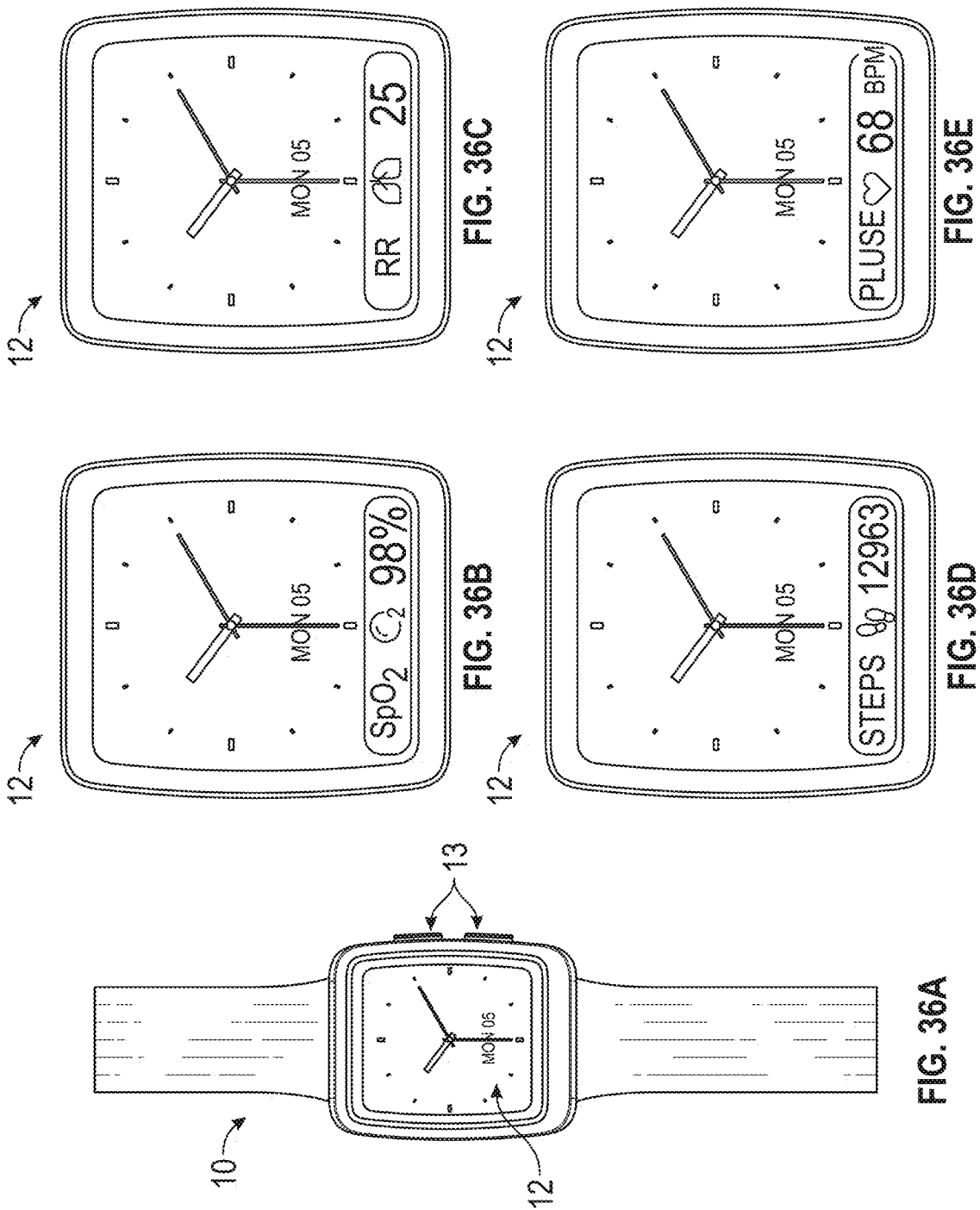

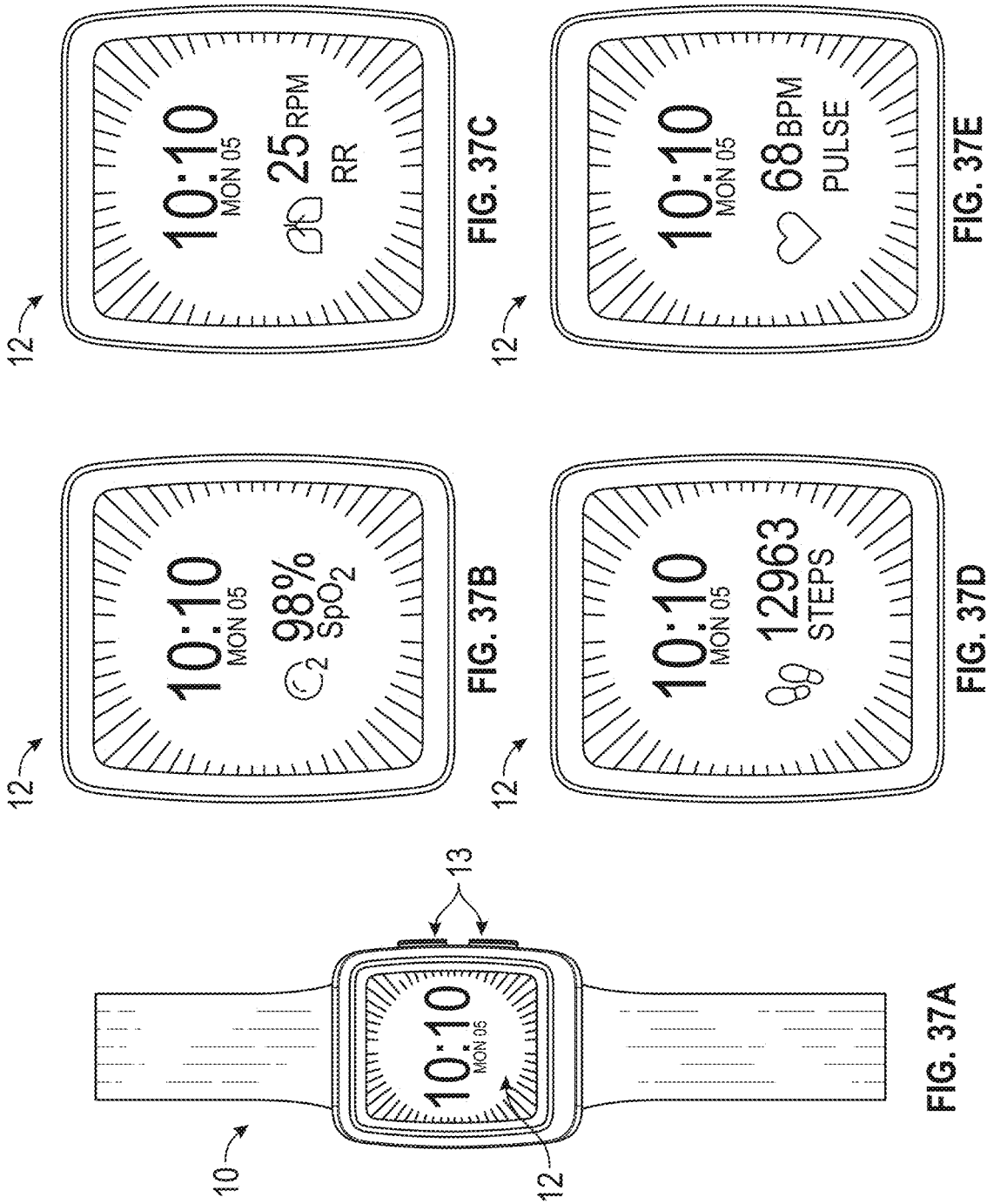

WEARABLE DEVICE WITH PHYSIOLOGICAL PARAMETERS MONITORING

CROSS-REFERENCE TO RELATED APPLICATIONS

This application claims the benefit of U.S. Provisional Application No. 63/252,893, filed Oct. 6, 2021, and U.S. Provisional Application No. 63/230,239, filed Aug. 6, 2021, and U.S. Provisional Application No. 63/221,385, filed Jul. 13, 2021. The entire disclosure of each of the above items is hereby made part of this specification as if set forth fully herein and incorporated by reference for all purposes, for all that it contains.

FIELD

The present disclosure relates to a wearable health monitoring device incorporating a plurality of sensors worn on the wrist.

BACKGROUND

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\varepsilon_{i,\lambda}$, at a particular wavelength $\lambda$.

In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \sum_{i=1}^{n} \varepsilon_{i,\lambda} \cdot c_i \quad (2)$$

where $\mu_{a,\lambda}$ is the bulk absorption coefficient and represents the probability of absorption per unit length. The minimum number of discrete wavelengths that are required to solve equations 1 and 2 is the number of significant absorbers that are present in the solution.

A practical application of this technique is pulse oximetry or plethysmography, which utilizes a noninvasive sensor to measure oxygen saturation and pulse rate, among other physiological parameters. Pulse oximetry or plethysmography relies on a sensor attached externally to the patient (typically for example, at the fingertip, foot, ear, forehead, or other measurement sites) to output signals indicative of various physiological parameters, such as a patient's blood constituents and/or analytes, including for example a percent value for arterial oxygen saturation, among other physiological parameters. The sensor has at least one emitter that transmits optical radiation of one or more wavelengths into a tissue site and at least one detector that responds to the intensity of the optical radiation (which can be reflected from or transmitted through the tissue site) after absorption by pulsatile arterial blood flowing within the tissue site. Based upon this response, a processor determines the relative concentrations of oxygenated hemoglobin ($HbO_2$) and deoxygenated hemoglobin (Hb) in the blood so as to derive oxygen saturation, which can provide early detection of potentially hazardous decreases in a patient's oxygen supply, and other physiological parameters.

A patient monitoring device can include a plethysmograph sensor. The plethysmograph sensor can calculate oxygen saturation ($SpO_2$), pulse rate, a plethysmograph waveform, perfusion index (PI), pleth variability index (PVI), methemoglobin (MetHb), carboxyhemoglobin (CoHb), total hemoglobin (tHb), respiration rate, glucose, and/or otherwise. The parameters measured by the plethysmograph sensor can display on one or more monitors the foregoing parameters individually, in groups, in trends, as combinations, or as an overall wellness or other index.

A pulse oximetry sensor is described in U.S. Pat. No. 6,088,607 entitled Low Noise Optical Probe; pulse oximetry signal processing is described in U.S. Pat. Nos. 6,650,917 and 6,699,194 entitled Signal Processing Apparatus and Signal Processing Apparatus and Method, respectively; a pulse oximeter monitor is described in U.S. Pat. No. 6,584,336 entitled Universal/Upgrading Pulse Oximeter; all of which are assigned to Masimo Corporation, Irvine, CA, and each is incorporated by reference herein in its entirety.

SUMMARY

A drawback to current pulse oximetry sensors is a need to be located near significant capillary beds on the body, including fingers, ears, toes, nose and forehead. Such locations are often inconvenient for monitoring a user during normal activities, outside of a healthcare facility. Further, although measuring through motion oxygen saturation technology exists, it is directed to the healthcare facility context and is not reliable for normal routines, which include sporting activities or other significant daily movement. Accordingly, the present disclosure provides a sensor which allows for measuring pulse oximetry at sparse capillary bed locations, including the wrist. The present disclosure also provides algorithms for measuring pulse oximetry though higher exertion everyday motion.

A physiological monitoring sensor or module, also referred to herein as a physiological parameter measurement sensor or module, or a module, can be integrated into a wearable device that is secured to a wrist of a person (the "wearer"), such as a wristwatch or watch. The sensor on the watch can be used to monitor the wearer's physiological parameters. The sensor can detect pulse rate, oxygen saturation, hydration status, respiratory rate, and/or other parameters, such as the parameters disclosed herein, of the wearer. The sensor can include a convex protrusion to improve pressure and contact, and therefore optical coupling, between the wearer's skin and the physiological parameter measurement sensor. The curvature of the sensor can be designed to balance the desired pressure by the watch on the wearer's wrist and the wearer's comfort. The sensor can include a light barrier between emitters and detectors of the module and/or light diffusing materials surrounding the emitters and the detectors, among other features, to improve signal strength and reduce noise. The sensor or the watch can include a connection port to receive another sensor, which can be configured to be coupled to the wearer at a different measurement site of the wearer's body than the wrist. The sensor can be configured to continuously, at certain time intervals, and/or upon the wearer's request, measure one or more of the physiological parameters. For example, the sensor can be configured to continuously measure the wearer's oxygen saturation and/or pulse rate when the watch is worn on the wearer's wrist.

An example optical physiological sensor of the present disclosure can be integrated into a watch configured to monitor health of a wearer. The optical physiological sensor can be configured to face tissue of the wearer when the watch is worn by the wearer. The optical physiological sensor can be configured to measure physiological parameters of the wearer using information from the optical physiological sensor. The optical physiological sensor can comprise: a printed circuit board (PCB); a first emitter group comprising a first plurality of light emitting diodes (LEDs) at a first location on the PCB; a second emitter group comprising a second plurality of LEDs at a second location on the PCB different from the first location, wherein the second emitter group comprises the same number and type of LEDs as the first emitter group; one or more first light blocks separating the first emitter group from the second emitter group; light diffusing material configured to diffuse light emitted by each of the first and second pluralities of LEDs; a plurality of detectors including six or more photodiodes on the PCB; one or more second light blocks separating each of the detectors of the plurality of detectors from (i) each of the other detectors of the plurality of detectors and from (ii) the first and second emitter groups; and a convex surface configured to be positioned between (i) the first and second emitter groups and the six or more photodiodes and (ii) the tissue of the wearer, the convex surface comprising one or more surface materials.

In some configurations, the first plurality of LEDs may be configured to emit light of at least five wavelengths and the second plurality of LEDs may be configured to emit light of at least five wavelengths.

In some configurations, the five wavelengths emitted by the first plurality of LEDs may be the same wavelengths as the five wavelengths emitted by the second plurality of LEDs.

In some configurations, the first plurality of LEDs may comprise LEDs of a same type as LEDs of the second plurality of LEDs.

In some configurations, the LEDs of the first plurality of LEDs may be arranged on the PCB to mirror, across a centerline of the sensor, an arrangement of the LEDs of the second plurality of LEDs on the PCB.

In some configurations, the first plurality of LEDs may comprise: a first LED configured to emit light of a first wavelength, a second LED configured to emit light of a second wavelength, a third LED configured to emit light of a third wavelength, a fourth LED configured to emit light of a fourth wavelength, and a fifth LED configured to emit light of a fifth wavelength, and the second plurality of LEDs may comprise: a sixth LED configured to emit light of the first wavelength, a seventh LED configured to emit light of the second wavelength, an eighth LED configured to emit light of the third wavelength, a ninth LED configured to emit light of the fourth wavelength, and a tenth LED configured to emit light of the fifth wavelength.

In some configurations, the first LED may be located on the PCB at a location that mirrors, across a centerline of the sensor, a location of the sixth LED on the PCB; the second LED may be located on the PCB at a location that mirrors, across a centerline of the sensor, a location of the seventh LED on the PCB; the third LED may be located on the PCB at a location that mirrors, across a centerline of the sensor, a location of the eighth LED on the PCB; the fourth LED may be located on the PCB at a location that mirrors, across a centerline of the sensor, a location of the ninth LED on the PCB; the fifth LED may be located on the PCB at a location that mirrors, across a centerline of the sensor, a location of the tenth LED on the PCB; and the centerline of the sensor may bisect at least one of the plurality of detectors.

In some configurations, the centerline of the sensor may bisect two of the plurality of detectors, and each of said two detectors may be configured to generate, responsive to detecting light emitted from the first and second plurality of emitters, one or more signals for normalizing a physiological parameter measurement of the sensor.

In some configurations, the first and sixth LEDs may each be located a same distance from at least one of the plurality of detectors; the second and seventh LEDs may each be located a same distance from at least one of the plurality of detectors; the third and eighth LEDs may each be located a same distance from at least one of the plurality of detectors; the fourth and ninth LEDs may each be located a same distance from at least one of the plurality of detectors; and the fifth and tenth LEDs may each be located a same distance from at least one of the plurality of detectors.

In some configurations, the plurality of detectors may comprise: a first detector group comprising at least two detectors; and a second detector group comprising at least two detectors, and the first emitter group may be proximal to the first detector group and distal to the second detector group, and the second emitter group may be proximal to the second detector group and distal to the first detector group.

In some configurations, the first and second emitter groups may be located at a central location of the PCB of the sensor.

In some configurations, the plurality of detectors may extend around a circumference of the PCB of the sensor.

An example optical physiological sensor of the present disclosure can be integrated into a watch configured to monitor health of a wearer. The optical physiological sensor can be configured to face tissue of the wearer when the watch is worn by the wearer. The optical physiological sensor can be configured to measure physiological parameters of the wearer using information from the optical physiological sensor. The optical physiological sensor can comprise: a printed circuit board (PCB); a first emitter group comprising a first plurality of light emitting diodes (LEDs) at a first location on the PCB; a second emitter group comprising a second plurality of LEDs at a second location on the PCB different from the first location, wherein the second emitter group comprises the same number and type of LEDs as the first emitter group; one or more first light blocks separating the first emitter group from the second emitter group; light diffusing material configured to diffuse light emitted by each of the first and second pluralities of LEDs; a plurality of detectors including six or more photodiodes on the PCB; one or more second light blocks separating each of the detectors of the plurality of detectors from each of the other detectors of the plurality of detectors; and a convex surface configured to be positioned between (i) the first and second emitter groups and the six or more photodiodes and (ii) the tissue of the wearer, the convex surface comprising one or more surface materials.

In some configurations, the first emitter group can define a first group of emitters, each emitter of the first group of emitters being located on the PCB less than 1.0 mm from each of the other emitters of the first group of emitters, and wherein the second emitter group can define a second group of emitters, each emitter of the second group of emitters being located on the PCB less than 1.0 mm from each of the other emitters of the second group of emitters.

In some configurations, the plurality of detectors can comprise: a first detector group which can comprise at least two detectors, wherein each detector of the at least two detectors can be proximal to the first emitter group; a second detector group which can comprise at least two detectors, wherein each detector of the at least two detectors can be distal to the first emitter group.

In some configurations, at least two of the plurality of detectors can each individually comprise an intermediate detector for the first emitter group and the second emitter group.

In some configurations, the first and second emitter groups can be located at a central location of the PCB of the sensor.

In some configurations, the plurality of detectors can extend around a circumference of the PCB of the sensor.

In some configurations, the PCB can comprise a conductive liquid adhesive.

In some configurations, the PCB can comprise a reflective surface.

In some configurations, the first plurality of LEDs can be configured to emit light of at least four wavelengths and wherein the second plurality of LEDs can be configured to emit light of at least four wavelengths.

In some configurations, the first plurality of LEDs can comprise: a first LED which can be configured to emit light of a first wavelength, a second LED which can be configured to emit light of a second wavelength, a third LED which can be configured to emit light of a third wavelength, and a fourth LED which can be configured to emit light of a fourth wavelength, and the second plurality of LEDs can comprise: a fifth LED which can be configured to emit light of the first wavelength, a sixth LED which can be configured to emit light of the second wavelength, a seventh LED which can be configured to emit light of the third wavelength, and an eighth LED which can be configured to emit light of the fourth wavelength.

In some configurations, the sensor can comprise a sensor processor configured to drive the first plurality of LEDs and the second plurality of LEDs at varying intensities.

In some configurations, the sensor processor can be configured to drive the intensities of the first plurality of LEDs and the second plurality of LEDs based, at least in part, on one or more of an attenuation of emitted light or a temperature of the first plurality of LEDs and the second plurality of LEDs.

In some configurations, the sensor may comprise a sensor processor configured to activate or deactivate some of the detectors of the plurality of detectors.

In some configurations, the sensor may comprise an ECG sensor, and the ECG sensor may comprise a reference electrode, a negative electrode, and a positive electrode and the reference and negative electrodes can be located on the sensor and a portion of a housing of the watch can form the positive electrode.

In some configurations, the reference and negative electrodes can be releasably coupled to the PCB of the sensor.

The present disclosure provides a system for monitoring physiological parameters. The system may comprise a wearable device which may comprise one or more physiological sensors configured to monitor one or more physiological parameters of a user. The system may comprise a computing device external to the wearable device and in wireless communication with the wearable device. The computing device may be configured to: receive, via an interactive user interface, user input; in response to receiving the user input, wirelessly transmit a first signal to the wearable device to instruct the wearable device to perform a physiological monitoring operation; receive, from the wearable device, physiological parameter data measured by the physiological monitoring operation; and cause presentation of the physiological parameter data in the interactive user interface.

In some configurations, the monitoring operation can comprise continuous measuring of the physiological parameters.

In some configurations, the monitoring operation can comprise: measuring the physiological parameters for a predetermined length of time; and ceasing to measure the physiological parameters upon expiration of the predetermined length of time.

In some configurations, the wearable device can be configured to: in response to receiving the first signal from the computing device, determine a power level of a battery of the wearable device; determine whether the power level is sufficient to perform the monitoring operation; and in response to determining that the power level is sufficient, perform the monitoring operation.

In some configurations, the wearable device can be configured to: in response to receiving the first signal from the computing device, determine a power level of a battery of the wearable device; determine whether the power level is sufficient to perform the monitoring operation; in response to determining that the power level is not sufficient, determine a modified monitoring operation based at least in part on the power level; and perform the modified monitoring operation.

In some configurations, the computing device can be further configured to: cause presentation, in the interactive user interface, of one or more of a graph, chart, or trend of historical and substantially real-time physiological parameter data.

In some configurations, the wearable device can be configured to: determine that one or more physiological parameters exceed a respective predetermined threshold; and in response to determining that the one or more physiological parameters exceed the respective predetermined threshold, transmit a second signal to the computing device to cause the computing device to generate an alarm.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a first emitter group comprising a first plurality of light emitting diodes (LEDs) at a first location; a second emitter group comprising a second plurality of LEDs at a second location different from the first location, wherein the second emitter group can comprise the same number and type of LEDs as the first emitter groups; one or more light blocks separating the first emitter group from the second emitter group; light diffusing material configured to diffuse light emitted by each of the first and second pluralities of LEDs; a plurality of detectors including four or more photodiodes; and a convex surface configured to be positioned between (i) the first and second emitter groups and the four or more photodiodes and (ii) the tissue of the wearer, the convex surface comprising one or more surface materials.

In some configurations, the one or more surface materials can comprise at least a portion of the one or more light blocks and a light transmission material.

In some configurations, the emitters in the first or second emitter groups may not be electrically connected to one another.

In some configurations, the first or second emitter groups can define a group of emitters located in close proximity.

In some configurations, the plurality of detectors can be individually both a near detector and far detector for each emitter group.

In some configurations, the first and second emitter groups can be located at non-central locations of a printed circuit board (PCB) of the sensor.

In some configurations, the one or more light blocks can extend from a surface of the sensor positioning the first and second pluralities of LEDs towards a tissue of the wearer when the watch is worn.

In some configurations, each of the first or second emitter group can be surrounded by its own diffusing material.

In some configurations, the light diffusing material surrounding the first emitter group can be different from the light diffusing material surrounding the second emitter group.

In some configurations, at least some of the plurality of detectors can extend around a circumference of the sensor.

In some configurations, the plurality of detectors can be positioned in a grid pattern and/or across from one another.

In some configurations, locations of the emitter groups can be interleaved with the plurality of detectors.

In some configurations, at least one of the plurality of detectors can be located between the first plurality of LEDs and the second plurality of LEDs, and at least one of the plurality of detectors can be located on each of at least two sides of each of the first plurality of LEDs and the second plurality of LEDs.

In some configurations, the sensor can further comprise a processor configured to determine an oxygen saturation measurement based on signals from the optical physiological sensor.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of emitters, the emitters configured to emit light of a plurality of different wavelengths, the plurality of different wavelengths comprising at least three different wavelengths; a plurality of detectors, the detectors configured to detect light emitted by the plurality of emitters and attenuated by tissue of the user when the watch is worn on the wrist of the wearer and output signals to a sensor processor for determining the physiological parameters of the wearer; and a sensor housing, the plurality of emitters and the plurality of detectors enclosed within the housing, wherein the sensor housing can comprise: a convex skin-facing light transmissive cover extending over the plurality of emitters and the plurality of detectors, the cover located at a first side of sensor housing, and a printed circuit board (PCB) located at a second side of the sensor housing opposite the first side, the plurality of emitters and detectors located on a skin-facing side of the PCB; and a plurality of light barriers extending from the PCB to the cover, the plurality of light barriers configured to form walls of chambers to block light or substantially all the light between the chambers, each chamber enclosing one or more emitters without detectors, or one or more detectors without emitters, wherein a skin-facing surface of the cover and at least one of the light barriers can define a skin-facing surface of the sensor, a surface area of the cover extending over the chambers that enclose one or more detectors is at least 50% of a surface area of the skin-facing surface of the sensor.

In some configurations, the surface area of the cover extending over the chambers that enclose one or more detectors can be at least 100 mm$^2$.

In some configurations, the surface area of the cover extending over the chambers that enclose one or more detectors can be at least 150 mm$^2$.

In some configurations, the surface area of the cover extending over the chambers that enclose one or more detectors can be at least 165 mm$^2$.

In some configurations, a surface area of the light transmissive cover that extends over the chambers that enclose one or more emitters can be at least 25 mm$^2$.

In some configurations, the surface area of the light transmissive cover that extends over the chambers that enclose one or more detectors can be at least 35 mm$^2$.

In some configurations, the skin-facing surface of the sensor can have a longer side and a shorter side, the longer side configured to be along a width of the wearer's wrist when the watch is worn.

In some configurations, more of the plurality of detectors can be located along the longer side than along the shorter side.

In some configurations, the plurality of emitters can comprise a first group of emitters and a second group of emitters, the chambers comprising a first emitter chamber enclosing the first group and a second emitter chamber enclosing the second group.

In some configurations, the plurality of detectors can comprise a first ring of detectors and a second ring of detectors, the first ring of detectors surrounding the first group of emitters and the second ring of detectors surrounding the second group of emitters.

In some configurations, at least one of the plurality of detectors can be located between the first and second group of emitters and can be shared by the first and second rings of detectors.

In some configurations, some of the plurality of detectors can be closer to the first group of emitters than a remainder of the plurality of detectors and some of the plurality of detectors can be closer to the second group of emitters than a remainder of the plurality of detectors.

In some configurations, the plurality of light barriers can extend to a skin-facing surface of the cover.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of emitters, the emitters configured to emit light of a plurality of different wavelengths, the plurality of different wavelengths comprising at least three different wavelengths; a plurality of detectors, the detectors configured to detect light emitted by the plurality of emitters and attenuated by tissue of the user when the watch is worn on the wrist of the wearer and output signals to a sensor processor for determining the physiological parameters of the wearer; and a sensor housing, the plurality of emitters and the plurality of detectors enclosed within the housing, wherein the sensor housing can comprise: a convex skin-facing light transmissive cover extending over the plurality of emitters and the plurality of detectors, the cover located at a first side of sensor housing, and a printed circuit board (PCB) located at a second side of the sensor housing opposite the first side, the plurality of emitters and detectors located on a skin-facing side of the PCB; and a plurality of light barriers extending from the PCB to the cover, the plurality of light barriers configured to form walls of chambers to block light or substantially all the light between the chambers, each chamber enclosing one or more emitters without detectors, or one or more detectors without emitters, wherein at least one of the plurality of light barriers can extend to a skin-facing surface of the cover.

In some configurations, all of the plurality of light barriers can extend to the skin-facing surface of the cover.

In some configurations, the skin-facing surface of the cover and the at least one of the light barriers can define a skin-facing surface of the sensor.

In some configurations, the skin-facing surface of the sensor can comprise a continuous curvature.

In some configurations, the cover can be a single lens or cover.

In some configurations, the cover can comprise individual lenses, each lens or cover covering a single chamber.

In some configurations, the cover can comprise a lens or cover covering all the chambers that extend over one or more detectors.

In some configurations, the lens or cover covering all the chambers that extend over one or more detectors may not cover a chamber that extends over one or more emitters.

In some configurations, the plurality of light barriers can comprise colored sapphire glass.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a first emitter comprising a first a plurality of light emitting diodes (LEDs) positioned on a surface of a substrate; a first photodiode positioned on the surface of the substrate; a curved surface extending over all the first plurality of LEDs and the first photodiode; and a first light barrier positioned between the first emitter and the first photodiode, and extending from the surface of the substrate to the curved surface.

In some configurations, the first light barrier can comprise one or more portions that together extend from the surface of the substrate to the curved surface.

In some configurations, the sensor can further comprise: a second emitter comprising a second plurality of LEDs positioned on the surface of the substrate; a second photodiode positioned on the surface of the substrate; a second light barrier positioned between (i) both the first and second emitters and (ii) the second photodiode, and extending from the surface of the substrate to the curved surface, wherein the curved surface can extend over all the second plurality of LEDs and the second photodiode.

In some configurations, the second light barrier can comprise one or more portions that together extend from the surface of the substrate to the curved surface.

In some configurations, portions of the curved surface positioned above the first and second emitters can comprise at least a first material, portions of the curved surface positioned and the first and second photodiodes can comprise at least a second material, and portions of the first and second barriers extending to the curved surface can comprise at least a third material different from the first and second materials.

In some configurations, at least the first, second, and third materials together can make up the curved surface.

In some configurations, the first and second materials can comprise the same material.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of light-emitting diodes (LEDs) configured to emit light to tissue of a wearer; a wall dividing the plurality of LEDs into at least a first group of LEDs and a second group of LEDs, the wall blocking at least some of the light emitted by the first group of LEDs from contacting the second group of LEDs; four or more photodiodes configured to detect the light emitted by the plurality of LEDs after attenuation by the tissue; and one or more covers covering the plurality of LEDs and the four or more photodiodes, the one or more covers together forming part of a convex surface configured to contact the tissue.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of emitters, the emitters configured to emit light of a plurality of different wavelengths, the plurality of different wavelengths comprising at least three different wavelengths; a plurality of detectors, the detectors configured to detect light emitted by the plurality of emitters and attenuated by tissue of the user when the watch is worn on the wrist of the wearer and output signals to a sensor processor for determining the physiological parameters of the wearer; and a sensor housing, the plurality of emitters and the plurality of detectors enclosed within the housing, wherein the sensor housing can comprise: a convex skin-facing light transmissive cover extending over the plurality of emitters and the plurality of detectors, the cover located at a first side of sensor housing, and a printed circuit board (PCB) located at a second side of the sensor housing opposite the first side, the plurality of emitters and detectors located on a skin-facing side of the PCB; and a plurality of light barriers extending from the PCB to the cover, the plurality of light barriers configured to form walls of chambers to block light or substantially all the light between the chambers, each chamber enclosing one or more emitters without detectors, or one or more detectors without emitters, wherein the plurality of detectors can comprise a plurality of far detectors that are further from at least some of the plurality of emitters than a remainder of the plurality of detectors.

In some configurations, the plurality of emitters can comprise a first group of emitters and a second group of emitters, the chambers comprising a first emitter chamber enclosing the first group and a second emitter chamber enclosing the second group.

In some configurations, the plurality of detectors can comprise a first ring of detectors and a second ring of detectors, the first ring of detectors surrounding the first group of emitters and the second ring of detectors surrounding the second group of emitters.

In some configurations, at least one of the plurality of detectors can be located between the first and second group of emitters and is shared by the first and second rings of detectors.

In some configurations, some of the plurality of detectors can be closer to the first group of emitters than a remainder of the plurality of detectors and some of the plurality of detectors are closer to the second group of emitters than a remainder of the plurality of detectors.

In some configurations, the sensor can further comprise the sensor processor, wherein the sensor processor is configured to determine a hydration status of a user based on signals from the plurality of far detectors.

In some configurations, at least one of the emitters can be configured to emit light of a wavelength more sensitive to water than a remainder of the different wavelengths.

In some configurations, the wavelength more sensitive to water can be about 970 nm.

In some configurations, the sensor processor can be configured to compare signals of the reflected light of the wavelength more sensitive to water and another wavelength less sensitive to water from the plurality of far detectors.

In some configurations, the sensor processor can be configured to selectively drive some of the plurality of emitters and/or activate or deactivate some of the plurality of detectors.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of emitters, the emitters configured to emit light of a plurality of different wavelengths, wherein at least one of the emitters can be configured to emit light of a reference wavelength; a plurality of detectors, the detectors configured to detect light emitted by the plurality of emitters and attenuated by tissue of the user when the watch is worn on the wrist of the wearer; a sensor processor, wherein the plurality of detectors can be configured to output signals to the sensor processor for determining at least some of the physiological parameters of the wearer based in part on a signal of the reflected light of the reference wavelength; and a sensor housing, the plurality of emitters and the plurality of detectors enclosed within the housing, wherein the sensor housing can comprise: a convex skin-facing light transmissive cover extending over the plurality of emitters and the plurality of detectors, the cover located at a first side of sensor housing, and a printed circuit board (PCB) located at a second side of the sensor housing opposite the first side, the plurality of emitters and detectors located on a skin-facing side of the PCB; and a plurality of light barriers extending from the printed circuit board to the cover, the plurality of light barriers configured to form walls of chambers to block light or substantially all the light between the chambers, each chamber enclosing one or more emitters without detectors, or one or more detectors without emitters.

In some configurations, the reference wavelength can be about 525 nm.

In some configurations, the light of the reference wavelength can be green or yellow.

In some configurations, the sensor processor can be configured to extract features from signals of other wavelengths based on the signal of the reflected light of the reference wavelength and calculate the at least some of the physiological parameters based on the extracted features.

In some configurations, at least one of the emitters can be configured to emit light of a wavelength more sensitive to oxygen saturation.

In some configurations, at least one of the emitters can be configured to emit light of a wavelength more sensitive to water.

In some configurations, at least one of the emitters can be configured to emit light of a normalizing wavelength.

In some configurations, the sensor processor can be configured to determine a hydration status of a user based on signals of the reflected light of the wavelength more sensitive to water and of the normalizing wavelength.

In some configurations, one or more physiological parameters can comprise a pulse rate, respiration rate, SpO2, PVI, PI, RRP, hydration, or a combination thereof.

In some configurations, the sensor can further comprise a thermistor located near the plurality of emitters.

In some configurations, the sensor can further comprise an accelerometer and/or gyroscope.

In some configurations, the sensor processor can be configured to selectively drive some of the plurality of emitters and/or activate or deactivate some of the plurality of detectors.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of emitters, the emitters configured to emit light of a plurality of different wavelengths, the plurality of different wavelengths comprising at least three different wavelengths; a plurality of detectors, the detectors configured to detect light emitted by the plurality of emitters and attenuated by tissue of the user when the watch is worn on the wrist of the wearer and output signals to a sensor processor for determining the physiological parameters of the wearer; and a sensor housing, the plurality of emitters and the plurality of detectors enclosed within the housing, wherein the sensor housing can comprise: a convex skin-facing light transmissive cover extending over the plurality of emitters and the plurality of detectors, the cover located at a first side of sensor housing, and a printed circuit board (PCB) located at a second side of the sensor housing opposite the first side, the plurality of emitters and detectors located on a skin-facing side of the PCB; a plurality of light barriers extending from the PCB to the cover, the plurality of light barriers configured to form walls of chambers to block light or substantially all the light between the chambers, each chamber enclosing one or more emitters without detectors, or one or more detectors without emitters, wherein each chamber that encloses one or more emitters can be filled with a diffusing material such that there is no air gap between the plurality of emitters and the cover.

In some configurations, the light diffusing material can comprise glass microspheres.

In some configurations, the cover can comprise glass microspheres.

In some configurations, the sensor housing can comprise one or more openings configured to receive a flow of light diffusing solution.

In some configurations, the light diffusion solution can be UV-cured after being injected into each chamber that encloses one or more emitters.

In some configurations, the sensor housing can comprise one or more air vent openings configured to receive air displaced from the chamber(s) by the flow of light diffusing solution.

In some configurations, each chamber that encloses one or more detectors can be filled with the diffusing material such that there is no air gap between the plurality of detectors and the cover.

In some configurations, the diffusing material in each chamber that encloses one or more emitters can be configured to improve mixing of light such that light emitted by one of the emitter in the same chamber appears to be emitted from the entire same chamber.

An example watch of the present disclosure can be configured to monitor physiological parameters of a wearer. The watch can comprise any of the optical sensor or physiological parameter measurement sensor configurations disclosed above; a watch processor separate from and in electrical communication with the sensor processor; a power source configured to power the watch and the sensor, and a display in communication with the processor, the display configured to display the plurality of physiological parameters monitored by the sensor.

In some configurations, the display can be configured to display the wearer's SpO2 and pulse rate that are monitored by the sensor.

In some configurations, the sensor can be configured to continuously monitor the wearer's SpO2 and pulse rate.

In some configurations, the display can be configured to continuously display the wearer's SpO2 and pulse rate.

In some configurations, the watch can further comprise an ECG sensor.

In some configurations, the ECG sensor can comprise a reference electrode, a negative electrode, and a positive electrode.

In some configurations, the reference and negative electrodes can be located on the sensor.

In some configurations, a portion of a housing of the watch can form the positive electrode.

In some configurations, the ECG sensor can be in electrical communication with the sensor processor.

In some configurations, the watch can further comprise a wireless transmitter such that the watch is configured to wireless connect to external devices and/or external sensors.

In some configurations, the wireless transmitter can be a Bluetooth chip.

In some configurations, the external devices and/or external sensors can comprise a bedside monitor, a mobile communication device, a tablet, a nurses' station system, or a different medical device.

A health monitoring watch of the present disclosure can comprise a strap and a housing. The housing can comprise: a first chamber comprising a first well comprising a first depth below a first surface configured to be in contact with a skin of a user; a first plurality of light emitting diodes positioned at the first depth inside the first well, said first plurality of light emitting diodes comprising a first light emitting diode configured to emit light at a first wavelength, a second light emitting diode configured to emit light at a second wavelength different than the first wavelength, and a third light emitting diode configured to emit light at a third wavelength different than the first wavelength and the second wavelength, and a first wall surrounding the first well; a second chamber comprising a second well comprising a second depth below a second surface configured to be in contact with the skin of the user, a second plurality of light emitting diodes positioned at the second depth inside the second well, said second plurality of light emitting diodes comprising a fourth light emitting diode configured to emit light at the first wavelength, a fifth light emitting diode configured to emit light at the second wavelength different than the first wavelength, and a sixth light emitting diode configured to emit light at the third wavelength different than the first wavelength and the second wavelength, and a second wall surrounding the second well; and four or more light sensors.

A wearable health monitoring device can be configured to be worn on a wrist of a user and monitor one or more physiological parameters indicative of the user's health. The wearable health monitoring device can comprise: a first emitter group, the first emitter group comprising a first plurality of light-emitting diodes (LEDs) configured to emit light of one or more wavelengths, wherein the first emitter group can be arranged at a first location, the first location being spaced from an axis extending through a center of the wearable health monitoring device; a second emitter group, the second emitter group comprising a second plurality of LEDs configured to emit light of one or more wavelengths, wherein the second emitter group can be arranged at a second location, the second location being spaced from the first location and spaced from the axis extending through the center of the wearable health monitoring device; one or more light blocks separating the first emitter group from the second emitter group; a first light diffusing material, the first light diffusing material configured to be positioned between the first emitter group and tissue of the user when the wearable health monitoring device is in use, wherein the first light diffusing material can be configured to spread light emitted from one or more of the first plurality of LEDs before the emitted light reaches the tissue; a second light diffusing material, the second light diffusing material configured to be positioned between the second emitter group and the tissue of the user when the wearable health monitoring device is in use, wherein the second light diffusing material can be configured to spread light emitted from one or more of the second plurality of LEDs before the emitted light reaches the tissue; a plurality of photodiodes configured to detect at least a portion of the light emitted from one or more of the first plurality of LEDs or one or more of the second plurality of LEDs after attenuation through the user's tissue, the plurality of photodiodes configured to output one or more signals responsive to the detected light; and a processor configured to receive and process one or more signals responsive to the one or more signals outputted by the plurality of photodiodes and further configured to determine a physiological parameter of the user based on the received and processed one or more signals.

The present disclosure provides an optical physiological sensor integrated into a wearable device. The optical physiological sensor can comprise: a substrate having an optical center; a first emitter group of light emitting diodes (LEDs) positioned adjacent to the optical center of the substrate and spaced at an offset from the optical center; a second emitter group of LEDs positioned adjacent to the optical center of the substrate at an offset to the optical center and spaced at an offset from the optical center opposite the first emitter group of LEDs relative to the optical center; and a plurality of detectors arranged in a spatial configuration that surrounds the first and the second emitter group. Each of the plurality of detectors can be positioned on the substrate a same distance away from the optical center of the substrate.

In some configurations, the spatial configuration includes an annulus.

In some configurations, the annulus has a same optical center as the substrate.

In some configurations, the annulus is concentric with a perimeter of the sensor.

In some configurations, the annulus includes a radius of between about 6.2 mm and about 6.6 mm.

In some configurations, the annulus includes a radius of between about 6.15 mm and about 6.45 mm.

In some configurations, the sensor includes a radius of between about 15.0 mm and about 15.5 mm.

In some configurations, a ratio of a radius of the annulus to a radius of the sensor is between about 40% and about 45%.

In some configurations, the second emitter group is spaced less than 1.5 mm away from the first emitter group.

In some configurations, the second emitter group is spaced about 1.28 mm away from the first emitter group.

In some configurations, the second emitter group is spaced about 1.2 mm away from the first emitter group.

In some configurations, the sensor can further comprise a light barrier construct mounted on the substrate and configured to isolate the first emitter group, the second emitter group, and the plurality of detectors.

In some configurations, the light barrier construct is a single integrated unit comprising a plurality of light barriers defining one or more chambers.

In some configurations, the light barrier construct comprises a plurality of light barriers configured to isolate the first and second emitter groups from each of the plurality of detectors.

In some configurations, the light barrier construct comprises a light barrier configured to isolate the first emitter group from the second emitter group.

In some configurations, the light barrier includes a width of between about 1.25 mm and about 1.35 mm separating the first and second emitter groups.

In some configurations, the light barrier includes a width of between about 1.1 mm and about 1.3 mm separating the first and second emitter groups.

In some configurations, the light barrier includes a width of less than a distance from an emitter chamber defined by the light barrier construct and housing the first emitter group to a detector chamber defined by the light barrier construct and housing a detector bisected by a centerline of the sensor.

In some configurations, the light barrier construct includes a height of between about 2.80 mm and about 2.90 mm extending away from the optical center of the substrate.

In some configurations, the light barrier construct includes a height of between about 2.55 mm and about 2.65 mm extending away from the optical center of the substrate.

In some configurations, the light barrier construct includes a height of between about 1.25 mm and about 1.35 mm extending away from a perimeter of the substrate.

In some configurations, the light barrier construct includes a height of between about 1.75 mm and about 1.85 mm extending away from a perimeter of the substrate.

In some configurations, a ratio of a maximum height of the light barrier construct extending away from the substrate to a minimum height of the light barrier construct extending away from the substrate is between about 215% and about 225%.

In some configurations, a ratio of a maximum height of the light barrier construct extending away from the substrate to a minimum height of the light barrier construct extending away from the substrate is between about 145% and about 155%.

In some configurations, the light barrier construct includes a maximum height extending away from the substrate at the optical center of the substrate.

In some configurations, the light barrier defines a plurality of chambers, including, at least, a detector chamber housing a detector bisected by a centerline of the sensor; a first emitter chamber housing the first emitter group; and a second emitter chamber housing the second emitter group.

In some configurations, a distance from the first emitter chamber to the detector chamber extending along a length parallel to the centerline of the sensor is the same as a distance from the second emitter chamber to the detector chamber extending along a length parallel to the centerline of the sensor.

In some configurations, a distance from the first emitter chamber to the detector chamber extending along a length parallel to the centerline of the sensor is less than half a width of the first emitter chamber along a length parallel to the centerline of the sensor.

In some configurations, a distance from the first emitter chamber to the detector chamber extending along a length parallel to the centerline of the sensor is greater than half a width of the first emitter chamber along a length parallel to the centerline of the sensor.

In some configurations, the first emitter group includes two or more LEDs and wherein the second emitter group includes two or more LEDs.

In some configurations, the first emitter group includes three or more LEDs and wherein the second emitter group includes three or more LEDs.

In some configurations, the first emitter group includes four or more LEDs and wherein the second emitter group includes four or more LEDs.

In some configurations, the first emitter group includes five LEDs and wherein the second emitter group includes five LEDs.

In some configurations, each LED in the first emitter group emits light at a different wavelength than each of the other LEDs in the first emitter group.

In some configurations, each LED in the second emitter group emits light at a different wavelength that each of the other LEDs in the second emitter group.

In some configurations, the first emitter group is configured to emit a same plurality of light wavelengths as the second emitter group.

In some configurations, an arrangement of the LEDs of the first emitter group on the substrate mirrors an arrangement of the LEDs of the second emitter group on the substrate across a centerline of the sensor that bisects the sensor.

In some configurations, the optical center of the substrate is located on the centerline of the sensor.

In some configurations, the centerline of the sensor bisects at least one of the plurality of detectors.

In some configurations, a distance from the first emitter group to the at least one of the plurality of detectors is substantially similar to a distance from the second emitter group to the at least one of the plurality of detectors.

In some configurations, the sensor further comprises an ECG sensor, and the ECG sensor comprises a reference electrode, a negative electrode, and a positive electrode and the reference and negative electrodes are located on the sensor and the positive electrode is located on a housing of the wearable device.

In some configurations, the reference and negative electrodes are releasably coupled to the substrate of the sensor via one or more springs configured to bias the reference and negative electrodes away from the substrate.

In some configurations, the reference electrode extends along a circumference of the sensor on a first side of the sensor, and wherein the negative electrode extends along a circumference of the sensor on a second side of the sensor.

In some configurations, the reference electrode is substantially semi-annular and wherein the negative electrode is substantially semi-annular.

In some configurations, the reference and negative electrodes surround the plurality of detectors.

In some configurations, the substrate comprises a conductive liquid adhesive configured to facilitate a conductive electrical connection between the electrodes of the ECG sensor and the substrate.

In some configurations, the substrate comprises a printed circuit board (PCB).

In some configurations, the substrate comprises a reflective surface.

In some configurations, the sensor further comprises a first temperature sensor positioned on the substrate adjacent to the first emitter group of LEDs, and a second temperature sensor adjacent to the second emitter group of LEDs.

In some configurations, the first emitter group of LEDs is configured to emit light of at least four wavelengths and wherein the second emitter group of LEDs is configured to emit light of at least four wavelengths.

In some configurations, the four wavelengths emitted by the first emitter group of LEDs are the same wavelengths as the four wavelengths emitted by the second emitter group of LEDs.

In some configurations, the first emitter group of LEDs comprise LEDs of a same type as the second emitter group of LEDs.

In some configurations, the first emitter group of LEDs comprises: a first LED configured to emit light of a first wavelength, a second LED configured to emit light of a second wavelength, a third LED configured to emit light of a third wavelength, and a fourth LED configured to emit light of a fourth wavelength, and the second emitter group of LEDs comprises: a fifth LED configured to emit light of the first wavelength, a sixth LED configured to emit light of the second wavelength, a seventh LED configured to emit light of the third wavelength, and an eighth LED configured to emit light of the fourth wavelength.

In some configurations, the first LED is located on the PCB at a location that mirrors, across a centerline of the sensor, a location of the fifth LED on the PCB; the second LED is located on the PCB at a location that mirrors, across the centerline of the sensor, a location of the sixth LED on the PCB; the third LED is located on the PCB at a location that mirrors, across the centerline of the sensor, a location of the seventh LED on the PCB; and the fourth LED is located on the PCB at a location that mirrors, across the centerline of the sensor, a location of the eighth LED on the PCB.

In some configurations, the first and fifth LEDs are each located a same distance from at least one of the plurality of detectors; the second and sixth LEDs are each located a same distance from at least one of the plurality of detectors; the third and seventh LEDs are each located a same distance from at least one of the plurality of detectors; and the fourth and eighth LEDs are each located a same distance from at least one of the plurality of detectors.

In some configurations, light emitted from the first emitter group of LEDs travels along a light path to a first detector of the plurality of detectors that is substantially similar in length to a light path along which light emitted from the second emitter group of LEDs travels to the first detector.

In some configurations, the plurality of detectors includes a first detector group and a second detector group.

In some configurations, the first detector group includes at least two detectors housed in respective detector chambers, and wherein the second detector group includes at least two detectors housed in respective detector chambers.

In some configurations, a distance between the first emitter group and the first detector group is greater than a distance between the second emitter group and the first detector group.

In some configurations, a distance between the first emitter group and a first detector of the first detector group is substantially similar as a distance between the first emitter group and a second detector of the first detector group.

In some configurations, a distance between the first emitter group and the first detector group is substantially similar to a distance between the second emitter group and the second detector group.

In some configurations, light emitted from the first emitter group travels to the first detector group along a light path that is shorter than a light path along which light emitted from the second emitter group travels to the first detector group.

In some configurations, light emitted from the second emitter group and detected by first detector group penetrates deeper into a tissue of the wearer than light emitted from the first emitter group and detected by first detector group.

In some configurations, the sensor further comprises a light barrier construct mounted on the substrate and configured to isolate the first emitter group, the second emitter group, and the plurality of detectors, wherein the light barrier construct comprises a plurality of light barriers defining one or more chambers.

In some configurations, the one or more chambers includes a first emitter chamber configured to house the first emitter group of light emitting diodes (LEDs).

In some configurations, the one or more chambers includes a second emitter chamber configured to house the second emitter group of light emitting diodes (LEDs).

In some configurations, the one or more chambers includes a plurality of detector chambers configured to house the plurality of detectors.

In some configurations, the light barrier construct is further configured to prevent the transmission of light therethrough.

In some configurations, the sensor further comprises a convex surface configured to be positioned between the tissue of the wearer and the emitter and detector chambers, the convex surface comprising at least a portion of the light barrier construct.

In some configurations, the convex surface further includes one or more lenses defining a surface of the emitter and detector chambers, wherein the one more lenses are further configured to transmit light.

In some configurations, the one or more lenses include polycarbonate and are configured to diffuse light.

In some configurations, the emitter and detector chambers enclose light diffusing material or encapsulant.

In some configurations, the light diffusing material or encapsulant includes glass beads or microspheres.

In some configurations, a height of the convex surface from the optical center of the substrate is between about 2.80 mm and about 2.90 mm.

In some configurations, a height of the convex surface from the optical center of the substrate is between about 2.55 mm and about 2.65 mm.

In some configurations, a centerline of the sensor bisects a first detector of the plurality of detectors, and wherein said first detector is configured to generate, responsive to detecting light emitted from the first and second emitter groups, one or more signals for calibrating or normalizing a physiological parameter measurement of the sensor.

In some configurations, the sensor processor is further configured to calibrate or normalize the physiological parameter measurement of the sensor based at least in part on comparing a first signal generated by the first detector responsive to light emitted from the first emitter group with a second signal generated by the first detector responsive to light emitted from the second emitter group.

In some configurations, the sensor further comprises a sensor processor configured to drive the LEDs of the first and second emitter groups at varying intensities.

In some configurations, the sensor processor is configured to drive the intensities of the LEDs of the first and second emitter groups based, at least in part, on one or more of an attenuation of emitted light or a temperature of the LEDs of the first and second emitter groups.

In some configurations, the sensor further comprises a sensor processor configured to activate or deactivate some of the detectors of the plurality of detectors.

The present disclosure provides an optical physiological sensor integrated into a wearable device. The optical physiological sensor can comprise: a first emitter group of light emitting diodes (LEDs) mounted on a substrate; a second emitter group of LEDs mounted on the substrate and spaced away from the first emitter group of LEDs, wherein the first emitter group is isolated from the second emitter group; and at least six detectors mounted on the substrate and arranged in a spatial configuration that surrounds the first and the second emitter group and isolated from each other, the first emitter group, and the second emitter group.

In some configurations, the spatial configuration includes an annulus.

In some configurations, the annulus has a same geometric center as the substrate or as the sensor.

In some configurations, the first and second emitter groups are located at a central location of the substrate.

In some configurations, the first and second emitter groups are located adjacent to a geometric center of the substrate or a geometric center of the sensor.

In some configurations, the sensor further comprises a light barrier construct mounted on the substrate and configured to isolate the first emitter group, the second emitter group, and the at least six detectors.

In some configurations, the sensor further comprises an ECG sensor, the ECG sensor comprises a reference electrode, a negative electrode, and a positive electrode and the reference and negative electrodes are located on the sensor and the positive electrode is located on a housing of the wearable device.

In some configurations, the reference and negative electrodes are releasably coupled to the substrate of the sensor via one or more springs configured to bias the reference and negative electrodes away from the substrate.

In some configurations, the reference electrode extends along a circumference of the sensor on a first side of the sensor, and wherein the negative electrode extends along a circumference of the sensor on a second side of the sensor.

In some configurations, the reference electrode is substantially semi-annular and the negative electrode is substantially semi-annular.

In some configurations, the reference and negative electrodes surround the plurality of detectors.

In some configurations, the substrate comprises a conductive liquid adhesive configured to facilitate a conductive electrical connection between the electrodes of the ECG sensor and the substrate.

In some configurations, the substrate comprises a printed circuit board (PCB).

In some configurations, the substrate comprises a reflective surface.

In some configurations, the first emitter group includes five LEDs and wherein the second emitter group includes five LEDs.

In some configurations, the sensor further comprises a first temperature sensor positioned on the substrate adjacent to the first emitter group of LEDs, and a second temperature sensor adjacent to the second emitter group of LEDs.

In some configurations, a centerline of the sensor bisects a first detector of the plurality of detectors, and said first detector is configured to generate, responsive to detecting light emitted from the first and second emitter groups, one or more signals for calibrating or normalizing a physiological parameter measurement of the sensor.

In some configurations, the sensor processor is further configured to calibrate or normalize the physiological parameter measurement of the sensor based at least in part on comparing a first signal generated by the first detector responsive to light emitted from the first emitter group with a second signal generated by the first detector responsive to light emitted from the second emitter group.

In some configurations, the sensor further comprises a sensor processor configured to drive the LEDs of the first and second emitter groups at varying intensities.

In some configurations, the sensor processor is configured to drive the intensities of the LEDs of the first and second emitter groups based, at least in part, on one or more of an attenuation of emitted light or a temperature of the LEDs of the first and second emitter groups.

In some configurations, the sensor further comprises a sensor processor configured to activate or deactivate some of the detectors of the plurality of detectors.

The present disclosure provides an optical physiological sensor integrated into a wearable device. The optical physiological sensor can comprise: a first emitter group of light emitting diodes (LEDs) mounted on a substrate; a second emitter group of LEDs mounted on the substrate and spaced away from the first emitter group of LEDs; and a plurality of detectors mounted on the substrate and arranged in an annular configuration that surrounds the first and the second emitter group, the detectors can be substantially rectangular having a first side of a length and a second side of a width, wherein the detectors are oriented on the substrate such that the first side of each detector having the length is substantially orthogonal to a radius of the annular configuration.

The present disclosure provides an optical physiological sensor integrated into a wearable device. The optical physiological sensor can comprise: a first emitter group of light emitting diodes (LEDs) mounted on a substrate; a second emitter group of LEDs mounted on the substrate and spaced away from the first emitter group of LEDs, wherein the LEDs of the first emitter group are arranged on the substrate to mirror, across a centerline of the sensor, an arrangement of the LEDs of the second emitter group on the substrate; and a plurality of detectors mounted on the substrate and arranged in a spatial configuration that surrounds the first and the second emitter group.

In some configurations, the centerline of the sensor bisects at least one of the plurality of detectors.

In some configurations, the first emitter group of LEDs is configured to emit light of at least four wavelengths and wherein the second emitter group of LEDs is configured to emit light of at least four wavelengths.

In some configurations, the four wavelengths emitted by the first emitter group of LEDs are the same wavelengths as the four wavelengths emitted by the second emitter group of LEDs.

In some configurations, the first emitter group of LEDs comprise LEDs of a same type as the second emitter group of LEDs.

In some configurations, the first emitter group of LEDs comprise: a first LED configured to emit light of a first wavelength, a second LED configured to emit light of a second wavelength, a third LED configured to emit light of a third wavelength, and a fourth LED configured to emit light of a fourth wavelength, and the second emitter group of LEDs comprises: a fifth LED configured to emit light of the first wavelength, a sixth LED configured to emit light of the second wavelength, a seventh LED configured to emit light of the third wavelength, and an eighth LED configured to emit light of the fourth wavelength.

In some configurations, the first LED is located on the PCB at a location that mirrors, across a centerline of the sensor, a location of the fifth LED on the PCB; and the second LED is located on the PCB at a location that mirrors, across the centerline of the sensor, a location of the sixth LED on the PCB; the third LED is located on the PCB at a location that mirrors, across the centerline of the sensor, a location of the seventh LED on the PCB; and the fourth LED is located on the PCB at a location that mirrors, across the centerline of the sensor, a location of the eighth LED on the PCB.

In some configurations, the first and fifth LEDs are each located a same distance from at least one of the plurality of detectors; the second and sixth LEDs are each located a same distance from at least one of the plurality of detectors; the third and seventh LEDs are each located a same distance from at least one of the plurality of detectors; and the fourth and eighth LEDs are each located a same distance from at least one of the plurality of detectors.

In some configurations, light emitted from the first emitter group of LEDs travels along a light path to a first detector of the plurality of detectors that is substantially similar in length to a light path along which light emitted from the second emitter group of LEDs travels to the first detector.

In some configurations, a centerline of the sensor bisects a first detector of the plurality of detectors, and wherein said first detector is configured to generate, responsive to detecting light emitted from the first and second emitter groups, one or more signals for calibrating or normalizing a physiological parameter measurement of the sensor.

In some configurations, the sensor processor is further configured to calibrate or normalize the physiological parameter measurement of the sensor based at least in part on comparing a first signal generated by the first detector responsive to light emitted from the first emitter group with a second signal generated by the first detector responsive to light emitted from the second emitter group.

In some configurations, the sensor further comprises a sensor processor configured to drive the LEDs of the first and second emitter groups at varying intensities.

In some configurations, the sensor processor is configured to drive the intensities of the LEDs of the first and second emitter groups based, at least in part, on one or more of an attenuation of emitted light or a temperature of the LEDs of the first and second emitter groups.

In some configurations, the sensor further comprises a sensor processor configured to activate or deactivate some of the detectors of the plurality of detectors.

The present disclosure provides an optical physiological sensor integrated into a wearable device. The optical physiological sensor can comprise: a first emitter group of light emitting diodes (LEDs) mounted on a substrate; a second emitter group of LEDs mounted on the substrate and spaced away from the first emitter group of LEDs, wherein the second emitter group is isolated from the first emitter group; and a plurality of detectors mounted on the substrate, wherein the plurality of detectors is arranged in a spatial configuration that surrounds the first and the second emitter group and isolated from each other, wherein the plurality of detectors includes a first detector group and a second detector group, and the first emitter group can be proximal to the first detector group and distal to the second detector group, and the second emitter group can be proximal to the second detector group and distal to the first detector group.

In some configurations, the first detector group includes at least two detectors housed in respective detector chambers, and wherein the second detector group includes at least two detectors housed in respective detector chambers.

In some configurations, a distance between the first emitter group and the first detector group is greater than a distance between the second emitter group and the first detector group.

In some configurations, a distance between the first emitter group and a first detector of the first detector group is substantially similar as a distance between the first emitter group and a second detector of the first detector group.

In some configurations, a distance between the first emitter group and the first detector group is substantially similar to a distance between the second emitter group and the second detector group.

In some configurations, light emitted from the first emitter group travels to the first detector group along a light path that is shorter than a light path along which light emitted from the second emitter group travels to the first detector group.

In some configurations, light emitted from the second emitter group and detected by first detector group penetrates deeper into a tissue of the wearer than light emitted from the first emitter group and detected by first detector group.

In some configurations, a centerline of the sensor bisects a first detector of the plurality of detectors, and wherein said first detector is configured to generate, responsive to detecting light emitted from the first and second emitter groups, one or more signals for calibrating or normalizing a physiological parameter measurement of the sensor.

In some configurations, the sensor processor is further configured to calibrate or normalize the physiological parameter measurement of the sensor based at least in part on comparing a first signal generated by the first detector responsive to light emitted from the first emitter group with a second signal generated by the first detector responsive to light emitted from the second emitter group.

In some configurations, the sensor further comprises a sensor processor configured to drive the LEDs of the first and second emitter groups at varying intensities.

In some configurations, the sensor processor is configured to drive the intensities of the LEDs of the first and second emitter groups based, at least in part, on one or more of an attenuation of emitted light or a temperature of the LEDs of the first and second emitter groups.

In some configurations, the sensor further comprises a sensor processor configured to activate or deactivate some of the detectors of the plurality of detectors.

The present disclosure provides an optical physiological sensor integrated into a wearable device. The optical physiological sensor can comprise: first and second emitter groups of light emitting diodes mounted on a substrate; a first emitter chamber housing the first emitter group of light emitting diodes (LEDs); a second emitter chamber housing the second emitter group of LEDs wherein the first emitter group is isolated from the second emitter group; a plurality of detector chambers housing detectors mounted on the substrate and arranged in a spatial configuration that surrounds the first and the second emitter chambers; a light barrier construct mounted on the substrate and including one or more light barriers configured to prevent the transmission of light therethrough, wherein the light barriers of the light barrier construct isolate the emitter chambers and the detector chambers; and a convex surface configured to be positioned between the tissue of the wearer and the emitter and detector chambers, the convex surface comprising at least a portion of the light barrier construct.

In some configurations, the convex surface further includes one or more lenses defining a surface of the emitter and detector chambers, wherein the one more lenses are further configured to transmit light.

In some configurations, the one or more lenses include polycarbonate and are configured to diffuse light.

In some configurations, the emitter and detector chambers enclose light diffusing material or encapsulant.

In some configurations, the light diffusing material or encapsulant includes glass beads or microspheres.

In some configurations, a height of the convex surface from a center of the substrate is between about 2.80 mm and about 2.90 mm.

In some configurations, a height of the convex surface from a center of the substrate is between about 2.55 mm and about 2.65 mm.

In some configurations, a centerline of the sensor bisects a first detector of the detectors, and wherein said first detector is configured to generate, responsive to detecting light emitted from the first and second emitter groups, one or more signals for calibrating or normalizing a physiological parameter measurement of the sensor.

In some configurations, the sensor processor is further configured to calibrate or normalize the physiological parameter measurement of the sensor based at least in part on comparing a first signal generated by the first detector responsive to light emitted from the first emitter group with a second signal generated by the first detector responsive to light emitted from the second emitter group.

In some configurations, the sensor further comprises a sensor processor configured to drive the LEDs of the first and second emitter groups at varying intensities.

In some configurations, the sensor processor is configured to drive the intensities of the LEDs of the first and second emitter groups based, at least in part, on one or more of an attenuation of emitted light or a temperature of the LEDs of the first and second emitter groups.

In some configurations, the sensor further comprises a sensor processor configured to activate or deactivate some of the detectors of the plurality of detectors.

The present disclosure provides an optical physiological sensor integrated into a wearable device. The optical physiological sensor can comprise: a circuit layer; a light barrier construct positioned proximate said circuit layer, the light barrier construct comprising a plurality of openings defining at least a first emitter chamber, a second emitter chamber, and a plurality of detector chambers. The first and second emitter chambers can be spaced from one another and are spaced inward from and surrounded by the plurality of detector chambers; and the first emitter chamber, the second emitter chamber, and the plurality of detector chambers can be isolated from one another by portions of the light barrier construct. In some configurations, the sensor comprises: a first plurality of emitters mounted on said circuit layer and positioned within the first emitter chamber of the light barrier construct; a second plurality of emitters mounted on said circuit layer and positioned within the second emitter chamber of the light barrier construct; and a plurality of detectors, each of the plurality of detectors mounted on said circuit layer and positioned within a different one of the plurality of detector chambers of the light barrier construct. In some configurations, each of the plurality of detector chambers includes only one detector.

In some configurations, the sensor further comprises a first electrocardiogram (ECG) electrode and a second ECG electrode, and wherein the first and second ECG electrodes partially surround the first plurality of emitters, second plurality of emitters, and plurality of detectors.

In some configurations, each of the first and second ECG electrodes comprises a semi-annular shape having a first end and a second end; and the first ends of the first and second ECG electrodes are separated from one another by a first gap and the second ends of the first and second ECG electrodes are separated from one another by a second gap.

In some configurations, the light barrier construct further comprises: a first recess sized and shaped to receive the first ECG electrode; and a second recess sized and shaped to receive the second ECG electrode; each of the first and second recesses comprises a semi-annular shape having a first end and a second end; the first ends of the first and second recesses are separated from one another by said first gap and the second ends of the first and second recesses are separated from one another by said second gap; and the first and second recesses partially surround the first emitter chamber, second emitter chamber, and plurality of detector chambers.

In some configurations, the plurality of detector chambers are spaced inward from the first and second recesses.

In some configurations, the sensor does not include any emitters positioned outward from the first and second ECG electrodes.

In some configurations, the sensor does not include any detectors positioned outward from the first and second ECG electrodes.

In some configurations, the first and second gaps are substantially equal.

In some configurations, first and second ends of the first and second ECG electrodes comprise a rounded shape.

In some configurations, each of the first and second gaps are between approximately 1.5 mm and approximately 1.75 mm.

In some configurations, each of the first and second gaps are between approximately 0.5 mm and approximately 0.75 mm.

In some configurations, the sensor does not include any emitters positioned within any of the plurality of detector chambers.

In some configurations, the sensor does not include any detectors positioned within any of the first and second emitter chambers.

In some configurations, the plurality of detector chambers are arranged in a circular configuration around said first and second emitter chambers.

In some configurations, said sensor does not include any emitters other than the first and second plurality of emitters.

In some configurations, said sensor does not include any detectors other than the plurality of detectors.

In some configurations, said circuit layer comprises a printed circuit board.

In some configurations, each of the first and second plurality of emitters comprises a light emitting diode (LED).

In some configurations, each of the plurality of detectors comprises a photodiode.

In some configurations, each of the first and second plurality of emitters are configured to emit light into tissue of a user; each of the plurality of detectors are configured to: (i) detect at least a portion of light emitted by at least one of the first and second plurality of emitters after attenuation by said tissue; and (ii) output at least one signal responsive to detected light; and the sensor further comprises one or more processors configured to receive and process the outputted at least one signal and determine at least one physiological parameter of the user.

The present disclosure provides a system for monitoring physiological parameters. The system can comprise: a wearable device comprising one or more physiological sensors configured to monitor one or more physiological parameters of a user; and a computing device external to the wearable device and in wireless communication with the wearable device, the computing device configured to: receive, via an interactive user interface, user input; in response to receiving the user input, wirelessly transmit a first signal to the wearable device to instruct the wearable device to perform a physiological monitoring operation; receive, from the wearable device, physiological parameter data measured by the physiological monitoring operation; and cause presentation of the physiological parameter data in the interactive user interface.

In some configurations, the monitoring operation comprises continuous measuring of the physiological parameters.

In some configurations, the monitoring operation comprises: measuring the physiological parameters for a predetermined length of time; and ceasing to measure the physiological parameters upon expiration of the predetermined length of time.

In some configurations, the wearable device is configured to: in response to receiving the first signal from the computing device, determine a power level of a battery of the wearable device; determine whether the power level is sufficient to perform the monitoring operation; and in response to determining that the power level is sufficient, perform the monitoring operation.

In some configurations, the wearable device is configured to: in response to receiving the first signal from the computing device, determine a power level of a battery of the wearable device; determine whether the power level is sufficient to perform the monitoring operation; in response to determining that the power level is not sufficient, determine a modified monitoring operation based at least in part on the power level; and perform the modified monitoring operation.

In some configurations, the wearable device is configured to: determine that one or more physiological parameters exceed a respective predetermined threshold; and in response to determining that the one or more physiological parameters exceed the respective predetermined threshold, transmit a second signal to the computing device to cause the computing device to generate an alarm.

In some configurations, the computing device is further configured to: cause presentation, in the interactive user interface, of one or more of a graph, chart, or trend of historical and substantially real-time physiological parameter data.

It is noted that "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood. Moreover, "oximetry" as used herein encompasses its broad ordinary meaning known to one of skill in the art, which includes at least those noninvasive procedures for measuring parameters of circulating blood through spectroscopy.

For purposes of summarization, certain aspects, advantages and novel features are described herein. Of course, it is to be understood that not necessarily all such aspects, advantages or features need to be present in any particular aspect.

BRIEF DESCRIPTION OF THE DRAWINGS

The drawings and the associated descriptions are provided to illustrate aspects of the disclosure and not to limit the scope of the claims. In the present disclosure, "bottom" refers to the side facing a wearer's wrist when an example wearable device disclosed herein is worn on the wearer's wrist and "top" refers to the side facing away from the wearer's wrist.

FIG. 1I illustrates a perspective view of an example strap configured to secure the wearable device disclosed herein to a wearer's wrist.

FIG. 4 illustrates an example physiological parameter measurement module of the wearable device.

FIG. 13B illustrates an example block diagram of emitters circuitry of the physiological parameter measurement module disclosed herein.

FIG. 13C illustrates an example block diagram of detectors circuitry of the physiological parameter measurement module disclosed herein.

FIG. 13D illustrates an example block diagram of temperature sensors circuitry of the physiological parameter measurement module disclosed herein.

FIG. 16E illustrates a bottom view of a variation of the example physiological parameter measurement module of FIG. 16B including ECG electrodes.

FIG. 16F illustrates a side view of the example physiological parameter measurement module of FIG. 16E.

FIG. 16G illustrates a bottom perspective view of the example physiological parameter measurement module of FIG. 16E with the opaque frame and light transmissive cover hidden to show ECG electrodes assembled with the sensor or module processor board.

FIG. 17A illustrates a bottom perspective view of an example physiological parameter measurement module incorporating the plethysmograph sensor arrangement of FIG. 16A.

FIG. 17B illustrates a bottom view of the example physiological parameter measurement module of FIG. 17A.

FIG. 17C illustrates a side view of the example physiological parameter measurement module of FIG. 17A.

FIG. 19A illustrate schematically an example plethysmograph sensor arrangement on a sensor or module processor board of a physiological parameter measurement module of a wearable device.

FIG. 19B illustrates a bottom view of an example physiological parameter measurement module incorporating the plethysmograph sensor arrangement of FIG. 19A.

FIG. 19C illustrates a side view of the physiological parameter measurement module of FIG. 19B.

FIG. 20A illustrates a bottom view of an example physiological parameter measurement module of a wearable device as worn on a schematic representation of a wearer's wrist.

FIG. 20B illustrates a side view of the physiological parameter measurement module of FIG. 20A.

FIG. 20H illustrates a third side view of the wearable device of FIG. 20E.

FIG. 20I illustrates a bottom perspective view of the wearable device of FIG. 20E.

FIG. 20J illustrates a top perspective view of the wearable device of FIG. 20E.

FIG. 23A illustrates a bottom perspective view of an example wearable device incorporating the physiological parameter measurement module of FIGS. 20A-20D.

FIG. 23B illustrates a side view of the wearable device of FIG. 23A.

FIG. 23C illustrates a top perspective view of the wearable device of FIG. 23A.

FIG. 23D illustrates a top view of the wearable device of FIG. 23A.

FIG. 23E illustrates a bottom view of the wearable device of FIG. 23A.

FIG. 24A illustrates a bottom view of another example physiological parameter measurement module of a wearable device.

FIG. 24B illustrates a side view of the physiological parameter measurement module of FIG. 24A.

FIG. 25A illustrates a bottom view of another example physiological parameter measurement module of a wearable device.

FIG. 25B illustrates a side view of the physiological parameter measurement module of FIG. 25A.

FIG. 25C illustrates a first side view of another example wearable device incorporating the physiological parameter measurement module of FIGS. 25A-25B.

FIG. 25D illustrates a bottom view of the wearable device of FIG. 25C.

FIG. 25E illustrates a second side view of the wearable device of FIG. 25C.

FIG. 25F illustrates a top perspective view of the wearable device of FIG. 25C.

FIG. 25G illustrates a third side view of the wearable device of FIG. 25C.

FIG. 25H illustrates a bottom perspective view of the wearable device of FIG. 25C.

FIG. 26A illustrates schematically a microneedle inserted into skin of a wearer.

FIG. 26B illustrates schematically a microneedle patch coupled to a body of the wearable device disclosed herein.

FIG. 26C illustrates schematically a microneedle patch coupled to a strap of the wearable device disclosed herein.

FIG. 27B illustrates an exploded view of an example aspect of a physiological parameter measurement sensor or module.

FIGS. 27K-27L illustrate an example physiological parameter measurement sensor or module and example light paths between emitters and detectors of the module.

FIGS. 30A-30D illustrate example spot check monitoring user interfaces of the health application.

FIGS. 31A-31D illustrate example measurement settings user interfaces of the health application.

FIG. 32 illustrates an example activity user interface of the health application.

FIGS. 34A-34C illustrate example sleep user interfaces of the health application.

FIG. 36A illustrates an example aspect of a wearable device with a display screen.

FIGS. 36B-36E illustrate example display screens of a wearable device.

FIG. 37A illustrates an example aspect of a wearable device with a display screen.

FIGS. 37B-37E illustrate example display screens of a wearable device.

FIG. 38A-38B illustrate example display screens of a wearable device.

FIG. 39 is a flowchart illustrating an example process for performing a monitoring operation of the wearable device.

FIG. 40 illustrates a block diagram of an example computing device that may implement one or more aspects of the present disclosure, according to various aspects of the present disclosure.

DETAILED DESCRIPTION

Figure 1C:
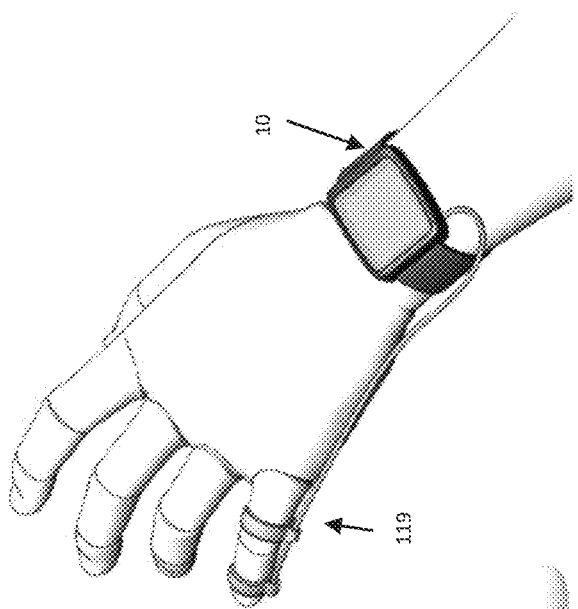
FIG. 1C illustrates an example fingertip sensor that can be coupled to the wearable device of the present disclosure.
Figure 1B:
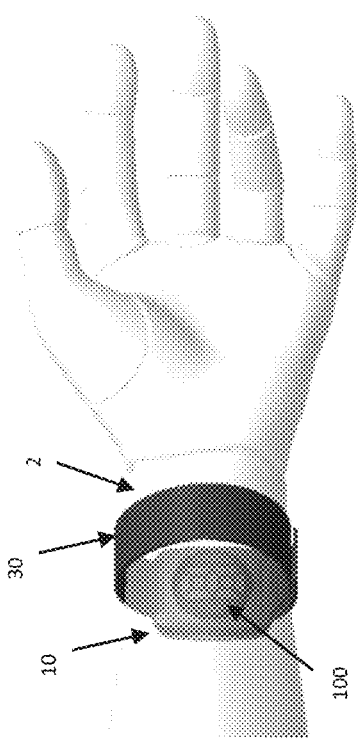
FIG. 1B illustrates a second view of the example wearable device of FIG. 1A worn on the wrist.
Figure 1A:
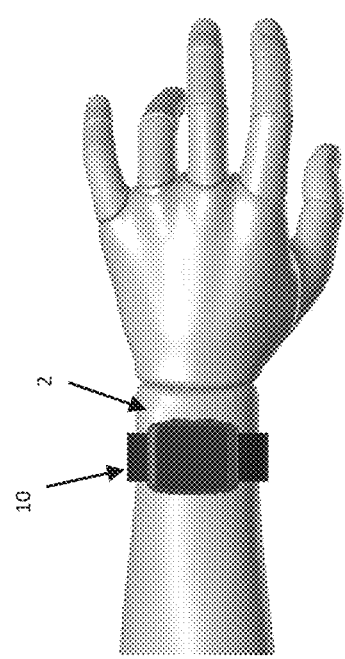
FIG. 1A illustrates a first view of an example wearable device including a physiological parameter measurement sensor or module worn on a wrist using straps.

Although certain aspects and examples are described below, those of skill in the art will appreciate that the disclosure extends beyond the specifically disclosed aspects and/or uses and obvious modifications and equivalents thereof based on the disclosure herein. Thus, it is intended that the scope of the disclosure herein disclosed should not be limited by any particular aspects described below.

Overview of Wearable Device Including a Physiological Parameter Measurement Sensor or Module Daily use of a wearable healthcare monitoring device, which can include oximetry- or plethmosmograph-based and/or ECG physiological parameters, can be beneficial to the wearer. The device, such as a device 10 as shown in FIGS. 1A-1H, can be a wristwatch incorporating a physiological parameter measurement sensor 100 or a wrist-worn physiological parameter measurement sensor with built-in watch or time-indicating functions. The device 10 can include an adjustable strap 30. Accordingly, the wearer needs not wear an additional sensor when going about daily activities and the appearance of the device attracts less attention from the general public so that the wearer may feel less self-conscious about wearing a pulse oximeter sensor on the wearer's body. The wearer can also connect additional sensors (for example, a fingertip plethysmograph sensor shown in FIG. 1C) and/or other physiological monitoring devices to the wearable device to expand the functionality of the wearable device.

The wearer can be informed of physiological parameters, such as vital signs including but not limited to heart rate (or pulse rate), and oxygen saturation by the wearable device 10. The device 10 can display one or more of the measured physiological parameters on its display 12. The information can be helpful in providing feedback to the wearer and/or a third party user, for example, a healthcare professional or the wearer's family member, when the wearer is exercising, or otherwise for warning the wearer of possible health-related conditions, including but not limited to changes in the wearer's physiological parameters in response to medication that is being administered to the wearer.

As shown in FIGS. 1A-1H, the wearable device 10 can be a watch, which can include a physiological parameter measurement sensor or module 100 configured to measure an indication of the wearer's physiological parameters, which can include, for example, pulse rate, respiration rate, oxygen saturation (SpO2), Pleth Variability Index (PVI), Perfusion Index (PI), Respiration from the pleth (RRp), hydration, glucose, blood pressure, and/or other parameters. The physiological parameter measurement sensor or module 100 can be an optical sensor. Additionally, the sensor or module 100 can optionally calculate a wellness index based on more than one individual physiological parameter measured by the module and/or received by the sensor or module 100 based on externally connected sensors and/or patient monitoring devices. The sensor or module 100 can perform intermittent and/or continuous monitoring of the measured parameters. The sensor or module 100 can additionally and/or alternatively perform a spot check of the measured parameters, for example, upon request by the wearer.

Figure 1E:
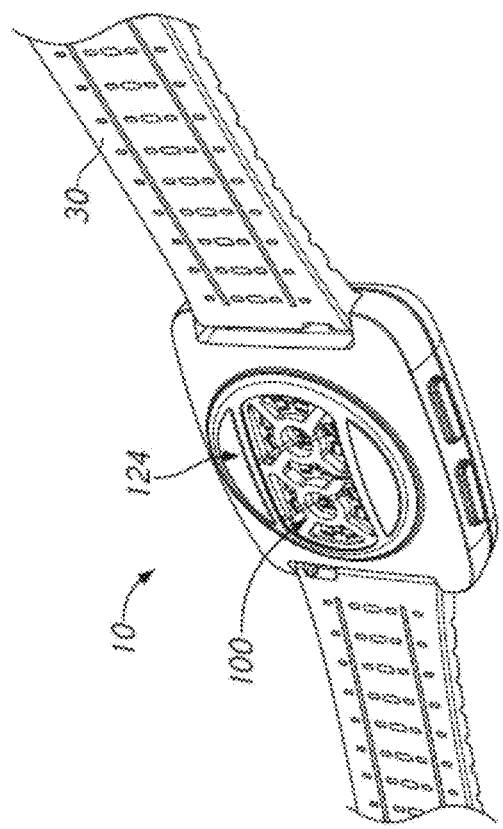
FIG. 1E illustrates a bottom perspective view of the example wearable device of FIG. 1D.
Figure 1D:
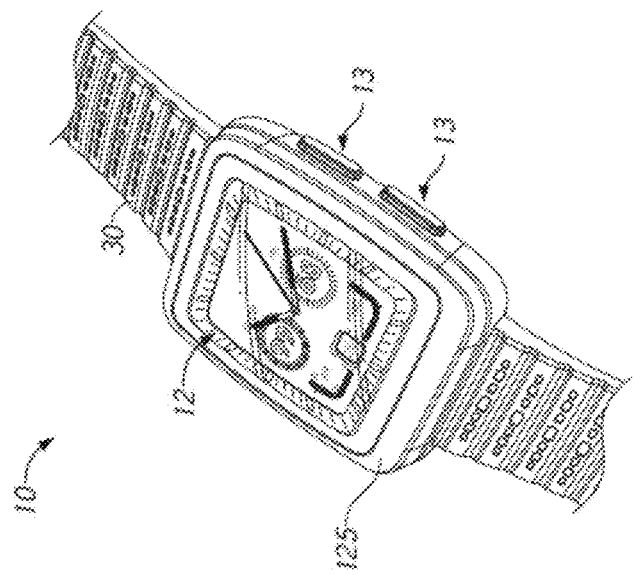
FIG. 1D illustrates a top perspective view of the example wearable device of FIGS. 1A-1C with a partial view of the straps.
Figure 1G:
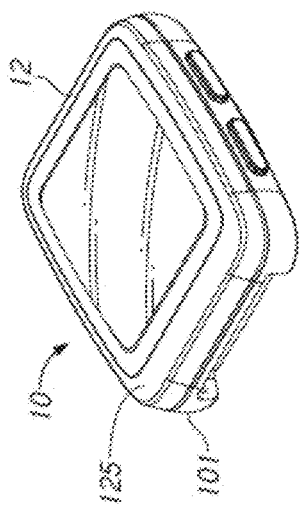
FIG. 1G illustrates a top perspective view of the example wearable device of FIG. 1F.
Figure 1H:
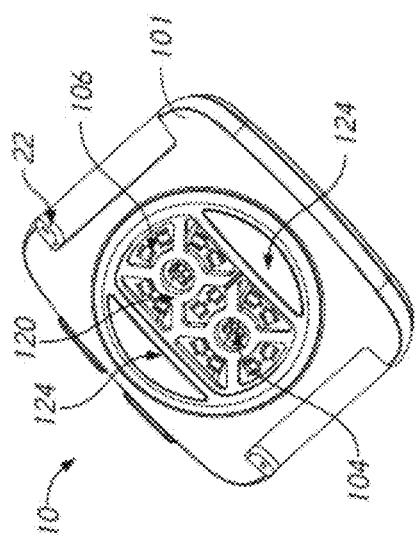
FIG. 1H illustrates a bottom perspective view of an example wearable device.
Figure 1F:
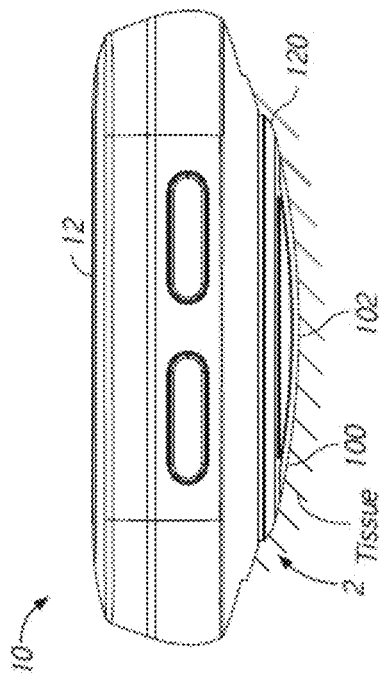
FIG. 1F illustrates a side view of an example wearable device without the straps when the device is interfacing with a wearer's skin.
Figure 11:
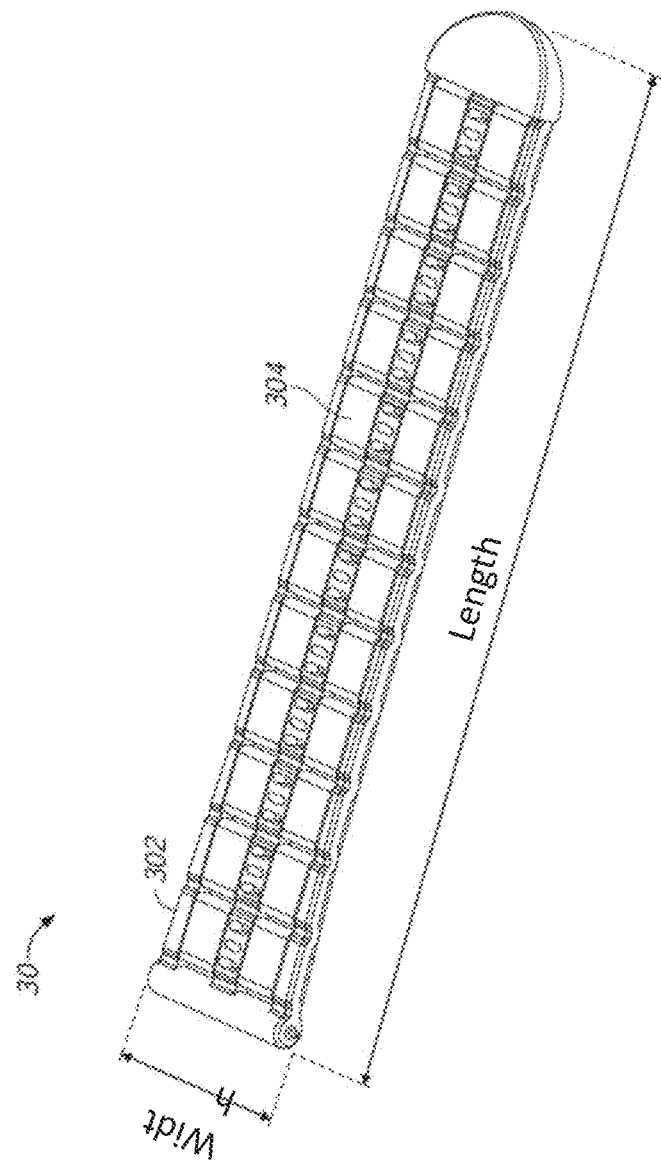
FIG. 11A illustrates a schematic system diagram of an example wearable device including a physiological parameter measurement module.
FIG. 11B illustrate a schematic diagram of an example device processor shown in FIG. 11A.
FIG. 11C illustrates a schematic system diagram of an example sensor or module processor shown in FIG. 11A.
FIG. 11D illustrates a block diagram of an example front end circuitry of the sensor or module processor of FIG. 11C.

As shown in FIGS. 1E and 1H, a bottom side of a device (or watch) housing 101 can include an opening sized to retain the physiological parameter measurement module 100 while still allowing the tissue-facing surface of the sensor or module 100 to be exposed. The retaining of the sensor or module 100 in the device housing 101 can be aided by any suitable retaining mechanisms. As shown in FIGS. 1F and 1H, the physiological parameter measurement module 100 can include a skin-interfacing light transmissive cover 102 that encloses a plurality of light emitters 104 (such as LEDs) and one or more photodetectors (also referred to as "detectors") 106. Additionally, the sensor or module 100 can optionally include an electrocardiogram (ECG) sensor, which can include a plurality of ECG electrodes 124, 125. As shown in FIGS. 1G and 1H, some of the ECG electrodes 125 can be located away from the sensor or module 100 and some of the ECG electrodes 124 can be located on the sensor or module 100. The cover 102 can include a plurality of lenses or covers or a single construct of lens or cover. The physiological parameter measurement module 100 is designed to reduce noise in the signals detected by the detectors 106, for example, by reducing mixing of the emitted light and the reflected light using light barriers that are substantially opaque. As shown in FIG. 1F, the light barrier 120 can include a first light barrier which can be placed between the emitters and the detectors of the sensor or module 100. The first light barrier can extend (for example, entirely extend) along an inner portion of the cover 102. The first light barrier can also suppress light emitted by the emitters at an angle. The sensor or module 100 can include additional light barriers, including for example, a side perimeter wall and additional light barriers to separate the detectors from the emitters, and/or separate different detector groups from one another.

FIG. 1F illustrates the device 10 being worn on the wrist 2 of the wearer, with the physiological parameter measurement module 100 facing the wrist 2. The physiological parameter measurement module 100 on the device 10 is designed so as to reduce and/or eliminate a gap between a surface of the physiological parameter measurement module 100 and the wearer's skin at the measurement site where the device 10 is worn. At the wrist, if the device 10 is worn too loosely (which can be the case when the device 10 is able to slide over the skin when the device 10 is moved), the gap between the tissue-facing surface of the physiological parameter measurement module 100 and the wearer's skin can cause inaccurate measurements. This is because the gap can result in both light-piping and in the emitted light not penetrating deep enough into the wearer's tissue, for example, by going no deeper than within a top skin layer (for example, the epidermis) of the wearer's tissue, which typically does not have any blood vessels present. Therefore, light cannot reach and or interact with tissues, such as the arterial blood in the dermis, located below the top skin layer. The gap can also result in loss of the attenuated and reflected light through the gap so that less of the attenuated and reflected light can arrive at the detectors 106.

The tightness of the device 10 on the wearer's body (for example, the wrist) can be adjusted by adjusting any suitable strap(s) 30 used to secure the device to the wearer's body. The strap(s) can be connected to the device 10 using any suitable strap connections 22. For example, the strap connections 22 can be compatible with third party watch bands, wearable blood pressure monitors, and/or the like. As shown in FIG. 1I, an example strap 30 can be stretchable and evenly distribute the pressure of the device 10 around the wrist so as to provide better contact between the sensor or module 100 and the wrist 2 while not compromising the comfort of the wearer and/or reducing the blood flow across the wrist 2 in a way that reduces the accuracy of the measurement by the sensor or module 100. As shown in FIG. 1L, a rubber base 302 can be molded through a plurality of metal loops 304 arranged along a length of a strap 30 to form the strap 30. The metal loops 304 can include a thin (for example, less than about 1 mm) wall of metal forming a closed loop with a through-hole in a direction generally transverse to the length (that is, along a width) of the strap 30 and perpendicular to a thickness of the strap 30. During the overmolding process, the rubber material can fill up or substantially fill up the space in the through-hole. The metal loops 304 can be arranged in two rows along the length of the strap 30. Alternatively, the metal loops can include a partial loop with an opening, or the strap may include more than one partial metal loop snapped onto each other around the rubber base. Additional details of the strap 30 are described in U.S. Provisional Application No. 63/068,256, filed Aug. 20, 2020 and titled "WEARABLE PHYSIOLOGICAL MONITORING DEVICE WITH ADJUSTABLE STRAPS", the entirety of which is incorporated herein by reference.

Additionally, the gap between a surface of the physiological parameter measurement module 100 and the wearer's skin at the measurement site can be reduced by the design of the light transmissive cover 102. As shown in FIG. 1F, a cover 102 of the physiological parameter measurement module 100 can include a convex curvature or convex protrusion on its skin-interfacing cover 102. As will be described in greater detail below, the curvature of the cover 102 of the sensor or module 100, which can include a plurality of lenses or covers or a single lens or cover, can be discontinuous or continuous.

As shown in FIG. 1F, when the device 10 is worn by the wearer, the convex cover 102 can be pressed onto the skin and the tissue 2 of the wearer can conform around the convex curvature. The contact between the convex cover 102 and the tissue 2 of the wearer can leave no air gaps between the tissue 2 and the convex cover 102. And as the emitters and/or detectors can be surrounded by a light-diffusing material (as will be described below), the physiological parameter measurement module 100 may leave no air gap between the tissue 2 and any of the emitters and/or detectors. Optionally, certain portion(s) of the cover 102 can protrude more into the skin than the remainder of the cover. The pressure exerted by the curvature of the cover 102 on the skin and/or the absence of air gap can increase a light illuminated and/or detection area, improve the optical coupling of the emitted light and the blood vessels and/or of the reflected light and the detectors, reduce light piping, and/or reduce stagnation of the blood. The cover curvature can be configured so as to balance the pressure needed to improve contact between the cover 102 and the skin, and the comfort of the wearer.

Figure 1J:
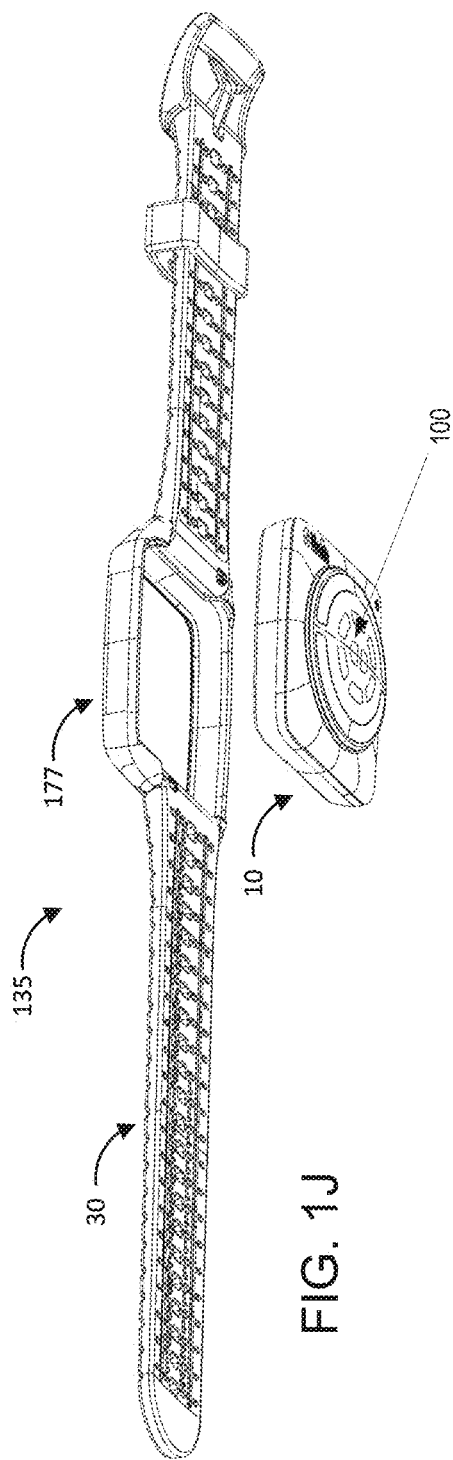
FIGS. 1J-1K illustrate perspective views of an example wearable device and physiological sensor or module removably secured to a wearable apparatus.
Figure 1K:
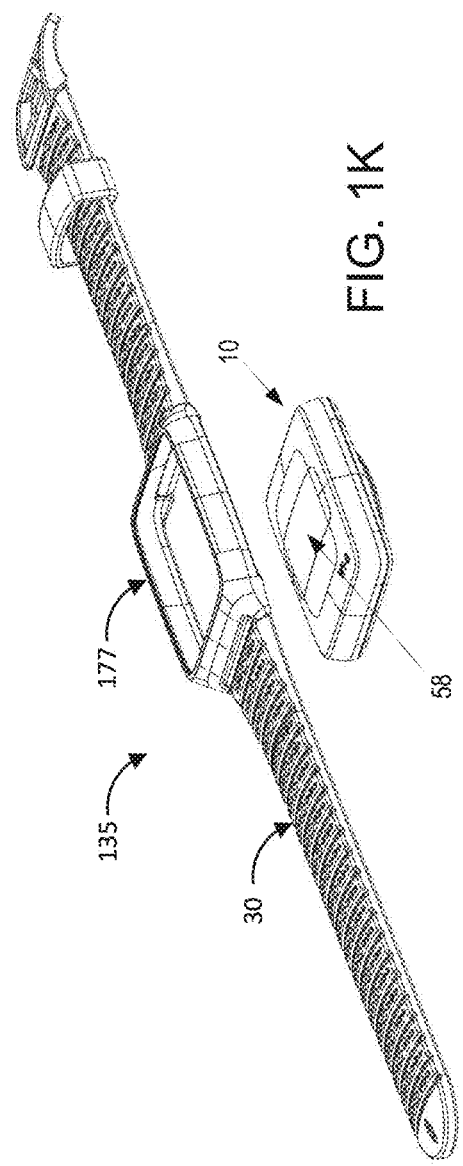

FIGS. 1J-1K illustrate perspective views of an example wearable device 10 removably secured to a wearable apparatus 135. The wearable apparatus 135 includes one or more straps 30 and a frame 177. The wearable device 10 may include a physiological sensor or module 100 and an electrode 58. The electrode may be a positive electrode. In some aspects, the wearable device 10 may include a screen or display. In some aspects, the wearable device 10 may not include a screen or display.

The device 10 may be removably secured to the frame 177. The frame 177 may hold the device 10 within the frame 177 via force-fit, friction-fit, snap-fit, or the like. The straps 30 may secure the apparatus 135 to a body part of a wearer. The wearable apparatus 135 may be configured to hold the wearable device 10 (e.g., the sensor or module 100) in contact with the skin of a wearer when the device 10 is secured within the frame 177 and the wearable apparatus 135 is secured to the body of a wearer. The wearable apparatus 135 (e.g., straps 30) may be sized and/or shaped to secure to a wrist of a wearer. In some aspects, the wearable apparatus 135 (e.g., straps 30) may be sized and/or shaped to secure to other portions of a wearer's body, including an ankle, a leg, an arm, a finger, a chest, a torso, a stomach, a back, a neck, a head, a forehead, as non-limiting examples.

Figure 2:
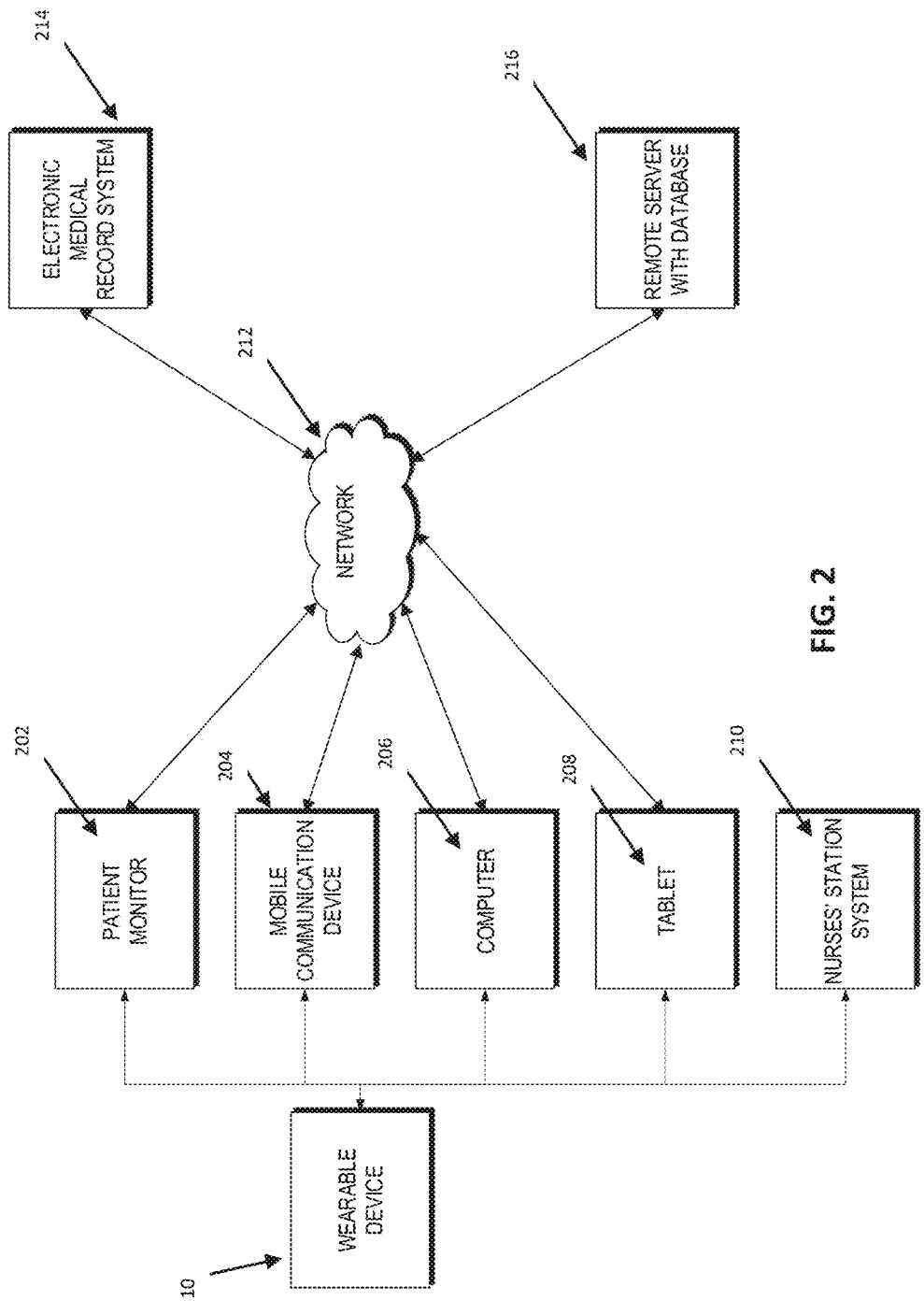
FIG. 2 is a diagram illustrating schematically a network of non-limiting examples of devices that can communicate with the wearable device disclosed herein.

The wearable device 10 can be used in a standalone manner and/or in combination with other devices and/or sensors. As shown in FIG. 2, the device 10 can connect (for example, wirelessly) with a plurality of devices, including but not limited to a patient monitor 202 (for example, a bedside monitor such as Masimo's Radical7®, Rad97® (optionally with noninvasive blood pressure or NomoLine capnography), and Rad8® bedside monitors, a patient monitoring and connectivity hub such as Masimo's Root® Platform, any handheld patient monitoring devices, and any other wearable patient monitoring devices), a mobile communication device 204 (for example, a smartphone), a computer 206 (which can be a laptop or a desktop), a tablet 208, a nurses' station system 201, glasses such as smart glasses configured to display images on a surface of the glasses and/or the like. The wireless connection can be based on Bluetooth technology, near-field communication (NFC) technology, and/or the like. Additionally, the wearable device 10 can connect to a computing network 212 (for example, via any of the connected devices disclosed herein, or directly). The network 212 may comprise a local area network (LAN), a personal area network (PAN) a metropolitan area network (MAN), a wide area network (WAN) or the like, and may allow geographically dispersed devices, systems, databases, servers and the like to connect (e.g., wirelessly) and to communicate (e.g., transfer data) with each other. The wearable device 10 can establish connection via the network 212 to one or more electronic medical record system 214, a remote server with a database 216, and/or the like.

Optionally, the device 10 can be integrated with more sensors and/or configured to connect to a plurality of external sensors, wirelessly or with a connecting cable. The connecting cable can be a universal connector configured to connect to any of the medical devices and/or sensors disclosed herein to provide communication between the wearable device 10 and the connected medical devices and/or sensors. The cable can optionally include a board-in-cable device that includes its own processor, but may not include its own display.

The device 10 can act as hub for the external sensors, for example, the sensors described in U.S. Patent Publication No. 2020/0138288, published on May 7, 2020 (the entirety of which is hereby incorporated herein by reference). The sensors described in U.S. Patent Publication No. 2020/0138288 can collect patient physiological data and provide power for a reusable pairing device. The reusable pairing device can establish wireless communication with a patient monitoring device. The wearable device 10 can replace the patient monitoring device in U.S. Patent Publication No. 2020/0138288. As another example, the device 10 can replace a patient monitor device described in U.S. Patent Publication No. 2020/0329993, published on Oct. 22, 2020, the entirety of which is hereby incorporated herein by reference. By replacing the patient monitor device in U.S. Patent Publication No. 2020/0329993, the wearable device 10 performs all the computations based on the sensor data so that the connected external sensors, for example, the ECG sensors disclosed in U.S. Patent Publication No. 2020/0329993, do not require heavy computing power.

The device 10 can include open architecture to allow connection of third party wireless sensor, and/or allow third party access to a plurality of sensors on the wearable device 10 or connected to the wearable device 10. The plurality of sensors can include, for example, a temperature sensor, an altimeter, a gyroscope, an accelerometer, emitters, LEDs, etc. Third party applications can be installed on the wearable device 10 and can use data from one or more of the sensors on the wearable device 10 and/or in electrical communication with the wearable device.

Optionally, the wearable device 10 can communicate with any other suitable noninvasive sensor, such as an acoustic sensor, a blood pressure sensor, temperature sensor, movement sensor, ECG sensor, etc. Examples of some of these devices include Masimo's Radius PPG™ sensor, Radius T™ sensor, and Centroid™ sensor, or otherwise. One or more of those sensors, for example, the Centroid™ sensor, can be used for stroke detection. The wearable device 10 can output an alert of stroke detection of the wearer and/or automatically initiate communication with a first respondent and/or the wearer's guardian or next-of-kin upon stroke detection.

The wearable device 10 can optionally communicate with chemical sensors, which can detect, for example, chemicals on the wearer's skin, and/or sweat, and/or the odor of certain chemicals in the air. The chemical sensors can include electrochemical sensors or any other suitable types of chemical sensors. A chemical sensor configured to analyze compositions of sweat can output measurements aiding the wearable device 10 in detecting stress and/or the wearer's hydration status. The wearable device 10 can optionally communicate with a skin impedance sensor, which can be used for monitoring the hydration status of the wearer.

Another example sensor that can be integrated into or connected to the device 10 and/or the sensor or module 100 can include a toxin and/or radiation detector configured to detect toxins in air (for example, pollution or contaminant particulates, carbon monoxide, smoke, and the like in the air). The toxin detection can aid care providers and/or firefighters who wear the device 10. Alternatively, the device 10 can be connected wirelessly to an external toxin and/or radiation detector. The toxin and/or radiation detector can be used with a smart mask. For example, the external toxin and/or radiation detector can be located on the mask, which can allow the mask to output a warning to the wearer of the mask when the mask filter or cartridge needs replacement.

Optionally, the wearable device 10 can communicate with glucose monitors, which can be invasive or minimally invasive such as finger prick type of glucose monitors, or a continuous noninvasive glucose monitor. The wearable device 10 can receive and display the wearer's glucose level from the glucose monitor. The wearable device 10 can also optionally be in communication with an insulin pump. The wearable device 10 can send a control signal to dispense insulin from the insulin pump to the wearer based on the monitored glucose level of the wearer.

Figure 3:
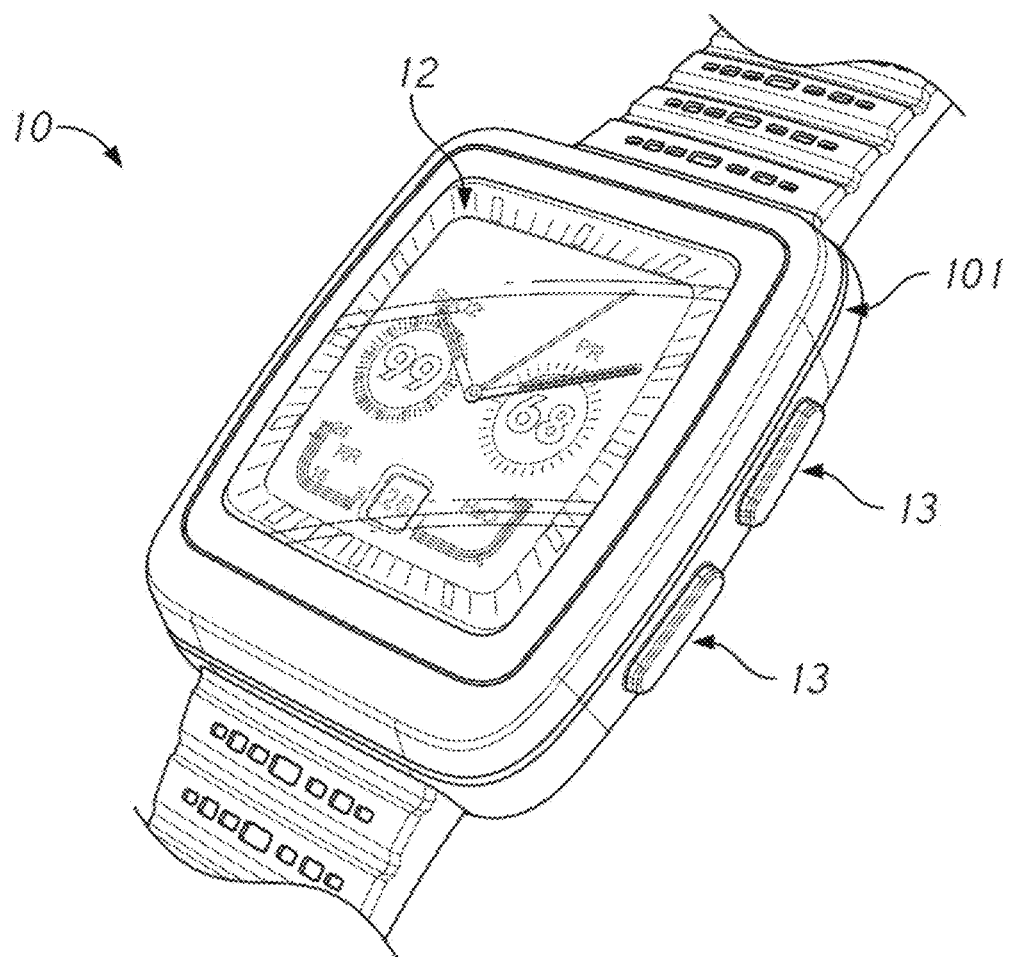
FIG. 3 illustrates an example display of physiological parameter measurements on the wearable device disclosed herein.
Figure 5B:
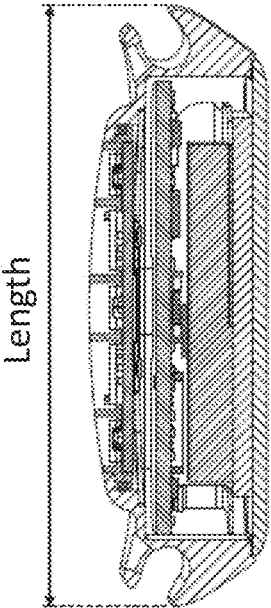
FIG. 5B illustrates a cross-sectional view of the example wearable device of FIG. 5A.
Figure 5D:
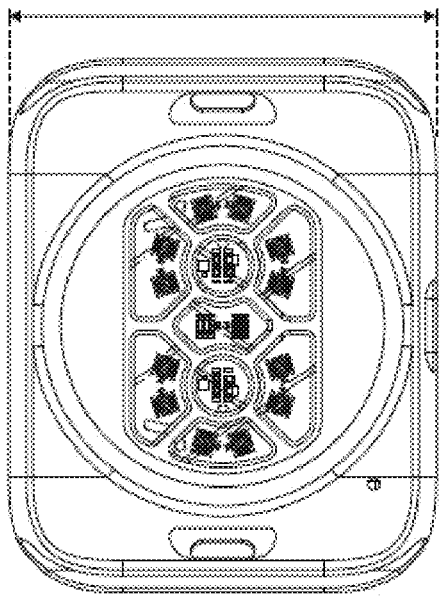
FIG. 5D illustrates a bottom view of the wearable device of FIG. 5A.
Figure 5A:
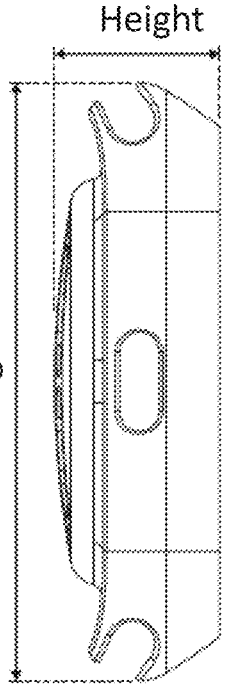
FIG. 5A illustrates a side view of an example wearable device incorporating an example physiological parameter measurement module.
Figure 5C:
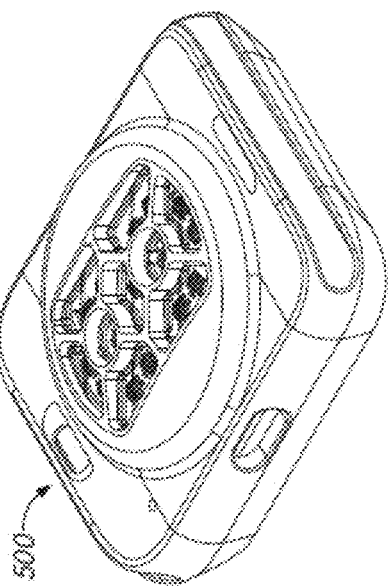
FIG. 5C illustrates a perspective view of the wearable device of FIG. 5A.

As shown in FIG. 3, the device 10 can include a display screen 12 positioned at a top side of the device housing 101. In addition to time and date indicators, one display layout (for example, the default display layout) of the display screen 12 can display the wearer's SpO2 measurement, the pulse rate (PR) measurement, the respiration rate (RR) measurement, and/or hydration status (H2O). The format of the measurement displayed is not limiting. For example, some measurements, such as the SpO2 measurement and the PR measurements, can be displayed as numerical values. As another example, some measurements, such as the RR measurements and hydration status, can be displayed as a sliding scale. In the illustrated example, the hydration status can be displayed as having three levels from low (L) to high (H). In the illustrated example, the respiration rate can be displayed as ranging from 5 bpm to 25 bpm. The wearer can optionally view individual display layouts for each measurements or a group of measurements by tapping on the display screen 12, which can be a touch screen, and/or pressing a button on the device 10. Each of the measurements can be displayed constantly, at certain intervals, and/or upon receiving instructions for display (for example, by the wearer tapping on the display screen 12 and/or pressing a button on the device 10). Each of the measurements can be configured to be displayed with different or the same frequencies. Time and certain physiological parameters (for example, SpO2 and pulse rate) can be immediately and/or intermittently available, and/or continuously measured (for example, at least every 5 to 10 measurements per minute or more) and the displayed values constantly updated. Optionally, the display can further show a trend line for some parameters, such as SpO2 and pulse rate. In one example, the display of the wearable device can be configured to display only time, SpO2, and pulse rate.

As shown in FIG. 4, the physiological parameter measurement module 100 can be preassembled before being integrated into the device 10. The physiological parameter measurement module 100 can be characterized before being assembled with the rest of the device 10. The preassembled physiological parameter measurement module 100 can be secured within the device housing 101 using various mechanical assembly mechanisms, for example, one or more screws or other fasteners. The sensor or module 100 of a wearable device 10 can be interchangeable and be replaced without replacing the memory in the device 10. For example, the sensor or module 100 can include a quick-connect (and/or quick-release) feature for attaching the sensor or module 100 to the remainder of the device 10, such as being attachable to the device 10 by magnets. An electrical connection can be established between the physiological parameter measurement sensor or module processor board and the circuit of the rest of the device 10, including for example, a device processor and the display 12. Optionally, the electrical connection can include a connector 32 on the sensor or module 100. The connector 32 is configured to be electrically connected to a flex circuit. The wearable device 10 and the sensor or module 100 are portable and can be moved from place to place. As described above, the functionality of the wearable device 10 can be integrated and/or interchangeable with various other patient monitoring devices, displays, etc.

The sensor or module 100 can be applied to locations on the body other than the wrist. Alternatively or additionally, multiple modules 100 can be applied to different locations of the body of the wearer. Other types of straps or fastening mechanism may be used to attach the multiple modules 100 onto other parts of the body. The other types of straps or fastening mechanism can optionally include a power source (for example, battery) to power a module 100 that is not integrated into the wearable device 10, but may not have its own display. For example, an optical sensor can be placed on the wearer's neck to measure arterial and venous oxygen saturation, which can be transmitted to and displayed on the wearable device 10. The wearer can view his or her oxygen consumption information on the wearable device 10 based on the signals from the optical sensor on the neck and/or the signals from the sensor or module 100 that is located on the wearable device 10.

As shown in FIGS. 5A-5D, an example wearable device 500 can include a watch housing 501. Features of the device 500 can be incorporated into features of the device 10 and features of the device 10 can be incorporated into features of the device 500. The watch housing 501 can have a length, for example, between about 40 mm and 50 mm, or between about 42 mm and 46 mm. The watch housing can have a width, for example, between about 32 mm to about 40 mm, or between about 35 mm to about 38 mm. When fully assembled, the watch 500 can have a thickness or height, for example, between 10 mm to about 15 mm, or between 12 mm to about 14 mm.

Figure 6:
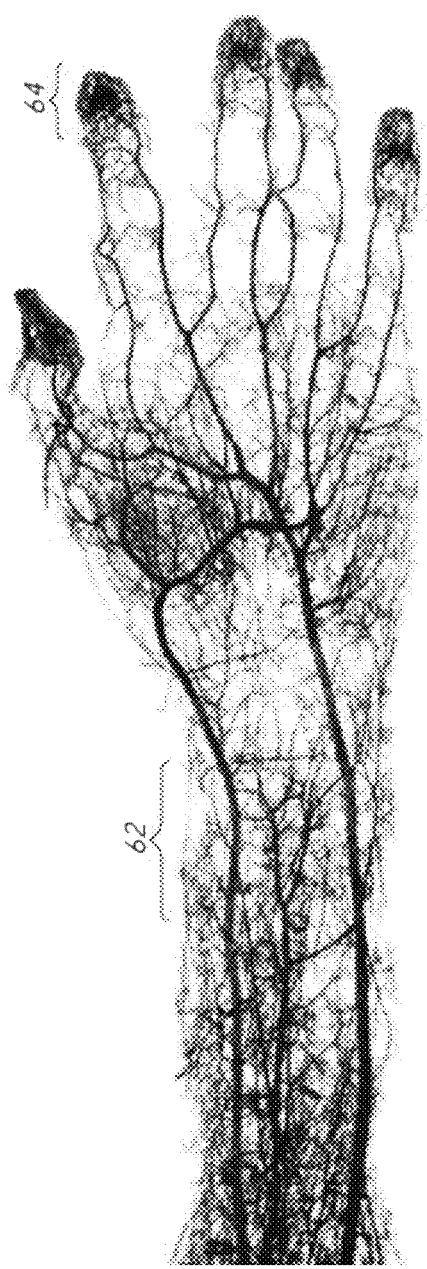
FIG. 6 illustrates schematically arteries and capillaries of a human hand and a proximal portion of a human forearm.

As described above, the physiological parameter measurement module can include a plurality of emitters and a plurality of detectors. The emitters can transmit optical radiation of a plurality of wavelengths into a tissue site (near the wrist of the wearer) and the detectors can respond to the intensity of the optical radiation (which can be reflected from the tissue site) after absorption by pulsatile arterial blood flowing within the tissue site. In addition to the light being attenuated by blood in the arteries, light interaction also happens at the capillary level. Arteries are located deeper below the skin surface than the capillaries, requiring LED emitters of greater light intensity and thus greater power consumption in order for the emitted light to reach the arteries. Moreover, measuring the light intensities signal of the light after attenuation by blood in the artery requires more selective placement of the emitters and detectors directly above the arteries to capture the pulsation of the blood. The physiological parameter measurement module disclosed herein is designed to utilize attenuation by blood in the capillaries and is not reliant on the blood flow in arteries. The patient parameter measurements made by the module disclosed herein can be accurate enough for clinical use. The module disclosed herein can provide plethysmograph-based patient parameter measurements with an accuracy of within about 4% error, or about 2% error. As shown in FIG. 6, the wrist 62 has fewer capillaries per volume than the fingertip 64. Accordingly, the module is designed to have a width to provide greater coverage area of the wearer's wrist, which can boost the signal from the sensors located on the module (which will be described in greater detail below).

When measuring oxygen saturation based on attenuation by blood in the capillaries, it is desirable to avoid veins. Because venous blood contains less oxygen, intensity signals of light attenuated by venous blood can cause errant readings oxygen saturation measurement. Optionally, the sensor or module processor of the physiological parameter measurement modules disclosed herein can reduce the effect of pulsing vein on the signal by comparing the signals from the plurality of detectors to determine which detectors receive better and/or clearer signals and deactivating the detectors that are more likely to cover and/or be around the pulsing veins. The sensor or module processor can dynamically adjust which detectors to deactivate. Deactivating the detectors can include deactivating operation of that detector and/or ignoring signals from that detector.

Optionally, the sensor or module processor of the physiological parameter measurement module can map the physiological parameter measurements calculated from signals received at the detectors and/or clusters of detectors located at different regions of the module. Variations (for example, if outside a certain range) in the mapped measurements can be an indication that the pressure distribution of the wearable device on the body of the wearer is unbalanced, and therefore the pressure of the device on the wearer is either too high or too low and/or the wearable device is tilted on the wrist. The wearable device can output an instruction to the wearer to readjust the tightness of the straps and/or to re-center of the wearable device on the wrist. Variations (for example, if outside a certain range) in the mapped measurements can additionally or alternatively provide an indication that a certain detector or cluster of detectors is/are placed over a large pulsing vein as described above. Readings from that certain detector or cluster of detectors can be ignored or the detector(s) suspected to be cover a pulsing vein may be deactivated. When two or more physiological parameter measurements, such as oxygen saturation measurements, do not agree among two or more detectors (for example, having a variation exceeding a certain range), the sensor or module processor can use the higher or highest measurement value, or alternatively use a combination of the measurement values from the two or more detectors (for example, using one of the two measurement values at different times or otherwise).

Alternatively or additionally, the mapped measurements can be compared with experimentally determined data at the same detector location or detector cluster location. The experimentally determined data can be obtained using, for example, a conventional reflectance type pulse oximeter taped over the corresponding detector location, or any other suitable known methods for making the same measurements, including the same wrist-based sensor arrangements described herein. The comparison between the mapped measurements and the experimentally determined data can provide indication of whether the device has achieved a desired pressure on the body of the wearer, whether certain detectors and/or clusters of detectors are placed over or near a pulsing vein, which may interfere with the physiological parameter measurements, or otherwise. For example, if the difference between the mapped measurements and the experimental data at a certain location falls outside a predetermined range, the sensor or module processor can determine that pressure is too high or too low at that location, and/or that the pressure distribution over the body is not sufficiently balanced to make accurate measurements, and/or a detector or cluster of detectors is/are placed over the wearer's pulsing vein. The experimental data can be stored in a memory device of the sensor or module processor.

The comparison among the mapped measurements and/or between the mapped measurements and the experimental data can be performed when the wearer first puts on the device and/or at certain time intervals in the duration when the device is worn on the wearer. Additionally, running the comparison-based diagnostics can allow the sensor or module processor to determine, at the start of the measurement and/or dynamically during use of the device, which detector(s) provide the most accurate and/or reliable measurements.

Various Example Components of the Wearable Device

Figure 7A:
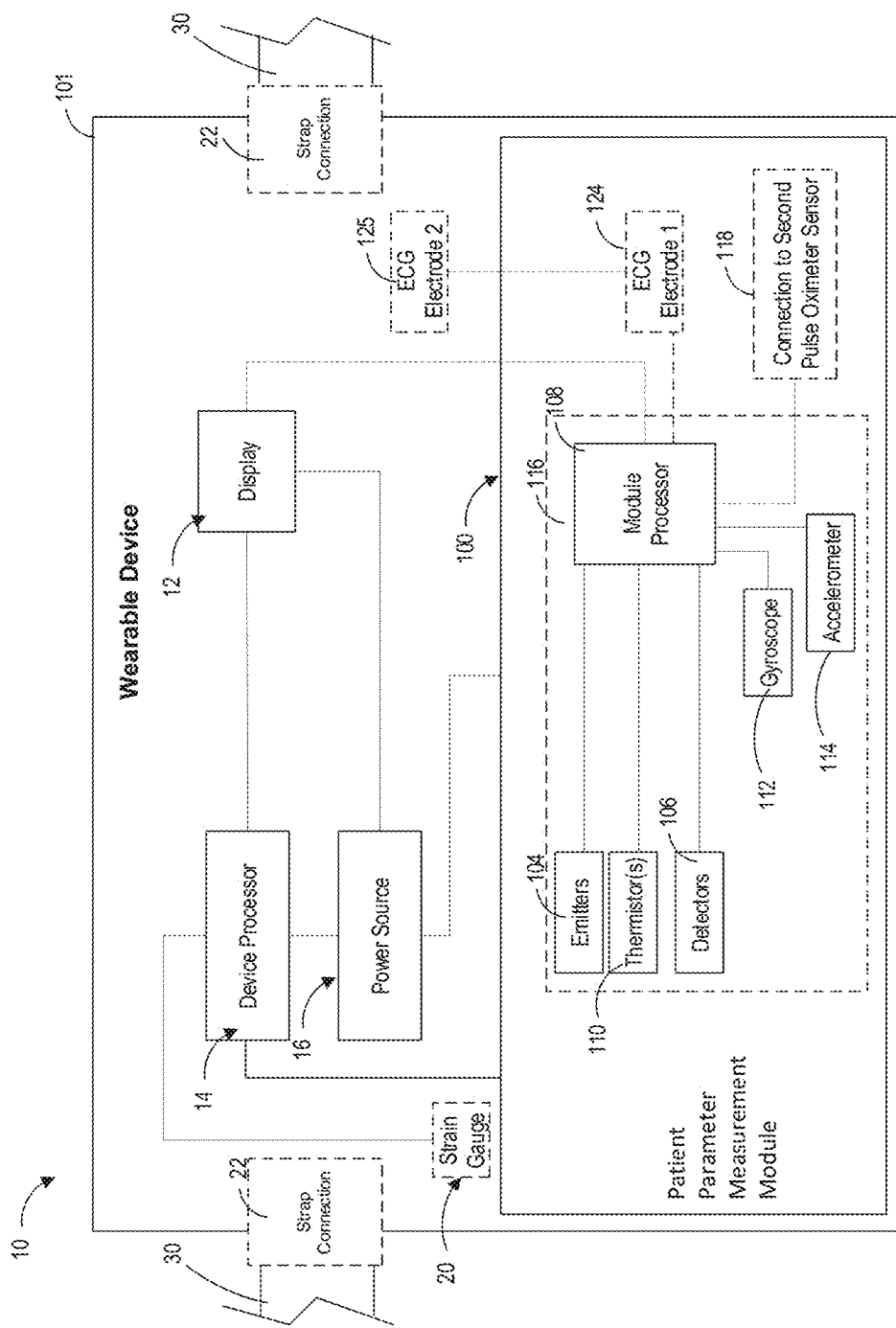
FIG. 7A illustrates a schematic system diagram of a wearable device including a physiological parameter measurement module.
Figure 7B:
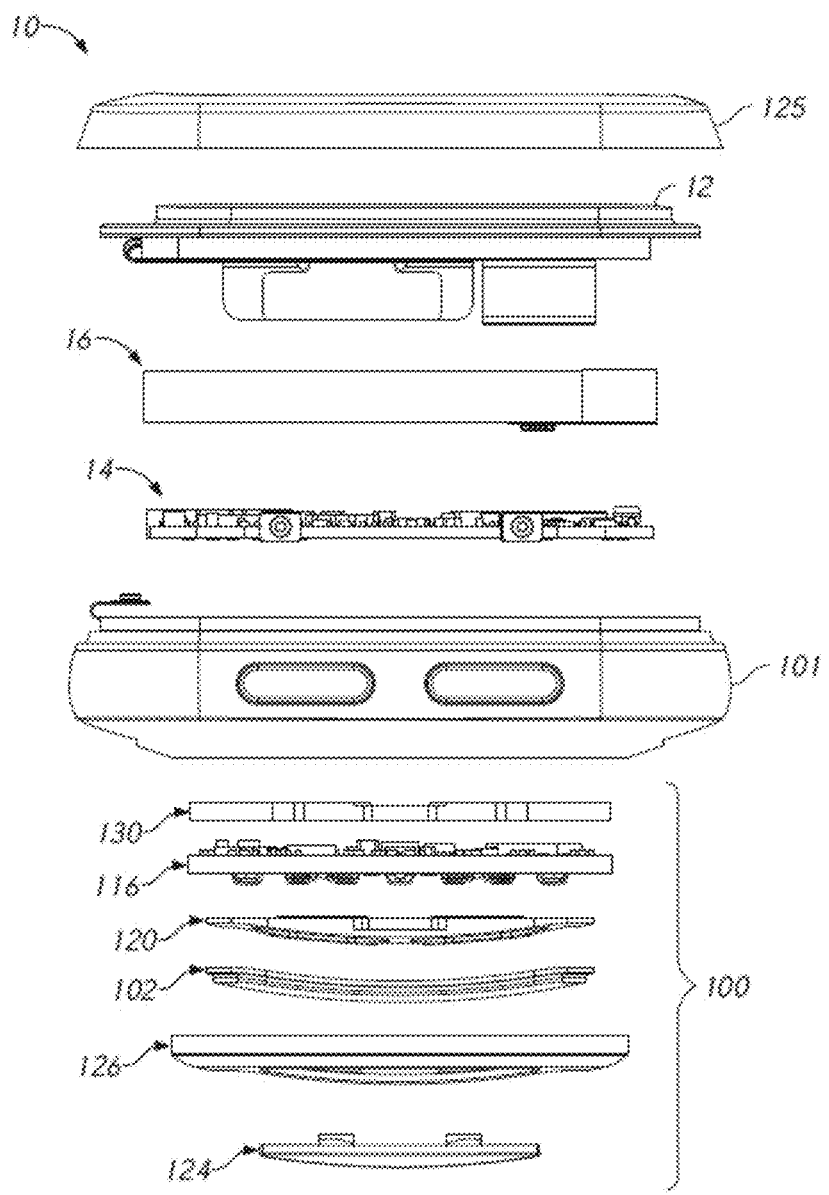
FIG. 7B illustrates a partially exploded view of an example wearable device.
Figure 7E:
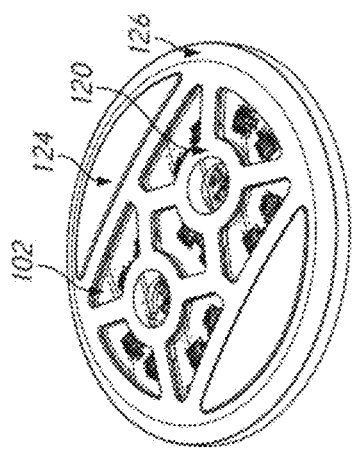
FIG. 7E illustrates a bottom perspective view of a physiological parameter measurement module incorporating the ECG electrodes, light transmissive cover(s), and a opaque frame of FIG. 7C or 7D.
Figure 7F:
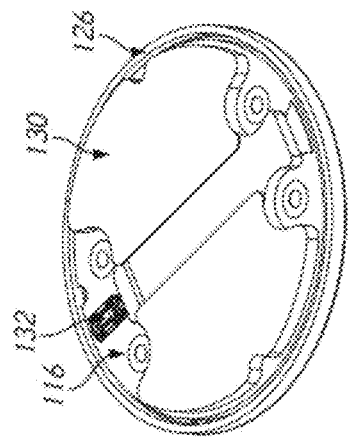
FIG. 7F illustrates a top perspective view of the example physiological parameter measurement module of FIG. 7E.

Components of the wearable device will now be described. As shown in FIGS. 7A and 7B, the device 10 can include its own device processor 14, which can be a digital/analog chip or other processor(s), such as a digital watch processor or a smartwatch processor. As shown in FIGS. 7B, 7G, and 7H, the device processor 14 can be located on a PCB. FIGS. 7G and 7H illustrate example layouts of the PCB for the device processor 14. As shown in FIGS. 7A and 7B, the device 10 can include a power source 16, which can be a battery, for powering the device processor 14, the display screen 12, and/or the physiological parameter measurement module 100. The battery 16 can last at least 10 hours, or at least 12 hours, or at least 14 hours, or at least about 16 hours after each charge, with continuous measurements and/or displaying of certain physiological parameters, such as SpO2 and pulse rate.

The device 10 can be configured to display time after the battery 16 has been depleted, even if other features (for example, measuring physiological parameters using the module) may not be available when the battery 16 has been depleted. Additionally, when the device 10 is used clinically, the display 12 can also continue displaying critical patient information (for example, the patient's name, date of admission, etc.) after the battery 16 has been depleted. The device 10 may include nonvolatile memory to store the critical patient information. The device 10 can include a dual-battery configuration with a main battery and a backup battery. Power management of the device 10 may switch automatically for the device 10 to be powered by the backup battery when the main battery has been depleted. The device can additionally or alternatively be configured to be solar-powered, for example, by including a solar panel on the dial or elsewhere of the wearable device 10. The display 12 of the device 10 can use e-ink or ULP (ultra low power screen) technology, which draws little amount of current for displaying information. The display 12 may automatically adjust the brightness, being brighter when outdoors and dimmer when indoors to further prolong battery life.

Figure 11A:
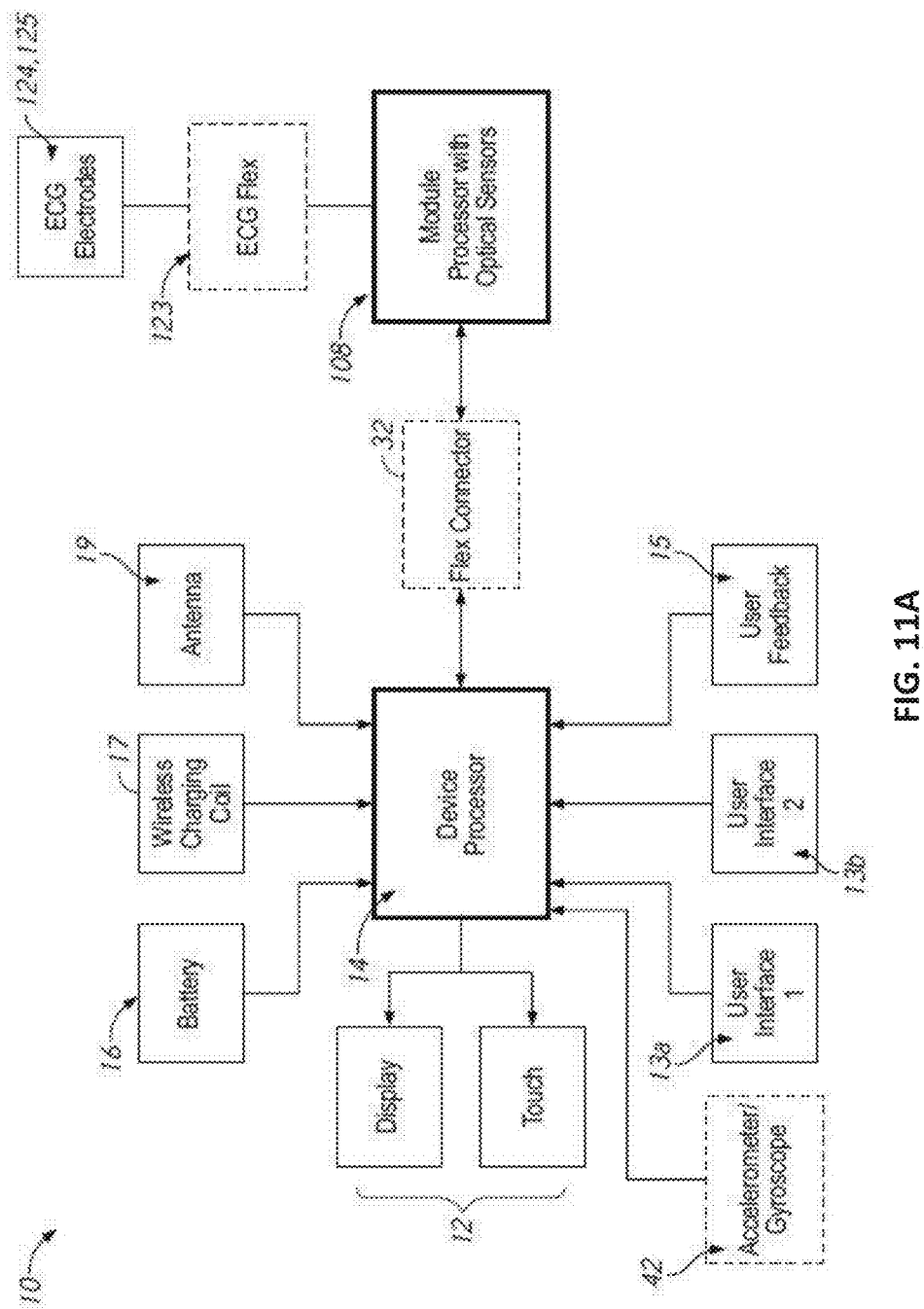
Figure 11B:
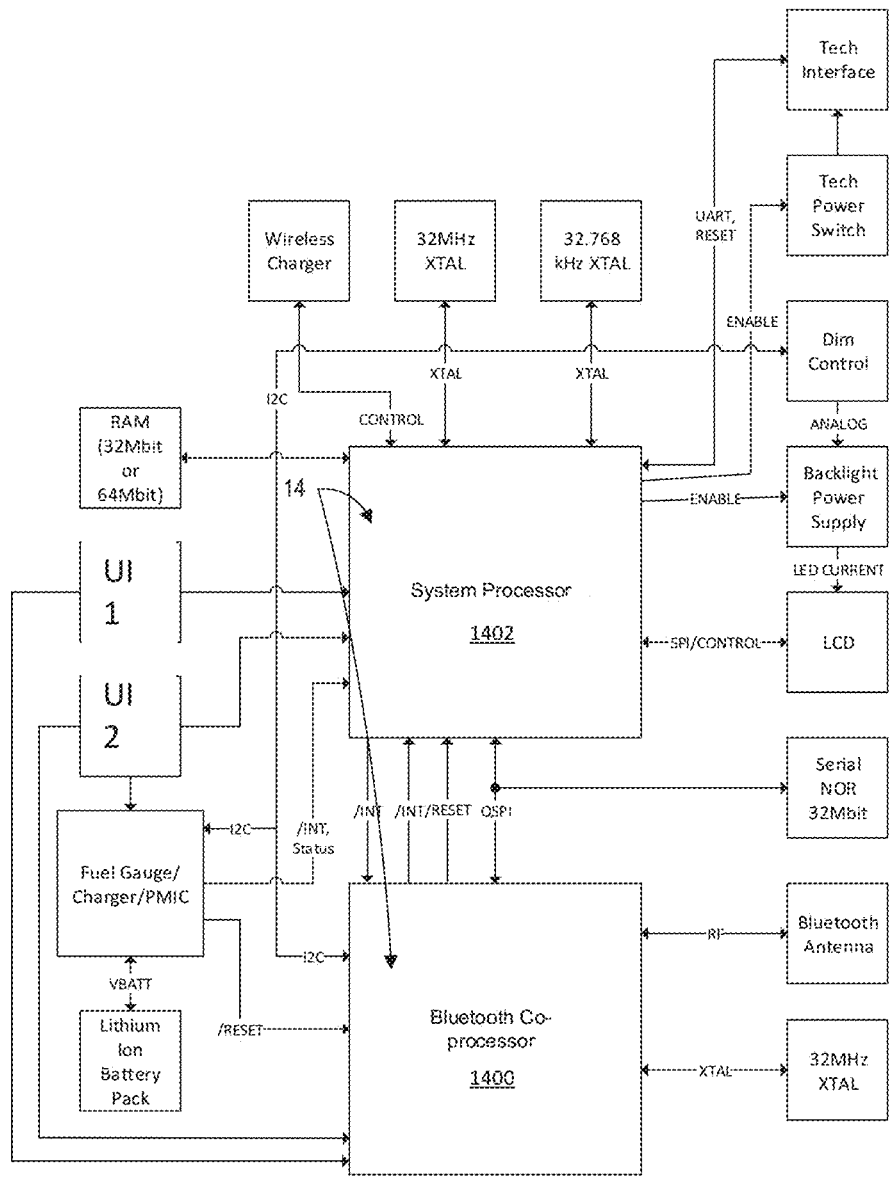
Figure 11C:
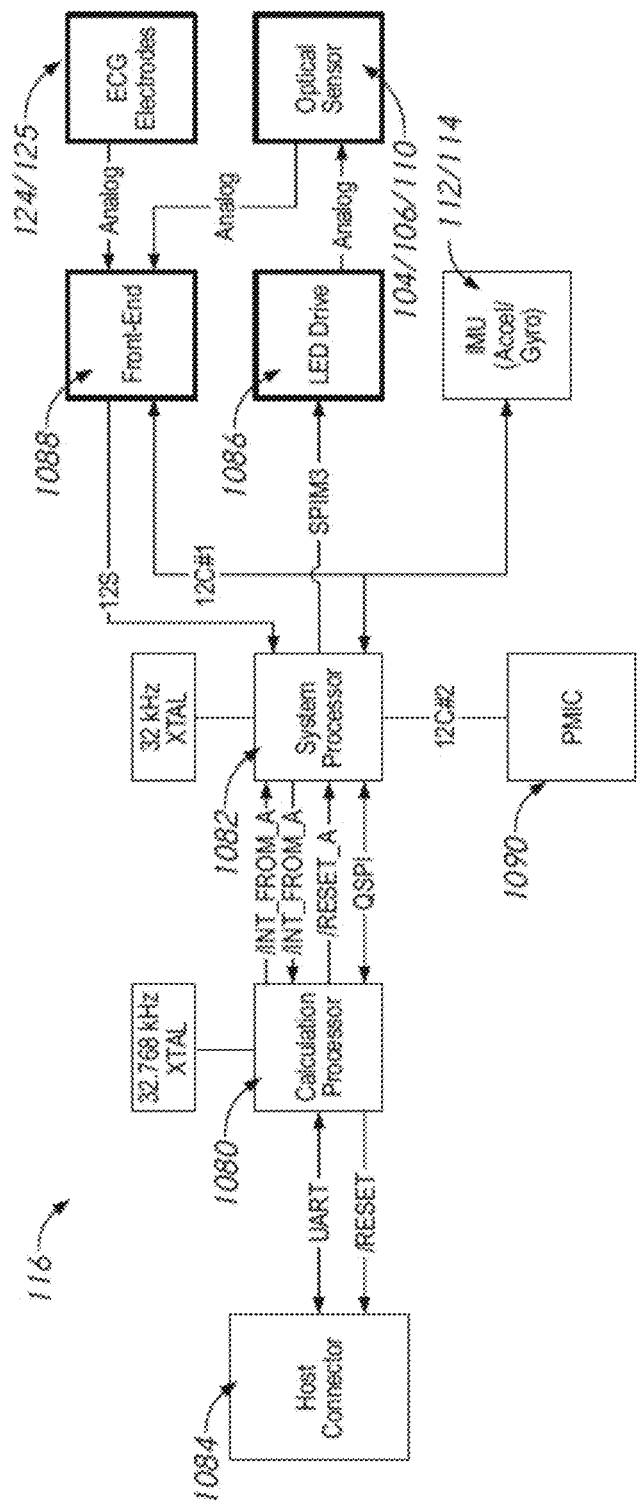

As shown in FIGS. 7A and 7B, the sensor or module 100 of the wearable device 10 can include a sensor or module processor 108 (which can include a memory and/or other electronics, such as shown in FIG. 11C). The sensor or module processor 108 can process signals from one or more of the sensors in the sensor or module 100 (or optionally other sensors in communication with the device 10) to determine a plurality of physiological parameters. All the processing of the raw sensor data of the sensors in communication (via a wired and/or wireless connection) with the sensor or module processor 108 is performed by the sensor or module processor 108. The sensor or module processor 108 can be configured to drive the emitters 104 to emit light of different wavelengths and/or to process signals of attenuated light after absorption by the body tissue of the wearer from the detectors 106. The sensor or module processor 108 can determine and output for display on the device display screen 12 the physiological parameters based on the detected signals. Optionally, the sensor or module 100 can send the signals from the detectors 106 (for example, preprocessed signals) to the device processor 14, which can determine and output for display the physiological parameters based on the detected signals. The absorption of light can be via transreflectance by the wearer's body tissue, for example, by the pulsatile arterial blood flowing through the capillaries (and optionally also the arteries) within a tissue site where the device 10 is worn (for example, the wrist). The sensor or module processor 108 can be located on a PCB 116, such as shown in FIG. 7B.

The sensor or module 100 can include more than one group or cluster of light emitters (such as LEDs) 104 and more than one group of photodetectors (also referred to as "detectors") 106. Each group of emitters 104 can be configured to emit four (or three) different wavelengths described herein. The sensor or module 100 can include one or more thermistors 110 or other types of temperature sensors. The thermistor(s) 110 can be placed near one or more groups of emitters 104. There can be at least one thermistor 110 near each group of emitters 104. The thermistor(s) 110 can provide for wavelength correction of the light emitted by the emitters 104. Optionally, the thermistor(s) 110 can additionally measure a temperature of the wearer of the device 10. Optionally there can be one or more thermistors 110 located at other places of the sensor or module 100. The emitters 104, the thermistor(s) 110, and/or the detectors 106 can be positioned on the PCB 116.

As shown in FIG. 7A, the device 100 can include a gyroscope 112, an accelerometer 114, and/or other position and/or posture detection sensor(s). The gyroscope 112 and/or the accelerometer 114 can be in electrical communication with the sensor or module processor 108. The sensor or module processor 108 can determine motion information from signals from the gyroscope 112 and/or the accelerometer 114. The motion information can provide noise reference for analysis of the pleth information and other signal processing (for example, processing of ECG signals) performed by the sensor or module processor 108. The gyroscope 112 and/or the accelerometer 114 can be located on the PCB 116.

Figure 8B:
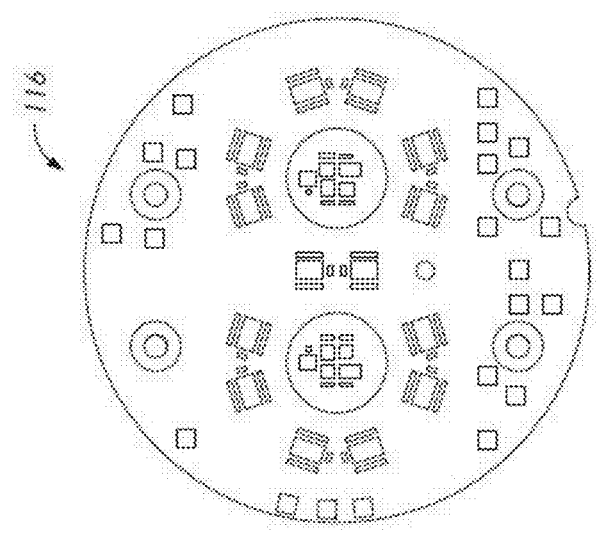
FIGS. 8A and 8B illustrate schematically top and bottom views of an example sensor or module processor board of an example physiological parameter measurement module.
Figure 8A:
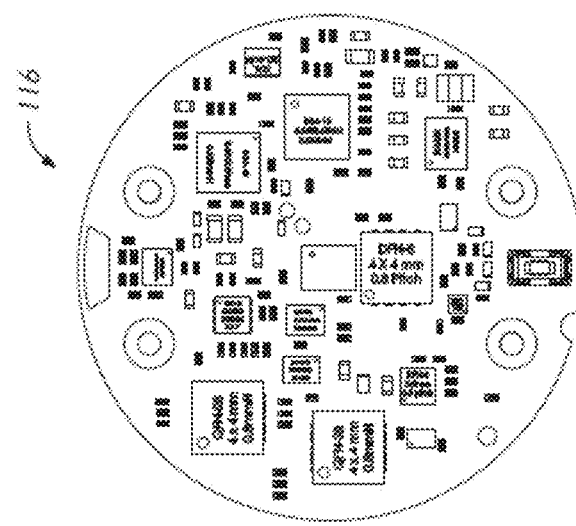
Figure 8E:
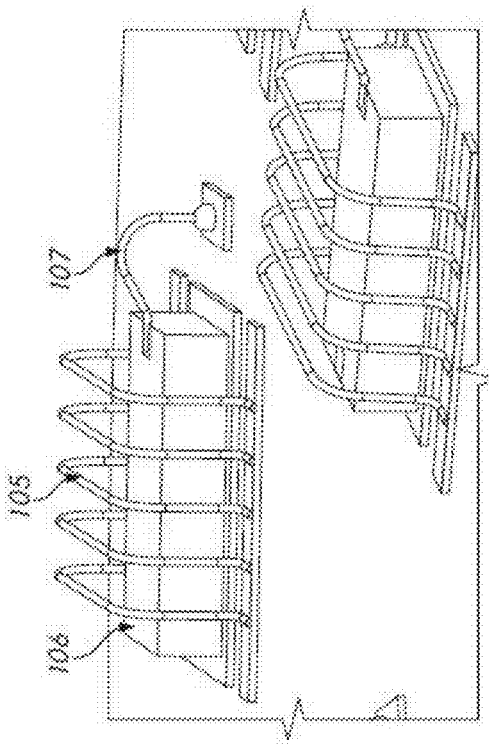
FIGS. 8C-8E illustrate various view of bonding of detectors to a PCB substrate of a physiological parameter measurement module.
Figure 8C:
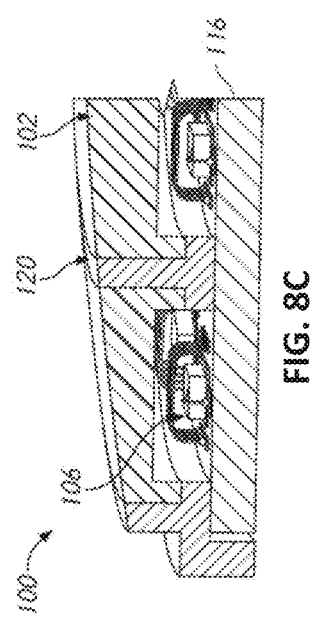
Figure 8D:
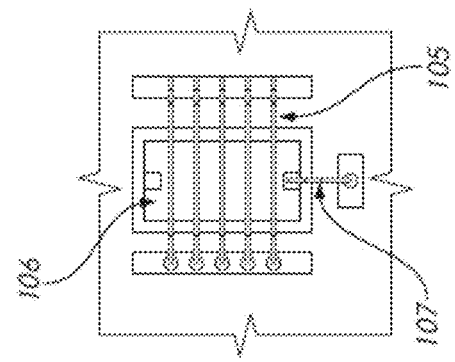
Figure 8F:
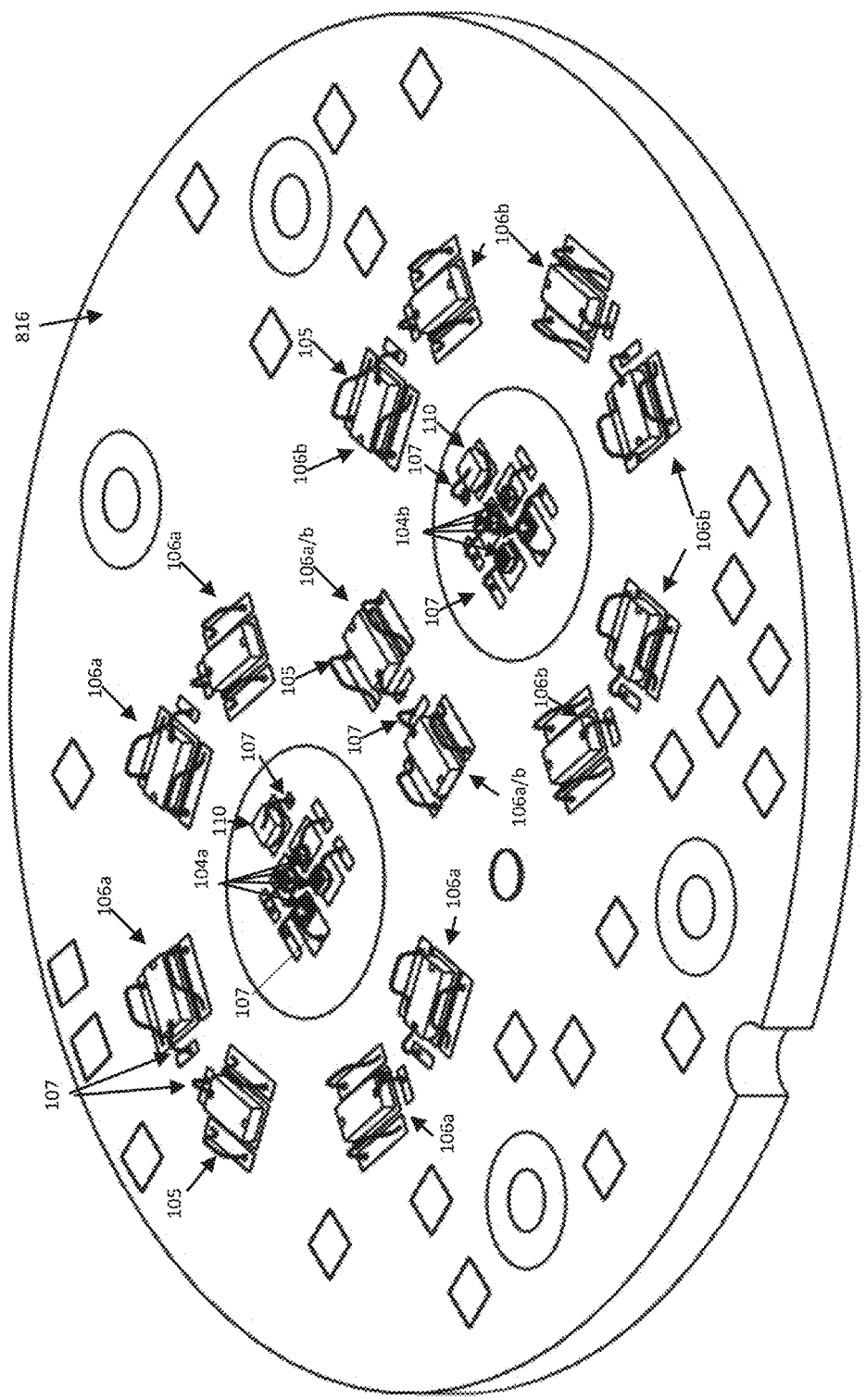
FIG. 8F illustrates a perspective view of a PCB substrate of a physiological parameter measurement module with different wire bonding arrangements than shown in FIGS. 8C-8E.

FIG. 8A illustrates example layouts of a top side of the PCB 116. FIG. 8B illustrates example layouts of a bottom side of the PCB 116. The first or bottom side of the PCB 116 can include the emitters 104, the detectors 106, the temperature sensor 110, and any other sensors, for example, the gyroscope, the accelerometer, and/or the like. FIGS. 8C-8E illustrate the detectors 106 being connected electrically to the PCB 116 via wire bonds 107. The module can include wires 105 extending over the detector 106 for shielding purposes. The number of wires 105 extending over the detector 106 may vary. The manner in which the wires 105 extend over the detector 106 may vary. The wires 105 may not extend all the way over the detectors 106 across the detector's width or length. For example, as shown in FIG. 8F, the detectors of detector groups 106a, 106b, 106a/b can each be connected electrically to the first side of the PCB 816 via wire bonds 107. A wire 105 can extend along each side of the detector for noise shielding. In the illustrated example, the wire 105 can extend along each long side of the detector. The wire 105 may extend parallel with the length of the detector. The wire 105 may not extend over the body of the detector 106a, 106b, 106a/b. In some aspects, a single wire 105 may extend along all four sides of the emitter for shielding. In some aspects, four wires 15 may each extend along one of the four sides of the emitter for shielding. In some aspects, a metal cover, such as a can shaped metal cover, may cover each of the detectors and/or emitters for shielding. The emitters in the emitter groups 104a, 104b can each be electrically connected to the first side of the PCB 816 via wire bonds 107. The thermistors 110 at each of the emitter groups 104a, 104b can be electrically connected to the first side of the PCB 816 via wire bonds 107. The detectors, emitters, and/or thermistor can alternatively be electrically connected to the PCB 116 via other suitable types of electrical connectors.

The second or top side of the PCB 116 can include the sensor or module processor 108 and other circuit hardware. The second side of the PCB 116 can be electrically noisy and is isolated from the sensors on the first side of the PCB 116 by the board. Electronics on the same side of the PCB 116 can be substantially entirely overmoulded to reduce or avoid components shifting in place or being damaged during use. On the second side of the PCB 116, which faces away from the light transmissive cover 102, the PCB 116 can be covered by melt plastic or other suitable electronics protective material 130, such as shown in FIGS. 7B and 7F. As shown in FIG. 7F, the electronic components on the second side of the PCB 116 can be generally sealed by the protective material 130 except that a connector 132 can extend from the second side of the PCB 116 and be exposed. The connector 132 can electronically connect the sensor or module 100 to circuitry of the wearable device 10.

Figure 7D:
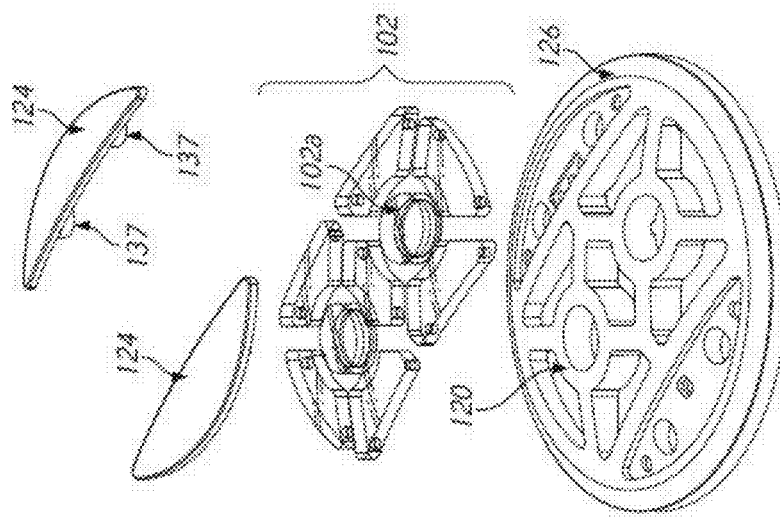
FIG. 7D illustrates an exploded view of ECG electrodes, light transmissive cover(s), and a opaque frame of the physiological parameter measurement module of FIG. 7B.

Optionally, as shown in FIGS. 7A, 7B, and 7D, the device 10 can include an electrocardiogram (ECG) sensor including a plurality of electrodes 124, 125 configured to make contact with the wearer's skin. One or more ECG electrodes 124 may be located on the sensor or module 100 (such as shown in FIGS. 7B and 7E). One or more ECG electrodes 125 may be located elsewhere on the device (for example, an ECG electrode 125 can form a part of the housing of the wearable device 10 as shown in FIG. 7B). The ECG sensor can be in electrical communication with the sensor or module processor 108 via an ECG connector.

Figure 7C:
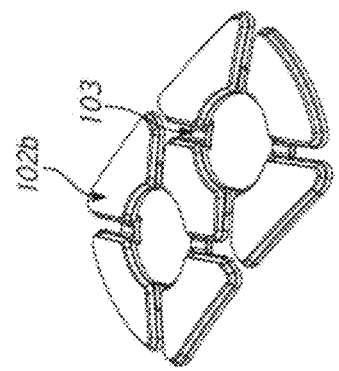
FIG. 7C illustrates an example light transmissive cover of the physiological parameter measurement module of FIG. 7B.
Figure 7H:
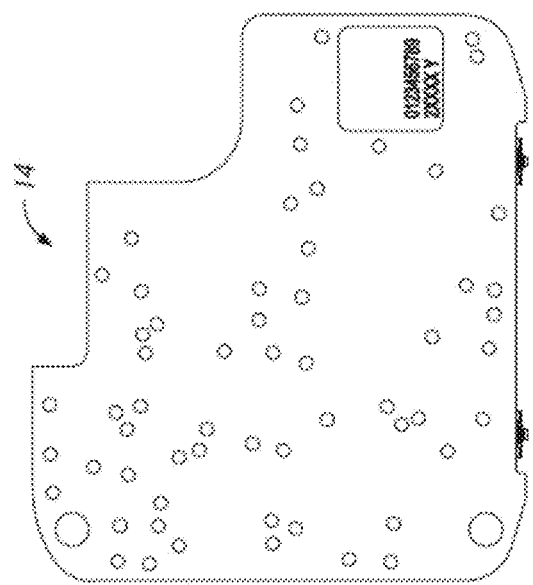
FIGS. 7G and 7H illustrate schematically top and bottom views of an example device processor board of the wearable device disclosed herein.
Figure 7G:
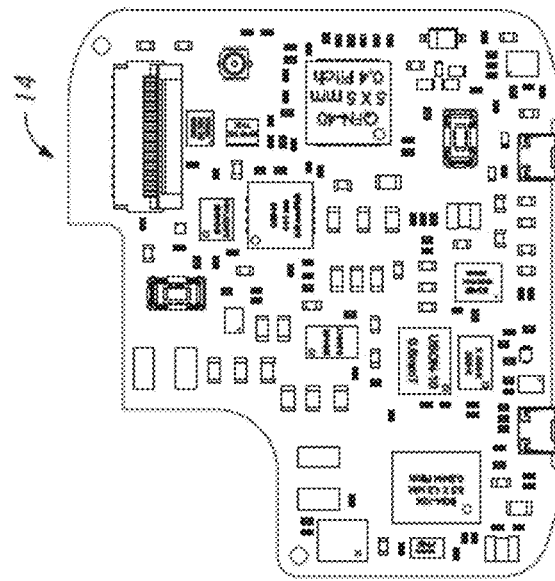

As shown in FIGS. 7B-7E, the physiological parameter measurement module 100 can include a skin-interfacing light transmissive cover 102 that encloses the first side of the PCB 116, which positions the plurality of light emitters 104 and detectors 106. The sensor or module 100 can include a light barrier construct 120 that is configured to divide the emitters 104 and the detectors 106 into different chambers such that light cannot travel or substantially cannot travel between the chambers. The light transmissive cover 102 can extend over the various emitter and detector chambers formed by the light barrier construct 120 and the PCB 116. The light transmissive cover 102 can include individual lenses or covers such as shown in FIG. 7D, a single lens or cover such as shown in FIGS. 17A-17C, or a combination of individual emitter chamber covering lenses or covers and a single lens or cover covering a plurality of detector chambers, such as shown in FIG. 7C. In the example lens or cover 102b shown in FIG. 7C, the individual lenses or covers that are configured to cover the detector chambers such as shown in FIG. 7D can be interconnected with bridging portions 103 between the detector chambers, forming a single piece of lens or cover. The lens or cover 102b can be combined with the lenses or covers 102a covering the emitter chambers to cover all the openings in the light barrier construct 120 for forming sealed emitter and detector chambers. The light barrier construct 120 can be overmoulded to the lens or cover 102b and the lenses or covers 102a. The lens or cover 102b may not be configured to cover the emitter chambers, which can be covered by individual lenses, so as to avoid any light traveling between an emitter chamber and a detector chamber.

As shown in FIG. 7B, the physiological parameter measurement module 100 can include an opaque frame 126. The opaque frame 126 can accommodate the light barrier construct 120. Alternatively, the opaque frame 126 and the light barrier construct 120 can form an integral piece, such as shown in FIG. 7D. The opaque frame 126 can include indentations having the shape and size to accommodate the ECG electrodes 124 or other components with a suitable shape and size. A front side of the electrodes 124 can have one or more posts 137 extending past openings in the opaque frame 126 into corresponding openings on the PCB 116. The posts 137 of the electrodes 124 can establish an electrical connection with the corresponding openings of the PCB 116. A plurality of screws (or other types of fasteners) can extend into the corresponding openings of the PCB 116 from the front side of the PCB 116 to secure the electrodes 124 to the sensor or module 100 by threadedly mating or otherwise with the posts 137. When a wearer puts the wearable device incorporating the sensor or module 100 onto the wearer's wrist, the electrodes 124 can make contact with the wearer's skin.

Figure 27A:
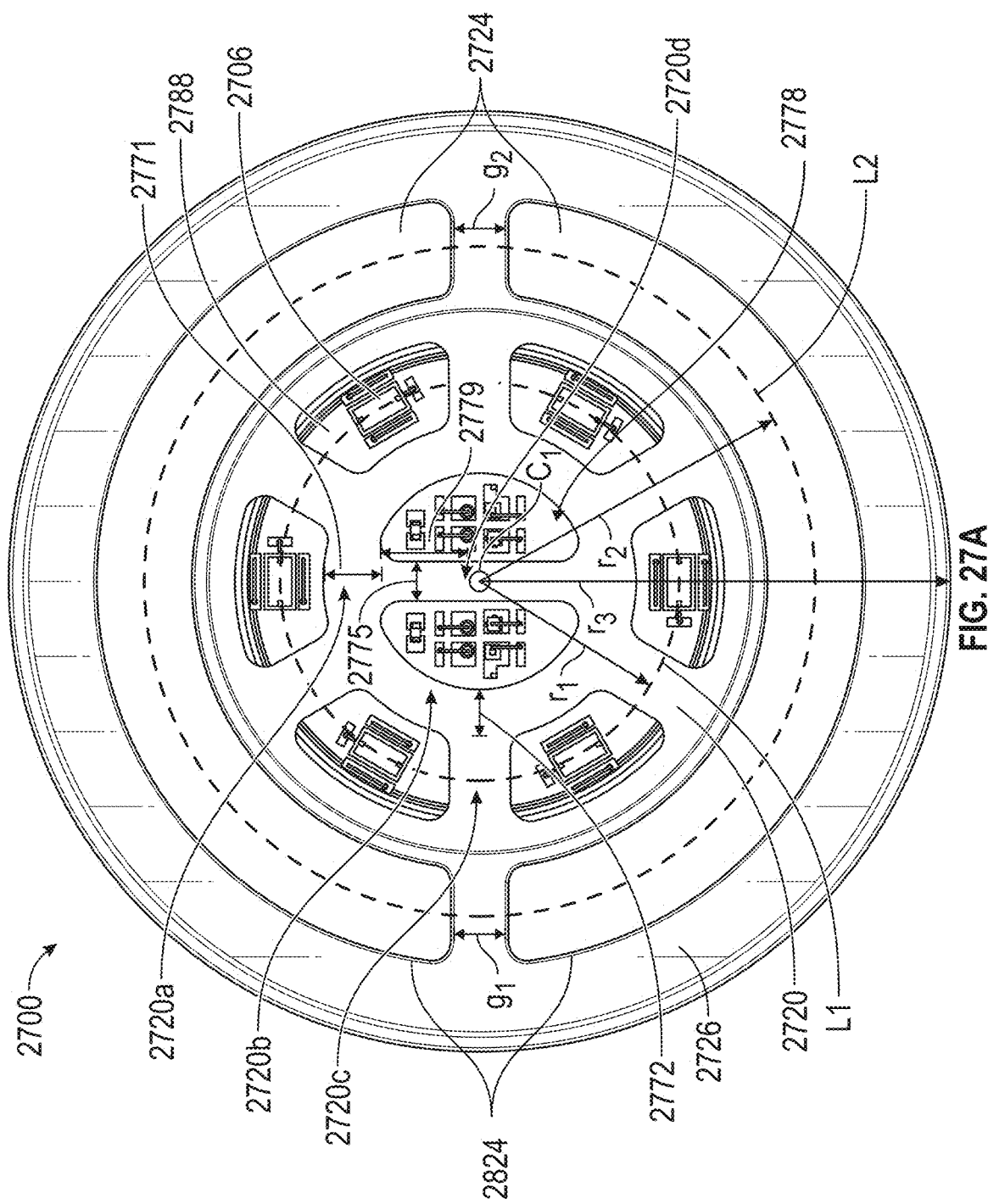
FIG. 27A illustrates a front view of an example aspect of a physiological parameter measurement sensor or module.
Figure 27D:
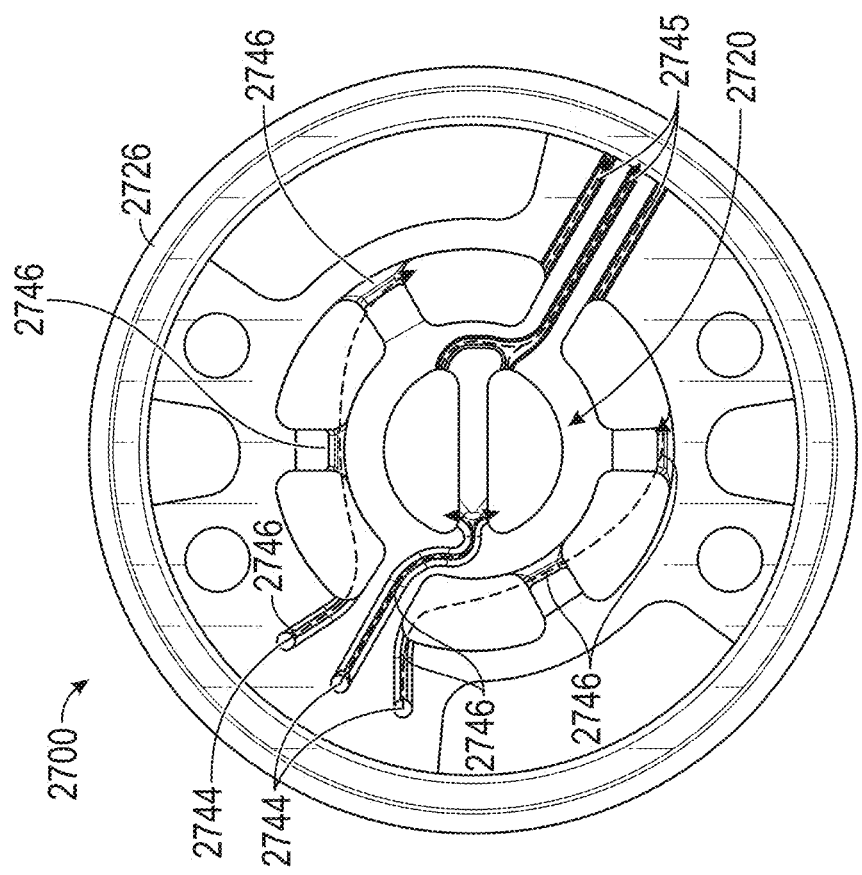
FIGS. 27C and 27D illustrate light diffusing material fill channels and air venting channels in an opaque frame of an example physiological parameter measurement sensor or module.
Figure 27C:
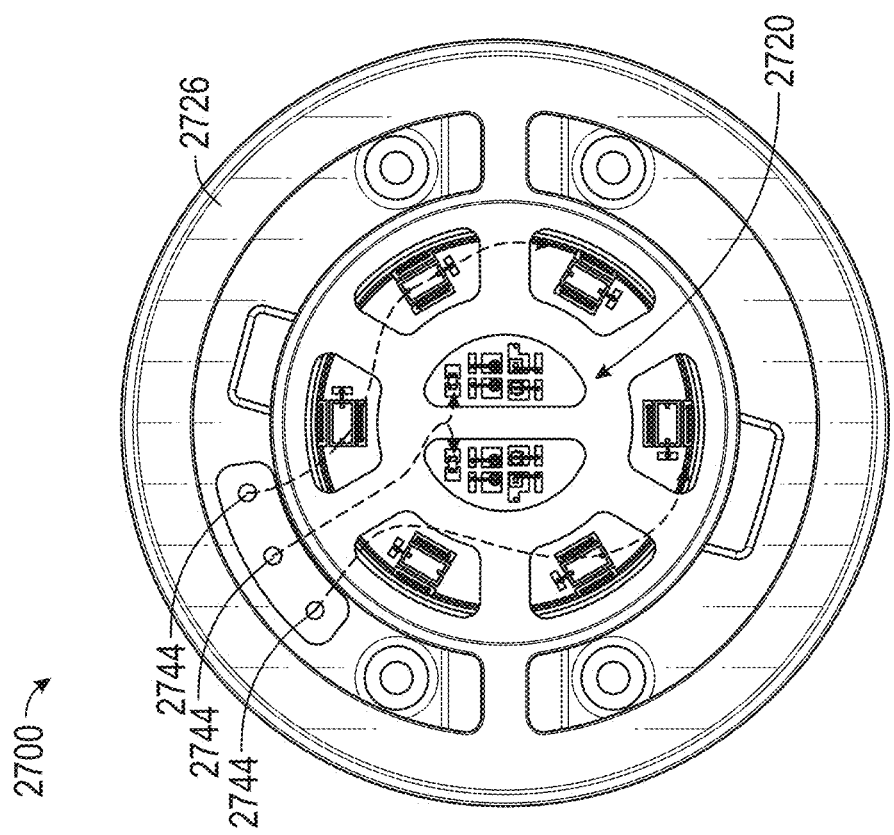
Figure 27E:
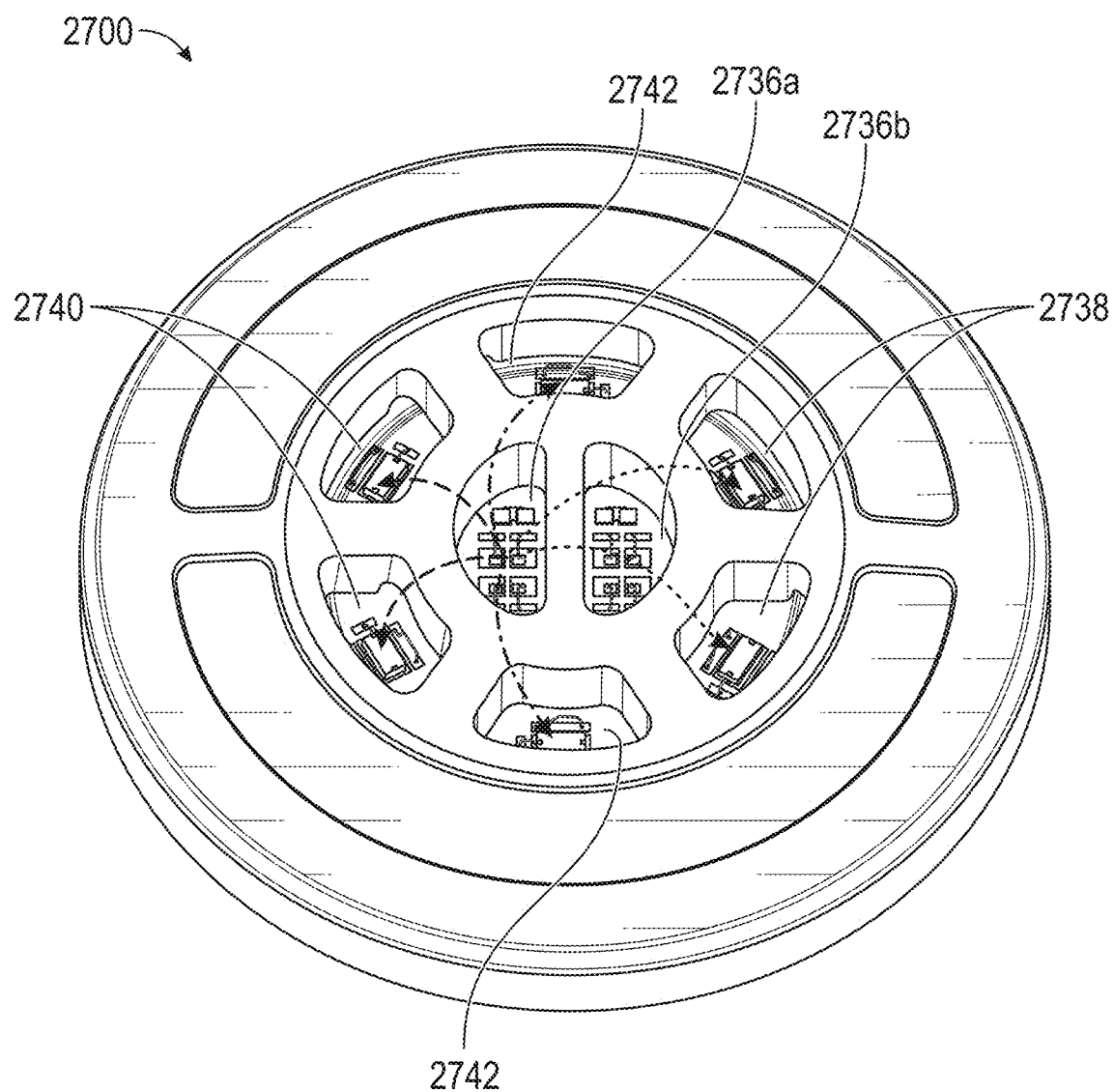
FIG. 27E illustrates an example physiological parameter measurement sensor or module and example light paths between emitters and detectors of the module.

FIGS. 27A, 27B, and 27E illustrate an additional example aspect of an optional electrocardiogram (ECG) sensor. The electrocardiogram (ECG) sensor may include a plurality of electrodes 2724 configured to make contact with the wearer's skin. The plurality of ECG electrodes 2724 may be located on the sensor or module 2700 (such as shown in FIGS. 27A, 27B and 7E). As disclosed herein, the wearable device incorporating the module can include another ECG electrode 125 located on the housing of the wearable device configured to make contact with the wearer's skin.

FIG. 27B is an exploded perspective view of an example aspects of a sensor or module 2700. As shown in FIG. 27B, the opaque frame 2726 can include recesses (which may also be referred to as "indentations") having the shape and size to accommodate the ECG electrodes 2724 or other components with a suitable shape and size. For example, in some implementations, frame 2726 includes recesses 2824. Recesses 2824 can be sized and/or shaped to receive ECG electrodes 2724. In some implementations, recesses 2824 have a depth (for example, measured from a plane of the frame 2726) that is substantially equal to a thickness of the ECG electrodes 2724. In some implementations, recesses 2824 have a size and/or shape that matches a size and/or shape of the ECG electrodes 2724. For example, in some implementations in which the ECG electrodes have a semi-annular shape (such as that illustrated in at least FIGS. 27A-27B), the recesses 2824 can have a semi-annular shape.

A front side of the electrodes 2724 can have one or more posts 2737 extending past openings in the opaque frame 2726 into corresponding openings on the substrate 2716. The posts 2737 of the electrodes 2724 can establish an electrical connection with the corresponding openings of the substrate 2716. A plurality of screws (or other types of fasteners) can extend into the corresponding openings of the substrate 2716 from the front side of the substrate 2716 to secure the electrodes 2724 to the sensor or module 2700 by threadedly mating or otherwise with the posts 2737. When a wearer puts the wearable device incorporating the sensor or module 2700 onto the wearer's wrist, the electrodes 2724 can make contact with the wearer's skin.

With continued reference to FIG. 27B, the substrate 2716 can include a printed circuit board (PCB). The substrate 2716 can include a conductive liquid adhesive 2739. The conductive liquid adhesive 2739 may be provided on the copper of the substrate 2716. The conductive liquid adhesive 2739 may facilitate conductive electrical connection between the electrodes 2724 and the substrate 2716.

With continued reference to FIG. 27B, one or more spring contacts (such as spring contacts 2755' shown in FIG. 27I) may be located between the electrodes 2724 and the substrate 2716. The shape, size, and/or number of the spring contacts can vary. The spring contacts can establish an electrical connection between the electrodes 2724 and the substrate 2716. The spring contacts can be biased toward the electrodes 2724 to ensure a firm electrical connection between the spring contacts and the electrodes 2724 and the substrate 2716.

The physiological parameter measurement module 100 can include diffusing materials or encapsulant, which can include, for example, microspheres or glass microspheres. As described above, the encapsulant can eliminate air gaps between the surface of the light transmissive cover 102 and the emitters 104 and/or the detectors 106. The encapsulant can be included around the emitters 104 to more evenly spread the emitted light, which appears to be emitted from an entire emitter chamber rather than from a point source (that is, a single LED emitter) if the encapsulant is absent. The encapsulant can allow the emitted light to travel through a greater volume of the tissue at the tissue site. The diffusing material can act as a beam shaper that can homogenize the input light beam from the emitter, shape the output intensity profile of the received light, and define the way (for example, the shape or pattern) the emitted light is distributed to a tissue measurement site. Such diffuser materials can, for example, deliver substantially uniform illumination over a specified target area in an energy-efficient manner. According to the Beer-Lambert law, the amount of light absorbed by a substance is proportional to the concentration of the light-absorbing substance in the irradiated solution (for example, the arterial blood). Therefore, by irradiating a larger volume of tissue and/or by increasing the amount of detected light, a larger sample size of light attenuated by the wearer's tissue can be measured. The larger sample size provides a data set that can be more representative of the complete interaction of the emitted light as it passes through the patient's blood as compared to a smaller sample size.

The diffusing materials can be any suitable materials, for example, glass, ground glass, glass beads, opal glass, greyed glass, polytetrafluoroethylene, or a microlens-based, band-limited, engineered diffuser that can deliver efficient and uniform illumination UV-cured flow glass microspheres injected into one or more openings on the sensor or module 100 (for example, after the sensor or module 100 has been assembled). Examples of engineered diffusers can include molded plastics with specific shapes, patterns, and/or textures designed to diffuse the emitter light across the entirety of a tissue surface. The diffusing material can be made of ground glass, which spreads the emitted light with a Gaussian intensity profile. The diffusing material can include glass beads. The diffusing material can be constructed so as to diffuse the emitted light in a Lambertian pattern. A Lambertian pattern is one in which the radiation intensity is substantially constant throughout the area of dispersion. One such diffusing material can be made from opal glass. Opal glass is similar to ground glass, but has one surface coated with a milky white coating to diffuse light evenly. The diffusing material can be capable of distributing the emitted light on the surface of a plane (for example, the surface of the tissue measurement site) in a predefined geometry (for example, a rectangle, square, circle, or otherwise), and with a substantially uniform intensity profile and energy distribution. The efficiency, or the amount of light transmitted by the diffusing material, can be greater than 70% of the light emitted by the emitter. The efficiency can be greater than 90% of the emitted light. Additional examples of the diffusing material are described in U.S. Pat. No. 10,448,871, the entirety of which is hereby incorporated herein by reference and should be considered part of the disclosure.

Additionally or alternatively, the physiological parameter measurement module 100 can include encapsulant or light diffusing materials in the detector chambers to more evenly spread the reflected light to so as to increase the amount of the reflected light reaching the detectors. The module can include light diffusing materials positioned around the detectors to scatter and/or deflect the reflected light so that more reflected light can be detected by the detectors. For example, the reflected light can keep bouncing off the diffusing materials until the reflected light reaches the detector. Accordingly, the light detecting surface area in the module can be greater than the surface area of the detectors. Having the light diffusing materials can reduce the power needed to drive the LEDs of the emitters and/or the number of detectors at a particular location of the module, which can reduce the power consumption of the module.

Figure 9B:
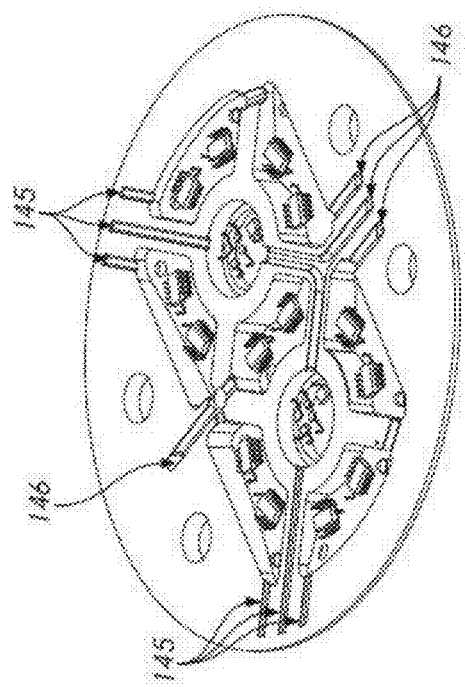
FIGS. 9A and 9B illustrate light diffusing material fill channels and air venting channels in a opaque frame of an example physiological parameter measurement module.
Figure 9A:
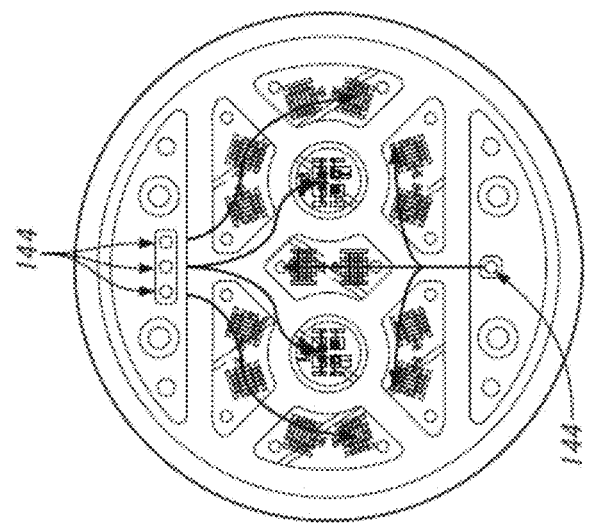

As shown in FIG. 9A, the opaque frame 126 of the sensor or module 100 can include a plurality of light diffusing material(s) (or encapsulant) fill holes 144. Light diffusing material(s) or encapsulant (for example, a flow of glass microspheres) can be injected into the plurality of chambers via the fill holes 144, and be directed to the respective emitter or detector chambers as illustrated by the arrows in FIG. 9A along a plurality of the fill channels 146 (see FIG. 9B) which are interconnected with the fill holes 144. The fill channels 146 can be located at a side of the opaque frame 126 facing away from the tissue of the wearer. As shown in FIG. 9B, the side of the opaque frame 126 facing away from the tissue of the wearer can further include a plurality of air vent channels 145. Air can escape into the vent channels 145 as the diffusing material solution or encapsulant is injected into the respective chambers via the fill holes 144, making it easier for the injected solution to flow into the respective chamber. As shown in FIG. 9B, the module 100 may not have air vent channels or fill channels between emitter and detector chambers to avoid light piping along such a channel. The encapsulant can be UV-cured after being injected into the respective chambers.

The opaque frame 126 may be configured such that the fill holes 144 and channels 146 allow the light diffusing materials to fill only the emitter chambers, or only the detector chambers, or both the emitter and detector chambers. Optionally, in addition or alternative to the light diffusing materials, the detector chamber can include light transmissive lens(es) or covers on the surface of the PCB that is not occupied by the detectors. The light transmissive lens(es) or covers may be polycarbonate. The light transmissive lens(es) or covers inside the detector chamber can help in focusing the reflected light onto the detectors inside the detector chamber.

FIGS. 27C and 27D illustrate another example opaque frame 2726 and light barrier construct 2720 of a sensor or module 2700. The opaque frame 2726 and/or light barrier construct 2720 can include a plurality of light diffusing material(s) (or encapsulant) fill holes 2744. Light diffusing material(s) or encapsulant (for example, a flow of glass microspheres) can be injected into the plurality of chambers via the fill holes 2744, and be directed to the respective emitter or detector chambers as illustrated by the red arrows in FIGS. 27C and 27D along a plurality of the fill channels 2746 (see FIG. 27D) which are interconnected with the fill holes 2744. The fill channels 2746 can be located at a side of the opaque frame 2726 facing away from the tissue of the wearer. The fill channels 2746 may travel through portions of the opaque frame 2726 and/or portions of the light barrier construct 2720. As shown in FIG. 27D, the side of the opaque frame 2726 facing away from the tissue of the wearer can further include a plurality of air vent channels 2745. Air can escape into the vent channels 2745 as the diffusing material solution or encapsulant is injected into the respective chambers via the fill holes 2744, making it easier for the injected solution to flow into the respective chamber. As shown in FIG. 27D, each of the fill channels 2746 and/or the vent channels 2745 may connect more than one emitter chamber or more than one detector chamber. However, the module 2700 may not have air vent channels or fill channels extending between emitter and detector chambers to avoid light piping along such a channel. The encapsulant can be UV-cured after being injected into the respective chambers.

The opaque frame 2726 may be configured such that the fill holes 2744 and channels 2746 allow the light diffusing materials to fill only the emitter chambers, or only the detector chambers, or both the emitter and detector chambers.

Figure 10:
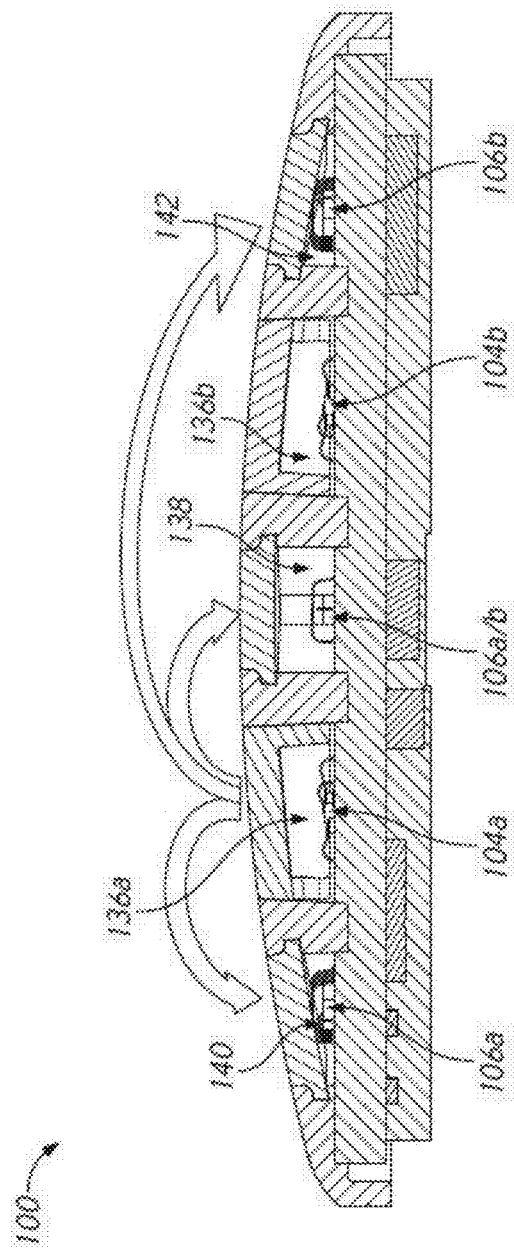
FIG. 10 illustrates a longitudinal cross-sectional view of an example physiological parameter measurement module and example light paths between emitters and detectors of the module.

In FIG. 10, a cross-sectional view of the sensor or module 100 illustrates some of the emitter and detector chambers. The chambers illustrated in FIG. 10 include a first emitter chamber 136a enclosing a first emitter group 104a, a second emitter chamber 136b enclosing a second emitter group 104b, a first detector chamber 140 enclosing one of first groups of detectors 106a that surround the first emitter group 104a, a second detector chamber 142 enclosing one of second groups of detectors 106b that surround the second emitter group 104b, and a third detector chamber 138 enclosing one of shared groups of detectors 106a/b that surround both the first and second emitter groups 104a, 104b on opposite sides of the third detector chamber 138.

As shown in FIG. 10, light from the first emitter group 104a can travel a shorter path, as indicated by the shorter arrows, to the first group of detectors 106a or the shared group of detectors 106a/b; and light from the first emitter group 104a can travel a longer path, as indicated by the longer arrows, to the second group of detectors 106b. The reverse is true for light from the second emitter group 104b, which can travel a shorter path to the second group of detectors 106b or the shared group of detectors 106a/b and a longer path to the first group of detectors 106a. As described herein, the different groups of emitters 104a, 104b and/or detectors 106a, 106b, 106a/b can be run independently and/or simultaneously. Signals outputted by the different groups of detectors 106a, 106b, 106a/b based on light emitted from the first emitter group 104a and/or the second emitter group 104b can provide different information due to the different light paths, which can travel through different areas of the tissue. The longer path penetrates deeper into the tissue and through a greater volume of the tissue to reach the "far" groups of detectors than the shorter path, which penetrates less deep into the tissue and travels through a smaller volume of tissue to reach the "near" group of detectors. The different information can be separated and/or combined to calculate a plurality of physiological parameters of the wearer of the sensor or module 100, for example, an indication of the wearer's hydration status, which will be described in greater detail below.

FIG. 27E is a front perspective view of an example aspect of a sensor or module 2700 including another example arrangement of emitter and detector chambers. The emitter and detector chambers may comprise one or more light blocks. The chambers illustrated in FIG. 27E include a first emitter chamber 2736a enclosing a first emitter group, a second emitter chamber 2736b enclosing a second emitter group, a first group of detector chambers 2740, a second group of detector chambers 2742, and a third group of detector chambers 2738. Each detector chamber can enclose one detector. The first and second emitter chambers 2736a, 2736b can be adjacent to each other. The first, second and third groups of detector chambers 2740, 2742, 2738 can extend around the first and second emitter chambers 2736a, 2736b.

As shown in FIG. 27E, light from the first and second emitter groups in the first and second emitter chambers, respectively, can emit light that travel paths of different lengths for example to different detectors. Light from the first emitter group can travel a shorter path, as indicated by the shorter arrows, to the first group of detector chambers 2740; and light from the first emitter group can travel an intermediate path, as indicated by the intermediate arrows, to the second group of detector chambers 2742; and light from the first emitter group can travel a longer path, as indicated by the longer arrows, to the third group of detector chambers 2738. The reverse is true for light from the second emitter group, which can travel a shorter path to the third group of detector chambers 2738, and an intermediate path to the second group of detector chambers 2742, and a longer path to the first group of detector chambers 2740.

As described herein, the different emitters can be run independently and/or simultaneously. For example, the emitters can be selectively activated (e.g., modulated) so that only one emitter (or subset of emitters) is emitting light at a given time. For example, in aspects wherein the first emitter group comprises four emitters, each of the four emitters of the first emitter group may be activated for a quarter cycle (e.g., a different quarter cycle than the other emitters) and off for the remaining three-quarters cycle. For example, a first emitter of the first emitter group may be activated to emit light during only a first quarter cycle, a second emitter of the first emitter group may be activated to emit light during only a second quarter cycle, a third emitter of the first emitter group may be activated to emit light during only a third quarter cycle and a fourth emitter of the first emitter group may be activated to emit light during only a fourth quarter cycle. The emitters of the second emitter group may operate in a similar manner as described.

As another example, in aspects wherein the first emitter group comprises four emitters, each of the four emitters of the first emitter group may be activated for an eighth of a cycle (e.g., a different eighth of the cycle than the other emitters) and off for the remaining seven-eighths cycle. An eighth of a cycle wherein no emitter is activated may occur between each of the cycles wherein an emitter is activated. For example, a first emitter of the first emitter group may be activated to emit light during only a first quarter cycle, a second emitter of the first emitter group may be activated to emit light during only a third quarter cycle, a third emitter of the first emitter group may be activated to emit light during only a fifth quarter cycle and a fourth emitter of the first emitter group may be activated to emit light during only a seventh quarter cycle. The emitters of the second emitter group may operate in a similar manner as described.

The above examples are not meant to be limiting. Alternative activation sequences for the emitters may be used to provide a time-multiplexed signal. In some aspects, the emitters can be selectively activated (e.g., modulated) so that two or more emitters are emitting light at a given time (e.g., during the same cycle or during overlapping cycles), for example in a manner similar to the examples given above.

The emitters may be modulated within an emitter group (e.g., first emitter group and second emitter group) or all of the emitters of the wearable device 10 may be modulated according to a single activation sequence. For example, the emitters of the first group may be modulated according to one activation sequence and the emitters of the second group may be modulated according to a second activation sequence. Alternatively, the emitters of the first and second emitters groups can all be modulated according to a single activation sequence.

In some aspects, the detectors may operate independently from and/or simultaneously with each of the other detectors. For example, each of the detectors may provide an individual signal to the module processor 108.

Signals outputted by the different detectors of the different detector chambers 2740, 2742, 2738 based on light emitted from the first emitter group and/or the second emitter group can provide different information due to the different light paths, which can travel through different areas of the tissue. The longer path penetrates deeper into the tissue and through a greater volume of the tissue to reach the detectors of the "far" group of detector chambers than the intermediate and shorter paths. The shorter path penetrates less deep into the tissue and travels through a smaller volume of tissue to reach the detectors of the "near" group of detector chambers than the intermediate and longer paths. The different information can be separated and/or combined to calculate a plurality of physiological parameters of the wearer of the sensor or module 2700.

For convenience, the terms "proximal" and "distal" are used herein to describe structures relative to the first emitter group or the second emitter group. For example, a detector may be proximal or distal to the first emitter group and may be proximal or distal to the second emitter group. The term "distal" refers to one or more detectors that are farther away from an emitter group than at least some of the other detectors. The term "proximal" refers to one or more detectors that are closer to an emitter group than at least some of the other detectors. The term "intermediate detector" refers to detectors that are closer to an emitter group than distal detectors and farther from an emitter group than proximal detectors. The term "proximal detector" may be used interchangeably with "near detector" and the term "distal detector" may be used interchangeably with "far detector".

A single detector may be both a proximal to one detector and distal to another detector. For example, a detector may be a proximal detector relative to the first emitter group and may be a distal detector relative to the second emitter group.

FIG. 11A illustrates schematically an example wearable device 10 disclosed herein. As described above, the device processor 14 can be connected to the module sensor 108 of the physiological parameter measurement module 100, which includes the emitters, the detectors, the thermistors, and other sensors disclosed herein. The electrical connection between the device processor 14 and the sensor or module processor 108 can be establish optionally via a flex connector 32. The sensor or module processor 108 can be coupled to the ECG electrodes 124, 125, optionally via an ECG flex connector 123.

The device processor 14 can be connected to a display 12, which can include the display screen and touch input from the wearer. The device processor 14 can include a battery 16, and optionally one or more wireless charging coils 17 to enable wireless charging of the battery 16. The device processor 14 can be connected to an antenna 19 for extending signals transmitted wirelessly, for example, to an external device as described with reference to FIG. 2. The device processor 14 can include connection to a first user interface (UI 1) 13a and a second user interface (UI 2) 13b on the device 10 to receive input from the wearer. As shown in FIG. 1D, example first and second user interface 13a, 13b can be in the form of buttons 13. Additionally or alternatively, the device 10 can include a microphone. The device 10 can receive user inputs via the user interfaces, which can be the buttons, the microphone, and/or the touchscreen. The user inputs can command the device 10 to turn on and/or off certain measurements, and/or to control externally connected devices, such as an insulin pump, a therapeutics delivery device, or otherwise. The device processor 14 can be connected to a user feedback output 15 to provide feedback to the wearer, for example, in the form of vibration, an audio signal, and/or otherwise. The device processor 14 can optionally be connected to an accelerometer and/or a gyroscope 42 located on the device 10 that is different from the accelerometer 114 and gyroscope 112 on the physiological parameter measurement module 100. The accelerometer and/or gyroscope 42 can measure position and/or orientation of the wearer for non-physiological parameter measurement functions, for example, for sensing that the wearer has woken up, rotating the display 12, and/or the like.

FIG. 11B illustrates example components of the device processor 14 PCB board. As shown in FIG. 11B, the device processor 14 can include a Bluetooth co-processor 1400 and a system processor 1402. The system processor 1402 can run the peripheral functions of the device 10, receive user (that is, the wearer) input and communicate to the sensor or module processor 108. The Bluetooth co-processor 1400 can focus on managing Bluetooth communication so as to allow the system processor 1402 to focus on the high memory utilization tasks, such as managing the display screen 12. The Bluetooth co-processor 1400 can be activated when there is incoming and/or outgoing Bluetooth communication. Alternatively, the Bluetooth co-processor 1400 can be replaced by a different wireless co-processor configured to manage wireless communication using a different wireless communication protocol.

FIG. 11C illustrates example components of the module processor PCB board 116. As shown in FIG. 11C, the sensor or module processor 108 can include a calculation processor 1080 and a system processor 1082. The calculation processor 1080 can manage host communication with the device processor 14 via a host connector 1084. The calculation processor 1080 can perform algorithm computations to calculate the physiological parameters based on the signals received from the ECG electrodes 124/125 and the optical sensor including the emitters 104, the detectors 106, and the temperature sensors 110, and optionally from other sensors in communication with the sensor or module processor 108. The calculation processor 1080 can have relatively large memory suitable for running algorithm computations. The system processor 1082 can be in communication with a power management integrated circuit (PMIC) 1090. The system processor 1082 can run the physical system of the sensor or module 100 (for example, including turning on and off the emitter LEDs, changing gain, setting current, reading the accelerometer 114 and/or the gyroscope 112, and the like) and decimate data to a lower sampling rate. The system processor 1082 can focus on data processing, taking measurements and diagnostics, and basic functions of the sensor or module processor 108. The system processor 1082 can allow the calculation processor 1082 to sleep (being inactive) most of the time, and only wake up when there is enough measurement data to perform calculations.

Figure 11D:
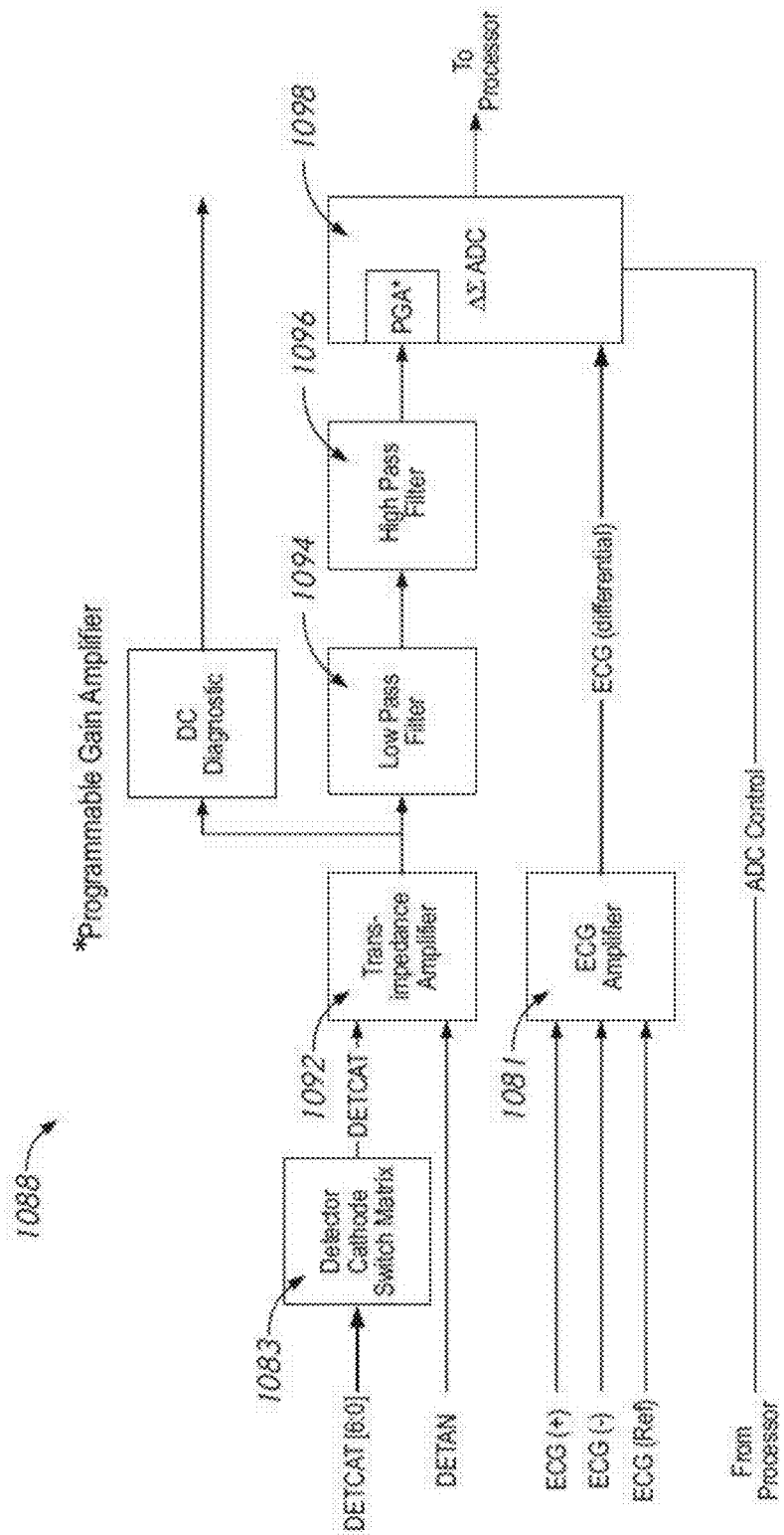

FIG. 11D illustrates an example front-end analog signal conditioning circuitry 1088 of the module PCB 116 shown in FIG. 11C. The entire front end circuitry 1088 can be located on a single application-specific integrated circuit (ASIC).

The front-end circuitry 1088 can include a transimpedance amplifier 1092 configured to receive analog signals from the optical sensor including the emitters 104, the detectors 106, and the temperature sensors 110, which can be preprocessed (for example, via a low pass filter 1094 and a high pass filter 1096) before being sent to an analog-digital converter 1098. The analog-digital converter 1098 can output a digital signal based on the analog signals from the optical sensor including the emitters 104, the detectors 106, and the temperature sensors 110 to the system processor 1082 and the calculation processor 1080. The front end circuitry 1088 can include a detector cathode switch matrix 1083 configured to activate the cathode of the detectors that are selected to be activated. The matrix 1082 can be further configured to deactivate (for example, by short-circuiting) anodes of the detectors that are selected to be deactivated in configurations in which the detectors share a common cathode and have different cathodes.

The front-end circuitry 1088 can include an ECG amplifier 1091 configured to receive analog signals from the ECG electrodes 124/125, which can output the amplified analog signals to the analog-digital converter 1096. The amplified analog signals can include an ECG differential between the positive and negative electrodes. The analog-digital converter 1098 can output a digital signal based on the analog signals from the ECG electrodes 124/125 to the system processor 1082 and the calculation processor 1080.

Figure 12B:
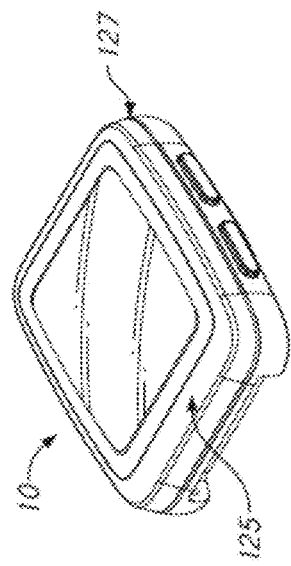
FIG. 12B illustrates a top perspective view of the example wearable device including a third ECG electrode.
Figure 12C:
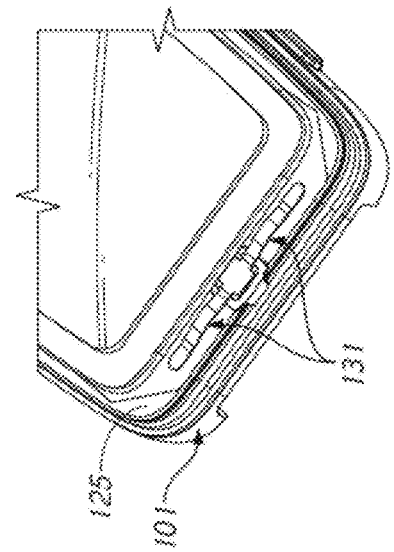
FIG. 12C illustrates a partial top perspective view of the example wearable device of FIG. 12B with the third ECG electrode shown as transparent to illustrate contact springs underneath the third ECG electrode.
Figure 12A:
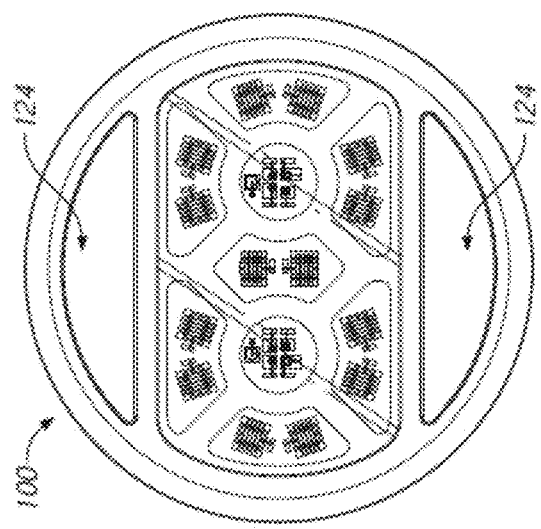
FIG. 12A illustrates a bottom view of an example physiological parameter measurement module with first and second ECG electrodes.

The ECG electrodes 124 can include a negative electrode, a positive electrode, and a reference electrode. As shown in FIG. 12A, the two electrodes 124 located on the sensor or module 100 can act as a reference electrode and a negative (or positive) electrode respectively. As shown in FIGS. 12B and 12C, a portion of the device housing 101 that surrounds the display screen 12 can function as another ECG electrode 125. An electrically insulating material 127 can separate the ECG electrode 125 from the remainder of the housing 101 so that an electrical current between the ECG electrode 125 and the ECG electrodes 124 would travel through the wearer's body. When the wearer wants to make a measurement using the ECG sensor that includes the ECG electrodes 124, 125, the wearer can press on or touch the electrode 125 using the wearer's finger or another part of the wearer's body such that the wearer's skin makes contact with the electrode 125.

In the illustrated examples, the ECG electrode 125 can be positive (or negative if one of the electrodes 124 servers as a positive electrode) electrode. As shown in FIG. 12C, the electrode 125 is illustrated as being transparent to show one or more spring contacts 131 located underneath the electrode 125. The shape, size, and/or number of the spring contacts 131 can vary from the example shown in FIG. 12C. The spring contacts 131 can establish an electrical connection between the electrode 125 and the electrode 125 and the sensor or module processor 108 of the sensor or module 100. For example, the spring contacts 131 can establish an electrical connection between the electrode 125 and the connector 132. The spring contacts 131 can be biased toward the electrode 125 to ensure a firm electrical connection between the spring contacts 131 and the electrode 125. Readings from the electrodes 124, 125 can allow the sensor or module processor 108 to obtain the wearer's ECG signal and optionally to make physiological measurements based on the obtained ECG, for example, the heart rate, the respiratory rate, and/or otherwise. The sensor or module processor 108 can communicate the ECG signals and/or ECG-related measurements to the wearable device processor 14. The wearer's ECG waveform and/or the measurements made from the ECG can be displayed on the display screen 12. [0281]

Figure 13A:
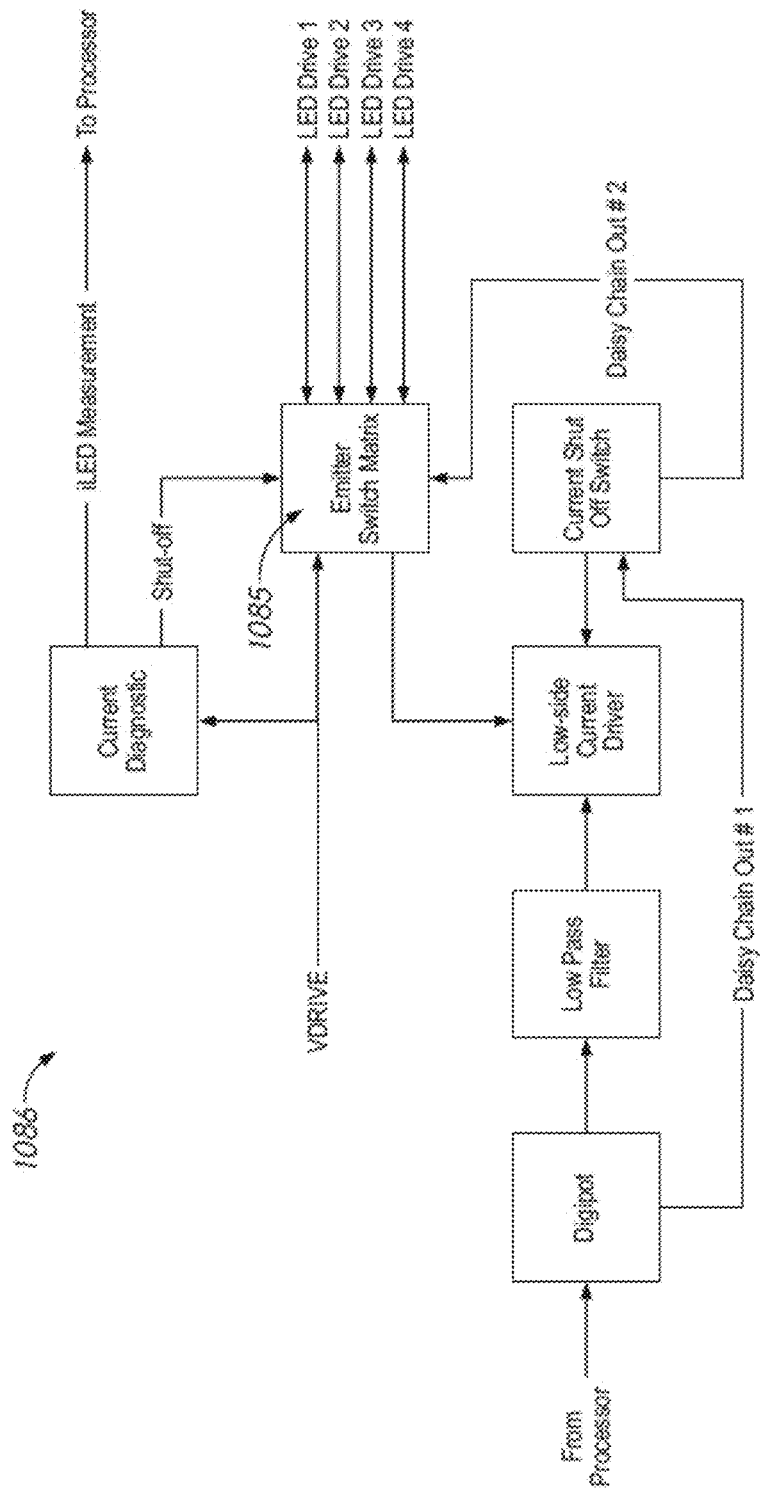
FIG. 13A illustrates an example block diagram of LED drive circuitry of the physiological parameter measurement module disclosed herein.

FIG. 13A illustrates an example LED driver circuitry 1086 of the module PCB 116 shown in FIG. 11C. The entire LED driver circuitry 1086 can be located on the single ASIC with the front end circuitry 1088. As described above, the system processor 1802 can output a control signal to turn on and off the emitter LEDs. As shown in FIG. 13A, the LED driver circuitry 1086 can include an emitter switch matrix 1085 configured to drive any of the emitters (or emitter groups) that are selected to be turned on or turn off any of the emitters (or emitter groups) that are selected to be turned off.

FIG. 13B illustrates an example emitter circuitry including eight different emitter LEDs 104. The number of LEDs may vary and can be less than or greater than eight. The emitters of the physiological parameter measurement module can be configured to emit a plurality of (for example, three, four, or more) wavelengths. Each of the emitters can be configured to emit light of a different wavelength than the other emitters. Alternatively, one or more of the emitters can emit light of more than one wavelength. In the illustrated example, the emitter circuitry can include four drivers to drive the eight emitter LEDs. Alternatively, the module can include more than four LEDs per emitter group. Each LED Drive can drive an LED to emit light of a different wavelength. The device or the module can grant access of some of the LEDs to a third party device, for example, for measurement purposes. The LED drivers can selectively drive some but not all the LEDs.

The emitters can be configured to emit light of a first wavelength providing an intensity signal that can act as a reference signal. The first wavelength can be more absorbent by the human body than light of other wavelengths emitted by the emitters. The reference signal can be stronger and less likely to be affected by noise than the signals from other wavelengths emitted by the emitters. The reference signal can be used by the physiological parameter measurement sensor or module processor to extract information from the other signals, for example, information relevant to and/or indicative of the pulsing rate, harmonics, or otherwise. The physiological parameter measurement sensor or module processor can focus the analysis on the extracted information for calculating physiological parameters of the wearer. Including the reference signal can reduce power consumption and saving the battery life of the device. The first wavelength can be from about 525 nm to about 650 nm, or from about 580 nm to about 585 nm, or from about 645 nm to about 650 nm, or about 525 nm, or about 580 nm, or about 645 nm. The light providing the reference signal can have an orange or yellow color. Alternatively, the light providing the reference signal can have a green color.

The emitters can be configured to emit light having a second wavelength having a red color. The second wavelength can be from about 620 nm to about 660 nm. Light of the second wavelength can be more sensitive to changes in oxygen saturation (SpO2) than light of other wavelengths emitted by the emitters. The second wavelength is preferably closer to 620 nm (for example, about 625 nm), which results in greater absorption by the body tissue of the wearer, and therefore a stronger signal and/or a steeper curve in the signal, than a wavelength that is closer to 660 nm. The physiological parameter measurement sensor or module processor 108 can extract information such as the pleth waveform from signals of the second wavelength.

The emitters can be configured to emit light having a third wavelength of about 900 nm to about 910 nm, or about 905 nm, or about 907 nm. The third wavelength can be in the infrared range. The sensor or module processor can use the third wavelength as a normalizing wavelength when calculating ratios of the intensity signals of the other wavelengths, for example, a ratio of the intensity signals of the second wavelength (red) to the third wavelength (infrared).

Additionally or optionally, the emitters can be configured to emit light having a fourth wavelength that is more sensitive to changes in water than the rest of the emitted wavelengths. The fourth wavelength can be in the infrared range and about 970 nm. The physiological parameter measurement sensor or module processor can determine physiological parameters such as a hydration status of the wearer based at least in part on a comparison of the intensity signals of the fourth wavelength and a different wavelength detected by certain detectors. The detectors used for hydration monitoring can be located a predetermined distance away from the emitters (that is, being a "far" detector disclosed herein) so that light travels through a certain depth of the tissue before being detected by those detectors.

The emitters in the physiological parameter measurement sensor or module can be placed in two emitter groups. Each emitter group can include four emitter LEDs configured to emit the first, second, third, and fourth wavelengths described above. The emitters in the same emitter group can be located in the same emitter chamber disclosed herein. Each of the four drivers are configured to drive the emitters to emit one of the four wavelengths described above.

In some aspects, drivers may drive the emitters at varying intensities. The intensity at which the drivers drive the emitters may affect the amount of light that is outputted (e.g., lumens), the strength of the light signal that is outputted, and/or the distance that the outputted light travels. The drivers may drive the emitters at varying intensities according to modeling, logic and/or algorithms. The logic and/or algorithms may be based, at least in part, on various inputs. The inputs may include historical data, the amount of light that is attenuated, for example as the light penetrates and travels through the tissue of the wearer, or the amount of blood with which the light is interacting, or the type of blood (e.g., venous, arterial) or type of blood vessel (e.g., capillary, arteriole) with which the light is interacting and/or the heat being generated by the emitters. For example, the drivers may increase the intensity at which they drive the emitters based upon a determination that too much light is being attenuated in the tissue or that the light is not interacting with enough blood. As another example, the drivers may decrease the intensity at which they drive the emitters based upon a determination that the emitters have exceeded a threshold temperature. The threshold temperature may be a temperature which may be uncomfortable for human skin.

In some aspects, each of the drivers may be capable of driving a corresponding emitter at various intensities independently of the other drivers. In some aspects, each of the drivers may drive a corresponding emitter at various intensities in unison with each of the other drivers.

Additionally, various LEDs may be used in various aspects. For example, certain LEDs may be used which are capable of outputting more light with the same amount of power as other LEDs. These LEDs may be more expensive. In some aspects, less expensive LEDs may be used. In some aspects, a combination of various types of LEDs may be used.

FIG. 13C illustrates an example detector circuitry including fourteen detectors 106. The total number of detectors on a module can vary. The fourteen detectors can form seven detector groups, each group including two detectors. The number of detectors in each group may vary. Detectors of the same detector group can be located in the same detector chamber disclosed herein. Each detector group can output one signal, which can be a combined signal of the two detectors in the same group. As shown in FIG. 13C, the detectors can share a common anode but have seven different cathodes, corresponding to the seven detector groups.

FIG. 13D illustrates an example thermistor circuitry. In the illustrated example, the physiological parameter measurement module can include two thermistors 110. The two thermistors can be located in the two emitter chambers near the two emitter groups respectively.

Example Signal Processing of the Physiological Parameter Measurement Module

Figure 14A:
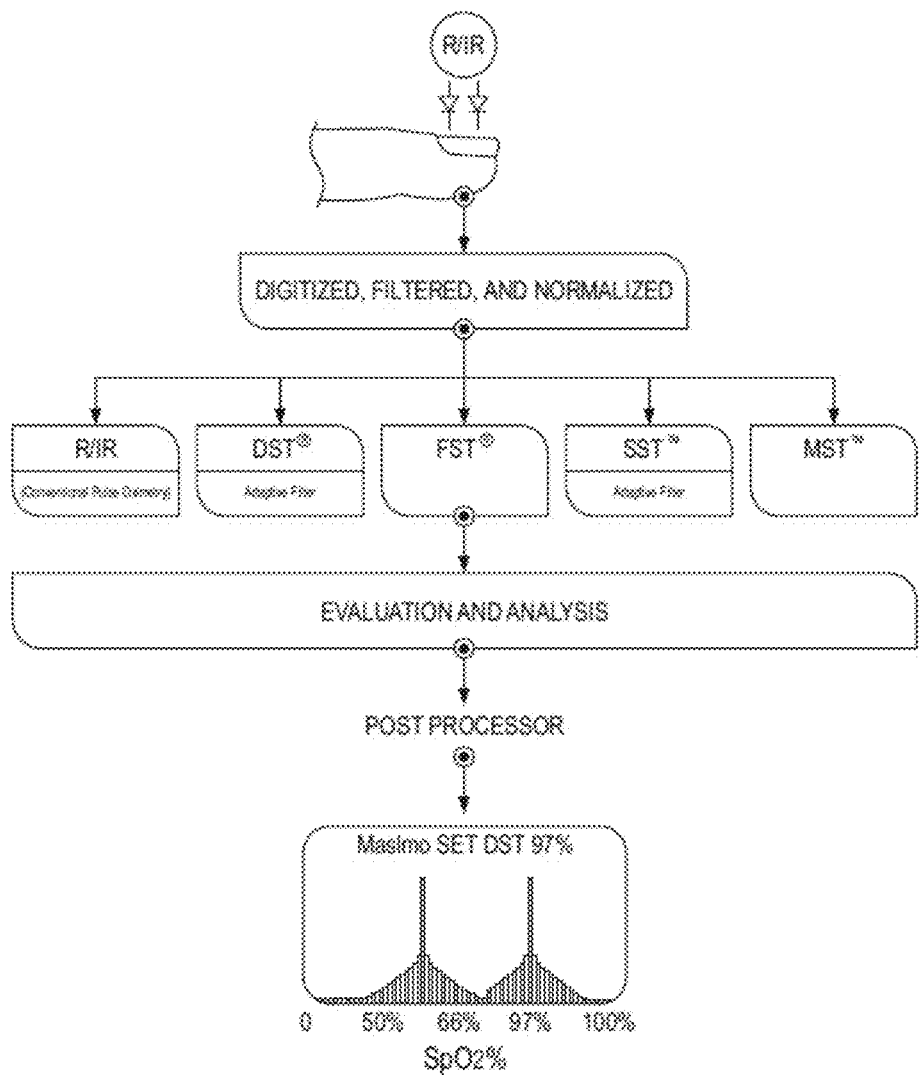
FIGS. 14A and 14B are example block diagrams illustrating signal processing of a conventional plethysmograph sensor.
Figure 14B:
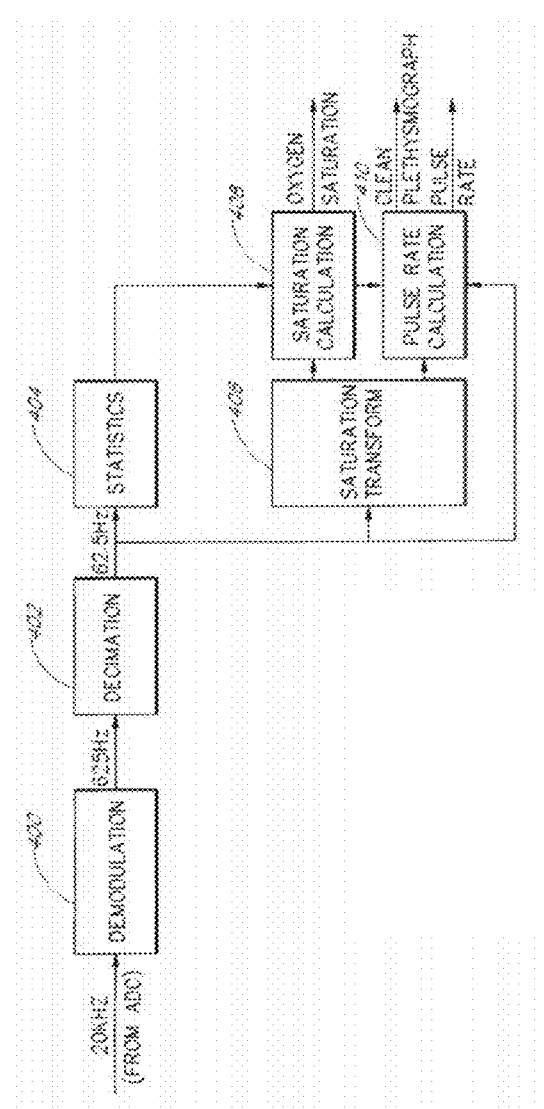

FIGS. 14A and 14B depict functional block diagrams of the operations of a conventional pulse oximeter carried out by the digital signal processing system. The signal processing functions described below are carried out by a digital signal processor (DSP) with a microcontroller providing system management. As shown in FIG. 14A, an analog signal from the detector(s) of the conventional pulse oximeter is digitized, filtered and normalized, and further processed using conventional pulse oximetry signal processing algorithms. Parallel signal processing engines—DST®, FST®, SST™, and MST™ are used to separate the arterial signal from sources of noise (including the venous signal) to measure SpO2 and pulse rate accurately, even during motion. FIG. 14B depicts a generalized functional block diagram for the operations performed on the 20 Khz sample data entering the digital signal processing system from an analog to digital converter (ADC). As illustrated in FIG. 14B, the DSP first performs a demodulation, as represented in a demodulation module 400. The processor performs decimation, as represented in a decimation module 402 on the resulting data from the demodulation. The processor calculates certain statistics, as represented in a statistics module 404, and performs a saturation transform, as represented in a saturation transform module 406, on the data resulting from the decimation operation. The processor forwards data subjected to the statistics operations and the data subjected to the saturation transform operations to saturation operations, as represented by a saturation calculation module 408 to output an oxygen saturation measurement and pulse rate operations, as represented in a pulse rate calculation module 410 to output a pulse rate value.

Figure 15A:
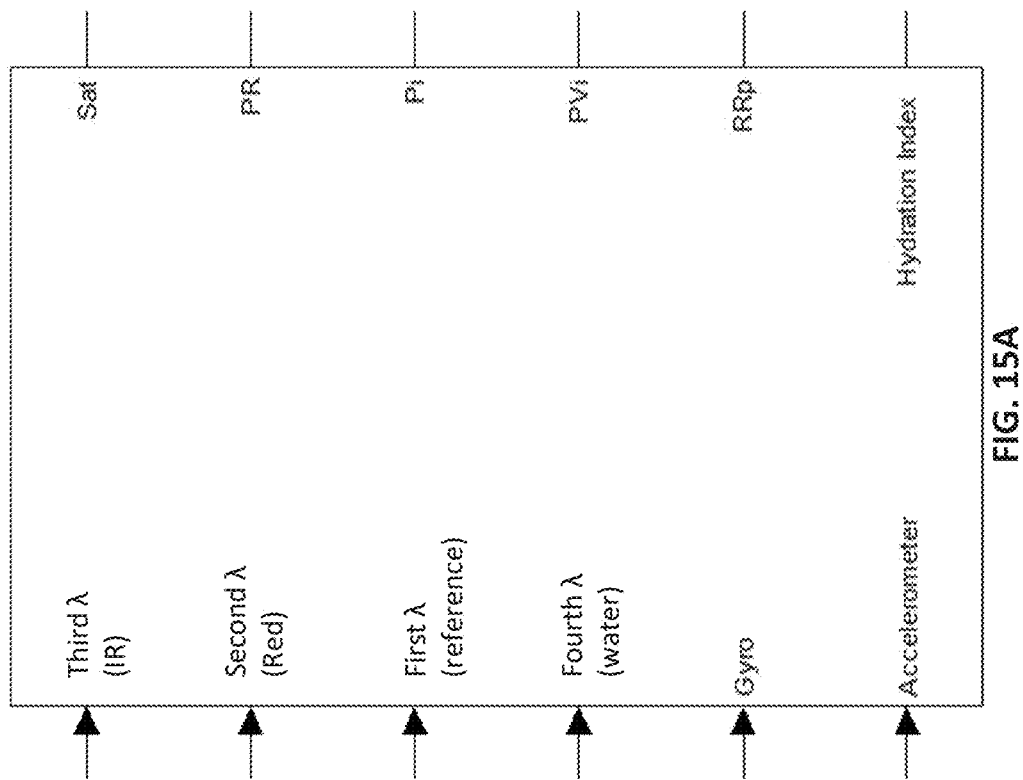
FIGS. 15A and 15B illustrate example schematic input and output flow diagrams of a physiological parameter measurement module disclosed herein.

FIGS. 15A-15G illustrate example signal processing of the physiological parameter measurement sensor or module disclosed herein. As shown in FIG. 15A, the sensor or module processor can receive intensity signals from the detectors in response to detected reflected light of the first (reference signal or signal of green or yellow light), second (signal of red light), third (signal of infrared light), and fourth (signal of infrared light with a wavelength of 970 nm) wavelengths described above, and signals from the gyroscope and accelerometer. The sensor or module processor can output a plurality of physiological parameters based on the input signals from the sensors described above. The plurality of physiological parameters can include, for example, SpO2 (Sat), pulse rate (PR), perfusion index (PI), pleth variability index (PVI), respiration rate from the pleth (RRp), and a hydration index.

Figure 15B:
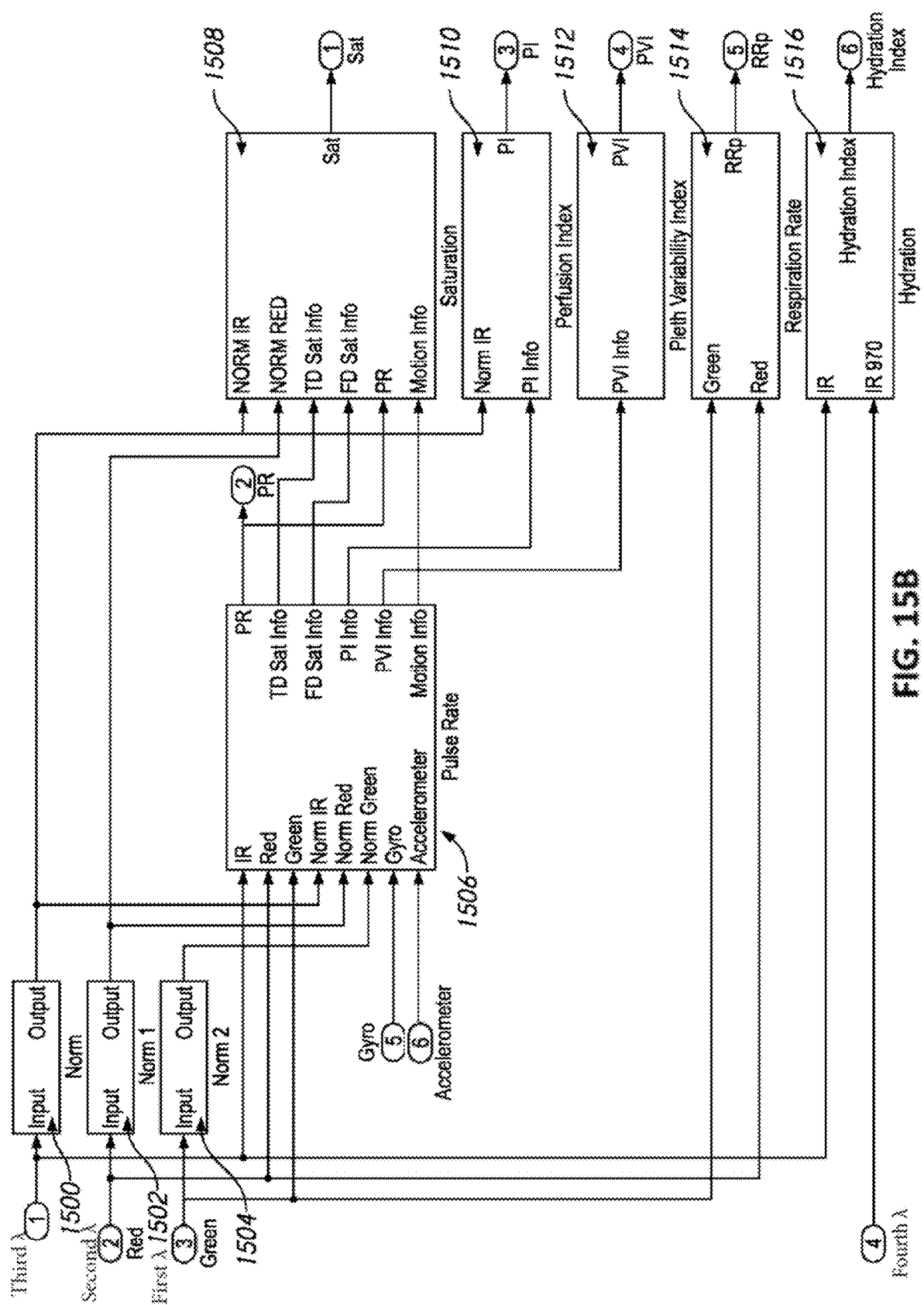

As shown in greater detail in FIG. 15B, the sensor or module processor can process the intensity signal in response to detected light of the first, second, and third wavelengths in the unnormalized form and a normalized form (in normalization modules "Norm" 1500, "Norm 1" 1502, and "Norm 2" 1504). As described above, the signal of the third wavelength can be used as the normalizing signal. The sensor or module processor can extract various information from the intensity signals in response to detected light of the first, second, and third wavelengths and signals from the accelerometer and the gyroscope, such as the PR (which can be output as the PR measurement), time domain (TD) saturation information, frequency domain (FD) saturation information, PI information, and PVI information, in a pulse rate determination module 1506.

Figure 15C:
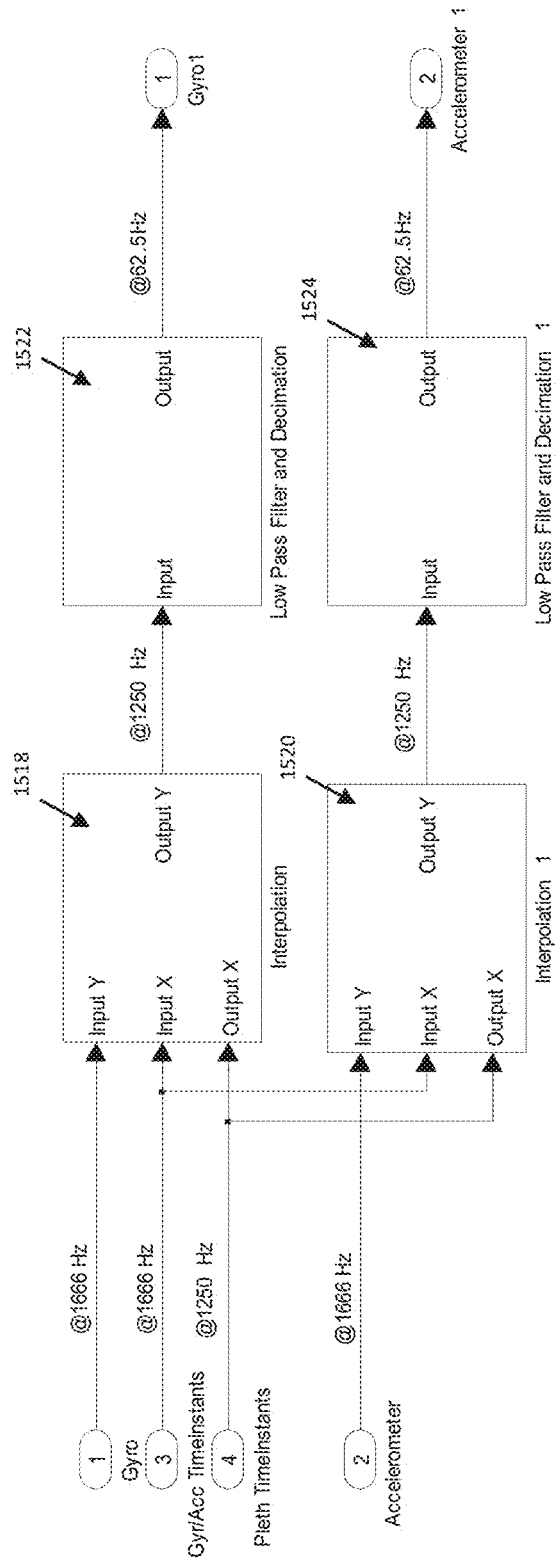
FIG. 15C illustrates an example schematic input and output flow diagram of the gyroscope and accelerometer of a physiological parameter measurement module disclosed herein.

FIG. 15C illustrates example processing of the raw signals from the accelerometer and the gyroscope to output the gyroscope and accelerometer signals. The sensor or module processor can combine each of the raw gyroscope and accelerometer signals (which can be raw signals from any axis of the gyroscope and/or accelerometer) with gyroscope/accelerometer time instants and pleth time instants signals in an interpolation module 1518 or interpolation 1 module 1520 respectively. The sensor or module processor can further process the outputs from the interpolation module 1518 or interpolation 1 module 1520 in a low pass filter and decimation module 1522 or low pass filter and decimation 1 module 1524 respectively to output a gyrol signal and an accelerometer 1 signal. The output gyre 1 and accelerometer 1 signals can be sent to the ASIC described above.

Figure 15D:
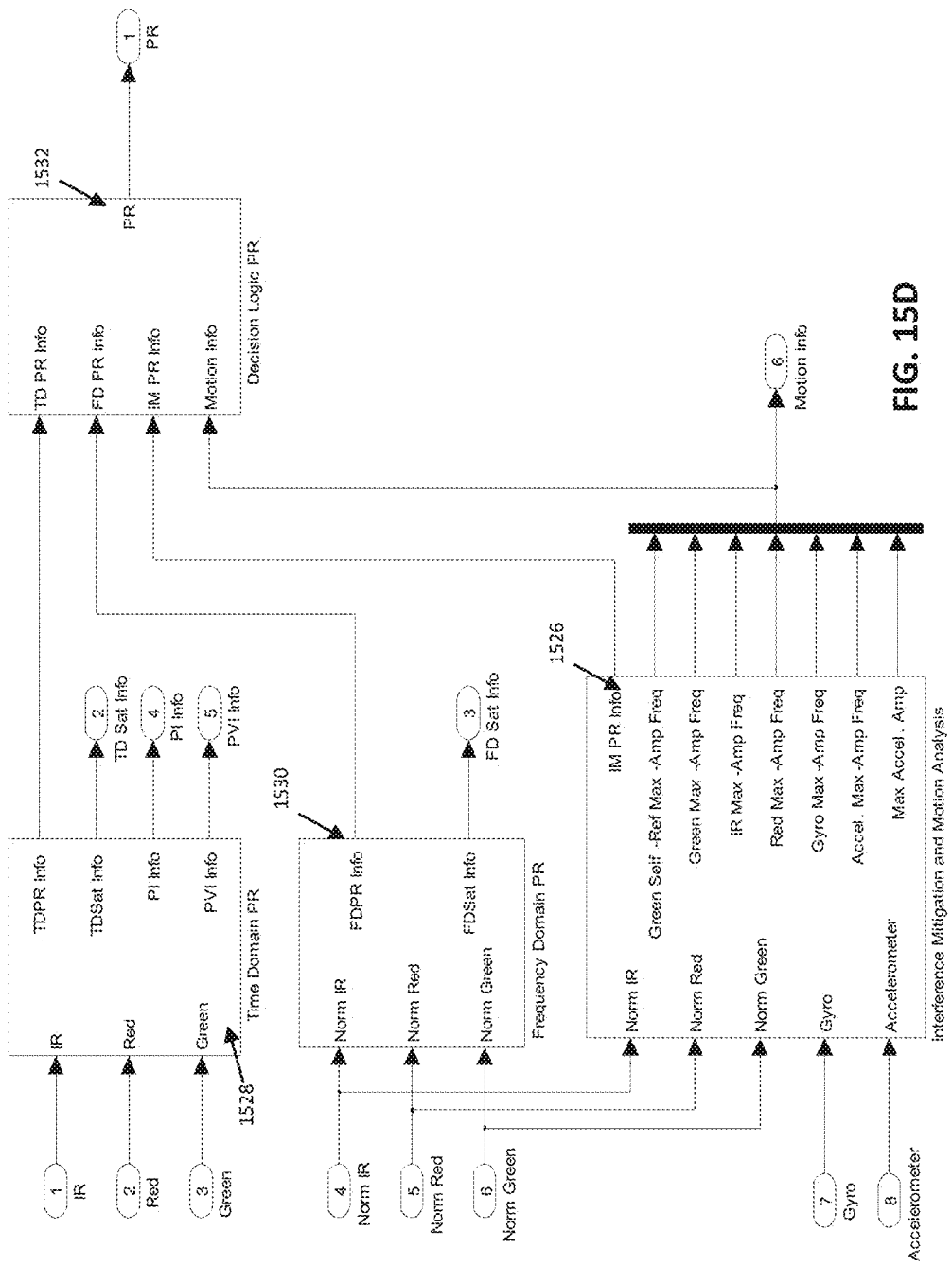
FIG. 15D illustrates an example schematic block diagram for determining pulse rate using a physiological parameter measurement module disclosed herein.

As shown in FIG. 15D, the sensor or module processor can extract motion information from the gyroscope and accelerometer input and the normalized signals of the first, second, and third wavelengths in an interference mitigation (IM) and motion analysis module 1526. As also shown in FIG. 15D, the sensor or module processor can obtain time domain pulse rate (TDPR) information, TD saturation information, PI information, and PVI information in a time domain pulse rate determination module 1528 from the intensity signals of the first, second, and third wavelengths. The sensor or module processor can obtain frequency domain pulse rate (FDPR) information and FD saturation information in a frequency domain pulse rate determination module 1530 based on normalized signals of the first, second, and third wavelengths. The sensor or module processor can determine and output a pulse rate in a pulse rate decision logic 1532 based on the TDPR information, FDPR information, interference mitigation (IM) PR information (output by the interference mitigation and motion analysis module 1526), and motion information.

Figure 15E:
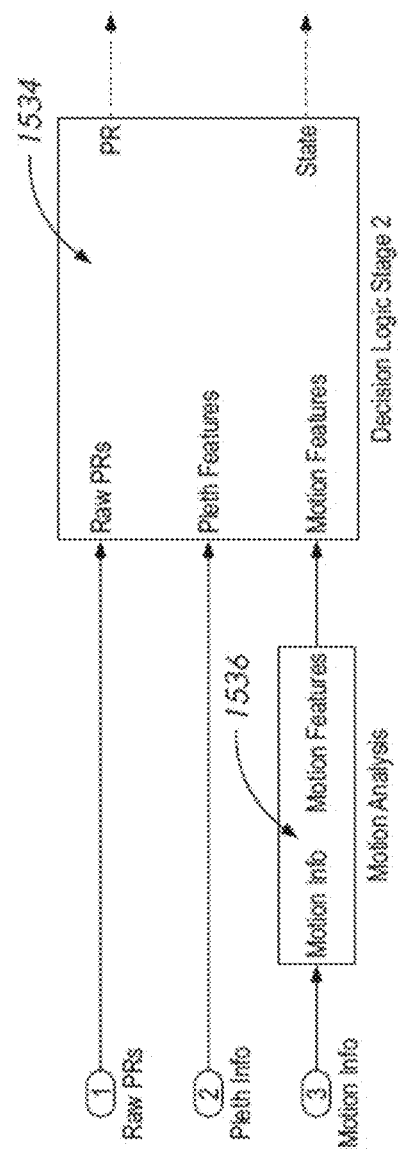
FIG. 15E illustrates an example decision logic for determining pulse rate using a physiological parameter measurement module disclosed herein.

FIG. 15E illustrates an example pulse rate determination decision logic. In this example, a decision logic stage 2 module 1534 can receive as input raw pulse rate calculations from individual pulse rate determination engines (for example, the time domain pulse rate determination module 1528, the frequency domain pulse rate determination module 1530 and the interference mitigation and motion analysis module 1526 as shown in FIG. 15D), pleth features including time domain and frequency domains from N channels (for example, N=4 or more) of pleth signals, and motion features obtained from a motion analysis module 1536. The motion analysis module 1536 can assess the amount of motion, define the type of motion, and calculate a motion rate (for example, per minute) if the motion is determined to be periodic, and/or the like based on motion information from a 6DOF (degree-of-freedom) inertia measurement unit (IMU). The IMU can include the accelerometer and the gyroscope on the physiological parameter measurement module.

Figure 15F:
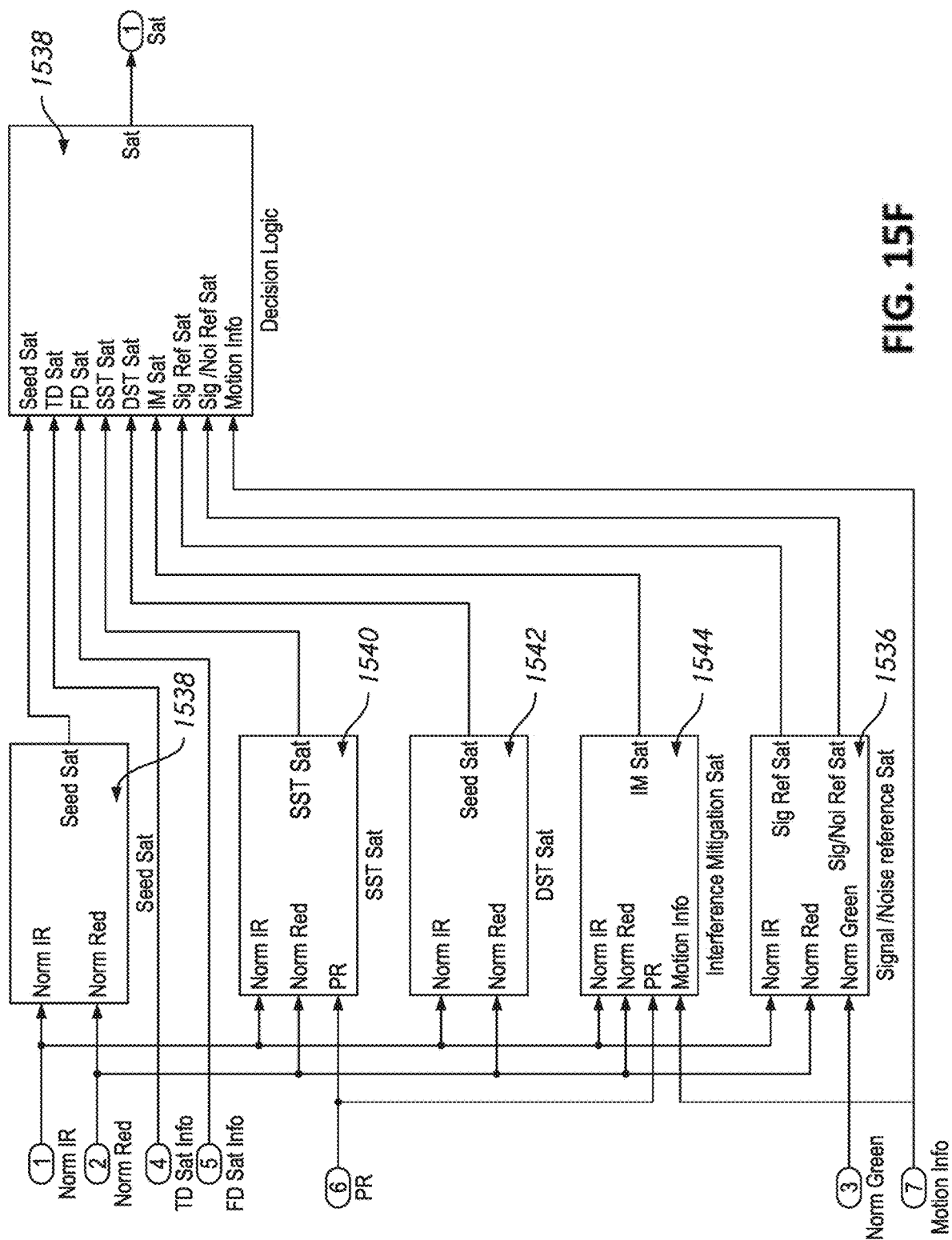
FIG. 15F illustrates an example schematic input and output flow diagram for determining oxygen saturation using a physiological parameter measurement module disclosed herein.
Figure 15G:
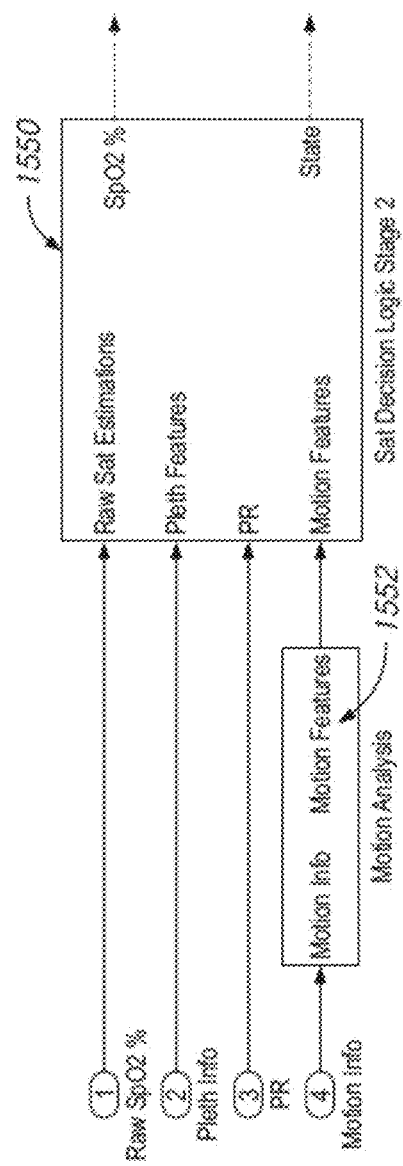
FIG. 15G illustrates an example decision logic for determining oxygen saturation using a physiological parameter measurement module disclosed herein.

With continued reference to FIG. 15B, the sensor or module processor can determine the oxygen saturation measurement based on the normalized signal of the third wavelength, the normalized signal of the second wavelength, the TD saturation information, the FD saturation information, the PR, and the motion information in an oxygen saturation determination module 1508. FIG. 15F illustrates an oxygen saturation determination module including a plurality of parallel signal processing engines, such as a Seed saturation module 1538, an SST saturation module 1540, a DST saturation module 1542, an interference mitigation (IM) saturation module 1544, and a signal/noise reference saturation module 1546, configured to feed individual raw oxygen saturation (SpO2) values to a decision logic 1548. The decision logic 1548 can further receive as input the motion information and output a final oxygen saturation measurement based on the motion information and the raw oxygen saturation values determined by the parallel engines.

FIG. 15E illustrates an example oxygen saturation determination decision logic. In this example, a saturation decision logic stage 2 module 1550 can receive as input raw oxygen saturation calculations from the parallel engines described above, pleth features, pulse rate, and motion features obtained from a motion analysis module 1552. The pleth features received by the module 1550 can include the features in the pulse rate decision logic shown in FIG. 15E. Additionally, the pleth features received by the module 1550 can include features related to saturation, for example, the DC ratio of the second and third wavelengths. The motion analysis module 1552 can receive the same features as the pulse rate decision logic shown in FIG. 15E.

With continued reference to FIG. 15B, the sensor or module processor can determine the PI measurement based on the normalized signal of the third wavelength and the PI information in a perfusion index determination module 1510. The sensor or module processor can determine the PVI measurement based on the PVI information in a pleth variability index determination module 1512. The sensor or module processor can determine the RRp measurement based on the intensity signals of the first and second wavelength in a respiration rate determination module 1514. The sensor or module processor can determine the hydration index in a hydration determination module 1516 based on the intensity signals (for example, from the "far detectors" disclosed herein) of the fourth wavelength, which is more sensitive to changes in water in the measurement site and another wavelength (for example, the third wavelength or about 905 nm) that is less sensitive to changes in water. The sensor or module processor can focus on the DC component of the signals for hydration status monitoring.

Various example physiological parameter measurement modules and wearable devices incorporating the same will be described below. Each of the example modules and devices can incorporate any of the features of the physiological parameter measurement module 100 and the device 10 described above, all of which are not repeated for brevity. Features of the example modules and devices disclosed herein can be incorporated into one another.

Figure 16B:
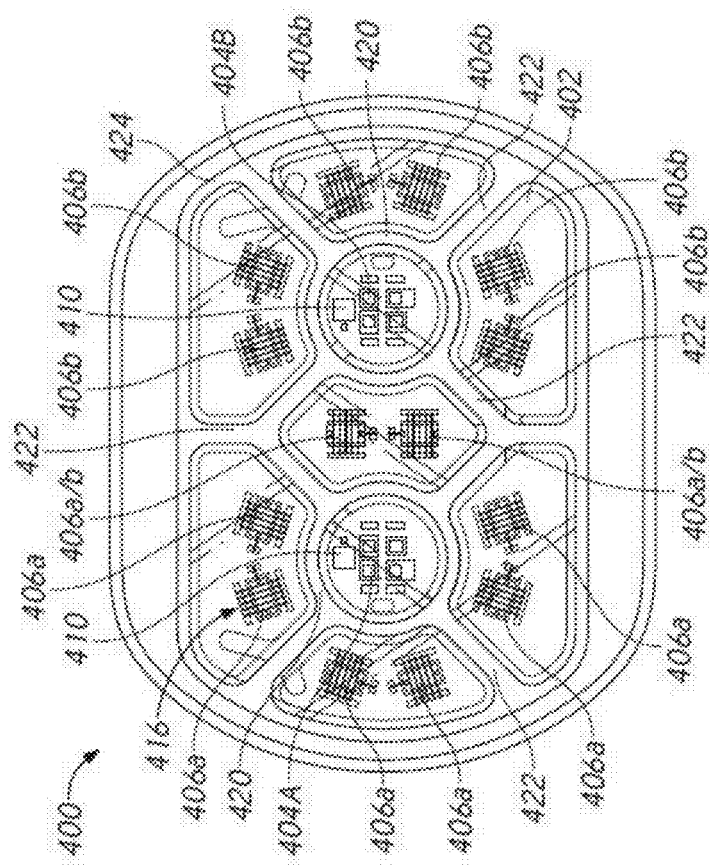
FIG. 16B illustrates a bottom view of an example physiological parameter measurement module incorporating the plethysmograph sensor arrangement of FIG. 16A.
Figure 16A:
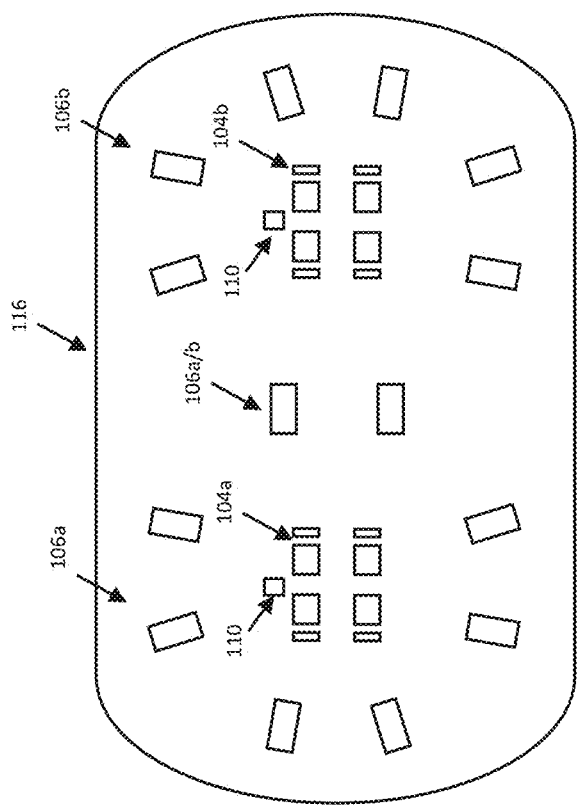
FIG. 16A illustrates schematically an example plethysmograph sensor arrangement on a sensor or module processor board of a physiological parameter measurement module of a wearable device.

Examples of Physiological Parameter Measurement Modules with Double Emitter Groups FIG. 16A illustrates schematically an example arrangement of an optical sensor, including emitters, detectors, and thermistors, on a sensor or module processor PCB 116. As shown in FIG. 16A, the PCB 116 can include a first group of emitters 104a and a second group of emitters 104b. Each group of emitters can include four emitters. The emitters in each group 104a, 104b can emit at least the first, second, third, and fourth wavelengths as described above. The first and second groups of emitters 104a, 104b can be located a distance from each other on a first side of a PCB 116. The PCB 116 can include a temperature sensor (such as a thermistor) 110 as described above located on the first side of the PCB 116. One temperature sensor 110 can be near the first group of emitters 104a. Another temperature sensor 110 can be near the second group of emitters 104b.

The PCB 116 can be elliptical in shape, although the shape of the PCB is not limiting. The two groups of the emitters 104a, 104b can be located on different parts of the first side of the PCB 116 divided along the minor diameter of the ellipse. Each of the two groups of the emitters 104a, 104b can be surrounded by a first light barrier and form an emitter chamber.

The first and second groups of emitters 104a, 104b can be surrounded by two rings of detectors 106a, 106b that are separated from the first and second groups of emitters 104a, 104b respectively by a distance. The two rings of detectors 106a, 106b can share a plurality of (for example, two or more) detectors 106a/b common to both rings. The detectors 106a/b common to both rings can be located along the minor axis of the ellipse. In the illustrated example, the PCB 116 can include fourteen detectors coupled to the PCB 116, but the total number of detectors can vary.

The detectors 106b can be the far detectors for the first group of emitters 104a and the detectors 106a, 106a/b can be the near detectors for the first group of emitters 104a. The detectors 106a can be the far detectors for the second group of emitters 104b and the detectors 106b, 106a/b can be the near detectors for the second group of emitters 104b. Accordingly, each detector 106a, 106b, 106a/b can receive two signals for each wavelength emitted by the first and second groups of emitters 104a, 104b respectively. As described above, signals outputted by the far and near detectors can provide different information due to the different light paths, which can travel through different areas of the tissue. In addition, the far detectors for each group of emitters 104a, 104b can detect the light emitted by the respective group of emitters 104a, 104b, for example, light of the fourth wavelength and another wavelength, and attenuated by tissue to provide an indication of the wearer's hydration status as described herein.

The detectors 106a, 106b, 106a/b can be separated or partitioned into seven detector regions. Each detector region can include two detectors, or any other number of detectors. Each detector region can form a detector chamber surrounded by light barriers. As described above, the sensor or module processor can process signals from a particular emitter and received at the detectors within the same detector region as one signal source. Accordingly, for each wavelength, the sensor or module processor can receive data from a total of fourteen signal sources, two from each detector region acting as the far and near detectors for the different groups of emitters respectively.

Figure 16D:
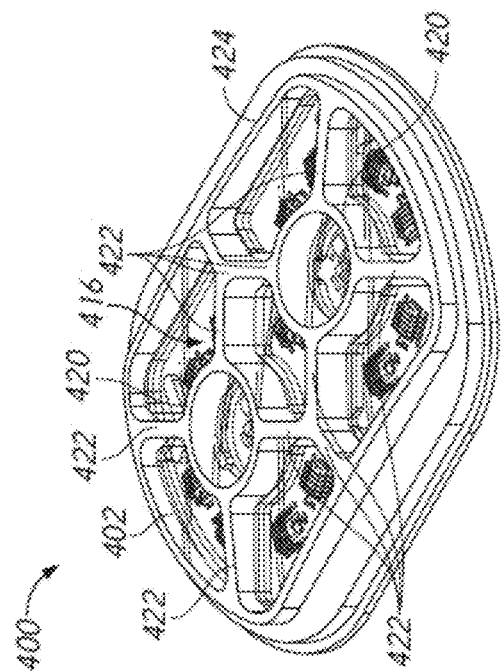
FIG. 16D illustrates a bottom perspective view of the example physiological parameter measurement module of FIG. 16B.
Figure 16C:
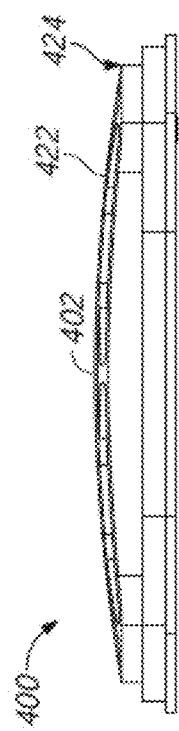
FIG. 16C illustrates a side view of the example physiological parameter measurement module of FIG. 16B.

FIGS. 16B-16D illustrate an example physiological parameter measurement module 400 of a wearable device. The module 400 can incorporate any of the features of the module examples described herein.

As shown in FIG. 16B, the physiological parameter measurement module 400 can include a first group of emitters 404a and a second group of emitters 404b incorporating the arrangement shown in FIG. 16A. Each group of emitters can include four emitters (or optionally a different number of emitters, such as six or eight emitters). The emitters in each group 404a, 404b can emit at least the first, second, third, and fourth wavelengths as described above. Each of the two groups of the emitters 404a, 404b can be surrounded by a first light barrier 420 and form an emitter chamber.

The first and second groups of emitters 404a, 404b in the module 400 can be surrounded by two rings of detectors 406a, 406b that are separated from the first and second groups of emitters 404a, 404b by the first light barrier 420. The two rings of detectors 406a, 406b can share a plurality of (for example, two or more) detectors 406a/b common to both rings. The detectors 406a, 406b, 406a/b can have the same arrangement as the detectors shown in FIG. 16A. In the illustrated example, the module 400 can include fourteen detectors, but the module 400 can also include a different total number of detectors.

As shown in FIGS. 16B and 16D, the detectors 406a, 406b, 406a/b can be separated or partitioned into seven detector chambers by a portion of the first light barrier 420 and second light barriers 422. Each detector region can include two detectors, or any other number of detectors. Along an outer perimeter of the module 400, the detectors 406a, 406b, 406a/b can be enclosed within a module side wall 424. A sensor or module processor of the module 400 can process signals from a particular emitter and received at the detectors within the same detector region as one signal source as described above. The arrangement of emitters 404a, 404b and detectors 406a, 406b, 406a/b and the light diffusing materials encapsulating the emitters 404a, 404b and/or detectors 406a, 406b, 406a/b can improve the sensing coverage on the wearer's wrist, which has fewer capillaries per volume than the fingertip as described above. The aggregate light detecting area of the 106a, 106b, 106a/b in FIG. 16B, that is, the aggregate surface area of all the detector chambers, can occupy about 50% or more of the tissue-facing surface of the physiological parameter measurement module. The aggregate light detecting area in FIG. 16B can be, for example, greater than about 100 mm$^2$, or greater than about 125 mm$^2$, or about 150 mm$^2$, or about 165 mm$^2$. The aggregate light emitting area in FIG. 16B, that is, the aggregate surface area of both emitters chambers, can be, for example, greater than about 25 mm$^2$, or about 30 mm$^2$, or about 35 mm$^2$. Any other physiological parameter measurement module examples disclosed herein can have the same or substantially similar aggregate light detecting area and/or light emitting area as the module 400 shown in FIG. 16B.

On the first side of the PCB 416, the module 400 can be enclosed by a curved light transmissive cover 402 with a convex protrusion. As shown in FIG. 16C, the cover 402 can have a continuous curvature. The first and second light barriers 420, 422 are configured to be in contact with the first side of the PCB 416 at one end. At the other end, the height of the first and second light barriers 420, 422, and of the side wall 424 can generally follow the curvature of the cover 402.

The side wall 424 can be shorter than the second light barrier 422. The height of the second light barrier 422 can increase from the perimeter of the module 400 toward a center of the module 400 until the second light barrier 422 merges with the first light barrier 420, which is the highest among the light barriers. The light barriers 420, 422 can extend to the tissue-facing surface of the cover 402 so that when the module 400 is pressed into the skin of the wearer of a device incorporating the module 400, the tissue-facing surfaces of the first and second light barriers 420, 422, and of the side wall 424 can be configured to contact the skin of the wearer. The cover 402 can include individual lenses or covers such as shown in FIG. 7D or a combination of individual emitter chamber covering lenses or covers and a lens or cover covering a plurality of detector chambers, such as shown in FIG. 7C. The lenses or covers may be polycarbonate. The tissue-facing surface of the module 400 can include a continuous convex curvature.

The first and second light barriers 420, 422 and the side wall 424 can optionally form a single light barrier construct. The single light barrier construct can be formed by any suitable manufacturing techniques and any suitable materials, for example, plastic, colored, or opaque sapphire glass, or others. The single light barrier construct can include at one end a recess that is shaped and sized to receive the PCB 416, including the electronics on the PCB 416. The first side of the PCB 416 can include the emitters 404a, 404b, detectors 406a, 406b, 406a/b, temperature sensor 410, and any other sensors, for example, the gyroscope, the accelerometer, and/or the like. The second side of the PCB 416 can include the sensor or module processor and other circuit hardware.

As described above, the module 400 can include a plurality of chambers such that light cannot travel between the chambers because of the various light barriers extending from the PCB 416 to the tissue-facing surface of the cover 402 as described herein. The light diffusing materials described above can be added above (for example, via the fill holes described herein) and around the emitters 404a, 404b, and/or optionally above and around the detectors 406a, 406b, 406a/b, to improve distribution of emitted lighted and/or detected light after attenuation by the tissue. The light diffusing materials can include a flow of glass microsphere solution, which can be injected into the chambers after the module 400 has been assembled. After being injected into the respective chamber, the solution can be UV-cured. Air can escape via the vent openings disclosed herein as the diffusing material solution is injected into the respective chambers via the injection openings, making it easier for the glass microsphere solution to flow into the respective chamber. The cover 402 can also include glass microspheres. The light diffusing materials in the cover 402 and inside the emitter chambers and/or the first light barrier 420 can make the emitted light leave the emitter chambers enclosing the emitters 404a, 404b in a direction generally parallel to the height of the first light barrier 420. The light diffusing materials in the cover 402 and the detector chambers can increase the amount of reflected light being directed to and detected by the detectors 406a, 406b, 406a/b.

FIGS. 16E-16G illustrate an example physiological parameter measurement modules 401 of a wearable device. The module 401 can include the same optical sensor arrangements as shown in FIGS. 16A-16D and have any of the features of the module 400 in FIGS. 16B-16D with the differences noted in the description of FIGS. 16E-16G. The module 401 can have any of the features of the other physiological parameter measurement module examples described herein.

The module 401 can include a generally circular outer shape. The generally circular outer shape can be defined by an opaque frame 426 extending over of the PCB 416 from a first side of the PCB 416. The opaque frame 426 can have a height such that a top side of the opaque frame 426 can be generally level with (or receding or protruding slightly from) a second side of the PCB 416. As shown in FIG. 16G, the PCB 416 can be generally circular in shape. The opaque frame 426 can be generally concentric with the PCB 416. The opaque frame 426 and the PCB 416 are not transmissive to light. The opaque frame 426 in FIGS. 16E and 16F can include the first light barrier 420 and second light barriers 422 as an integral piece.

The module 401 can include one or more (for example, two or otherwise) ECG electrodes 424. In the illustrated examples of FIGS. 16E-16G, one of the ECG electrodes 424 can be a reference electrode and the other one of the ECG electrode 424 can be a negative or positive electrode. The opaque frame 426 can have indentations having the shape and size to accommodate the electrodes 424, similar to the indentations on the opaque frame 126 shown in FIG. 7D. As shown in FIG. 16F, a bottom surface of the electrodes 424 can have a curvature that is generally continuous with the curvature of the opaque frame 426 and the light-transmissive cover 402. As shown in FIG. 16G, a top side of the electrodes 424 can have one or more posts 437 extending past openings in the opaque frame 426 into corresponding openings on the PCB 416. The posts 437 of the electrodes 424 can establish an electrical connection with the corresponding openings of the PCB 416. A plurality of screws (or other types of fasteners) can extend into the corresponding openings of the PCB 416 from the front side of the PCB 416 to secure the electrodes 424 to the module 401 by threadedly mating with the posts. When a wearer puts the wearable device incorporating the module 401 onto the wearer's wrist, the electrodes 424 can make contact with the wearer's skin. The electrodes 424 can have the same polarity as the electrodes 124 disclosed herein. As disclosed herein, the wearable device incorporating the module 401 can include another ECG electrode 125 located on the housing of the wearable device configured to make contact with the wearer's skin.

On the second side of the PCB 416, which faces away from the cover 402, the PCB 416 can be covered by melt plastic or other suitable electronics protective material 430 (similar to the protective material 130 disclosed herein) except that a flex connector 432 can remain exposed. The flex connector 432 can be configured to connect the module 401 electrically to the wearable device incorporating the module 401.

FIGS. 17A-17C illustrate an example physiological parameter measurement modules 403 of a wearable device. The module 403 can include the same optical sensor arrangements as shown in FIGS. 16A-16G and have any of the features of the module 400 in FIGS. 16B-16D and any of the features of the module 401 in FIGS. 16E-16G with the differences noted in the description of FIGS. 17A-17C. The module 401 can have any of the features of the other physiological parameter measurement module examples described herein.

As shown in FIGS. 17A-17C, the opaque frame 426 can include an opening fitted with the light transmissive cover 402. The cover 402 extending over emitter chambers or detector chambers formed by the light barriers 420, 422, 423 and the PCB 415 can include a single lens or cover. The cover 402 can be elliptical in shape. The cover 402 can have a continuous convex curvature. As shown in FIG. 17C, the light barriers 420, 422, 423 may not extend to the tissue-facing surface of the cover 402 and can extend to below the cover 402 such that when a wearer puts on a wearable device incorporating the module 402, the wearer's tissue comes into contact with the cover 402 and the electrodes 424, but not with any of the light barriers 420, 422, 423.

FIGS. 18A-19C illustrate other non-limiting examples of a physiological parameter measurement module with two emitter groups in two separate emitter chambers formed by a light barrier. In those configurations, the perimeter of the module can have a different shape. For example, FIG. 19A illustrates schematically a module 300 having an outer shape of two circles partially overlapped with each other. The circle in the module 300 can have a radius, for example, between about 6 mm and about 12 mm, or between about 8 mm and about 10 mm. The module 300 can have any of the features of the other modules disclosed herein. The module 300 can include the substantially the same arrangement of emitters 300a, 300b and detectors 306a, 306b, 306a/b as the module 400, 401, 403 described above except that each emitter group 304a, 304b includes three emitters. The module 300 can include a thermistor near each emitter group 304a, 304b. The module 300 can have a length of, for example, between about 22 mm and about 28 mm, or between about 24 mm and about 26 mm.

Figure 18B:
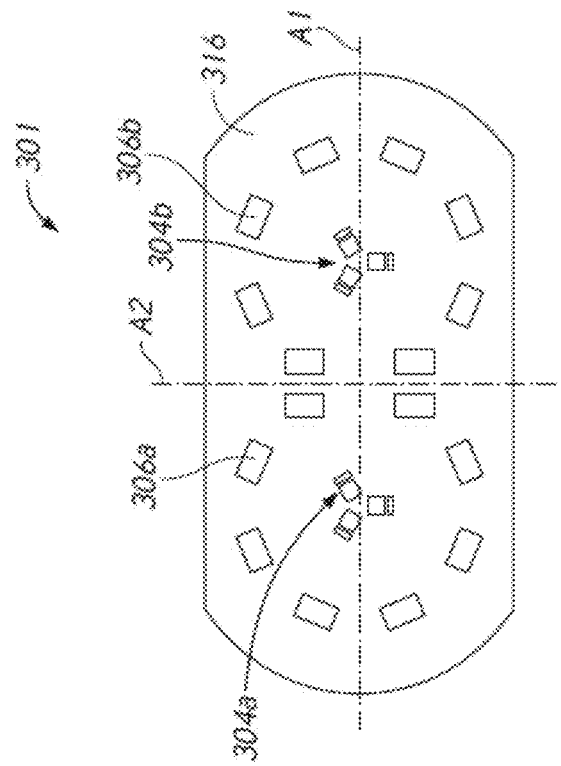
FIG. 18B illustrate schematically an example plethysmograph sensor arrangement on a sensor or module processor board of a physiological parameter measurement module of a wearable device.
Figure 18A:
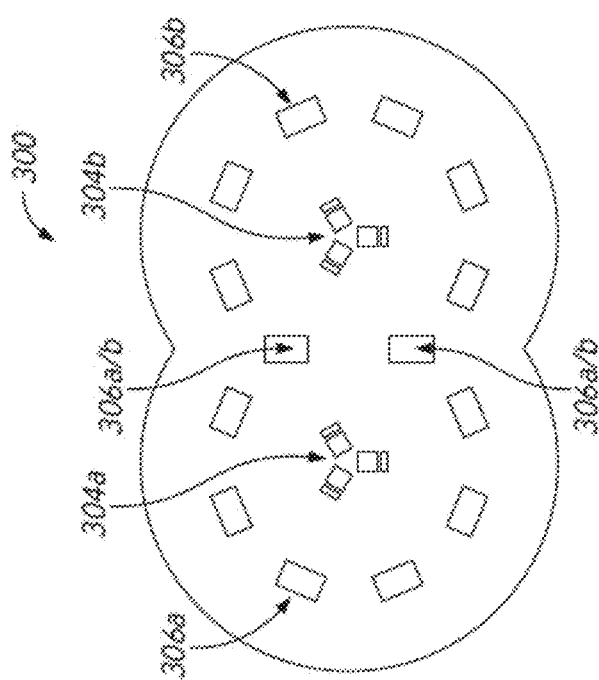
FIG. 18A illustrates schematically an example plethysmograph sensor arrangement on a sensor or module processor board of a physiological parameter measurement module of a wearable device.

FIG. 18B illustrates a physiological parameter measurement module 301 including a variation of the arrangement of emitters and detectors of the module 300 in FIG. 18A, and can include any of the features of the module 300 except for the differences described herein. The module 301 differs from the module 300 by not sharing detectors located between the two groups of emitters 304a, 304b. The first group of emitters 304a can be surrounded by a first ring of detectors 306a on a first side of the minor axis A2 and the second group of emitters 304b can be surrounded by a second ring of detectors 306b that are on a second side of the minor axis A2.

FIG. 19A illustrates a physiological parameter measurement module 201 including a variation of the arrangement of emitters and detectors of the module 300 in FIG. 18A. The physiological parameter measurement module 201 can have any of the features of the modules 300, with the differences noted in the description of FIG. 19A. The module 201 can have any of the features of the other modules disclosed herein. In the module 201, the two overlapping circles of detectors 206a, 206b are closer to each other than in the module 300. The detectors 206a/b can be further away from each other than in the module 300 and may not be located between or separating the two emitter groups 204a, 204b. The module 201 can include two groups of emitters that are separated from each other by one light barrier. Each of the detectors in the module 201 can form its own detector chamber with one or more light barriers. The circle can have a radius, for example, between about 6 mm and about 12 mm, or between about 8 mm and about 10 mm. The module 300 can have a length of, for example, between about 18 mm and about 24 mm, or between about 20 mm and about 22 mm.

FIGS. 19B and 19C illustrate a variation of the module 201 in FIG. 19A with the differences noted in the description of FIGS. 19B and 19C. The module 200 in FIGS. 19B and 19C can have any of the features of the module examples described herein. In FIGS. 19B and 19C, a physiological parameter measurement module 200 can include two groups of emitters 204a, 204b surrounded by one ring of detectors 206. The module 200 can have a width, for example, between about 16 mm and about 22 mm, or between about 18 mm and about 20 mm. The module 200 can have a length, for example, between about 20 mm and about 28 mm, or between about 22 mm and about 25 mm.

Each group of the emitters 204a, 204b can include three of emitters. Each group of the emitters 204a, 204b can emit at least the first, second, and third wavelength described above. Optionally, each emitter group 204a, 204b can include a fourth emitter configured to emit the fourth wavelength that is more sensitive to water. The emitters can be located at or near a center portion of a PCB 216 of the module 200. The module 200 can include a temperature sensor located on the PCB 216 near each group of the emitters 204a, 204b.

The emitters can be covered by an inner lens or cover 202a. In the illustrated example, the inner lens or cover 202a can be generally elliptical. In other examples, the inner lens or cover may have any other shapes. The two groups of the emitters 204a, 204b can be located on two parts of the central portion of the PCB divided along the minor diameter of the ellipse. The two groups of the emitters 204a, 204b can be divided by an opaque divider barrier 228, which can reduce mixing of light emitted by the two groups of the emitters 204a, 204b. As shown in FIG. 19C, the divider barrier 228 can have a same or substantially the same height as the highest point of the inner lens or cover 202a when assembled in the module 200. The inner lens or cover 202a can include two components divided by the divider barrier 228.

The module 200 can include a plurality of detectors 206 (for example, about six, eight, ten, or more) that can be arranged on the PCB so that the detectors 206 are spaced apart around the emitters 204a, 204b. The emitters groups 204a, 204b and the detectors 206 can be separated by a first light barrier 220. The first light barrier 220 can extend along and surround the inner lens or cover 202a. The divider barrier 228 and the first light barrier 220 can form two emitter chambers 234a, 234b, each enclosing one of the two emitter groups 204a, 204b. The first light barrier 220 and the divider barrier 228 can also suppress light emitted by the emitters 204a, 204b at an angle so the light emitted by each group of emitters 204a, 204b can exit the inner lens or cover 202a in a direction generally parallel to the height of the first light barrier 220. The detectors 206 can be enclosed within a module side wall 224. The module side wall 224 can define a perimeter of the module 200. As shown in FIG. 19B, the perimeter of the module 200 can have a generally elliptical outer shape. The detectors 206 can be further separated from one another by a plurality of divider barriers 226, forming detector chambers 236, each containing one detector 206.

As shown in FIG. 19C, the first light barrier 220 can protrude slightly from, that is, proud of the edge of the inner lens or cover 202a and the other lenses or covers that will be described below. The detectors 206 can be covered by an outer lens or cover 202b. The outer lens or cover 202b can be generally concentric with the inner lens or cover 202a. In the illustrated examples, the outer lens or cover 202b can be an elliptical disc as shown in FIG. 19B. In other examples such as those disclosed herein, the outer lens or cover can have other shapes. As shown in FIG. 19C, the outer lens or cover 202b can have a smaller curvature than the inner lens or cover 202a such that the inner lens or cover 202a protrudes more than if the inner lens or cover had the same curvature as the outer lens or cover 202b.

As shown in FIG. 19C, the side wall 224 can be shorter than the first light barrier 220. The height of the side wall 224 can be configured such that the tissue-facing end of the side wall 224 is generally continuous with the curvature of outer lenses or covers 202b. The divider barriers 226 can have a height lower than the first light barrier 220. The height of the divider barriers 226 can be configured to accommodate the outer lens or cover 202b such that when assembled, the outer lens or cover 202b forms a substantially smooth surface with the module side wall 224. The tissue-facing ends of the first light barrier 220 and the side wall 224, and the tissue-facing surfaces of the inner lens or cover 202a and the outer lens or cover 202b can form the tissue-facing surface of the module 200. The slightly protruding first light barrier 220 and/or inner lens or cover 202a can be pressed into the wearer's skin at a higher pressure than the remainder of the lens or cover or light barriers.

The light diffusing materials described above can be included in one or more of the chambers 234a, 234b, 236 of the module 200 to improve distribution of emitted lighted and/or detected light. As shown in FIG. 19B, one or more of the lenses or covers 202a, 202b can include an injection opening 244 so that the light diffusing materials, which can include a flow of glass microsphere solution, can be injected into the respective chambers 234a, 234b, 236 after the module 200 has been assembled. After the injection, the solution can be UV-cured. The lenses or covers 202a, 202b can include one or more venting openings that are smaller than the injection openings 244. Air can optionally escape via separate vent openings as the diffusing material solution is injected into the respective chambers 234a, 234b, 236 via the injection openings 244. The inner lens or cover 202a and the outer lens or cover 202b can also include glass microspheres so as to act as light diffusers.

Figure 27F:
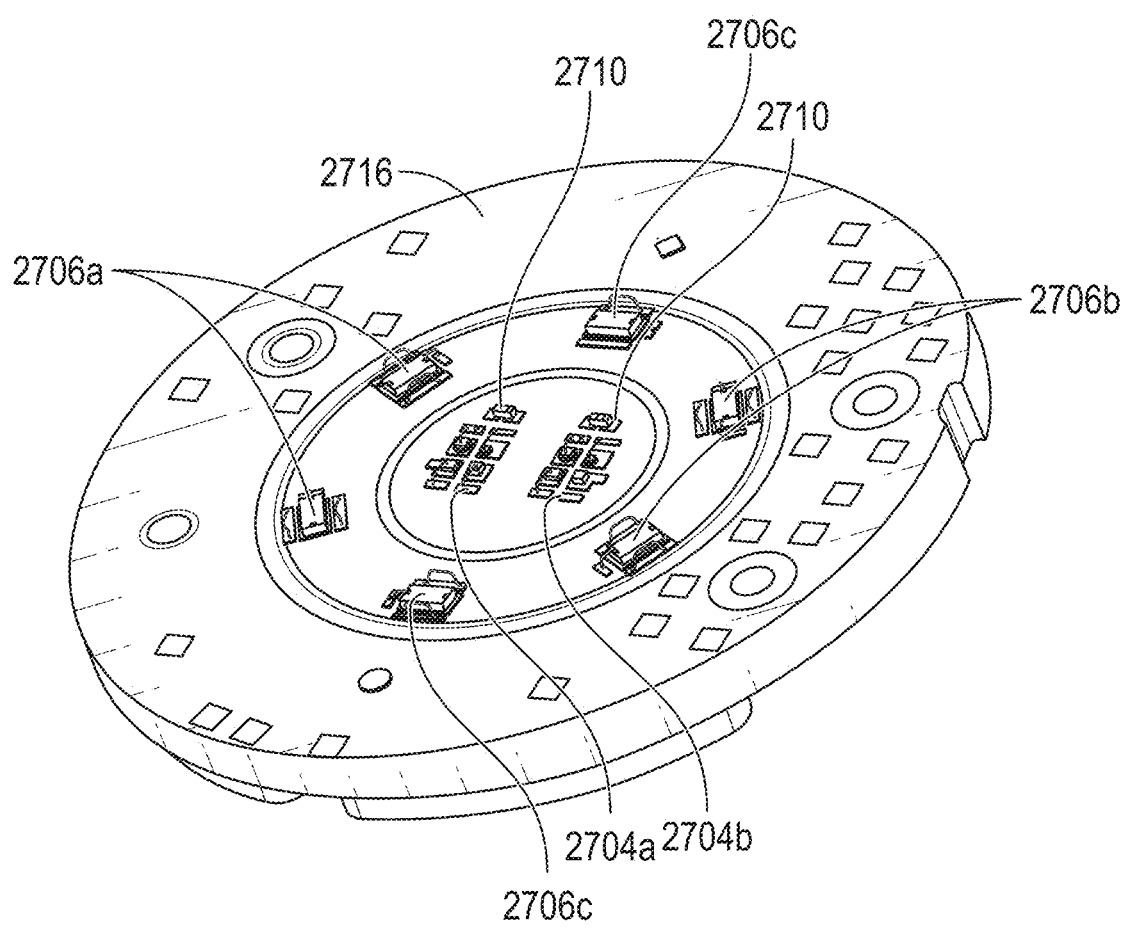
FIG. 27F illustrates a perspective view of PCB substrate of a physiological parameter measurement sensor or module with example plethysmograph sensor arrangement.

FIGS. 27A-27J illustrate other non-limiting examples of a physiological parameter measurement module 2700 of a wearable device. The module 2700 can incorporate any of the features of the module examples described herein. FIG. 27F illustrates an example arrangement of an optical sensor, including emitters, detectors, and thermistors, on a sensor or module processor substrate 2716. The substrate 2716 can include a printed circuit board (PCB). As shown in FIG. 27F, the substrate 2716 can include a first group of emitters 2704a and a second group of emitters 2704b. Each of the first and second groups of emitters 2704a, 2704b can include four emitters (or optionally a different number of emitters, such as three, six or eight emitters or any other number of emitters as required or desired). Each of the emitters of the first and second groups of emitters 2704a, 2704b may comprise an LED.

The emitters in the first and second group of emitters 2704a, 2704b can include operational and/or structural features discussed above, for example with reference to FIGS. 13A-13B. For example, the first and second group of emitters 2704a, 2704b can be configured to emit a plurality of (for example, three, four, or more) wavelengths. In some aspects, each of the emitters (e.g., within a group) can be configured to emit light of a different wavelength than the other emitters (e.g., of that group). Alternatively, one or more of the emitters can emit light of more than one wavelength. The emitters in the first and second group of emitters 2704a, 2704b can emit at least the first, second, third, and fourth wavelengths as described above with reference to FIG. 13B.

Each of the emitters in the first group of emitters 2704a may be located within close proximity to each of the other emitters in the first group of emitters 2704a. For example, each of the emitters of the first group of emitters 2704a may be located on the PCB between 0.2 mm and 2 mm from each of the other emitters in the first group of emitters 2704a. For example, each of the emitters of the first group of emitters 2704a may be located on the PCB about 0.5 mm from each of the other emitters of the first group of emitters 2704a. In some aspects, each of the emitters in the first group of emitters 2704a are positioned such that no more than a certain distance is between each of the emitters in the first group of emitters 2704a, such as 0.5 mm, 1 mm, 1.5 mm and/or 2 mm, or any other distance as required or desired. Each of the emitters in the second group of emitters 2704b may be located within close proximity to each of the other emitters in the second group of emitters 2704b, for example as described above with reference to the first group of emitters 2704a.

Each of the two groups of the emitters 2704a, 2704b can be surrounded by a first light barrier and form emitter chambers for the group of emitters 2704a and group of emitters 2704b, respectively. The first and second groups of emitters 2704a, 2704b can be located a distance from each other on a first side of a substrate 2716. The substrate 2716 can include one or more temperature sensor(s) (such as a thermistor) 2710 as described above located on the first side of the substrate 2716. One temperature sensor 2710 can be near the first group of emitters 2704a within the respective emitter chamber. Another temperature sensor 2710 can be near the second group of emitters 2704b within the respective emitter chamber.

The substrate 2716 can be circular in shape, although the shape of the PCB is not limiting. The two groups of the emitters 2704a, 2704b can be located on different parts of the first side of the substrate 2716 divided along a center line of the circle. Each of the two groups of the emitters 2704a, 2704b can be surrounded by a first light barrier and form an emitter chamber.

The first and second groups of emitters 2704a, 2704b can be surrounded by detectors 2706. As described in greater detail with reference to FIG. 27A, the detectors 2706 can be positioned on the substrate 2716 in a substantially circular or annular arrangement. The detectors 2706 may surround and/or enclose the first and second groups of 2704a, 2704b. Each of the detectors may be a similar or same distance from a geometric center of the substrate 2716 and/or the sensor or module 2700. In some aspects, the detectors 2706 may be rectangular including longer sides and shorter sides. The detectors 2706 may be positioned on the substrate 2716 such that a long side of each detector is orthogonal to a radius of the substrate 2716. In the illustrated example, the substrate 2716 includes six detectors coupled to the substrate 2716, but the total number of detectors can vary.

The detectors 2706b can be the far detectors for the first group of emitters 2704a. The detectors 2706a can be the near detectors for the first group of emitters 2704a. The detectors 2706a can be the far detectors for the second group of emitters 2704b. The detectors 2706b can be the near detectors for the second group of emitters 2704b. The detectors 2706c can be the intermediate detectors for the first and second groups of emitters 2704a, 2704b. Accordingly, each detector 2706a, 2706b, 2706c can receive two signals for each wavelength emitted by the first and second groups of emitters 2704a, 2704b respectively. As described above, signals outputted by the far, near and intermediate detectors can provide different information due to the different light paths, which can travel through different areas of the tissue.

In some aspects, the sensor or module processor may evaluate the various signals outputted by the detectors for example by comparing the signal quality of the detectors. The sensor or module processor may select less than all of the detector signals for processing for each of the far, near and intermediate detectors. For example, the sensor or module processor may rely on signals from one or two detectors from the four possible far detectors, and one or two detectors from the four possible near detectors, and one or two detectors from the four possible intermediate detectors.

In addition, the far detectors for each group of emitters 2704a, 2704b can detect the light emitted by the respective group of emitters 2704a, 2704b, for example, light of the fourth wavelength and another wavelength, and attenuated by tissue to provide an indication of the wearer's hydration status as described herein.

The detectors 2706a, 2706b, 2706c can be separated or partitioned into six detector regions. Each detector region can include one detector, or any other number of detectors. Each detector region can form a detector chamber surrounded by light barriers (as shown in FIG. 26E). As described above, the sensor or module processor can process signals from a particular emitter and received at the detectors within the same detector region as one signal source.

The module 2700 can include individual lenses or covers or a combination of individual emitter chamber covering lenses or covers and a lens or cover covering a plurality of detector chambers. The lenses or covers may be polycarbonate. The tissue-facing surface of the module 2700 can include a continuous convex curvature.

Figure 27G:
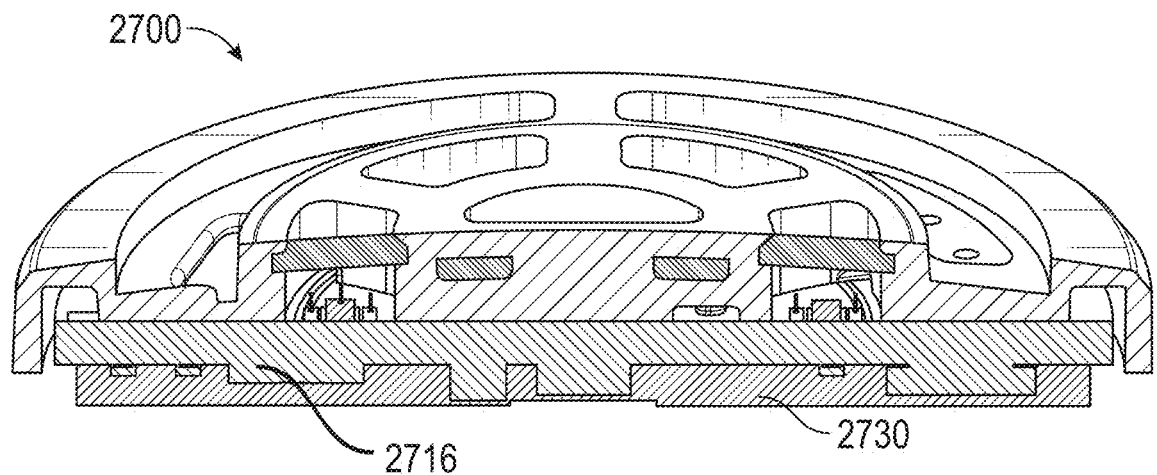
FIG. 27G illustrates a longitudinal cross-sectional view of an example physiological parameter measurement sensor or module.
Figure 27H:
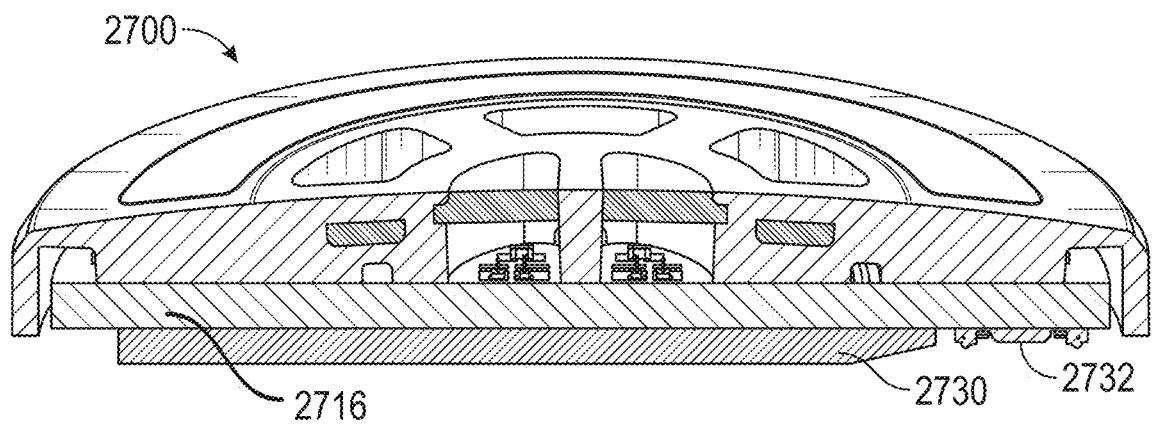
FIG. 27H illustrates a longitudinal cross-sectional, that is orthogonal to the view of FIG. 27G, of an example physiological parameter measurement sensor or module.
Figure 27I:
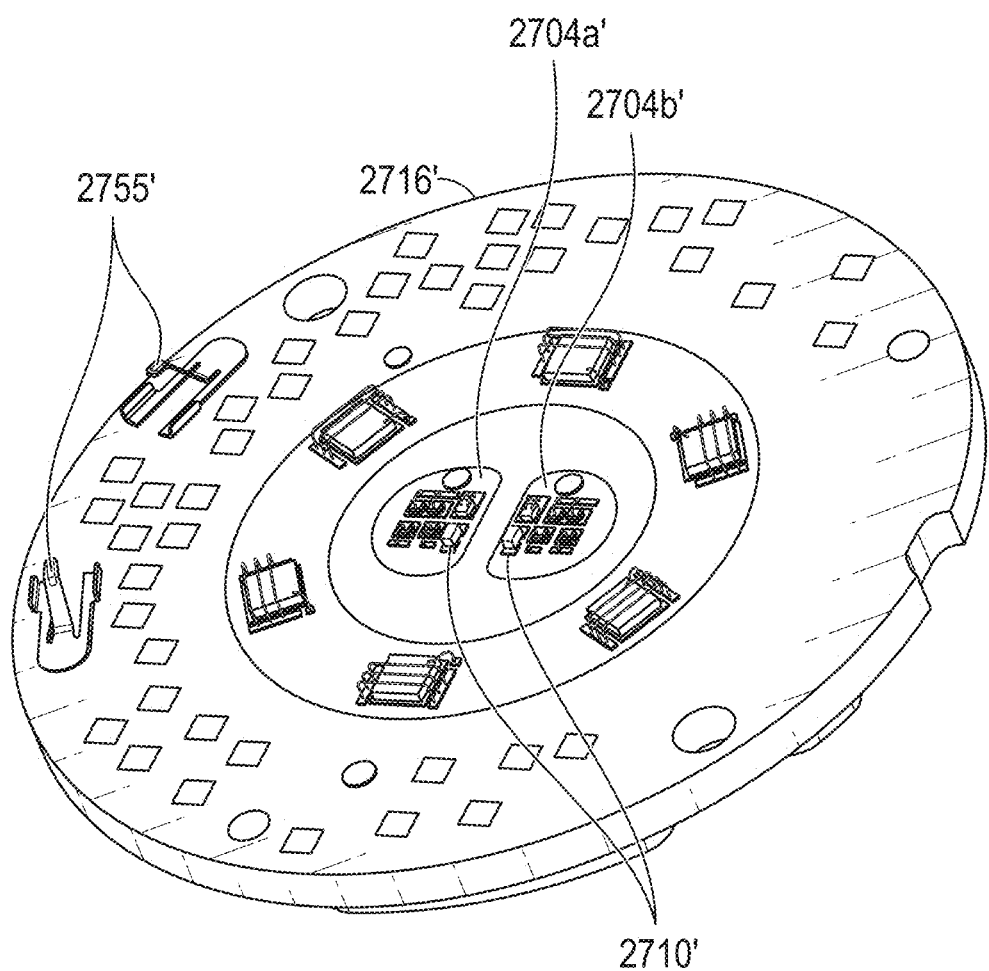
FIG. 27I illustrates a perspective view of PCB substrate of a physiological parameter measurement sensor or module with example plethysmograph sensor arrangement.

FIG. 27I illustrates another example arrangement of an optical sensor, including emitters, detectors, and thermistors, on a sensor or module processor substrate 2716'. The substrate 2716' of FIG. 27I can include structural and/or operational features similar to those discussed above with reference to FIG. 27F. As shown in FIG. 27I, each of the first and second groups of emitters 2704a', 2704b' can include five emitters (or optionally a different number of emitters as required or desired). Each of the emitters of the first and second groups of emitters 2704a', 2704b' may comprise an LED and can be configured to emit light at various wavelengths such as any of the wavelengths discussed herein, for example, a first wavelength of about 525 nm to about 650 nm (such as about 525 nm or about 580 nm or about 645 nm), a second wavelength from about 620 nm to about 660 nm (such as about 625 nm), a third wavelength from about 650 nm to about 670 nm (such as about 660 nm), a fourth wavelength from about 900 nm to about 910 nm, and a fifth wavelength at about 970 nm.

As shown in FIG. 27I, the substrate 2716' can include spring contacts 2755' for facilitating physical and/or electrical connection between the substrate 2716' and electrodes (e.g., electrodes 2724 shown in FIG. 27B, for example).

As shown in FIGS. 27G-27H, on the second side of the substrate 2716, which faces away from the cover, the substrate 2716 can be covered by melt plastic or other suitable electronics protective material 2730 (similar to the protective material 130 disclosed herein) except that a flex connector 2732 can remain exposed. The flex connector 2732 can be configured to connect the module 2700 electrically to the wearable device incorporating the module 2700.

Figure 27J:
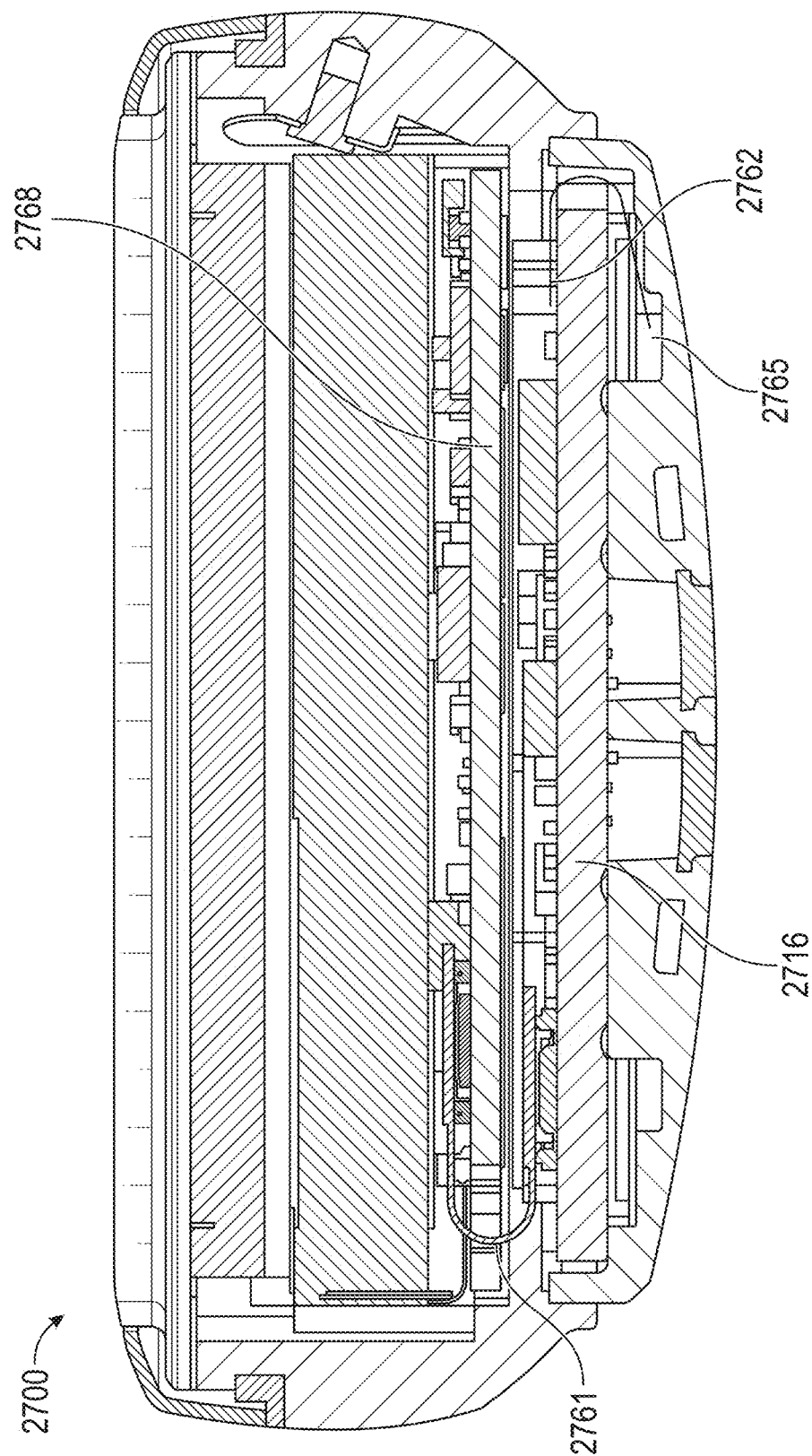
FIG. 27J illustrates a perspective cross-sectional view of an example physiological parameter measurement sensor or module.

FIG. 27J illustrates a perspective cross-sectional view of an example physiological parameter measurement sensor or module 2700. As shown, the sensor or module 2700 can include a first circuit board (e.g., substrate 2716) and a second circuit board (e.g., instrument PCB 2768. The sensor or module 2700 can include an induction coil 2765. The induction coil 2765 can be electrically and/or physically connected to the substrate 2716, for example via solder and/or a flex connector connection 2762. The induction coil can provide a voltage to the substrate 2716, for example via the solder and/or flex connector connection 2762. The substrate 2716 can include charging circuitry which can be configured to receive and/or control a voltage received from the induction coil 2765. The substrate 2716 can be configured to transfer voltage received from the induction coil 2765 to the instrument PCB 2768, for example via a flex connector 2761. The instrument PCB 2768 can be configured to transfer voltage received from the substrate 2716 to a battery or to other components of the sensor or module 2700 as required or desired.

Figure 20C:
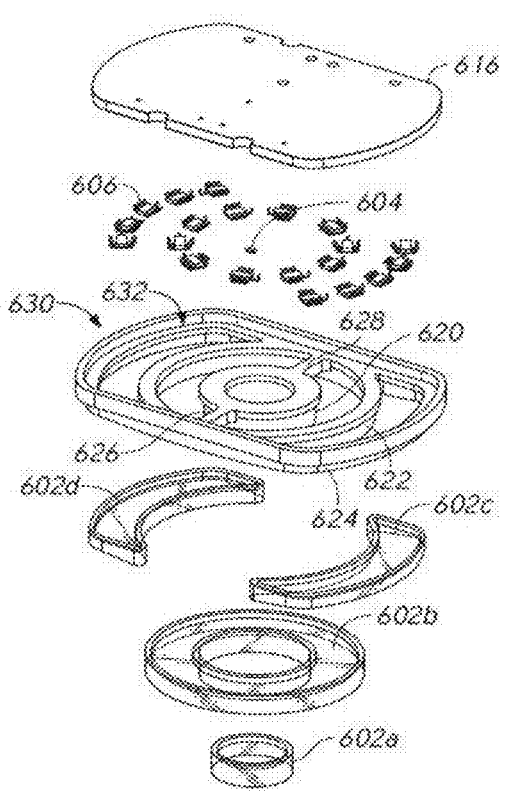
FIGS. 20C and 20D illustrate exploded views of the physiological parameter measurement module of FIG. 20A.

Examples of Physiological Parameter Measurement Modules with Inner and Outer Detector Groups and Examples of Wearable Devices Incorporating the Same FIGS. 20A-20D illustrate an example physiological parameter measurement module 600 of a wearable device. The module 600 can have any of the features of the module examples described herein, with the differences noted in the description of FIGS. 20A-20D. The physiological parameter measurement module 600 can include a single emitter group having a plurality of emitters 604, such as four emitters as shown in FIG. 20A, six emitters, or eight emitters. The emitters 604 of the module 600 can emit at least the first, second, third, and fourth wavelengths as described above. The emitters 604 can be located at or near a center portion of a PCB 616 of the module 600. The module 600 can include a temperature sensor 610 located on the PCB 616 near the emitters 604.

The module 600 can include a plurality of detectors 606 that can be arranged on the PCB 616 as an inner group of detectors 606 and an outer group of detectors 606. The inner group 606c of detectors 606, which can include, for example, about ten (or a different number of) detectors 606, can surround the emitters 604 and be spaced apart from one another.

The outer group of detectors 606 can be located further away from the emitters 604 than the inner group of detectors 606. The outer group of detectors 606 can be separated into a first outer group 606a and a second outer group 606b of detectors 606. As shown in FIG. 20A, the module 600 can have a first axis A1 and a second axis A2. The outer groups 606a, 606b of detectors 606 can be located further away from the emitters 204 than the inner group of detectors 606 generally along the first axis A1. The two outer groups 606a, 606b of detectors 606 are on opposite sides of the inner group of detectors along the first axis A1. The first and second outer groups 606a, 606b of detectors 606 can be generally symmetrical about the first axis A2 and the second axis A2. Each of the first or second outer groups 606a, 606b of detectors 606 can include about five (or a different number) of detectors 606 that are spaced apart from one another generally along the second axis A2. The outer groups 606a, 606b of detectors 606 can be arranged to be generally concentric with the inner group 606c of detectors 606.

The module 600 can be longer in the first axis A1 than in the second axis A2. The module 600 can have a dimension of about 25.4 mm (1 inch) along the first axis A1. The module can have a dimension of about 19.1 mm (0.75 inch) along the second axis A2. As shown in FIG. 20A, when a watch incorporating the module 600 is worn on the wrist of a wearer, the first axis A1 can be generally parallel to the width of the wrist and generally perpendicular to the direction of blood flow along the wrist (that is, along a direction between the hand and the forearm) and the second axis A2 can be generally perpendicular to the width of the wrist and generally parallel to the direction of blood flow along the wrist. The distribution of the detectors 606 along the first axis A1 can improve detection of the light attenuated by the pulsing arterial blood in the capillaries as the detectors 606 are arranged to cover a greater cross-section of the blood flow through the wrist. Similarly, in the other example modules described herein, such as the sensor or module 100, 400, 401, 403, 300, 301, 200, 201, the physiological parameter measurement module is incorporated in the wearable device such that the longer side of the module is generally perpendicular to the direction of the blood flow along the wrist (see, for example, FIG. 1B) when the wearable device is worn on the wrist.

As shown in FIG. 20A, the emitters 604 can be covered by an inner lens or cover 602a. In the illustrated example, the inner lens or cover 602a can be generally circular. In other examples such as disclosed herein, the inner lens or cover may not be generally circular, but can have other shapes, for example, elliptical, rectangular, square, diamond, or otherwise. The inner group 606c of detectors 606 can be covered by a first outer lens or cover 602b. The first outer lens or cover 602b can be generally concentric with the inner lens or cover 602a. In the illustrated example, the first outer lens or cover 602b can be disc shaped. The first and second outer groups 606a, 606b of detectors 606 can be covered by a second outer lens or cover 606c and a third outer lens or cover 606d respectively. The second and third outer lenses or covers 606c, 606d can be symmetrical about the second axis A2. As shown in FIG. 20B, the first, second, and third outer lenses or covers 602b, 602c, 602d can have substantially the same curvature. The inner lens or cover 602a can be more curved than the outer lenses or covers 602b, 602c, 602d such that the inner lens or cover 602a protrudes more than if the inner lens or cover 602a had same curvature as the outer lenses or covers 602b, 602c, 602d.

The inner group 606c of detectors 606 and the emitters 604 can be separate by a first light barrier 620. The first light barrier 620 can extend along and surround the inner lens or cover 602a, forming an emitter chamber. The first and second outer groups 606a, 606b of detectors 606 can be separated from the inner group 606c of detectors 606 by a second light barrier 622. The second light barrier 622 can be shorter than the first light barrier 620. The first and second outer groups 606a, 606b of detectors 606 can be enclosed within a module side wall 624 enclosing a perimeter of the module 600. The perimeter of the module 600 can be elliptical or any other shape. The side wall 624 can be shorter than the second light barrier 622. The height of the first and second light barriers 620, 622, and of the side wall 624 can generally follow or be substantially continuous with the curvature of the first, second, and third outer lenses or covers 602b, 602c, 602d. The first and second light barriers 620, 622, and of the side wall 624 can have a height so as to be configured to contact the skin of the wearer. Accordingly, the tissue-facing surface of the module 600 can be defined by the tissue-facing side of the first and second light barriers 620, 622, and of the side wall 624 and tissue-facing surfaces of the inner lens or cover 602a and the first, second, and third outer lenses or covers 602b, 602c, 602d.

Figure 20D:
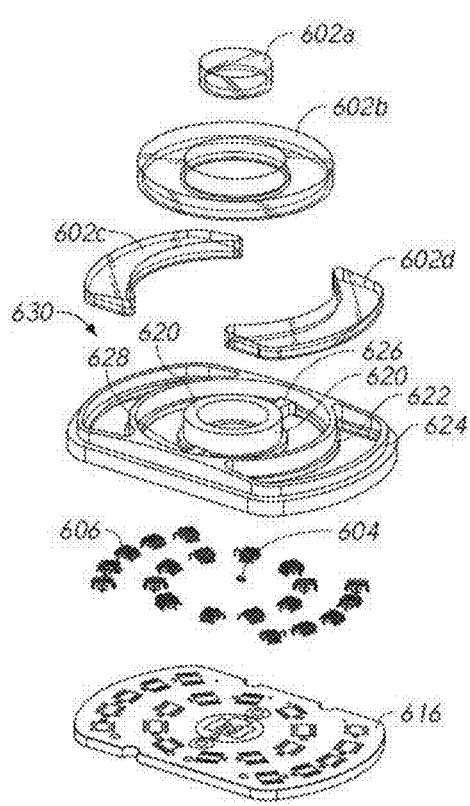
Figure 20G:
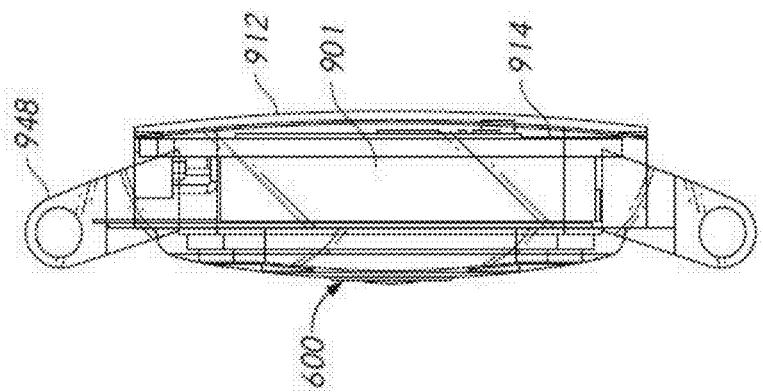
FIG. 20G illustrates a second side view of the wearable device of FIG. 20E.

In the illustrated example, the inner group 606c of detectors 606 can be separated by a third light barrier 626 and a fourth light barrier 628 (see FIGS. 20C and 20D). The third and fourth light barriers 626, 628 can have a height lower than the first light barrier 620 or the second light barrier 622. The height of the third and fourth light barriers 626, 628 can be configured to accommodate the first outer lens or cover 602b such that when assembled, the first outer lens or cover 602b forms a substantially smooth surface with the second and third outer lenses or covers 602c, 602d. The first outer lens or cover 602b can sit on top of the third and fourth light barriers 626, 628.

The first light barrier 620 can protrude slightly from, that is, sit proud of the edge of the inner lens or cover 602a and the outer lenses or covers 602b, 602c, 602d. The slightly protruding first light barrier 620 and/or inner lens or cover 602a can be pressed into the wearer's skin at a higher pressure than the remainder of the lenses or covers or light barriers. The first light barrier 620 can also reduce mixing of the emitted and reflected light and/or suppress light emitted by the emitters 604 at an angle so that the emitted light exits the inner lens or cover 602a generally in a direction parallel to the height of the first light barrier 620.

As shown in FIGS. 20C and 20D, the first, second, third, and fourth light barriers 620, 622, 626, 628 and the side wall 624 can optionally form a single light barrier construct 630. The single light barrier construct 630 can be formed by any suitable manufacturing techniques. The single light barrier construct 630 can include at one end a recess 632 (see FIG. 20C) that is configured to receive the PCB 616 (and the emitters 604, detectors 606, temperature sensor 610, and any other sensors, for example, the gyroscope, the accelerometer, and/or the like, and the sensor or module processor, which are located on the PCB 616). The single light barrier construct 630 can receive the lenses, including the inner lens or cover 602a, the first, second, and third outer lenses or covers 602b, 602c, 602d at another end that is opposite to the end including the recess 632.

The module housing can include a plurality of chambers such that light cannot travel between the chambers because of the various light barriers described herein. As described above, the first chamber can be enclosed by the inner lens or cover 602a, the first light battier 620, and a portion of the PCB 616. The first chamber 634 enclose the emitters 604. A second chamber and a third chamber can be enclosed by the first outer lens or cover 602b, the first light barrier 620, the second light barrier 622, the third light barrier 626, the fourth light barrier 628, and a portion of the PCB 616. The second and third chambers can enclose the inner group 606c of detectors 606, with half of the inner group 606c of detectors enclosed by each of the second and third chambers. A fourth chamber can be closed by the second outer lens or cover 602c, the second light barrier 622, the side wall 624, and part of the PCB 616. A fifth chamber can be enclosed by the third outer lens or cover 602d, the second light barrier 622, the side wall 624, and part of the PCB 616. The fourth and fifth chambers can enclose the first and second outer groups 606a, 606b of detectors 606 respectively.

Light from the emitters 604 can travel a shorter path to the inner group 606c of detectors 606 and a longer path to the first and second outer groups 606a, 606b of detectors 606. The inner group 606c of detectors 606 and the first and second outer groups 606a, 606b of detectors 606 can be run independently and/or simultaneously. Signals outputted by the inner and outer groups 606a, 606b of detectors 606 can provide different information due to the different light paths, which can travel through different areas of the tissue. The longer path penetrates deeper into the tissue and through a greater volume of the tissue to reach one of the outer groups 606a, 606b of detectors 606 than the short path, which penetrates less deep into the tissue and travels through a smaller volume of tissue to reach one of the inner group 606c of detectors 606. The different information can be separated and/or combined to calculate a plurality of physiological parameters of the wearer of the module 600, for example, an indication of the wearer's hydration status, which will be described in greater detail below.

The light diffusing materials described above can be included in one or more chambers of the module 600 to improve distribution of emitted lighted and/or detected light after attenuation by the tissue. As shown in FIG. 20A, one or more of the lenses or covers 602a, 602b, 602c, 602d can include an injection opening 644 so that the light diffusing materials, which can include a flow of glass microsphere solution, can be injected into the respective chambers after the module 600 has been assembled. After being injected into the respective chamber, the solution can be UV-cured. The lenses or covers 602a, 602b, 602c, 602d can include one or more venting openings 645 that are smaller than the injection openings 644. Each of the lenses or covers can include at least one venting opening 645. Air can escape via the vent openings 645 as the diffusing material solution is injected into the respective chambers via the injection openings 644, making it easier for the glass microsphere solution to flow into the respective chamber. The inner lens or cover 602a and/or the outer lenses or covers 602b, 602c, 602d can also include glass microspheres. The light diffusing materials in the inner lens or cover 602a and the UV-cured material in the first chamber 634 and/or the first light barrier 620 can make the emitted light leave the first chamber 634 in a direction generally parallel to the height of the first light barrier 620. The light diffusing materials in the outer lenses or covers 602b, 602c, 602d and the UV-cured material in the other chambers 636, 638, 640, 642 can increase the amount of reflected light being directed to the detectors 606.

Figure 20F:
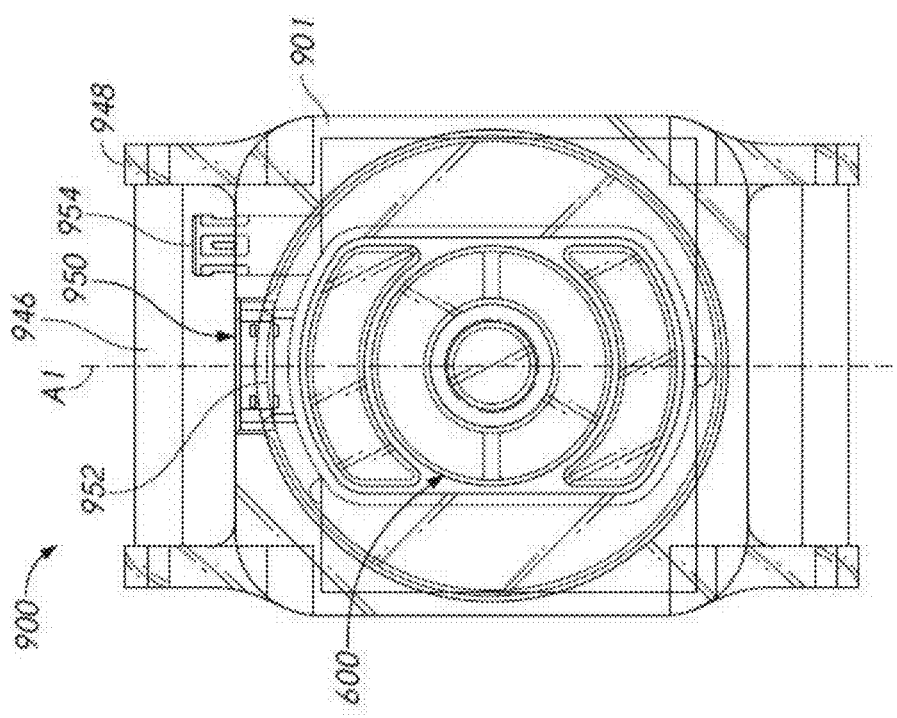
FIG. 20F illustrates a bottom view of the wearable device of FIG. 20E.
Figure 20E:
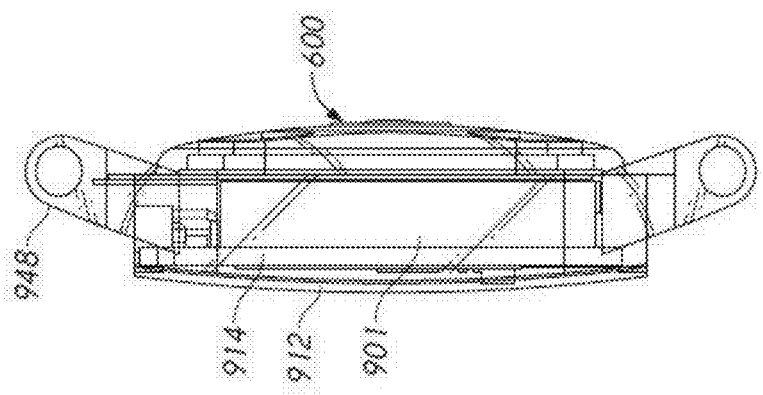
FIG. 20E illustrates a first side view of an example wearable device incorporating the physiological parameter measurement module of FIGS. 20A-20D.

The module 600 shown in FIGS. 20A-20D can be incorporated in a wearable device disclosed herein, such as a watch 900 shown in FIGS. 20E-20J. The watch processor 914 and power source can be enclosed within the watching housing 901. The watch housing 901 can include a connection port opening 950 configured to allow access to a connection port 952 that is in electrical communication with the watch processor 914 and/or the power source. The connection port opening 950 can be located at one end of the watch housing 901 transverse to the first axis A1 of the module 600. The connection port 952 can allow for charging of the power source and/or data transfer to and from the watch processor 914. Optionally, as shown in FIGS. 20F and 20I, the watch 900 can include a cable connector 945 extending outward from the watch housing 901. The cable connector 945 can be located adjacent to or near the connection port opening 950.

The watch 900 can include a display screen 912 positioned at a first side of the watch housing 901. The watch housing 901 has a second side that is opposite the first side. The second side of the watch housing 901 can include an opening sized to retain the physiological parameter measurement module 600 while still allowing the tissue-facing surface of the module 600 to be exposed. The second side of the watch housing 901 can be removably attached to the first side of the watch housing 901 without using external fasteners or alternatively via one or more fasteners. An electrical connection can be established between the physiological parameter measurement module PCB and the watch circuit, for example, using a flex connector as disclosed herein.

The watch housing 901 can include strap coupling extensions 948 on opposing sides of the watch 900 along the length of the housing 901 (that is, along the first axis A1 of the module 600). The extensions 948 can include a bar 946 for coupling to any suitable watch straps.

Figure 21A:
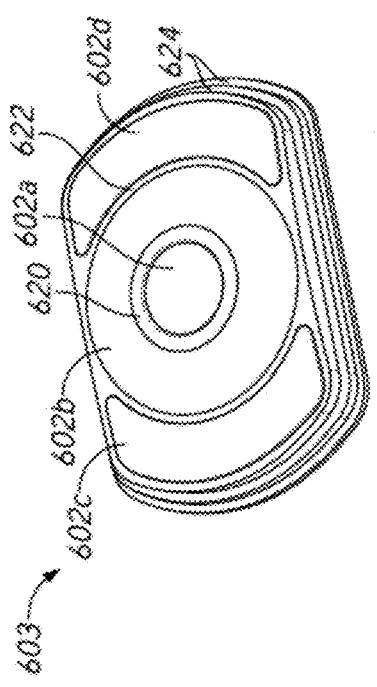
FIGS. 21A and 21B illustrate perspective views of an example physiological parameter measurement module with alternative light transmissive cover curvatures from the module in FIG. 20A.
Figure 21B:
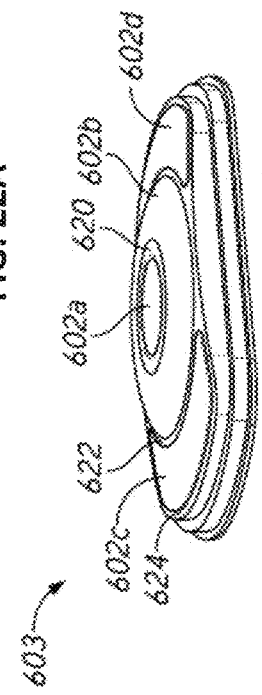
Figure 21C:
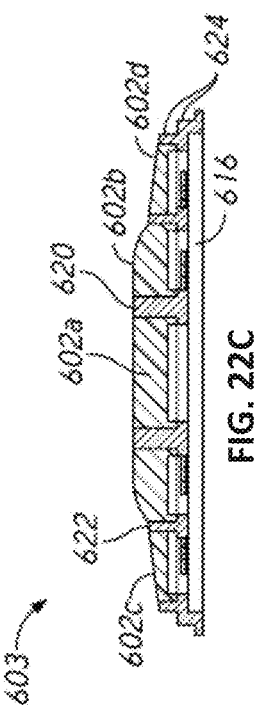
FIG. 21C illustrates a longitudinal cross-sectional view of the physiological parameter measurement module of FIGS. 21A and 21B.
Figure 22A:
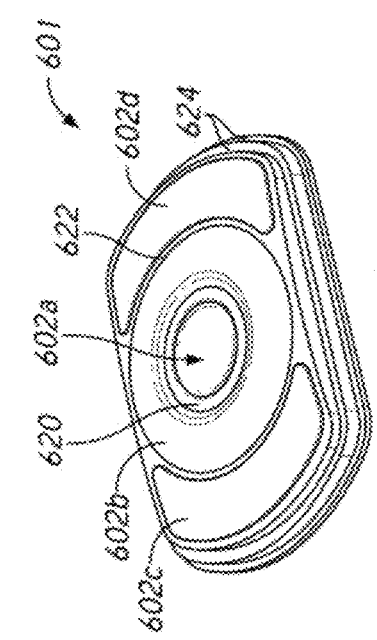
FIGS. 22A and 22B illustrate perspective views of an example physiological parameter measurement module with another alternative light transmissive cover curvatures from the module in FIG. 20A.
Figure 22B:
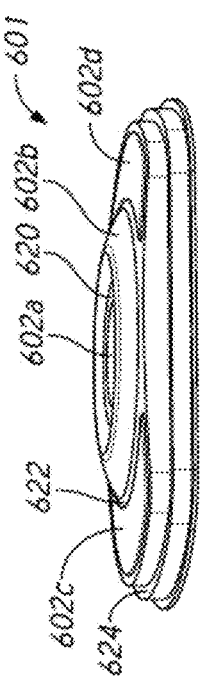
Figure 22C:
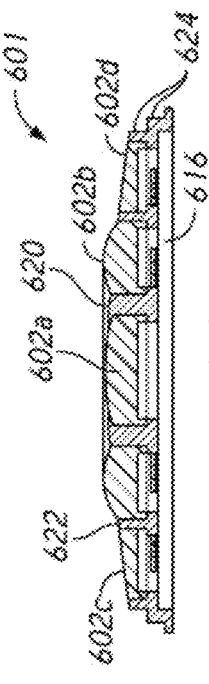
FIG. 22C illustrates a longitudinal cross-sectional view of the physiological parameter measurement module of FIGS. 22A and 22B.

FIGS. 21A-21C and 22A-22C illustrate alternative lens or cover curvatures of the physiological parameter measurement module 600 of FIGS. 20A-20D and can incorporate any of the features of the module 600 of FIGS. 20A-20D except the differences described below. As shown in FIGS. 21A-21C, the first outer lens or cover 602b of the module 601 can be more convex (that is, protrude more) than the inner lens or cover 602a the second and third outer lenses or covers 602c, 602d. The curvatures of the tissue-facing side of the second light barrier 622 and of the side wall 624 can be substantially continuous with the curvature of the second and third outer lenses or covers 602c, 602d. The second light barrier 622 can be shorter than the first light barrier 620. The first light barrier 620 can be higher than an outer edge of the inner lens or cover 602a, which can facilitate separation of light emitted by the emitters 604 and light being detected by the detectors 606 before the light is attenuated by the wearer's body tissue. In the FIGS. 22A-22C, the module 603 can be different from the module 601 in FIGS. 21A-21C in that the inner lens or cover 602a can have the same height as the first light barrier 620 and the first outer lens or cover 602b. The inner lens or cover 602a can have a generally flat surface or a slight curvature that can be substantially continuous from the curvature of the first outer lens or cover 602b. The module 601, 603 in FIGS. 21A-22C can facilitate pressing the first outer lens or cover 602b or the first outer lens or cover 602b and the inner lens or cover 602a into the skin of the wearer more than the remainder of the tissue-facing surface of the module 600.

FIGS. 23A-23E illustrate a watch 700 that can incorporate the physiological parameter measurement module 600. The watch 700 can have any of the features of the watch 900 with the differences noted in the description of FIGS. 23A-23E. As shown in FIGS. 23A-23E, the watch housing 701 of the watch 700 can include a flap 750 on a side of the housing 701 along a length of the watch housing 701, which is along the first axis A1 of the physiological parameter measurement module (see FIG. 23E). The flap 750 can be opened to give access to a connection port (such as the connection port in the watch 900) in electrical communication with the watch processor 714 and/or the power source 716. The connection port can allow for charging of the power source 716 and/or data transfer to and from the watch processor 714. The flap 750 can be closed when the connection port 752 is not in use.

The watch 700 can include a display screen positioned at a first side of the watch housing 701. The watch housing 701 has a second side that is opposite the first side. The second side of the watch housing 701 can include an opening sized to retain the physiological parameter measurement module 600 while still allowing the tissue-facing surface of the module 600 to be exposed. The second side of the watch housing 701 can be removably attached to the first side of the watch housing 701 via one or more screws 718 or other fasteners. When fully assembled, the watch 700 can have a thickness or height, for example, between 10 mm to about 15 mm, or between 12 mm to about 14 mm.

The watch housing 701 can include suitable strap connections configured to couple to watch strap(s). The strap connections in the watch housing 701 can be different from the strap connections shown in the watch 900. In an example, a plurality of strap openings can be at opposite ends of the watch and the watch housing can additionally and/or alternatively include strap slots on the same opposite ends of the watch as the strap openings. In this example, the strap slots can be configured to slidably receive ends of watch straps that include a shape corresponding to the shape of the strap slots. The strap openings can be configured to receive spring-biased buttons near the ends of the watch straps to releasably retain the straps after the ends of the watch straps are received into the strap slots. Alternatively, the watch may not include strap openings. The strap(s) coupled to the watch examples disclosed herein can be configured to allow adjusting of tightness around the wearer's wrist, for example, using a buckle connector, a Velcro connector, and/or the like.

Hydration Monitoring by Wearable Devices Incorporating Examples Physiological Parameter Measurement Modules with "Near" and "Far" Detectors or Detector Groups The physiological parameter measurement module examples disclosed herein can monitor a hydration status of the wearer. This is because water in the body tissue can allow a greater portion of the light of the third (or first or second) wavelength disclosed herein to go through (that is, acting as a light pipe), but can bulk absorb the light of the fourth wavelength disclosed herein. The physiological parameter measurement processor can compare intensity signals of the fourth wavelength and another wavelength that is less sensitive to changes in water from the same detector(s). When the wearer's hydration status is in a normal range such that the wearer is not considered dehydrated in a medical sense, the signals of the fourth wavelength and the other wavelength can show opposite trends, that is, one is increasing when the other one is decreasing. When the wearer becomes dehydrated in a medical sense, the opposite trends can become less distinct, for example, by falling below a threshold.

Hydration monitoring can be performed when the physiological parameter measurement module, such as the sensor or module 100, is configured such that at least some of the detectors 106 are located further away (far detector) from one of the emitters 104 (or emitter groups than the other detectors 106 (near detector), such as illustrated in FIG. 10. In configurations where there are two emitter groups, each detector 106 or detector region (which can include more than one detector 106 placed enclosed in the same detector chamber) can act as a near (or shallow) detector or detector region for the group of emitters that are closer to that detector 106 or detector region and as a far (or deeper) detector or detector region for the group of emitters that are further away from that detector 106 or detector region.

The physiological parameter measurement module 400, 401, 403 illustrates an example configuration for hydration monitoring of the wearer. The detectors 406a can be the far detectors for the second group of emitters 404b and the detectors 406b, 406a/b can be the near detectors for the second group of emitters 404b. The detectors 406b can be the far detectors for the first group of emitters 404a and the detectors 406a, 406a/b can be the near detectors for the first group of emitters 404a. The physiological parameter measurement modules 300, 301 illustrate similar detector arrangements in configurations (except that in the module 301, there are no shared detectors between the two groups of emitters 304a, 304b) where the modules 300, 301 include a fourth emitter in at least one of the emitter groups configured to emit light of the four wavelength.

The physiological parameter measurement modules 200, 201 illustrate additional example detectors configurations that can include "near" detectors for one emitter group and "far" detectors for another emitter group, in configurations where the modules 200, 201 include a fourth emitter configured to emit light of the fourth wavelength. For example, the detectors 206 on the far side of each group of emitters 204a, 204b can act as "far" detectors for detecting the light emitted by the respective group of emitters 204a, 204b, for example, light of the fourth wavelength and another wavelength, and attenuated by tissue to provide an indication of the wearer's hydration status The physiological parameter measurement module 600 illustrates an example configuration for hydration monitoring of the wearer, with the inner group 606c of detectors 606 acting as the "near" detectors and the outer groups 606a, 606b of the detectors acting as the "far" detectors.

In the above-described configurations, each detector or detector region can provide two measurements calculated from the signals received from the closer emitter group and the signals from the further emitter group respectively. Signals detected at the far detectors can provide indication of the hydration status of the wearer as light travels through a deeper portion of the tissue of the wearer to reach the far detectors than to reach the near detectors). Signals detected at the near detectors can optionally be used as reference or for comparison with the signals detected at the far detectors when the physiological parameter measurement sensor or module processor determines the wearer's hydration status. The sensor or module processor of the physiological parameter measurement module disclosed herein can compare intensity signals of the fourth wavelength and another wavelength (for example, the third wavelength or about 905 nm) that is less sensitive to changes in water from one of the "far" detectors. The module processor can focus on the DC component, or the DC bulk absorption measurement of the signals detected by the "far" detectors for hydration status monitoring. At the DC level, water can act as a light block (that is, less transmissive of light) for the fourth wavelength and as a lens or cover (that is, more transmissive of light) for the other wavelength.

Additionally and/or alternatively, any of the modules disclosed herein can monitor the wearer's hydration status by monitoring the wearer's PVI values. The module can determine a baseline PVI value of the wearer, and can output a notification that the wearer is dehydrated or hydrated based on fluctuations in the PVI value from the baseline.

The module can further combine the hydration status monitoring by the optical detectors and other sensors (such as a sweat sensor or a skin impedance sensors) in outputting a final hydration status indication of the wearer. The module can calculate an average, a weight average or otherwise of raw hydration index values calculated based on signals from the different sensors, and/or rely on the different hydration monitoring sensors for redundancy.

As a person's hydration status is not expected to change rapidly, the physiological parameter measurement module can optionally make a measurement of the hydration status less frequently than making measurements related to the wearer's pulse rate or SpO2 or other parameters. For example, the physiological parameter measurement sensor or module processor can make a measurement of hydration status every 5 minutes, or longer, and/or upon (for example, only upon) a request by the wearer, such as when the wearer presses a button (a physical button and/or a touch button on the display) on the device or otherwise instructs the device using voice commands, hand gestures, and/or the like.

Examples of Generally Circular Physiological Parameter Measurement Modules and Examples of Wearable Devices Incorporating the Same A physiological parameter measurement module can alternatively include an inner portion of emitters and an outer ring of detectors as shown in FIGS. 24A-24B and FIGS. 25A-25B. The sensor or module 1000 in FIGS. 24A-24B and the module 1100 in FIGS. 25A-25B can have any of the features of the module examples described herein, with the differences noted in the description of FIGS. 24A-24B and 25A-25B. Such a physiological parameter measurement module can have a generally circular outer shape. The sensor or module 1000 in FIGS. 24A-24B can be smaller than the module 1100 in FIGS. 25A-25B. For example, the sensor or module 1000 can have an outer diameter between about 12 mm and about 16 mm, or between about 14 mm and about 15 mm. For example, the module 1100 can have an outer diameter between about 16 mm and about 22 mm, or between about 18 mm and about 20 mm.

The physiological parameter measurement module 1000, 1100 can each include a single emitter group having a plurality of emitters 1004, 1104, such as three emitters. The emitters 1004, 1104 of the sensor or module 1000, 1100 can emit at least the first, second, and third wavelengths as described above. The emitters 1004, 1104 can be located at or near a center portion of a PCB of the sensor or module 1000, 1100. The sensor or module 1000, 1100 can include a temperature sensor located on the PCB near the emitters 1004, 1104.

The sensor or module 1000, 1100 can include a plurality of detectors 1006, 1106 (for example, about six, eight, or more) that can be arranged on the PCB so that the detectors 1006, 1106 are spaced apart around the emitters 1004, 1006. The emitters 1004, 1104 and the detectors 1006, 1106 can be separated by a first light barrier 1020, 1120. The first light barrier 1020, 1120 can surround the emitters 1004, 1104. The first light barrier 1020, 1120 can also suppress light emitted by the emitters 1004, 1104 at an angle so that the emitted light exits the inner lens or cover 1002a, 1102a in a direction generally parallel to the height of the first light barrier 1020, 1120.

The emitters 1004, 1104 can be covered by an inner lens or cover 1002a, 1102a. In the illustrated example, the inner lens or cover 1002a, 1102a can be generally circular. The detectors 1006, 1106 can be covered by an outer lens or cover 1002b, 1102b. The outer lens or cover 1002b, 1102b can be generally concentric with the inner lens or cover 1002a, 1102a. In the illustrated examples, the outer lens or cover 1002b, 1102b can be a disc when viewed directly above from the sensor or module 1000, 1100. In other examples such as those disclosed herein, the outer lens or cover can have other shapes, for example, being elliptical or otherwise. The outer lens or cover 1002b, 1102b can have a smaller curvature than the inner lens or cover 1002a, 1102a such that the inner lens or cover 1002a, 1102a protrudes more than if the inner lens or cover had the same curvature as the outer lens or cover 1002b, 1102b. As shown in FIGS. 24B and 25B, the first light barrier 1020, 1120 can protrude slightly from, that is, proud of the outer edge of the inner lens or cover 1002a, 1102a. The slightly protruding first light barrier 1020, 1120 and/or inner lens or cover 1002a, 1102a can be pressed into the wearer's skin at a higher pressure than the remainder of the light barriers or lenses or covers of the sensor or module 1000, 1100.

The detectors 1006, 1106 can be enclosed within a module side wall 1024, 1124 that defines a perimeter of the sensor or module 1000, 1100. The perimeter can be generally circular or of any other shape. The side wall 1024, 1124 can be shorter than the first light barrier 1020, 1120. The height of the side wall 1024, 1124 can be such that the tissue-facing end of the side wall 1024, 1124 is generally continuous with the curvature of outer lenses or covers 1002b, 1102b. In the illustrated example, the detectors 1006, 1106 can be separated from one another by a plurality of generally opaque divider barriers 1026, 1126. The divider barriers 1026, 1126 can have a height lower than the first light barrier 1020, 1120. The height of the divider barriers 1026, 1126 can be configured to accommodate the outer lens or cover 1002b, 1102b such that when assembled, the outer lens or cover 1002b, 1102b forms a substantially smooth surface with the module side wall 1024, 1124. The outer lens or cover 1002b, 1102b can sit on top of the divider barriers 1026, 1126. The tissue-facing end of the first light barrier 1020, 1120 and the side wall 1024, 1124, and the tissue-facing surfaces of the inner lens or cover 1002a, 1102a and the outer lens or cover 1002b, 1102b can be configured to contact the skin of the wearer and form the tissue-facing surface of the sensor or module 1000, 1100.

The first light barrier 1020, 1120, the side wall 1024, 1124, and the divider barriers 1026, 1126 can optionally form a single light barrier construct. The single light barrier construct can receive the PCB of the sensor or module 1000, 1100, and the emitters 1004, 1104, detectors 1006, 1106, temperature sensor, and any other sensors, for example, the gyroscope, the accelerometer, and/or the like, and the sensor or module processor that are located on the PCB. The single light barrier construct can receive the lenses, including the inner lens or cover 1002a, 1102a and the outer lens or cover 1002b, 1102b on another end that is opposite the end receiving the PCB. As shown in FIGS. 25A and 25B, the light barrier construct of the module 1100 or the PCB can additionally include a plurality of (for example, four or otherwise) extension prongs 1152. The plurality of extension prongs 1152 can be generally equally spaced around the side wall 1124.

The sensor or module 1000, 1100 can include a plurality of chambers such that light cannot travel between the chambers because of the various light barriers described herein. A first chamber 1034, 1134 can be enclosed by the inner lens or cover 1002a, 1102a, the first light battier 1020, 1120, and a portion of the PCB. The first chamber 1034, 1134 can enclose the emitters 1004, 1104. A plurality of second chambers 1036, 1136 can be enclosed by the outer lens or cover 1002b, 1102b, the first light barrier 1020, 1120, the divider barriers 1026, 1126, the side wall 1024, 1124, and part of the PCB. Each of the second chambers 1036, 1136 can enclose one detector 1006, 1106.

The light diffusing materials described above can be included in one or more of the chambers 1034, 1134, 1036, 1136 of the module housing to improve distribution of emitted lighted and/or detected light. The inner lens or cover 1002a, 1102a and the outer lens or cover 1002b, 1102b can also include glass microspheres as described above.

The watch 1200 in FIGS. 25C-25H is illustrated as incorporating the module 1100 shown in FIGS. 25A-25B. However, any of the example watches disclosed herein can incorporate the physiological parameter measurement module 1000, 1100 shown in FIGS. 24A-24B or FIGS. 25A-25B. The watch 1200 can have any of the features of the wearable devices disclosed herein, such as the watch 700, 900, all of which are not repeated for brevity. The watch processor 1214 and power source can be enclosed within the watching housing 1201. The watch housing 1201 can include a connection port opening 1250 configured to allow access to a connection port 1252 in electrical communication with the watch processor 1214 and/or the power source. The opening 1250 can be on one side of the watch 1200 perpendicular to the first axis A1 of the module 1100, closer to the strap coupling mechanisms. The connection port 1252 can allow for charging of the power source and/or data transfer to and from the watch processor 1214. Optionally, as shown in FIGS. 25D, 25F, and 25H, the watch 1200 can include a cable connector 845 extending outward from the watch housing 1201. The cable connector 1245 can be located adjacent to or near the connection port opening 1250.

The watch 1200 can include a display screen 1212 positioned at a first side of the watch housing 1201. The watch housing 1201 has a second side that is opposite the first side. The second side of the watch housing 1201 can include an opening sized to retain the physiological parameter measurement module 1100 while still allowing the tissue-facing surface of the module 1100 to be exposed. The extension prongs 1152 of the module 1100 can be received into corresponding structures, for example, recesses, on the second side of the watch housing 1201, which can prevent rotation of the module 1100 when being installed in the watch 1200. The second side of the watch housing 1201 can be removably attached to the first side of the watch housing 1201 without using external fasteners or via one or more fasteners as described above. An electrical connection can be established between the physiological parameter measurement module circuit and the watch circuit. Optionally, the electrical connection can include a flex circuit.

The watch housing 1201 can include strap coupling extensions 1248 on opposite sides of the watch 1200 along the first axis A1 of the module 1100. The extensions 1248 can include a bar 1246 for coupling to any suitable watch straps.

Example Second Sensor Connection on Physiological Parameter Measurement Modules for Preventing Opioid Overdose The physiological parameter measurement module examples disclosed herein can include an optional connector 118 (see FIG. 7A) for receiving a second sensor, which can be a plethysmograph sensor or other suitable sensors. The connector 118 can be oriented such that the second sensor can extend from a housing of the device 10 with reduced or no impingement of the tissue at the device/tissue interface, resulting in less or no effect of the connection of a second sensor to the connector 118 on the blood flow through the device measurement site. The second plethysmograph sensor can include any suitable plethysmograph sensors, for example, a fingertip sensor configured to monitor opioid overdose as described in U.S. Pub. No. 20190374173, the entirety of which is incorporated herein by reference and should be considered part of the disclosure. FIG. 1C illustrates a non-limiting example of the second sensor 119 that is a fingertip sensor. The second sensor 119 can extend from a wearable device as shown in FIG. 1C or any of the wearable device examples disclosed herein.

Alternative to the connection to a wearable device as shown in FIG. 1C, the connector from the watch disclosed herein can extend from an opening on a tissue-facing side of the device housing, for example, on a raised platform 703, 903 (FIGS. 20I and 23A). The connector can be coupled to the PCB 616 via a cable, which can optionally have a length configured to extend around the raised platform 703, 903, for example, in a groove of the raised platform 703, 903, or otherwise. Having the cable extending around the raised platform 703, 903 can allow adjustment of the slack of the cable when the connector connects to the second sensor. Having the connector extending from an opening on the raised platform 703, 903 can also avoid the connector and/or the cable impinging on the tissue at the watch/tissue interface as described above. The connector can alternatively be located at other suitable locations on the watch 700, 900.

The second plethysmograph sensor can have a higher measurements accuracy than the physiological parameter measurement module disclosed herein. The wearer can disconnect and/or deactivate the second sensor while the wearer is awake and/or moving about. The wearer can connect and activate the second sensor, for example, when going to sleep or resting. The sensor or module processor can ignore signals from the detectors of the module when the second sensor is activated so that the sensor or module processor can output physiological parameters based on the readings from the second sensor. Alternatively, the sensor or module processor can output physiological parameters based on a combination of the readings from the second sensor and the detectors of the module. The wearer can have the flexibility of choosing to use the physiological parameter measurement module and/or the second sensor, depending on the wearer's need.

The second plethysmograph sensor can aid in detection of opioid overdose in a wearer who uses opioid (for example, for medical reasons), in particular, by detecting low saturation of oxygen in the blood of the wearer. Depressed breathing is the most dangerous side effect of opioid overdose. Lack of oxygen to the brain can not only result in permanent neurologic damage, but may also be accompanied by the widespread failure of other organ systems, including the heart and kidneys. If a person experiencing an opioid overdose is left alone and asleep, the person could easily die as the respiratory depression worsens. The second plethysmograph sensor can be configured to detect depressed breathing by detecting decreased oxygen saturation in the blood of the wearer. The wearable device can be configured to automatically notify a first responder and/or the wearer's family or guardian in response to detecting opioid overdose of the wearer.

Optionally, the device processor of the wearable device can be in communication (for example, via Bluetooth or NFC communication, or via the network) with a processor of a drug delivery apparatus that is wearable by the wearer and configured to deliver one or more doses of a therapeutic drug, such as opioid. The drug delivery apparatus can include a delivery device that includes a dose of a therapeutic drug stored in a reservoir, a drug delivery channel, a dispensing device to dispense the therapeutic drug from the reservoir through the drug delivery channel, and activation circuitry to activate the dispensing device. The processor of the drug delivery apparatus can receive the parameters measured by the second plethysmograph sensor of the wearable device disclosed herein. The processor of the drug delivery apparatus can store memory-storing instructions and be configured to execute the instructions to at least compare the received parameters from the wearable device to a threshold that is indicative of opioid overdose. The processor of the drug delivery apparatus can determine whether an overdose event is occurring or likely to occur based on the comparison and send at least one activation signal to the drug delivery apparatus to dispense at least one dose of the therapeutic drug based on the determination.

Alternatively, the sensor or module processor of the physiological parameter measurement module can perform the comparison of the parameters measured by the second plethysmograph sensor to the predetermined opioid overdose threshold. Optionally, a microneedle patch may be used for providing a medication that can counteract opioid overdose. The wearer can apply the microneedle patch containing the medication to the skin when the wearable device outputs an alert that the wearer's physiological parameters (for example, SpO2) has exceeded a threshold (which may be indicative of opioid overdose).

Alternatively or additionally, the second sensor can be any other suitable noninvasive sensor disclosed herein. Alternatively or additionally, the physiological parameter measurement module examples disclosed herein can connect to a second sensor via wireless connection, for example, using Bluetooth technology. The module can receive measured parameters from the connected second sensor and/or process the sensor data received from the second sensor to calculate additional physiological parameters.

Example Microneedle Patch

In addition and/or alternative to delivering medication to prevent opioid overdose as described herein, a microneedles patch can be used for other purposes in combination with the wearable device. Microneedles have been used in recent years as a painless alternative to hypodermic needles to deliver drugs to the body. Microneedles on a patch can be placed on an arm or leg, or other parts of the body, which then create small holes in the skin's outermost layer, allowing the drugs coated on each needle to diffuse into the body. Microneedles can be made from silicon, metals, synthetic polymers, or natural, biodegradable materials such as silk and chitin.

Because of the small size, microneedles are minimally invasive and cause less pain compared to larger needles (for example, hypodermic needles). Additionally, the microneedle patch are easier to apply by the wearer than a hypothermal needle. In comparison, larger needles may require correct injection depth and injection angle to ensure that the drugs are injected at a right location.

FIG. 26A illustrates schematically a microneedle 3100 of a microneedle patch that has penetrated the tissue surface 2 of the wearer. Depending on its height, the microneedle 3100 may have varying injection depths. For example, the microneedle 3100 may puncture just the epidermis (including the stratum corneum, which is the outer layer of the epidermis) 42. In other examples, the microneedle 102 may puncture the epidermis 42 and dermis 44, with a tip of the microneedle 3102 terminating in the dermis 44. In other examples such as shown in FIG. 26A, the microneedle 3100 may puncture the epidermis 42 and dermis 44, with the tip 3102 end in the subcutaneous tissues 46.

Depending on the use, the microneedles 3100 with different heights may be used for delivery of medication and/or irrigation fluid 3104 into different parts of the wearer's tissue. The microneedles 3100 can be used to deliver a broad range of drugs, biotherapeutics, and vaccines. The microneedles 3100 can be hollow with internal reservoirs to store and deliver drugs or irrigation fluid 3104. Alternatively, the microneedles 3100 can be solid and coated with drugs 3104, and optionally other surfactant/thickening agents. Optionally, the microneedle 3100 can be dissolvable and encapsulate the drug in a nontoxic polymer that can dissolve once inside the skin.

Alternatively or additionally, the microneedles 3100 can be used to extract a tissue fluid sample 3104 (for example, the interstitial fluid of the wearer) for detection and/or analysis of analytes in the sample 3104. Optionally, the microneedle 3100 can irrigate the tissue of the wearer with a fluid before extracting the fluid (which, for example, may have equilibrated with the chemical composition of the wearer's bodily fluid sample) back into the microneedles 3100. The microneedles 3100 can be hollow and can extract a fluid sample via surface tension. The analyte detection and/or analysis can provide information such as the hydration status, glucose concentration, hemoglobin concentration, and/or orthogonal information about the fluid. The analyte detection and/or analysis can provide additional information related to, for example, sodium, potassium, glucose, chloride, bicarbonate, blood urea nitrogen, magnesium, creatinine, LDL cholesterol, HDL cholesterol, triglyceride, pH, and the like.

A microneedle patch may be located under one of the straps or the body of the wearable device, or be applied remotely (anywhere else on the wearer's body) from the wearable device without contacting the device. A plurality of microneedle patches can be applied to the wearer at different locations on the wearer's body. As shown in FIGS. 26B and 26C, the microneedles 3100 may be connected to a patch body 3106, forming a microneedle patch 3108. The patch body 3106 may be circular, oval, rectangular, square, triangular, tear-drop shaped, or of any other shape. The size of the patch body 3106 is not limiting. A surface of the patch body 3106 that is not connected to the microneedles 3100 can include an adhesive layer for releasably attach the patch 3108 to the wearable device. The adhesive layer may be covered by a back layer, which can be peeled off before applying the patch 3108 to the wearable device.

As shown in FIG. 26B, the microneedle patch 3108 can be placed on the body of the device 10. The patch 3108 can be applied under the skin-facing surface of the physiological parameter measurement sensor or module 100. The microneedles 3100 of the microneedle patch 3108 can face the skin of the wearer of the device 10 when the device 10 is worn. Accordingly, when the device 10 is worn, for example, on the wrist of the wearer with the straps wrapped around the wearer's wrist, the microneedles 3100 can puncture the skin on the wrist.

Additionally or alternatively, the microneedle patch 3108 may be integrated or releasably secured to an inner side of the adjustable strap 30 of the wearable device 10, such as shown in FIG. 26C. The microneedles 3100 can be pointing toward the skin around the wrist of the wearer when the device 10 is worn. When the strap 30 is wrapped around the wrist of the wearer, the microneedle patch 3108 may come in contact with the skin around the wrist of the wearer and the microneedles 3100 can penetrate the skin of the wearer.

Figure 26D:
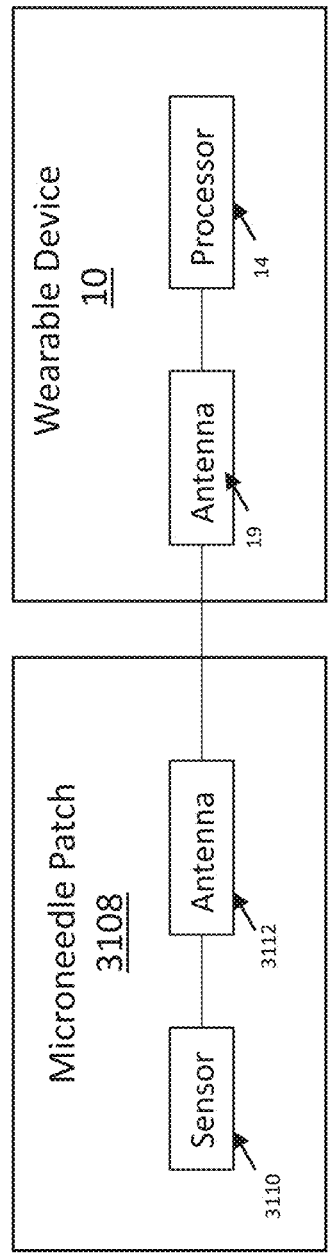
FIG. 26D illustrates schematically a simplified system diagram of the microneedle patch and the wearable device.

As shown in FIG. 26D, the microneedle patch 3108 can communicate with the wearable device 10, using the wearable device 10 as a platform or hub to detect and/or analyze analytes in the fluid sample collected in the microneedles patch 3108. The patch 3108 can optionally include a sensor 3110, for example, an electrochemical sensor (with electrodes built into the microneedles), a colorimetric sensor, or otherwise. Alternatively, the patch 3108 can be brought to an external sensor for analyte detection and analysis. The patch 3108 can include an antenna 3112, which may be an NFC antenna or otherwise. The sensor 3100 can output a signal via the antenna 3112. The wearable device can receive the signal from the sensor 3100 via the antenna 19. The device processor 14 (or optionally the sensor or module processor of the physiological parameter measurement sensor or module on the device 10) can process the signal from the sensor 3100 to determine the presence and/or concentration of certain analyte(s) in the fluid sample.

Examples Device Tightness Monitoring Systems and Methods

A desired tightness and/or pressure of the device on the body can be indicated by the skin interfacing with the wearable device moving with the device when the device is moved. If there is insufficient tightness and/or pressure of the device on the body of the wearer, ambient light entering the device-skin interface can result in noises in the signals detected by the detectors, and therefore inaccurate measurements made by the device. If the device is worn too tight (and/or the pressure exerted by the device on the body is too high), blood pulsation and circulation at the wrist can be restricted, which can lead to a decrease in oxygen saturation readings of the wearer of the device. Optionally, the device can output a warning that the device is worn too tight (which can include a message displayed on the device to the wearer to loosen the straps) when the device has determined that the wearer's oxygen saturation readings are decreasing by a certain percentage, at a certain rate, and/or at a certain rate within a predetermined amount of time.

The device 10 can include an optional strain gauge 20 (see FIG. 7A) to measure a pressure of the device 10 on the wearer. The strain gauge 20 can be located in a device housing 101 between the physiological parameter measurement module 100 and other components of the device 10, for example, the power source 16, the device processor 14, or otherwise. For example, the strain gauge 20 can be flanged between the physiological parameter measurement module 100 and the device processor 14. When the device 10 is worn on the wearer, for example, on the wrist, the pressure exerted by the module, particularly by the convex protrusion of the cover 102 against the tissue can be transmitted to and measured by the strain gauge 20. The strain gauge 20 can also be incorporated in the other wearable device examples disclosed herein.

Readings from the strain gauge 20 can be communicated to the device processor 14, which can process the readings and output an indication of the pressure asserted by the device 10 on the wearer to be displayed on the display 12. The indication can be in a variety of suitable forms, for example, using different colors to indicate whether the pressure is too low, appropriate, or too high for obtaining accurate or reliable measurements using the physiological parameter measurement module 100. In one example, the device 10 can display a green light when the pressure on the wearer is suitable for using the physiological parameter measurement module 100 and display a red or other colored light for a pressure that is too high or too low than the desired pressure or pressure range. The physiological parameter measurement module 100 may not be activated unless the readings from the strain gauge 20 indicate that the desired pressure or pressure range has been achieved. Optionally, the device processor can also deactivate the physiological parameter measurement module 100, and/or any other sensors on or attached to the device 10, in response to not detecting any readings from the strain gauge 20, indicating that the device 10 is not worn on the wearer. Automatically turning on and/or off the sensors on or attached to the device 10 can reduce power consumption and increase battery life of the device 10.

Optionally, the wearable device 10 can include a motor to adjust tightness of the straps based on a monitored tightness of the straps and/or pressure exerted by the sensor or module 100 on the wearer's skin.

Example Additional Features of the Wearable Device

The wearable device examples disclosed herein can provide protection of the wearer's safety by sending an alert to a first responder (for example, a hospital emergency room, a firefighter, 911, security at the facility where the wearer is located, or otherwise) and/or the wearer's family or guardian when the wearer is in danger, for example, when the wearer is drowning. The wearable device can include a swim mode, which the wearer can activate when going swimming. The physiological parameter measurement module of the wearable device can monitor one or more parameters to determine that the wearer is likely drowning (such as drowning of a child in water), for example, by determining that the wearer's respiratory rate has become irregular (such as showing fluctuations greater than a predetermined number per minute), or the wearer's SpO2 value declines by a predetermined amount, or otherwise. Alternatively, the module processor can determine that wearer is likely drowning based on the gyroscope and/or accelerometer readings, which can further be combined with the parameters monitored by the other sensors. In response to determining that the wearer is likely drowning, the module can send a notification to the processor of the wearable device, which can send an alert to a first responder and/or the wearer's family or guardian. Additionally or alternatively, the wearable device can include a distress button that the wearer can push in an emergency, such as when the wearer is drowning, has sustained a fall (which can alternatively or additionally be determined using the gyroscope and/or accelerometer readings, which can further be combined with the parameters monitored by the other sensors) while being alone, or otherwise.

The physiological parameters (for example but not limited to, SpO2, PR, PI, PVI, RR, Hydration, ECG-related parameters, etc.) measured by the module disclosed herein can be reliable enough for healthcare or medical purposes, for example, in hospitals. The module can be configured to take measurements at the same time every day. The wearable device (or the physiological parameter measurement module of the device) can further include a hospital patient ID tag on a near-field communication (NFC) or Bluetooth chip, or a watch strap or band. Essential patient information, such as the patient's name, admission date, reason for admission, blood type, drug allergies, etc. can be stored on the memory device of the watch or the physiological parameter measurement module. The patient ID tag cannot be easily removed and/or may include special tools like theft prevention devices, for example, requiring the patient to cut the watch strap off. Alternatively, the wearable device can display the patient information (for example, name, admission date, etc.) on the screen when the patient is admitted to the hospital. The patient ID tag can be either disposable after the patient is discharged or reusable after disinfection. The physiological parameter measurement module can be removed and replaced when the patient ID tag (for example, the watch band) is changed. If the wearable device is worn by a caregiver, the caregiver can use the wearable device for communications with other caregivers (for example, to share critical, substantially real-time information about patients, update changes in patient status, and/or the like), replacing the need for specialized communication tools, for example, Vocera®, Spok®, etc.

Additional Example Aspects and Implementations of a Sensor or Module

FIG. 27A is a front view of an example aspect of a sensor or module 2700. The sensor or module 2700 includes an opaque frame 2726, one or more electrodes 2724, one or more detector chambers 2788, one or more emitter chambers 2778, and a light barrier construct 2720.

The opaque frame 2726 can include one or more materials configured to prevent or block the transmission of light. In some aspects, the opaque frame 2726 may form a single integrated unit. In some aspects, the opaque frame 2726 may be formed of a continuous material. The light barrier construct 2720 can include one or more materials configured to prevent or block the transmission of light. In some aspects, the light barrier construct 2720 may form a single integrated unit. In some aspects, the light barrier construct 2720 may be formed of a continuous material. In some aspects, the light barrier construct 2720 and the opaque frame 2726 may form a single integrated unit. In some aspects, the light barrier construct 2720 and the opaque frame 2726 may be separably connected.

The light barrier construct 2720 may include one or more light barriers, such as light barriers 2720a, 2720b, 2720c, 2720d, which are provided as non-limiting examples. In some aspects, light barriers may be also be referred to as light blocks herein. The light barriers may form one or more portions of the light barrier construct 2720. The light barrier construct 2720 (or light barrier portions thereof) may prevent light from passing therethrough. The light barrier construct 2720 may include spaces between various light barriers which may define one or more chambers (e.g., detector chambers 2788, emitter chambers 2778). In some aspects, the one or more chambers (e.g., detector chambers 2788, emitter chambers 2778) may be enclosed by the light barrier construct 2720 or light barrier portions thereof, a surface of a substrate (e.g., PCB), and a lens or cover. In some aspects, light may only enter the chambers through the lens or cover.

An example of a light barrier is provided with reference to example light barrier 2720a. Light barrier 2720a forms a portion of light barrier construct 2720. Light barrier 2720a may prevent (e.g., block) light from passing therethrough between adjacent chambers. For example, light barrier 2720a may prevent light from passing through the light barrier construct 2720 between an emitter chamber 2778 and a detector chamber 2788. Light barrier 2720a, or portions thereof, may include a width 2771. In some aspects, width 2771 may be less than about 1.85 mm. In some aspects, width 2771 may be less than about 1.9 mm. In some aspects, width 2771 may be less than about 1.95 mm. In some aspects, width 2771 may be about 1.88 mm. In some aspects, the width 2771 may be less (e.g., smaller) than length 2779. In some aspects, width 2771 may be less than about 55% of length 2779. In some aspects, width 2771 may be less than about 60% of length 2779. In some aspects, width 2771 may be less than about 65% of length 2779. In some aspects, width 2771 may be about 58.9% of length 2779.

Another example of a light barrier is provided with reference to example light barrier 2720b. Light barrier 2720b forms a portion of light barrier construct 2720. Light barrier 2720b may prevent (e.g., block) light from passing therethrough between adjacent chambers. For example, light barrier 2720b may prevent light from passing through the light barrier construct 2720 between an emitter chamber 2778 and a detector chamber 2788. Light barrier 2720b, or portions thereof, may include a width 2772. In some aspects, width 2772 may be less than about 1.35 mm. In some aspects, width 2772 may be less than about 1.40 mm. In some aspects, width 2772 may be less than about 1.45 mm. In some aspects, width 2772 may be about 1.37 mm. In some aspects, the width 2772 may be substantially similar to width 2771. In some aspects, the width 2772 may be less (e.g., smaller) than width 2771. In some aspects, width 2772 may be less than about 70% of width 2771. In some aspects, width 2772 may be less than about 75% of width 2771. In some aspects, width 2772 may be less than about 80% of width 2771. In some aspects, width 2772 may be about 72.9% of width 2771.

Another example of a light barrier is provided with reference to example light barrier 2720c. Light barrier 2720c forms a portion of light barrier construct 2720. Light barrier 2720c may prevent (e.g., block) light from passing therethrough between adjacent chambers. For example, light barrier 2720c may prevent light from passing through the light barrier construct 2720 between adjacent detector chamber 2788.

Another example of a light barrier is provided with reference to example light barrier 2720d. Light barrier 2720d forms a portion of light barrier construct 2720. Light barrier 2720d may prevent (e.g., block) light from passing therethrough between adjacent chambers. For example, light barrier 2720d may prevent light from passing through the light barrier construct 2720 between adjacent emitter chambers 2778. In some aspects, light barrier 2720d may have a width 2775 separating adjacent emitter chambers of less than about 1.30 mm. In some aspects, width 2775 may be less than about 1.25 mm. In some aspects, width 2775 may be less than about 1.20 mm. In some aspects, width 2775 may be about 1.20 mm. In some aspects, width 2775 may be substantially similar to width 2772. In some aspects, width 2775 may be less (e.g., smaller) than width 2772. In some aspects, width 2775 may be less than about 95% of width 2772. In some aspects, width 2775 may be less than about 90% of width 2772. In some aspects, width 2775 may be less than about 85% of width 2772. In some aspects, width 2775 may be about 87.6% of width 2772.

The emitter chambers 2778 are positioned within a central region of the sensor or module 2700. The emitter chambers 2778 may be positioned adjacent to one another across a centerline of the sensor or module 2700 as described in greater detail with reference to FIG. 27K, for example. The emitter chambers 2778 may be positioned adjacent the center point $C_1$. Each of the emitter chambers 2778 may be a similar size and/or shape. The emitter chambers 2778 may be separated, at least in part, by light barrier 2720d of the light barrier construct 2720. In some aspects, as shown in this example, the light barrier 2720d may form an entire distance between emitter chambers 2778. For example, emitter chambers 2778 may be separated by only the light barrier 2720d such that other components (e.g., detectors, detector chambers, etc.) are not positioned between the emitter chambers 2778.

A portion of the emitter chambers 2778 may extend a length 2779 away from center point $C_1$. In some aspects, length 2779 may be less than about 3.15 mm. In some aspects, length 2779 may be less than about 3.20 mm. In some aspects, length 2779 may be less than about 3.25 mm. In some aspects, length 2779 may be about 3.19 mm. In some aspects, the length 2779 may be greater (e.g., larger) than a width of a light barrier separating an emitter chamber from a detector chamber such as width 2771. In some aspects, length 2779 may be greater than about 165% of width 2771. In some aspects, length 2779 may be greater than about 170% of width 2771. In some aspects, length 2779 may be greater than about 175% of width 2771. In some aspects, length 2779 may be about 169.7% of width 2771.

As shown in this example aspect, the detector chambers 2788 are arranged in a substantially circular pattern. Each of the detector chambers 2788 houses a detector 2706 positioned on a substrate (e.g., PCB) in a substantially circular or annular pattern. The detectors 2706 may be positioned in a central region of each of the respective detector chambers 2778. The detector chambers 2788 are arranged along a ring defined by ring $L_1$. In some aspects, such as shown in this example aspect, detectors 2706 of respective detector chambers 2788 may also be arranged along a same ring along which the detector chambers 2788 are arranged (such as in aspects where detectors are positioned in a central region of respective chambers). The ring $L_1$ may intersect a central region of the detector chambers 2788. In this example aspect, the ring $L_1$ encloses an entirety of the emitter chambers emitter chambers 2778 such that the emitter chambers 2778 are positioned within an interior region (e.g., a central region) of the ring $L_1$ defined by the detector chambers 2788. In some aspects, each of the detector chambers 2788 (and corresponding detectors 2706 within respective detector chambers 2788) may be positioned at a substantially similar or same distance away from the center point $C_1$ (e.g., center of sensor or module 2700). In some aspects, the detectors 2706 may be rectangular including longer sides and shorter sides. The detectors 2706 may be positioned on a substrate of the sensor or module 2700 such that a long side of each detector is orthogonal to a radius extending away from center point $C_1$ (e.g., radius $r_1$, radius $r_2$, radius $r_3$). Advantageously, orienting the detectors 2706 on the sensor or module 2700 in an annular arrangement with a long side of the detectors 2706 orthogonal the center point $C_1$ may improve an accuracy of physiological measurements by ensuring that light from emitters travels along a known path length from emitters to the detectors 2706 and may also reduce processing requirements of the sensor or module 2700 by reducing the amount of variables (e.g., number of light path lengths) required to process in order to determine physiological data.

The electrodes 2724 can include a reference electrode and a negative electrode (and/or a positive electrode). In some aspects, a wearable device such as a watch incorporating the sensor or module 2700 can include another ECG electrode (e.g., a positive electrode) located on the housing of the wearable device configured to make contact with the wearer's skin. In some configurations, a surface of the electrodes 2724 may be flush with a surface of the opaque frame 2726.

The electrodes 2724 are positioned within or along a portion of the opaque frame 2726 such as shown in FIG. 27B for example. In some aspects, the electrodes 2724 can be substantially semicircular. In some aspects, the electrodes 2724 can be substantially semiannular. In the example aspect shown, each of the electrodes 2724 forms a substantial half annulus. Advantageously, an annular shaped electrode may improve contact with the skin of a wearer (e.g., by contacting a diverse area of skin) while simultaneously reducing the amount of surface area of the electrode. In some aspects, each of the electrodes 2724 may be a similar size and/or shape. In some aspects, the electrodes 2724 may be various sizes and/or shapes. In this example aspect, the electrodes 2724 are positioned within the sensor or module 2700 (e.g., within the opaque frame 2726) along ring defined by $L_2$. In various aspects described herein, the ring $L_2$ may include various radii which may advantageously provide improved contact between the electrodes 2724 and the skin of a wearer of the device.

The opaque frame 2726 includes one or more gaps (e.g., $g_1$, $g_2$) between electrodes 2724. The gaps $g_1$, $g_2$, (or other portions of the opaque frame 2726) may electrically insulate each of the electrodes 2724 from one another. Each of the electrodes 2724 includes substantially straight edge along a portion of respective gaps $g_1$, $g_2$. In some aspects, the gaps $g_1$, $g_2$, may be a similar or a same size. In some aspects, the gaps $g_1$, $g_2$, may be a different size than each other. In some aspects, the gaps $g_1$, $g_2$, may be less than about 1.6 mm. In some aspects, the gaps $g_1$, $g_2$, may be less than about 1.65 mm. In some aspects, the gaps $g_1$, $g_2$, may be less than about 1.7 mm. In some aspects, the gaps $g_1$, $g_2$, may be about 1.62 mm. As discussed above, in some implementations the frame 2726 includes recesses 2824 sized and/or shaped to receive the ECG electrodes 2724. In some implementations, each of such recesses 2824 includes first and second ends, the first ends of the recesses 2824 are separated from one another by gap $g_1$, and the second ends of the recesses 2824 are separated from one another by gap $g_2$.

The ring $L_1$ may be concentric with an outer perimeter of the sensor or module 2700. The ring $L_2$ may be concentric with an outer perimeter of the sensor or module 2700. The ring $L_2$ may be concentric with a ring defined by positions of the detector chambers 2788 such as ring $L_1$. Center point $C_1$ may define a geometric center of ring $L_1$. Center point $C_1$ may define a geometric center of ring $L_2$. Center point $C_1$ may define a geometric center of an outer perimeter of the sensor or module 2700. In some aspects, such as shown in FIG. 27A, each of $L_1$, $L_2$, and an outer perimeter of the sensor or module 2700 are concentric with each other and share a same geometric center shown as $C_1$.

The ring $L_1$ may include a radius $r_1$. In some aspects, radius $r_1$ may be less than about 6.25 mm. In some aspects, radius $r_1$ may be less than about 6.50 mm. In some aspects, radius $r_1$ may be less than about 6.75 mm. In some aspects, radius $r_1$ may be about 6.34 mm. In some aspects, the radius $r_1$ may be less (e.g., smaller) than radius $r_2$. In some aspects, radius $r_1$ may be less than about 55% of $r_2$. In some aspects, radius $r_1$ may be less than about 60% of $r_2$. In some aspects, radius $r_1$ may be less than about 65% of $r_2$. In some aspects, radius $r_1$ may be about 59% of $r_2$. In some aspects, the radius $r_1$ may be less (e.g., smaller) than radius $r_3$. In some aspects, radius $r_1$ may be less than about 40% of $r_3$. In some aspects, radius $r_1$ may be less than about 45% of $r_3$. In some aspects, radius $r_1$ may be less than about 50% of $r_3$. In some aspects, radius $r_1$ may be about 41.7% of $r_3$.

The ring $L_2$ may include a radius $r_2$. In some aspects, radius $r_2$ may be less than about 10.5 mm. In some aspects, radius $r_2$ may be less than about 10.75 mm. In some aspects, radius $r_2$ may be less than about 11.0 mm. In some aspects, radius $r_2$ may be about 10.73 mm. In some aspects, the radius $r_2$ may be less (e.g., smaller) than radius $r_3$. In some aspects, radius $r_2$ may be less than about 65% of $r_3$. In some aspects, radius $r_2$ may be less than about 70% of $r_3$. In some aspects, radius $r_2$ may be less than about 75% of $r_3$. In some aspects, radius $r_2$ may be about 70.6% of $r_3$.

In some aspects, the sensor or module 2700 (e.g., an outer perimeter of the sensor or module 2700) may include a radius $r_3$. In some aspects, radius $r_3$ may be less than about 14.5 mm. In some aspects, radius $r_3$ may be less than about 15.0 mm. In some aspects, radius $r_3$ may be less than about 15.50 mm. In some aspects, radius $r_3$ may be less than about 16.0 mm. In some aspects, radius $r_3$ may be about 15.19 mm.

Figure 27L:
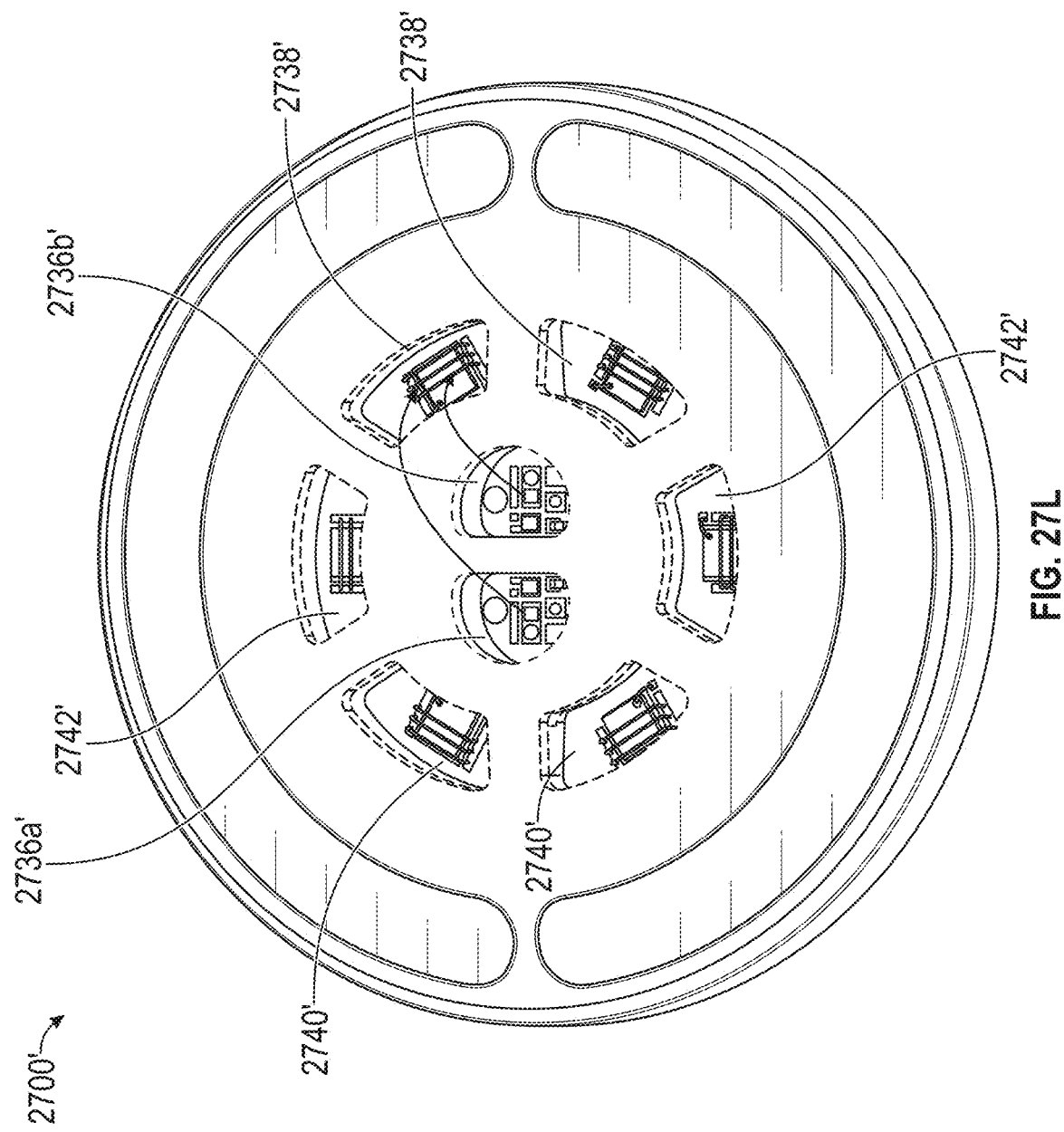

FIGS. 27K-27L illustrate an example physiological parameter measurement sensor or module 2700' and example light paths between emitters and detectors of the module 2700'.

FIG. 27K illustrates an example arrangement of emitter and detector chambers of the sensor or module 2700'. As shown, the sensor or module 2700' can include a first emitter chamber 2736a' enclosing a first emitter group comprising one or more emitters, a second emitter chamber 2736b' enclosing a second emitter group comprising one or more emitters, one or more first detector chambers 2740', one or more second detector chambers 2742', and one or more third detector chambers 2738'. In some aspects, each detector chamber may enclose one detector.

The first emitter group of the first emitter chamber 2736a' may comprise the same number and type of emitters as the second emitter group of the second emitter chamber 2736b'.

In other words, each emitter of the first emitter group may correspond to an emitter of the same type (e.g., same wavelength) of the second emitter group. The emitters of the first emitter group may be arranged in a configuration that mirrors the emitters of the second emitter group across a centerline 2750 of the sensor or module 2700' as shown in FIG. 27K. For example, each emitter of the first group of emitters may be located a distance away from a centerline 2750 of the sensor or module 2700' that is a same distance that a corresponding emitter of the second group of emitters is located away from the centerline 2750 of the sensor or module 2700'. For example, the first and second emitter groups may each include an emitter that emits light of a first wavelength and that are positioned at locations that are mirror images of each other across a centerline 2750 of the sensor or module 2700'. Additionally, the first and second emitter groups may each include an emitter that emits light of a second wavelength and that are positioned at locations that are mirror images of each other across a centerline 2750 of the sensor or module 2700'. Each of the emitters of the first emitter group may correspond to an emitter of the second emitter group located at a mirror image position, and vice versa.

The one or more second detector chambers 2742' may be bisected by a centerline 2750 of the sensor or module 2700'. Each of the detectors of the respective one or more second detector chambers 2742' may be bisected by a centerline 2750 of the sensor or module 2700'. In other words, the one or more second detector chambers 2742' and the respective detectors and the sensor or module 2700' may each share a same (e.g., parallel) centerline 2750. The sensor or module 2700' may be oriented (e.g., rotated) with respect to the tissue of a wearer in any orientation. In an example implementation where the sensor or module 2700' is worn on a wrist of a user, the sensor or module 2700' may be rotated in any direction with respect to the wrist or forearm of the wearer. In one example configuration, the sensor or module 2700' may be oriented with respect to the forearm (or other body part) of a wearer such that the centerline 2750' of the sensor or module is perpendicular to a line extending along a length of the forearm of the wearer (e.g., from the elbow to the wrist). Advantageously, such a configuration may improve physiological measurements by facilitating light emitted from the emitter chambers and detected at the detector chambers (e.g., light travelling from emitter chamber 2736a' to detector chamber 2738') to penetrate into soft tissue of the wearer (e.g., blood vessels) rather than other tissues such as bone. In another example configuration, the sensor or module 2700' may be oriented with respect to the forearm (or other body part) of a wearer such that the centerline 2750' of the sensor or module is parallel to a line extending along a length of the forearm of the wearer (e.g., from the elbow to the wrist). Advantageously, such a configuration may improve physiological measurements by facilitating light emitted from the emitter chambers and detected at the detector chambers (e.g., light travelling from emitter chamber 2736a' to detector chamber 2742') to penetrate into soft tissue of the wearer (e.g., blood vessels) rather than other tissues such as bone.

As shown in FIG. 27K, emitters of the first and second emitter groups that correspond to each other (e.g., emit the same wavelength and mirror each other) may each emit light that travels along respective paths to the detectors of the one or more second detector chambers 2742'. The respective paths of light from the corresponding emitters may be of equal length. This may be because the corresponding emitters are each positioned an equal distance away from a detector of a chamber 2742'. The corresponding emitters may each be an equal distance away from a detector of a chamber 2742' because they are positioned at mirror images of each other across a centerline 2750 of the sensor or module 2700' that bisects the one or more second detector chambers 2472' and respective detectors.

The one or more second detector chambers 2742' and their respective detectors may be used, at least in part, for calibration, for example to characterize the emitters, by providing known information such as a known ratio. For example, information corresponding to a wavelength detected at a detector of a chamber 2742' from an emitter of the first group of emitters may be similar or the same as information corresponding to that wavelength detected at the detector of the chamber 2742' from an emitter of the second group of emitters and a comparison (e.g., subtracting, dividing, etc.) of the information resulting from the first and second groups of emitters may yield a known number such as zero or one because the corresponding emitters from the first and second emitter groups may be an equal distance from the detector of chamber 2742' and light emitted therefrom may travel a same distance to the detector of chamber 2742'. As an example of normalization, ratios of wavelengths detected at detectors of chambers 2738', 2740' may be normalized (e.g., divided by) ratios of wavelengths detected at detectors of chambers 2742'. In instances where the information resulting from detection of light from the first and second groups of emitters is not the same or is substantially different (e.g., as a result of emission intensity variations or other such discrepancies) the information may be adjusted or normalized (e.g., calibrated) to account for such differences. This normalization or on-board calibration or characterization of the emitters may improve accuracy of the physiological measurements and provide for continuous calibration or normalization during measurements. In some aspects, a processor may be configured to calibrate or normalize the physiological parameter measurement of the sensor continuously. In some aspects, a processor may be configured to calibrate or normalize the physiological parameter measurement of the sensor while the optical physiological sensor measures physiological parameters of the wearer.

FIG. 27L illustrates an example arrangement of emitter and detector chambers of the sensor or module 2700'. As shown, the sensor or module 2700' can include a first emitter chamber 2736a', a second emitter chamber 2736b', one or more first detector chambers 2740', one or more second detector chambers 2742', and one or more third detector chambers 2738', for example as discussed elsewhere herein.

The first and second emitter chambers 2736a', 2736b' may be located at non-equal distances away from each of the chambers of the one or more detector chambers 2738', 2740'. Thus, with respect to each detector chamber of the chambers 2738', 2740', the first and second emitter chamber 2736a', 2736b', may each be a "near" or "far" emitter chamber. In other words, each detector of the detector chambers 2738', 2740' may detect light, of any given wavelength, from both a "near" emitter and a "far" emitter, with the near and far emitters being included in either the first or second emitter group, respectively.

As an example, as shown in FIG. 27L, light of a given wavelength may travel along a path from an emitter in the first emitter group to the detector of detector chamber 2738' and light of the same wavelength may travel along a path from an emitter in the second emitter group to the same detector. The light from the first emitter group may travel along a longer path than light from the second emitter group before reaching the detector of chamber 2738'. Thus, for any detector of detector chambers 2738' or 2740', the detector may receive light of a given wavelength from both a near (e.g., proximal) emitter and a far (e.g., distal) emitter. This may not be the case for detectors of chambers 2742' because the first and second emitter groups may each be located a same distance away from any given detector of detector chambers 2742', as described herein.

For convenience, the terms "proximal" and "distal" may be used herein to describe structures relative to any of the detector chambers or their respective detectors. For example, an emitter may be proximal to a detector chamber of the first detector chambers and distal to a detector of the second detector chambers. The term "distal" refers to one or more emitters that are farther away from a detector chamber than at least some of the other emitters. The term "proximal" refers to one or more emitters that are closer to a detector chamber than at least some of the other emitters. The term "proximal emitter" may be used interchangeably with "near emitter" and the term "distal emitter" may be used interchangeably with "far emitter".

A single emitter may be both proximal to one detector and distal to another detector. For example, an emitter may be a proximal emitter relative to a detector of the first detector chambers and may be a distal emitter relative to a detector of the second detector chambers.

Light of a given wavelength that is detected at a detector may provide different information depending on the length of the path it has travelled from the emitter (e.g., along a long path from a distal emitter or along a short path from a proximal emitter). For example, light that has travelled along a long path from a distal emitter may penetrate deeper into the tissue of a wearer of the device and may provide information pertaining to pulsatile blood flow or constituents. The use of a proximal and distal emitter for each wavelength may improve accuracy of the measurement, for example information pertaining to light that has travelled along a long path from a distal emitter may be normalized by (e.g., divided by) information pertaining to light that has travelled along a short path from a proximal emitter.

FIGS. 27M-27P illustrate an example physiological parameter measurement sensor or module 2700' and example light barriers or light blocks between emitter and detector chambers of the module 2700'.

Figure 27M:
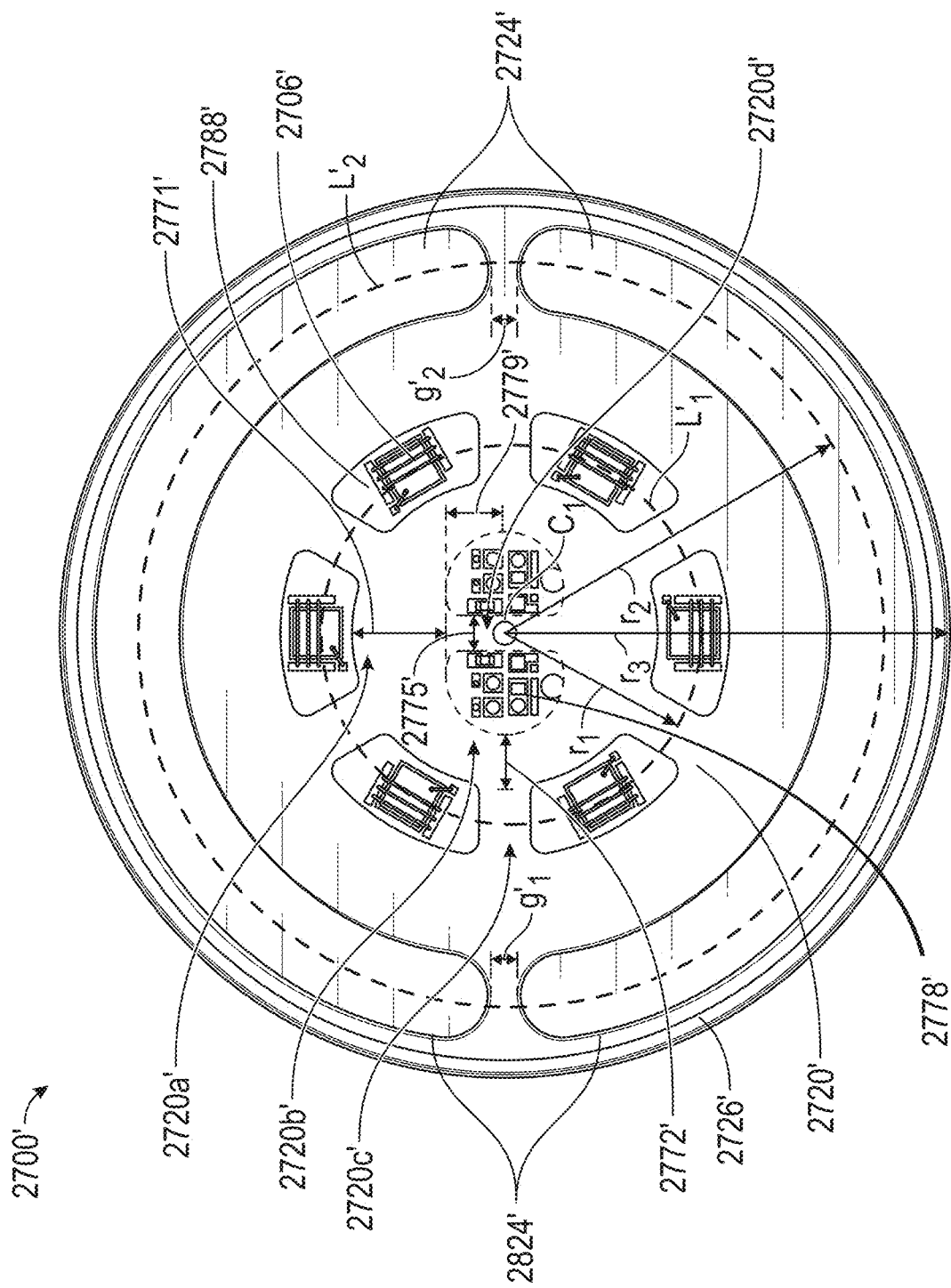
FIGS. 27M-27P illustrate an example physiological parameter measurement sensor or module and example light barriers or light blocks between emitter and detector chambers of the module.

FIG. 27M is a front view of an example aspect of a sensor or module 2700'. The sensor or module 2700' includes an opaque frame opaque frame 2726', one or more electrodes 2724', one or more detector chambers 2788', one or more emitter chambers 2778', and a light barrier construct 2720'.

The opaque frame 2726' can include one or more materials configured to prevent or block the transmission of light. In some aspects, the opaque frame 2726' may form a single integrated unit. In some aspects, the opaque frame 2726' may be formed of a continuous material. The light barrier construct 2720' can include one or more materials configured to prevent or block the transmission of light. In some aspects, the light barrier construct 2720' may form a single integrated unit. In some aspects, the light barrier construct 2720' may be formed of a continuous material. In some aspects, the light barrier construct 2720' and the opaque frame 2726' may form a single integrated unit. In some aspects, the light barrier construct 2720' and the opaque frame 2726' may be separably connected.

The light barrier construct 2720' may include one or more light barriers, such as light barriers 2720a', 2720b', 2720c', 2720d', which are provided as non-limiting examples. In some aspects, light barriers may be also be referred to as light blocks herein. The light barriers may form one or more portions of the light barrier construct 2720'. The light barrier construct 2720' (or light barrier portions thereof) may prevent light from passing therethrough. The light barrier construct 2720' may include spaces between various light barriers which may define one or more chambers (e.g., detector chambers 2788', emitter chambers 2778'). In some aspects, the one or more chambers (e.g., detector chambers 2788', emitter chambers 2778') may be enclosed by the light barrier construct 2720' or light barrier portions thereof, a surface of a substrate (e.g., PCB), and a lens or cover. In some aspects, light may only enter the chambers through the lens or cover.

An example of a light barrier is provided with reference to example light barrier 2720a'. Light barrier 2720a' forms a portion of light barrier construct 2720'. Light barrier 2720a' may prevent (e.g., block) light from passing therethrough between adjacent chambers. For example, light barrier 2720a' may prevent light from passing through the light barrier construct 2720' between an emitter chamber 2778' and a detector chamber 2788'. Light barrier 2720a', or portions thereof, may include a width 2771'. In some aspects, width 2771' may be less than about 3.30 mm. In some aspects, width 2771' may be less than about 3.25 mm. In some aspects, width 2771' may be less than about 3.20 mm. In some aspects, width 2771' may be about 3.24 mm. In some aspects, the width 2771' may be greater (e.g., larger) than length 2779. In some aspects, width 2771' may be less than about 165% of length 2779. In some aspects, width 2771' may be less than about 160% of length 2779. In some aspects, width 2771' may be less than about 155% of length 2779. In some aspects, width 2771' may be about 160% of length 2779. Advantageously, a greater width 2771' (e.g., a wider light barrier separating the emitter chambers 2778' and detector chambers 2788') may cause light emitted from the emitter chambers 2778' to travel a greater distance before reaching the detector chambers 2788'. Light that travels a greater distance may penetrate deeper into the tissue of the wearer which may improve accuracy of a physiological measurement.

Another example of a light barrier is provided with reference to example light barrier 2720b'. Light barrier 2720b' forms a portion of light barrier construct 2720'. Light barrier 2720b' may prevent (e.g., block) light from passing therethrough between adjacent chambers. For example, light barrier 2720b' may prevent light from passing through the light barrier construct 2720' between an emitter chamber 2778' and a detector chamber 2788'. Light barrier 2720b', or portions thereof, may include a width 2772'. In some aspects, width 2772' may be less than about 1.65 mm. In some aspects, width 2772' may be less than about 1.60 mm. In some aspects, width 2772' may be less than about 1.55 mm. In some aspects, width 2772' may be about 1.59 mm. In some aspects, the width 2772' may be less (e.g., smaller) than width 2771'. In some aspects, width 2772' may be less than about 60% of width 2771'. In some aspects, width 2772' may be less than about 55% of width 2771'. In some aspects, width 2772' may be less than about 50% of width 2771'. In some aspects, width 2772' may be about 49% of width 2771'. Advantageously, a greater width 2772' may cause light emitted from the emitter chambers 2778' to travel a greater distance before reaching the detector chambers 2788'. Light that travels a greater distance may penetrate deeper into the tissue of the wearer which may improve accuracy of a physiological measurement Another example of a light barrier is provided with reference to example light barrier 2720c'. Light barrier 2720c' forms a portion of light barrier construct 2720'. Light barrier 2720c' may prevent (e.g., block) light from passing therethrough between adjacent chambers. For example, light barrier 2720c' may prevent light from passing through the light barrier construct 2720' between adjacent detector chamber 2788'.

Another example of a light barrier is provided with reference to example light barrier 2720d'. Light barrier 2720d' forms a portion of light barrier construct 2720'. Light barrier 2720d' may prevent (e.g., block) light from passing therethrough between adjacent chambers. For example, light barrier 2720d' may prevent light from passing through the light barrier construct 2720' between adjacent emitter chambers 2778'. In some aspects, light barrier 2720d' may have a width 2775' separating adjacent emitter chambers of less than about 1.40 mm. In some aspects, width 2775' may be less than about 1.35 mm. In some aspects, width 2775' may be less than about 1.30 mm. In some aspects, width 2775' may be about 1.28 mm. In some aspects, width 2775' may be less (e.g., smaller) than width 2771'. In some aspects, width 2775' may be less than about 50% of width 2771'. In some aspects, width 2775' may be less than about 45% of width 2771'. In some aspects, width 2775' may be less than about 40% of width 2771'. In some aspects, width 2775' may be less than about 35% of width 2771'. In some aspects, width 2775' may be about 39.5% of width 2771'.

The emitter chambers 2778' are positioned within a central region of the sensor or module 2700'. The emitter chambers 2778' may be positioned adjacent to one another across a centerline of the sensor or module 2700' as described in greater detail with reference to FIG. 27K, for example. The emitter chambers 2778' may be positioned adjacent the center point $C'_1$. Each of the emitter chambers 2778' may be a similar size and/or shape. The emitter chambers 2778' may be separated, at least in part, by light barrier 2720d' of the light barrier construct 2720'. In some aspects, as shown in this example, the light barrier 2720d' may form an entire distance between emitter chambers 2778'. For example, emitter chambers 2778' may be separated by only the light barrier 2720d' such that other components (e.g., detectors, detector chambers, etc.) are not positioned between the emitter chambers 2778'.

A portion of the emitter chambers 2778' may extend a length 2779 away from center point $C'_1$. In some aspects, length 2779 may be less than about 2.15 mm. In some aspects, length 2779 may be less than about 2.10 mm. In some aspects, length 2779 may be less than about 2.05 mm. In some aspects, length 2779 may be less than about 2.0 mm. In some aspects, length 2779 may be about 2.02 mm. In some aspects, the length 2779 may be less (e.g., smaller) than a width of a light barrier separating an emitter chamber from a detector chamber such as width 2771'. In some aspects, length 2779 may be less than about 70% of width 2771'. In some aspects, length 2779 may be less than about 65% of width 2771'. In some aspects, length 2779 may be less than about 60% of width 2771'. In some aspects, length 2779 may be about 62.3% of width 2771'.

As shown in this example aspect, the detector chambers 2788' are arranged in a substantially circular pattern. Each of the detector chambers 2788' houses a detector 2706 positioned on a substrate (e.g., PCB) in a substantially circular or annular pattern. The detectors 2706 may be positioned in a central region of each of the respective detector chambers 2778'. The detector chambers 2788' are arranged along a ring defined by ring $L'_1$. In some aspects, such as shown in this example aspect, detectors 2706 of respective detector chambers 2788' may also be arranged along a same ring along which the detector chambers 2788' are arranged (such as in aspects where detectors are positioned in a central region of respective chambers). The ring $L'_1$ may intersect a central region of the detector chambers 2788'. In this example aspect, the ring $L'_1$ encloses an entirety of the emitter chambers emitter chambers 2778' such that the emitter chambers 2778' are positioned within an interior region (e.g., a central region) of the ring $L'_1$ defined by the detector chambers 2788'. In some aspects, each of the detector chambers 2788' (and corresponding detectors 2706 within respective detector chambers 2788') may be positioned at a substantially similar or same distance away from the center point $C'_1$ (e.g., center of sensor or module 2700'). In some aspects, the detectors 2706 may be rectangular including longer sides and shorter sides. The detectors 2706 may be positioned on a substrate of the sensor or module 2700' such that a long side of each detector is orthogonal to a radius extending away from center point $C'_1$ (e.g., radius $r'_1$, radius $r'_2$, radius $r'_3$). Advantageously, orienting the detectors 2706 on the sensor or module 2700' in an annular arrangement with a long side of the detectors 2706 orthogonal the center point $C'_1$ may improve an accuracy of physiological measurements by ensuring that light from emitters travels along a known path length from emitters to the detectors 2706 and may also reduce processing requirements of the sensor or module 2700' by reducing the amount of variables (e.g., number of light path lengths) required to process in order to determine physiological data.

The electrodes 2724' can include a reference electrode and a negative electrode (and/or a positive electrode). In some aspects, a wearable device such as a watch incorporating the sensor or module 2700' can include another ECG electrode (e.g., a positive electrode) located on the housing of the wearable device configured to make contact with the wearer's skin. In some configurations, a surface of the electrodes 2724' may be flush with a surface of the opaque frame 2726'.

The electrodes 2724' are positioned within or along a portion of the opaque frame 2726' such as shown in FIG. 27B for example. In some aspects, the electrodes 2724' can be substantially semicircular. In some aspects, the electrodes 2724' can be substantially semi-annular. In the example aspect shown, each of the electrodes 2724' forms a substantial half annulus. Advantageously, an annular shaped electrode may improve contact with the skin of a wearer (e.g., by contacting a diverse area of skin) while simultaneously reducing the amount of surface area of the electrode. In some aspects, each of the electrodes 2724' may be a similar size and/or shape. In some aspects, the electrodes 2724' may be various sizes and/or shapes. In this example aspect, the electrodes 2724' are positioned within the sensor or module 2700' (e.g., within the opaque frame 2726') along ring defined by L'2. In various aspects described herein, the ring L'2 may include various radii which may advantageously provide improved contact between the electrodes 2724' and the skin of a wearer of the device. In some implementations, frame 2726' includes recesses that 2824' are sized and/or shaped to accommodate the ECG electrodes 2724'. In some implementations, recesses 2824' have a depth (for example, measured from a plane of the frame 2726') that is substantially equal to a thickness of the ECG electrodes 2724'. In some implementations, recesses 2824' have a size and/or shape that matches a size and/or shape of the ECG electrodes 2724'. For example, in some implementations in which the ECG electrodes have a semi-annular shape, the recesses 2824' can have a semi-annular shape.

The opaque frame 2726' includes one or more gaps (e.g., $g'_1$, $g'_2$) between electrodes 2724'. The gaps $g'_1$, $g'_2$, (or other portions of the opaque frame 2726') may electrically insulate each of the electrodes 2724' from one another. Each of the electrodes 2724' includes a curved edge along a portion of respective gaps $g'_1$, $g'_2$. In some aspects, the gaps $g'_1$, $g'_2$, may be a similar or a same size. In some aspects, the gaps $g'_1$, $g'_2$, may be a different size than each other. In some aspects, the gaps $g'_1$, $g'_2$, may be less than about 0.6 mm. In some aspects, the gaps $g'_1$, $g'_2$, may be less than about 0.65 mm. In some aspects, the gaps $g'_1$, $g'_2$, may be less than about 0.7 mm. In some aspects, the gaps $g'_1$, $g'_2$, may be about 0.62 mm. As discussed above, in some implementations the frame 2726' includes recesses 2824' sized and/or shaped to receive the ECG electrodes 2724'. In some implementations, each of such recesses 2824' includes first and second ends, the first ends of the recesses 2824' are separated from one another by gap $g'_1$, and the second ends of the recesses 2824' are separated from one another by gap $g'_2$ (see FIG. 27M). In some implementations, such as that illustrated in at least FIG. 27M, ends of the recesses 2824' and/or ends of ECG electrodes 2724' have a rounded shape.

The ring $L'_1$ may be concentric with an outer perimeter of the sensor or module 2700'. The ring $L'_2$ may be concentric with an outer perimeter of the sensor or module 2700'. The ring $L'_2$ may be concentric with a ring defined by positions of the detector chambers 2788' such as ring $L'_1$. Center point $C'_1$ may define a geometric center of ring $L'_1$. Center point $C'_1$ may define a geometric center of ring $L'_2$. Center point $C'_1$ may define a geometric center of an outer perimeter of the sensor or module 2700'. In some aspects, such as shown in FIG. 27M, each of $L'_1$, $L'_2$, and an outer perimeter of the sensor or module 2700' are concentric with each other and share a same geometric center shown as $C'_1$.

The ring $L'_1$ may include a radius $r'_1$. In some aspects, radius $r'_1$ may be less than about 6.5 mm. In some aspects, radius $r'_1$ may be less than about 6.45 mm. In some aspects, radius $r'_1$ may be less than about 6.40 mm. In some aspects, radius $r'_1$ may be about 6.40 mm. In some aspects, the radius $r'_1$ may be less (e.g., smaller) than radius $r'_2$. In some aspects, radius $r'_1$ may be less than about 60% of $r'_2$. In some aspects, radius $r'_1$ may be less than about 55% of $r'_2$. In some aspects, radius $r'_1$ may be less than about 50% of $r'_2$. In some aspects, radius $r'_1$ may be about 50.9% of $r'_2$. In some aspects, the radius $r'_1$ may be less (e.g., smaller) than radius $r'3$. In some aspects, radius $r'_1$ may be less than about 40% of $r'_3$. In some aspects, radius $r'_1$ may be less than about 45% of $r'3$. In some aspects, radius $r'_1$ may be less than about 50% of $r'_3$. In some aspects, radius $r'_1$ may be about 42% of $r'_3$.

The ring $L'2$ may include a radius $r'_2$. In some aspects, radius $r'_2$ may be less than about 13 mm. In some aspects, radius $r'_2$ may be less than about 12.75 mm. In some aspects, radius $r'_2$ may be less than about 12.5 mm. In some aspects, radius $r'_2$ may be about 12.59 mm. In some aspects, the radius $r'_2$ may be less (e.g., smaller) than radius $r'_3$. In some aspects, radius $r'_2$ may be less than about 80% of $r'_3$. In some aspects, radius $r'_2$ may be less than about 85% of $r'_3$. In some aspects, radius $r'_2$ may be less than about 90% of $r'_3$. In some aspects, radius $r'_2$ may be about 82.7% of $r'_3$.

In some aspects, the sensor or module 2700' (e.g., an outer perimeter of the sensor or module 2700') may include a radius $r'_3$. In some aspects, radius $r'_3$ may be less than about 15 mm. In some aspects, radius $r'_3$ may be less than about 15.0 mm. In some aspects, radius $r'_3$ may be less than about 15.25 mm. In some aspects, radius $r'_3$ may be less than about 15.5 mm. In some aspects, radius $r'_3$ may be about 15.22 mm.

Figure 27N:
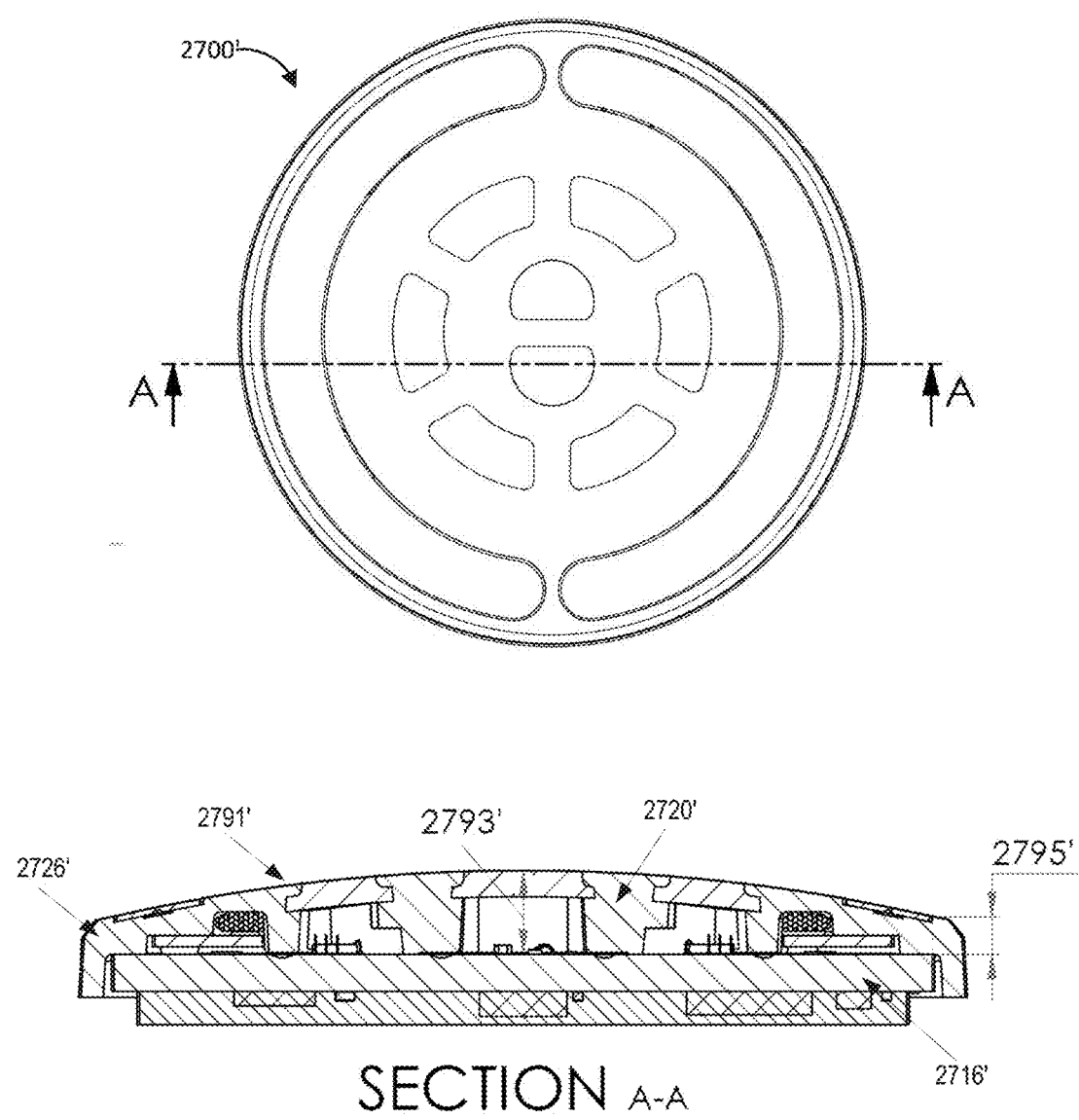

FIG. 27N is a side cutaway view of an example aspect of a sensor or module 2700'. The sensor or module 2700' includes a barrier construct 2720', an outer surface 2791', and a substrate 2716'. The outer surface 2791' may include light barrier construct portions, lens portions, opaque frame portions, and/or electrode portions. The outer surface 2791' of the sensor or module 2700' may face and/or contact the skin of a wearer and may include a generally convex shape. A central region of the sensor or module 2700' may have a height 2793'. For example, the height of the light barrier construct 2720' at a central region of the sensor or module 2700' may correspond to height 2793'. The height 2793' may be a maximum distance the outer surface 2791' extends perpendicularly away from the substrate 2716' (e.g., toward the skin of a wearer). An outer region (e.g., along a perimeter of the substrate 2716') of the sensor or module 2700' may have a height 2795'. For example, the height of the light barrier construct 2720' and/or opaque frame 2726' at an outer region of the sensor or module 2700' may correspond to height 2795'. The height 2795' may be a minimum distance the outer surface 2791' extends perpendicularly away from the substrate 2716' (e.g., toward the skin of a wearer).

In some aspects, height 2793' may be less than about 2.95 mm. In some aspects, height 2793' may be less than about 2.90 mm. In some aspects, height 2793' may be less than about 2.85 mm. In some aspects, height 2793' may be less than about 2.80 mm. In some aspects, height 2793' may be about 2.85 mm. In some aspects, height 2793' may be less than about 2.70 mm. In some aspects, height 2793' may be less than about 2.65 mm. In some aspects, height 2793' may be less than about 2.60 mm. In some aspects, height 2793' may be less than about 2.55 mm. In some aspects, height 2793' may be about 2.58 mm.

In some aspects, height 2795' may be less than about 1.40 mm. In some aspects, height 2795' may be less than about 1.35 mm. In some aspects, height 2795' may be less than about 1.30 mm. In some aspects, height 2795' may be less than about 1.25 mm. In some aspects, height 2795' may be about 1.29 mm. In some aspects, height 2795' may be less than about 1.90 mm. In some aspects, height 2795' may be less than about 1.85 mm. In some aspects, height 2795' may be less than about 1.80 mm. In some aspects, height 2795' may be less than about 1.75 mm. In some aspects, height 2795' may be about 1.78 mm.

In some aspects, the height 2793' may be greater (e.g., larger) than height 2795'. In some aspects, height 2793' may be less than about 230% of height 2795'. In some aspects, height 2793' may be less than about 225% of height 2795'. In some aspects, height 2793' may be less than about 220% of height 2795'. In some aspects, height 2793' may be less than about 215% of height 2795'. In some aspects, height 2793' may be about 221% of height 2795'. In some aspects, height 2793' may be less than about 155% of height 2795'. In some aspects, height 2793' may be less than about 150% of height 2795'. In some aspects, height 2793' may be less than about 145% of height 2795'. In some aspects, height 2793' may be less than about 140% of height 2795'. In some aspects, height 2793' may be about 145% of height 2795'.

Advantageously, a greater height 2793' (and/or greater ratio of height 2793' to 2795') (for example, a taller light barrier at a central region of the sensor or module 2700 may cause light emitted from emitter chambers to travel a greater distance before reaching the detector chambers. Light that travels a greater distance may penetrate deeper into the tissue of the wearer which may improve accuracy of a physiological measurement. A smaller height 2793' (and/or smaller ratio of height 2793' to 2795') may reduce discomfort to the wearer wearing the wearable device 10 or may reduce obstruction to blood flow of the wearer by reducing the amount of pressure the wearable device places on the wearer. The height 2793' and/or height 2795' may be selected to balance the above-mentioned considerations such as increasing the depth which light penetrates into the tissue and reducing discomfort or blood flow obstruction of the wearer.

Figure 27O:
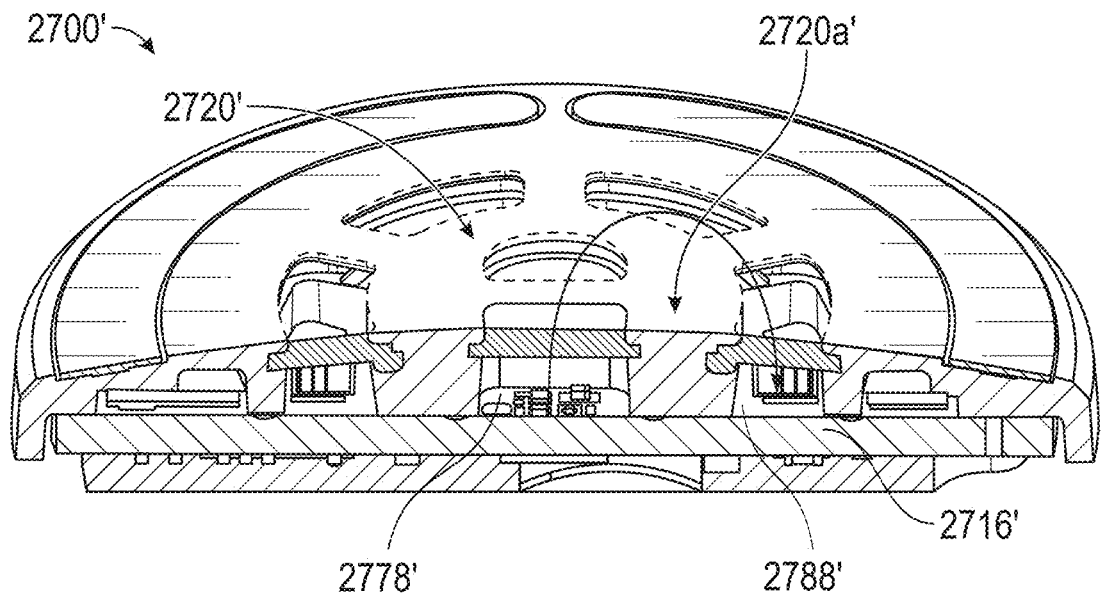
Figure 27P:
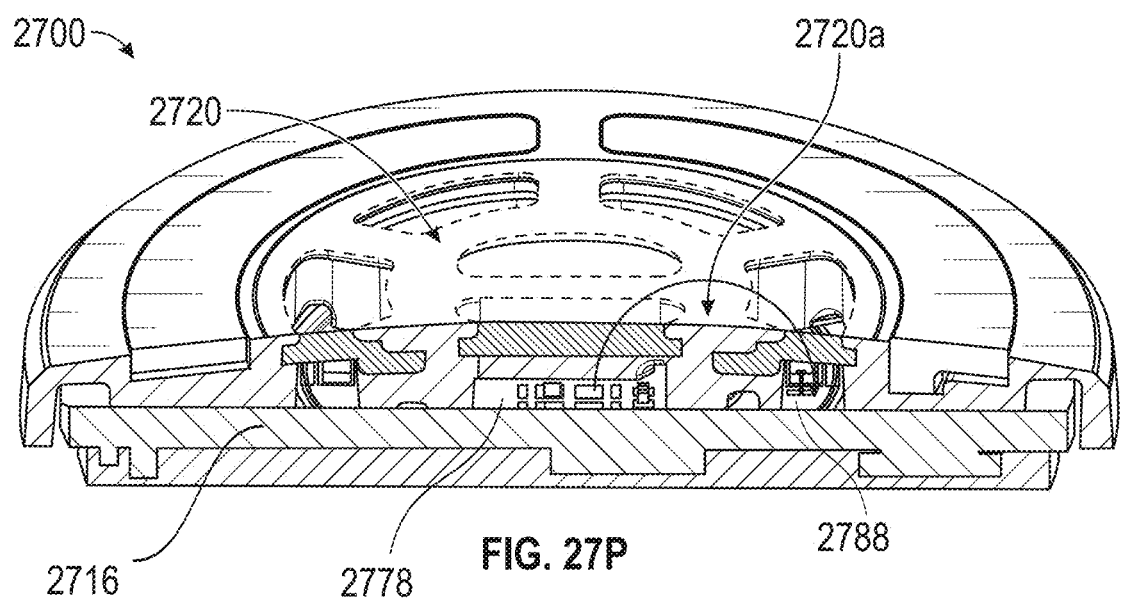

FIG. 27O and FIG. 27P illustrate two example aspects of a sensor or module 2700' with different light barrier construct configurations. FIGS. 27O and 27P also show an example light path from an emitter chamber to a detector chamber. The light barrier construct 2720' (or portions thereof) shown in the example aspect of FIG. 27O may be taller (e.g., extending away from a surface of the substrate 2716) and/or wider than the light barrier construct 2720 (or portions thereof) shown in the example aspect of FIG. 27P. The greater height and/or width of the light barrier construct 2720' in the aspect of FIG. 27O may cause the light emitted from an emitter chamber 2778' to travel a greater distance before reaching a detector chamber and thus penetrate deeper into the tissue of the wearer than in the aspect of FIG. 27P. Thus, adjusting the height and/or width of the light barrier construct may affect the path the light travels from the emitter chamber to the detector chamber which may affect an accuracy of a physiological measurement. The height and/or width of the light barrier construct may be adjusted, according to various aspects, as required or desired.

Figure 27Q:
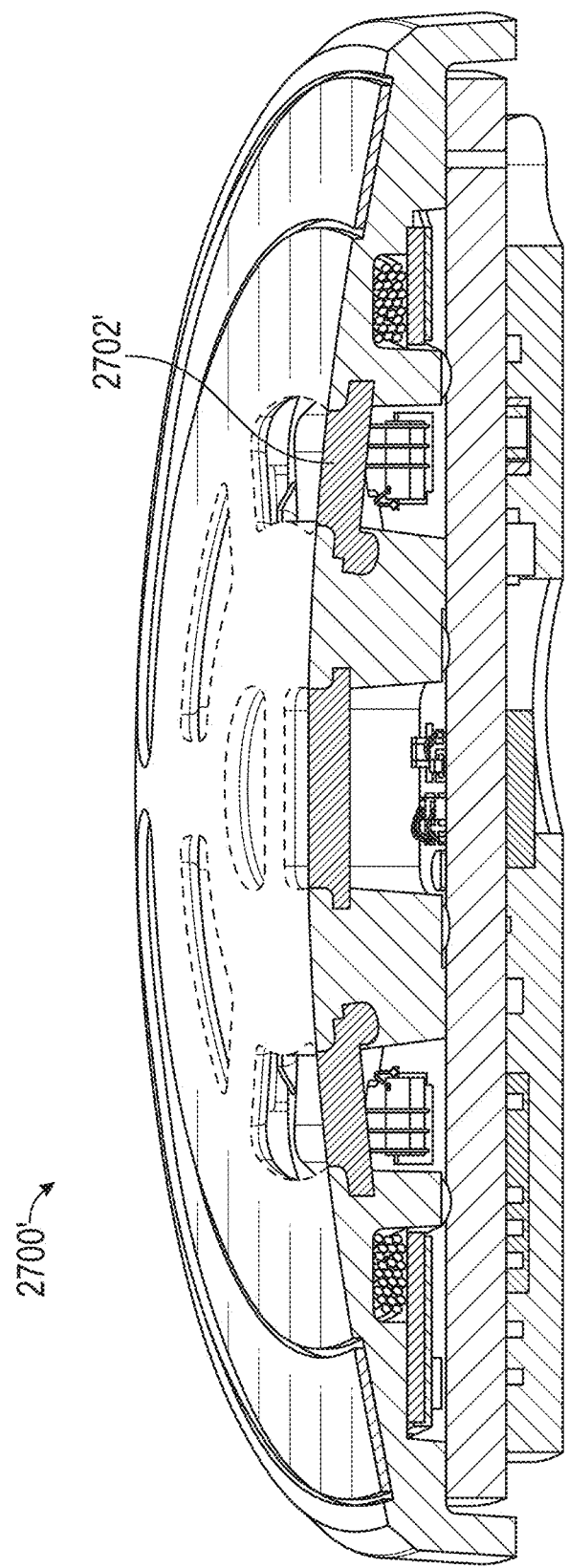
FIG. 27Q illustrates an example physiological parameter measurement sensor or module and example light diffusing material and light transmissive lens(es) or cover(s).

FIG. 27Q illustrates a cutaway side view of an example sensor or module 2700' showing light transmissive lens(es) or cover(s) 2702' and light diffusing material. The light diffusing materials can be included in one or more of the emitter or detector chambers to improve distribution of emitted lighted and/or detected light. The diffusing materials or encapsulant, can include, for example, microspheres or glass microspheres. The encapsulant can eliminate air gaps between the surface of the light transmissive cover 2702' and the emitters and/or the detectors. The encapsulant can be included around the emitters to more evenly spread the emitted light, causing the emitted light to appear to be emitted from an entire emitter chamber rather than from a point source (that is, a single LED emitter) if the encapsulant were absent. The light transmissive lens(es) or cover(s) 2702' may include polycarbonate.

Example Graphical User Interfaces of External Devices

Figure 28:
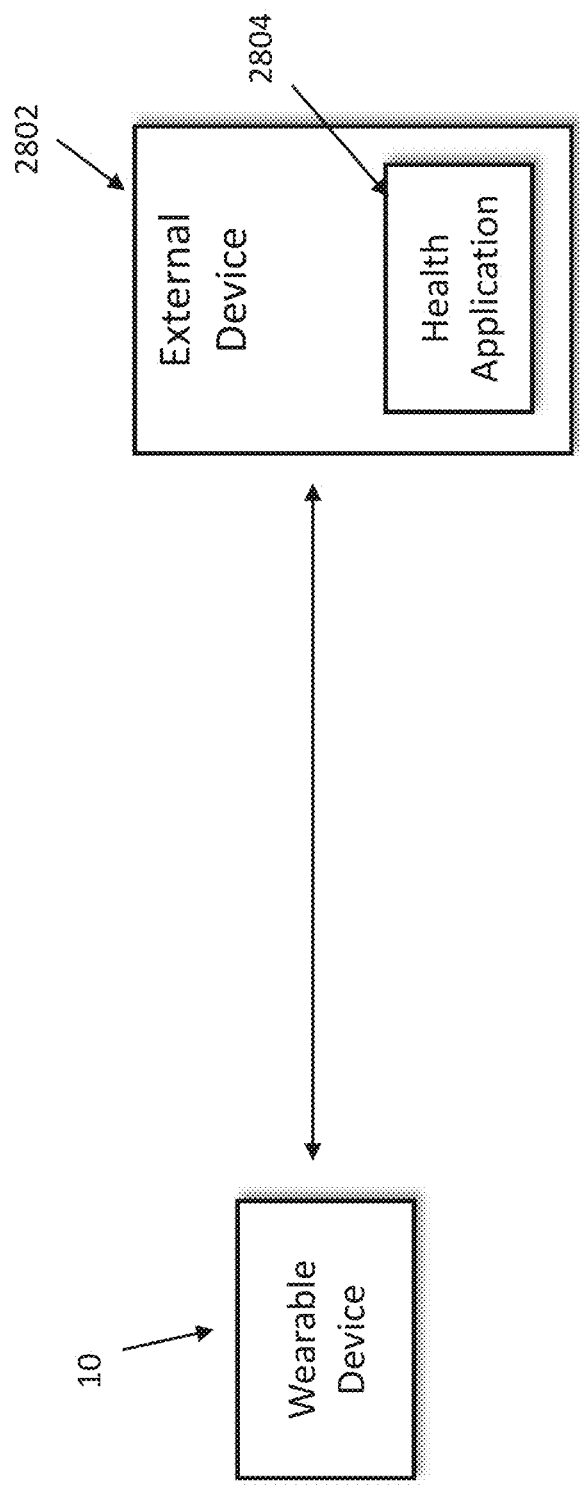
FIG. 28 shows a block diagram illustrating an example aspect of the wearable device in communication with an external device via a network.

As discussed herein and as shown in FIG. 2, the wearable device 10 can be in communication, for example wirelessly, to an external device. FIG. 28 shows a block diagram illustrating an example aspect of the wearable device 10 in communication with an external device 2802. The communication may be wireless, such as, but not limited to, Bluetooth and/or near-field communication (NFC) wireless communication. As shown in FIG. 2, the wearable device 10 may be in communication with any number and/or types of external devices 2802 which may include a patient monitor 202 mobile communication device 204 (for example, a smartphone), a computer 206 (which can be a laptop or a desktop), a tablet 208, a nurses' station system 201, glasses such as smart glasses configured to display images on a surface of the glasses and/or the like. The external device 2802 may include a health application 2804. "External device" and "computing device" may be used interchangeably herein.

A user may operate the external device 2802 as described herein. A wearer may wear the wearable device 10. In some implementations, the user of the external device 2802 and the wearer of the wearable device 10 are different people. In some implementations, the user of the external device 2802 and the wearer of the wearable device 10 are the same person. The terms "user" and "wearer" and "patient" may be used interchangeably herein and may all refer to a person wearing the wearable device 10 and/or a person using the health application 2804 and their uses in any of the given examples are not meant to be limiting of the present disclosure.

The wearable device 10 may communicate information such as physiological data of the wearer/user to the external device 2802. The external device 2802 may display the physiological parameters received from the wearable device 10, as described herein.

The external device 2802 may control operation of the wearable device 10, for example via a wireless connection as described herein. For example, the external device 2802 may cause the wearable device 10 to start or stop taking measurements of a wearer's physiological parameters. In some aspects, the wearable device 10 may continuously measure and communicate a wearer's physiological parameters to the external device 2802. In some aspects, the external device 2802 may continuously display the wearer's physiological parameters received from the wearable device 10. In some aspects, the wearable device 10 may measure and communicate physiological parameters to an external device 2802 for a finite amount of time, such as 1 minute, upon receiving user input at the external device 2802 communicated to the wearable device 10.

FIGS. 29, 30A-30H, 31A-31D, 32, 33A-33C, 34A-34C and 35A-35B illustrate example graphical user interfaces of a health application 2804, according to some aspects of the present disclosure. In various aspects, aspects of the user interfaces may be rearranged from what is shown and described below, and/or particular aspects may or may not be included. The health application 2804 can execute on the external device 2802 to present the graphical user interfaces of FIGS. 29, 30A-30H, 31A-31D, 32, 33A-33C, 34A-34C and 35A-35B. As described herein, the health application 2804 can receive a respective client configuration package that causes the presentation of the graphical user interfaces of FIGS. 29, 30A-30H, 31A-31D, 32, 33A-33C, 34A-34C and 35A-35B. The graphical user interfaces of FIGS. 29, 30A-30H, 31A-31D, 32, 33A-33C, 34A-34C and 35A-35B may have similar user interface elements and/or capabilities.

Figure 29:
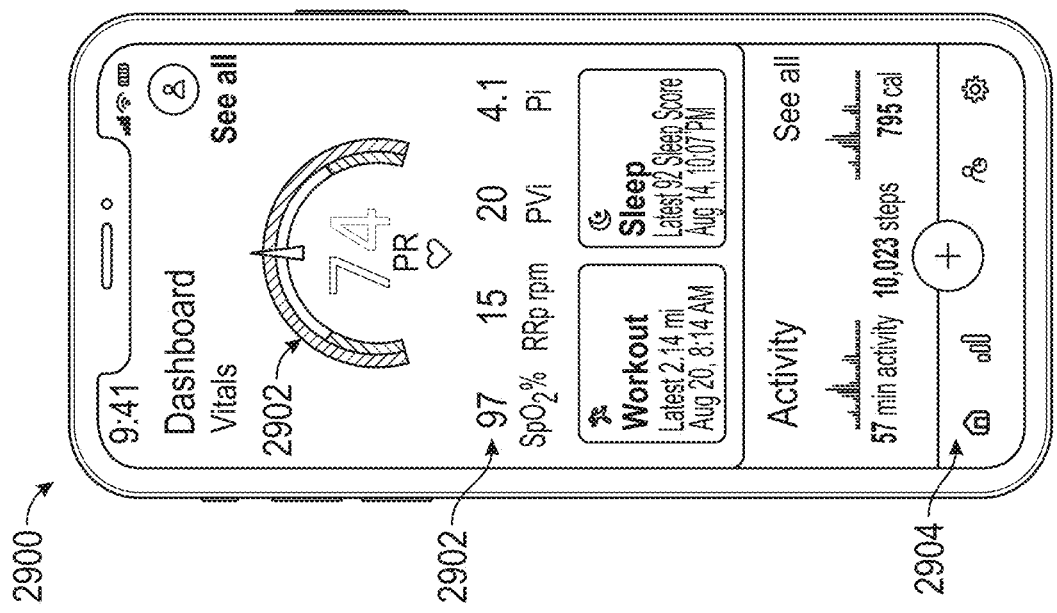
FIG. 29 illustrates an example dashboard user interface of the health application.

FIG. 29 illustrates an example dashboard user interface 2900 of the health application 2804. The dashboard user interface 2900 can display current physiological parameters 2902 of a wearer such as pulse rate, SpO2, RRp, PVi, Pi and the like. In addition to the presentation of current wearer physiological parameter(s) 2902, the dashboard user interface 2900 can present indicator(s) associated with one or more of the physiological parameters 2902 that visually indicate a status of the parameters 2902 and various status ranges for each parameter 2902. The indicator(s) may be color coded or otherwise show a severity or status of a physiological parameter 2902. The dashboard user interface 2900 may additionally display a history of wearer statistics/information such as workout history information, sleep information, activity levels, steps taken, and/or calories burned.

The dashboard user interface 2900 may additionally display one or more navigation selectors 2904 configured for selection by a user. The one or more navigation selectors 2904 may include a home navigation selector, an activity navigation selector, a workout navigation selector, a vitals navigation selector, a sleep navigation selector, a history navigation selector, a share navigation selector and/or a settings navigation selector. Selection of the navigation selectors 2904 may cause the health application 2804 to display any of the graphical user interfaces described herein associated with the selected navigation selector 2904. The navigation selectors 2904 may be displayed in any of the graphical user interfaces described herein.

FIGS. 30A-30D illustrate example spot check monitoring user interfaces of the health application 2804. The wearable device 10 may be configured to perform spot checks. A spot check may be a discrete period of time during which the wearable device 10 performs physiological measurements of a wearer. For example, during a spot check the wearable device 10 may perform physiological measurements for one minute. A user/wearer may initiate a spot check at any desirable time, for example via the health application 2804 of the external device 2802.

FIG. 30A illustrates an example spot check monitoring user interface 3000 of the health application 2804. A user/wearer may initiate a spot check by selecting a start spot check selectable component 3002. Upon selection of the start spot check selectable component 3002 via the health application 2804, the external device 2802 may cause the wearable device 10 to commence measuring physiological parameters as described herein. In some aspects, upon selection of the start spot check selectable component 3002 via the health application 2804, the external device 2802 may check the power level of the wearable device 10 (for example, by checking a charge and/or voltage level of the power source 16) prior to causing the wearable device to start the spot check to determine if the wearable device 10 has sufficient power to perform the spot check. Upon determining that the wearable device 10 has sufficient power, the external application may cause the wearable device 10 to perform the spot check. Upon determining that the wearable device 10 does not have sufficient power, the external application may not cause the wearable device 10 to perform the spot check and/or may cause the spot check to be performed only for certain physiological parameters. In some aspects, upon receiving a command from the external device 2802 to perform a spot check, the wearable device 10 may check its power level (for example, by checking a charge and/or voltage level of the power source 16) prior to commencing physiological measurements for the spot check to determine if it has sufficient power to perform the spot check. Upon determining that it has sufficient power, the wearable device 10 may commence performing the spot check. Upon determining that it does not have sufficient power, the wearable device 10 may not perform the spot check.

In some aspects, the wearable device 10 may perform a spot check for a predetermined amount of time, for example three minutes, two minutes, one minute, 30 seconds, 15 seconds or any amount of time as required or desired. In some aspects, a user may select the predetermined amount of time for which the spot check is to be performed, for example before or after selecting the selectable component 3002. In some aspects, the wearable device 10 may perform a spot check until it receives a command to stop performing the spot check. For example, the external device 2802 may cause the wearable device 10 to stop performing a spot check upon receiving a user command, for example via a selectable component (e.g., similar to selectable component 3002) of the health application 2804.

FIG. 30B illustrates an example spot check monitoring user interface 3010 of the health application 2804. The spot check monitoring user interface 3010 may display the substantially real-time measurements of physiological parameters as measured by the wearable device 10 during the spot check such as pulse rate, SpO2, RRp, PVi, Pi and the like. As described herein, substantially real-time measurements, waveforms, parameters and/or the like may refer to physiological measurements that are displayed (e.g., via user interfaces of the health application) at the same time or substantially the same time (e.g., neglecting any small delays such as those that are imperceptible to humans such as delays arising from electrical conduction or transmission) that they are obtained by the wearable device 10. The spot check monitoring user interface 3010 may display the substantially real-time waveforms 3012 of any of the physiological parameters such as pulse waveform and/or plethysmograph waveform obtained during the spot check.

FIG. 30C illustrates an example spot check monitoring user interface 3020 of the health application 2804. The spot check monitoring user interface 3020 may display substantially real-time measurements of wearer physiological parameters such as those described with reference to FIG. 30B. The spot check monitoring user interface 3020 can further include historical data. In particular, the spot check monitoring user interface 3020 can include a visualization(s) that present historical trends of wearer physiological parameters. As shown, the visualization(s) can include one or more graphs with an x-axis of time and a y-axis of parameter values.

Figure 30F:
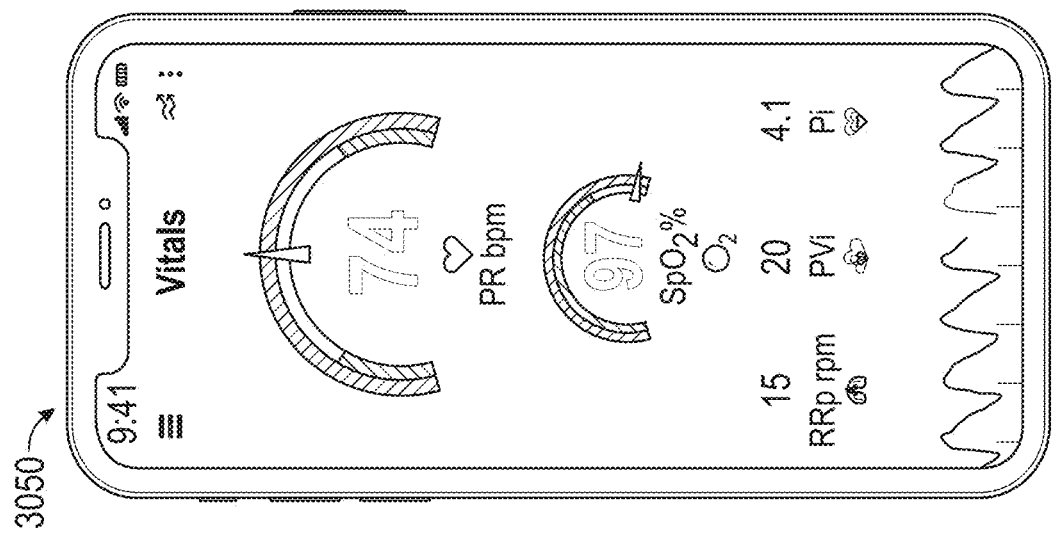
FIGS. 30E-30H illustrate example continuous monitoring user interfaces of the health application.
Figure 30E:
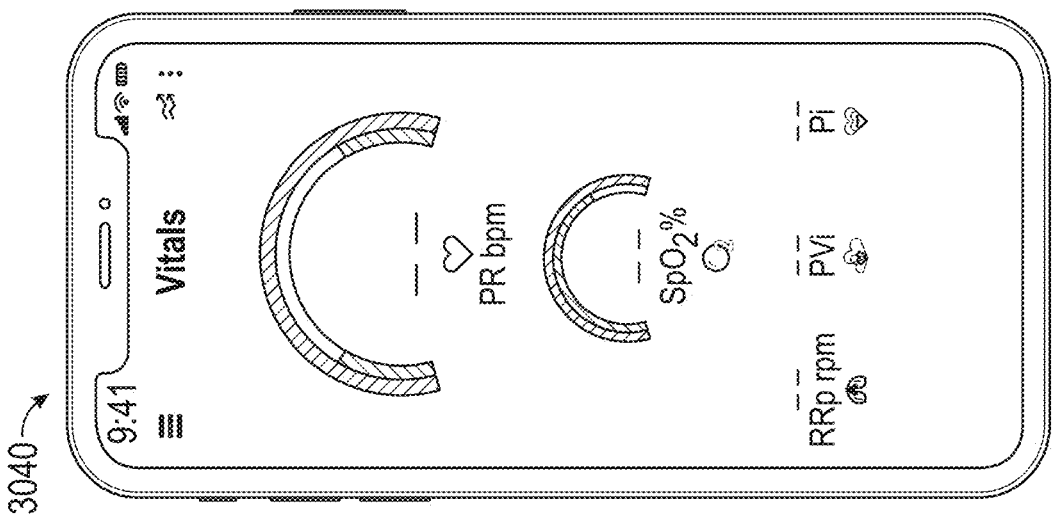
Figure 30D:
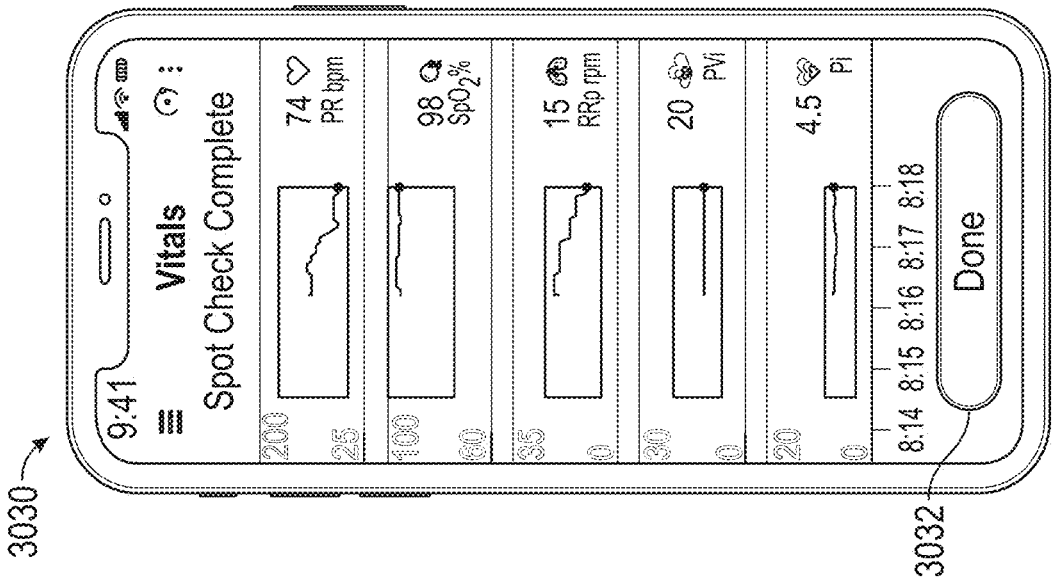

FIG. 30D illustrates an example spot check monitoring user interface 3030 of the health application 2804. The spot check monitoring user interface 3030 may be displayed when the wearable device 10 has completed the spot check. In some aspects, as depicted in FIG. 30D, the user interface 3030 may display physiological parameters obtained during the spot check in a similar format to that shown in user interface 3020 of FIG. 30C. In some aspects, the user interface 3030 may display physiological parameters obtained during the spot check in a similar format to that shown in user interface 3010 of FIG. 30B.

In some aspects, the spot check monitoring user interface 3030 may be displayed for a predetermined length of time, such as one minute, after the spot check has terminated, and after the predetermined length of time the health application 2802 may display another user interface such as any of the user interfaces described herein, such as the dashboard user interface 2900 or the spot check monitoring user interface 3000. In some aspects, a user may navigate to another user interface such as any of the user interfaces described herein, such as the dashboard user interface 2900 or the spot check monitoring user interface 3000, upon selection of the selectable component 3032. In some aspects, the health application 2804 may display the user interface 3030 until a user selects the selectable component 3032.

FIGS. 30E-30H illustrate example continuous monitoring user interfaces of the health application 2804. The wearable device 10 may be configured to perform continuous measurements of physiological parameters of a wearer. For example, the wearable device may continuously measure a wearer's physiological parameters indefinitely, for example as long as the device is powered on or until a user selects to cease the continuous operation mode and/or until a user selects operation of a non-continuous monitoring mode of operation such as the spot check as described herein.

In some aspects, the external device 2802 may check the power level of the wearable device 10 (for example by checking a charge and/or voltage level of the power source 16) prior to causing the wearable device to enter a continuous monitoring mode and/or during continuous monitoring to determine if the wearable device 10 has sufficient power to perform continuous monitoring. Upon determining that the wearable device 10 has sufficient power, the external application may cause the wearable device 10 to initiate continuous monitoring and/or to continue continuous monitoring. Upon determining that the wearable device 10 does not have sufficient power, the external application may not cause the wearable device 10 to initiate continuous monitoring and/or may cause the wearable device 10 to discontinue continuous monitoring, and/or may cause the wearable device 10 to initiate a mode of operation that is different than continuous monitoring such as a modified continuous monitoring mode or a spot check mode. In some aspects, upon receiving a command, for example from the external device 2802 to perform continuous monitoring, the wearable device 10 may check its power level (for example by checking a charge and/or voltage level of the power source 16) prior to commencing and/or during continuous monitoring to determine if it has sufficient power to perform continuous monitoring. Upon determining that it has sufficient power, the wearable device 10 may commence performing continuous monitoring and/or may continue performing continuous monitoring. Upon determining that it does not have sufficient power, the wearable device 10 may not initiate continuous monitoring and/or may discontinue continuous monitoring, and/or may cause the wearable device 10 to initiate a mode of operation that is different than continuous monitoring such as a modified continuous monitoring mode or a spot check mode.

FIG. 30E illustrates an example continuous monitoring user interface 3040 of the health application 2804. User interface 3040 may be displayed when the wearable device 10 is operating in continuous monitoring mode and is simultaneously unable to obtain physiological measurements (or the physiological measurements obtained are determined to fall below an accuracy threshold), for example when the wearable device 10 not being worn (or not being worn properly) by a wearer.

FIG. 30F illustrates an example continuous monitoring user interface 3050 of the health application 2804. The continuous monitoring user interface 3050 may display the substantially real-time measurements of physiological parameters as measured by the wearable device 10 during continuous monitoring in a similar manner as explained with reference to the display of physiological parameters during a spot check in example user interface 3010 of FIG. 30B.

Figure 30H:
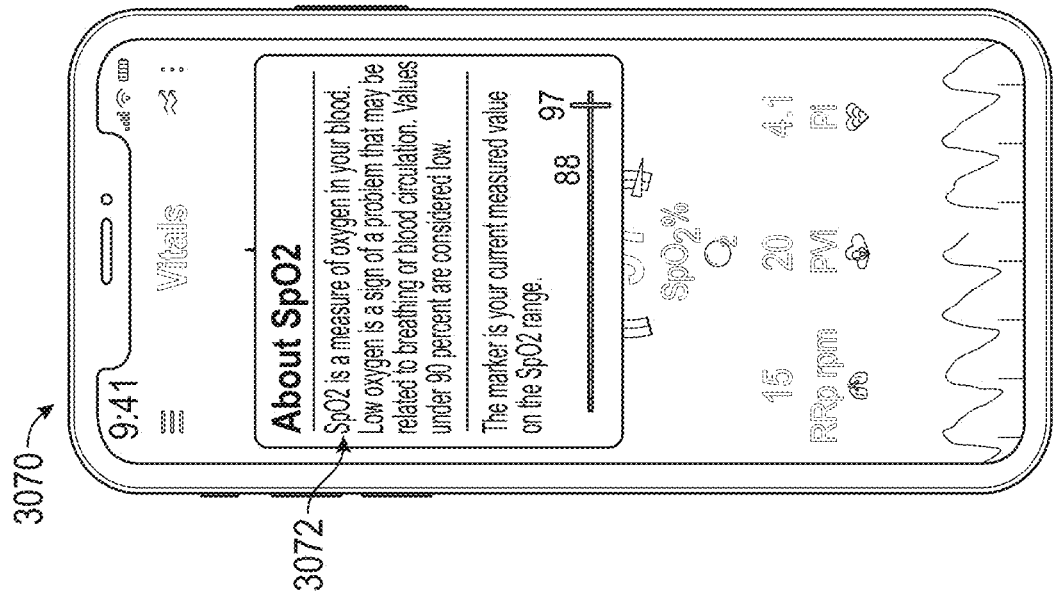
Figure 30G:
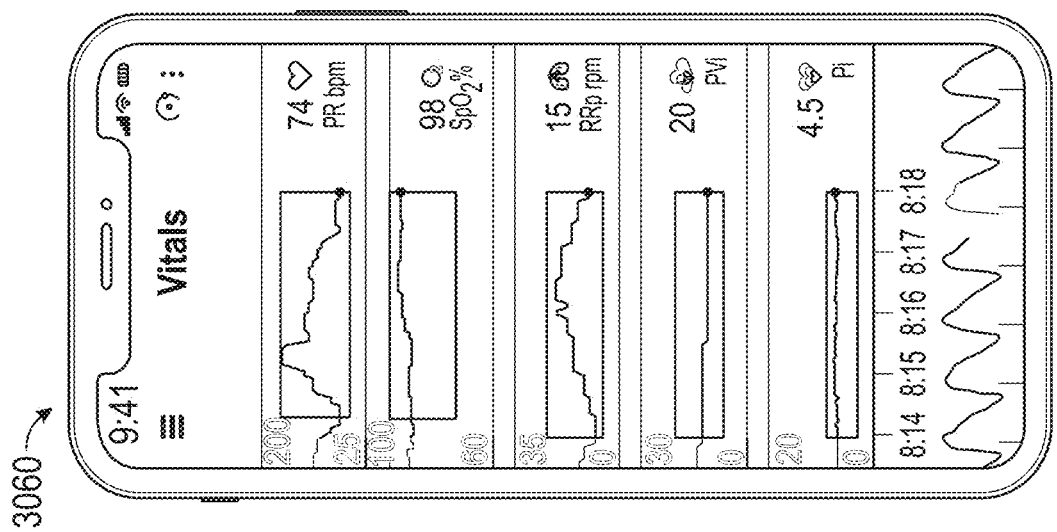

FIG. 30G illustrates an example continuous monitoring user interface 3060 of the health application 2804. The continuous monitoring user interface 3060 may display substantially real-time measurements of wearer physiological parameters such as those described with reference to FIG. 30F or FIG. 30B. The continuous monitoring user interface 3060 can further include historical data. In particular, the continuous monitoring user interface 3060 can include a visualization(s) that present historical trends of wearer physiological parameters. As shown, the visualization(s) can include one or more graphs with an x-axis of time and a y-axis of parameter values.

FIG. 30H illustrates an example continuous monitoring user interface 3070 of the health application 2804. The continuous monitoring user interface 3070 may display information 3702 relating to any of the physiological parameters discussed herein such as those displayed in any of the graphical user interfaces discussed herein. The information 3072 may help a user/wearer understand the physiological parameter. In the example of FIG. 30H, the continuous monitoring user interface 3070 displays information 3072 relating to SpO2 physiological parameter. The continuous monitoring user interface 3070 may display information relating to a physiological parameter in response to a user selection of the displayed corresponding physiological parameter. In some aspects, as depicted in FIG. 30H, a user may select a physiological parameter from a displayed format similar to that shown in user interface 3050 of FIG. 30F to display information 3072. In some aspects, a user may select a physiological parameter from a displayed format similar to that shown in user interface 3060 of FIG. 30G to display information 3072.

FIGS. 31A-31D illustrate example measurement settings user interfaces of the health application 2804. As discussed with reference to the example measurement settings interfaces, a user may adjust the settings of the health application 2804 with regards to at least the physiological measurements and/or may adjust the mode of operation of the wearable device 10.

Figure 31C:
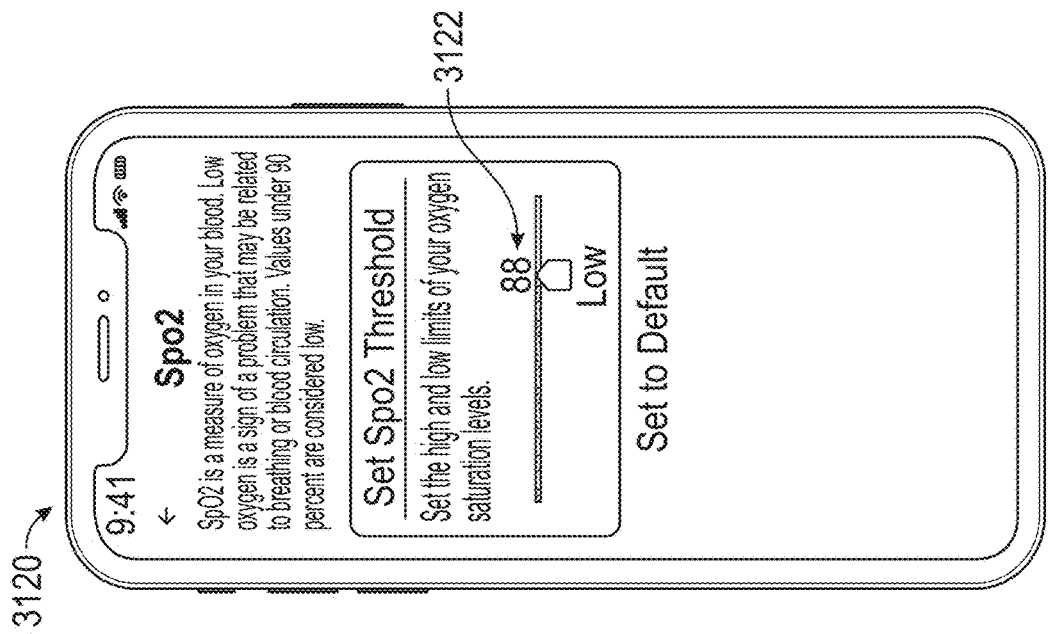
Figure 31B:
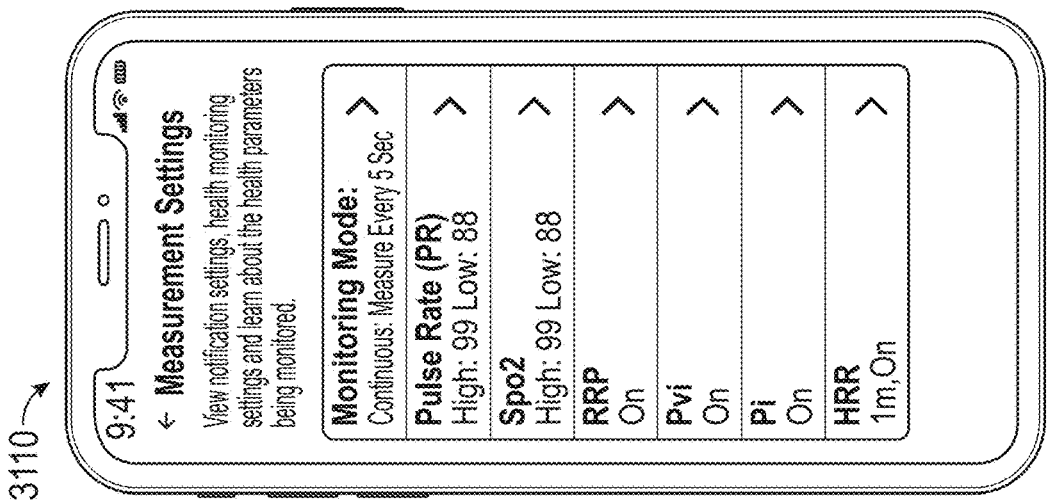
Figure 31A:
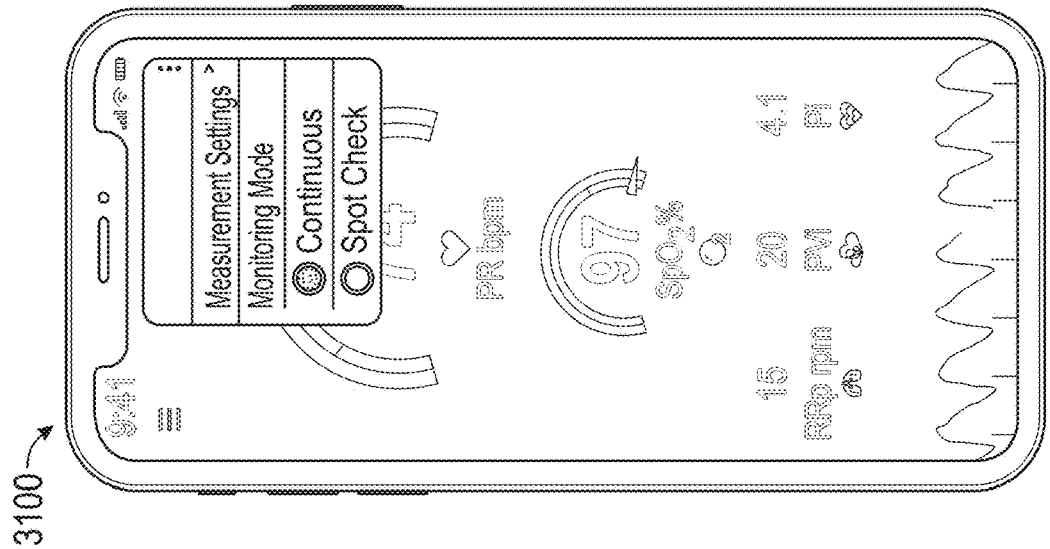

FIG. 31A illustrates an example measurement settings user interface 3100 of the health application 2804. The measurement settings user interface 3100 may allow a user to select a mode of operation of the wearable device 10. For example, a user may select, via user interface 3100, whether the wearable device operates in continuous monitoring mode or spot check mode. A user may also navigate, via selection in the user interface 3100, to additional measurement settings user interfaces such as user interface 3110.

FIG. 31B illustrates an example measurement settings user interface 3110 of the health application 2804. User interface 3110 may display various physiological parameters, as shown. A user may select any of the displayed physiological parameters to edit and/or adjust the settings associated with the selected physiological parameter. User selection of the physiological parameters may navigate a user to additional measurement settings user interfaces such as user interfaces 3120 or 3130.

FIG. 31C illustrates an example measurement settings user interface 3120 of the health application 2804. User interface 3120 may allow a user to set one or more threshold levels relating to a physiological parameter such as any of the physiological parameters measured by the wearable device 10 and/or displayed by the graphical user interfaces as discussed herein. In some aspects, when the physiological parameter value as measured by the wearable device 10 reaches the threshold level, the external device 2802 may generate a notification. For example, if a threshold level is breached, then the external device 2802 can cause an emergency notification to be generated. The emergency notification may be displayed on the graphical user interface of the external device 2802 and/or communicated to another device such as the wearable device 10, another external device 2802 and/or a third-party device. In some aspects, the generation of physiological parameter notification(s) can be activated or deactivated by the user.

The example measurement settings user interface 3120 displays a slidable component 3122 relating to SpO2 threshold. A user may slide the slidable component 3122 to adjust and/or select the threshold SpO2 limit. As shown, a user has set the SpO2 threshold limit to 88%. As discussed herein, in some aspects, when the wearable device 10 measures an SpO2 level of the wearer to be 88% or less than 88%, the health application 2804 of the external device 2802 may generate a notification and/or alert.

FIG. 31D illustrates an example measurement settings user interface 3130 of the health application 2804. The example measurement settings user interface 3130 displays a slidable component 3134 relating to RRp threshold. A user may slide the slidable component 3134 to adjust and/or select an upper and lower RRp threshold limit. As shown, a user has set the RRp lower threshold limit to 6 and has set the RRp upper threshold limit to 30. As discussed herein, in some aspects, when the wearable device 10 measures an RRp level of the wearer to be less than 6 or greater than 30, the health application 2804 of the external device 2802 may generate a notification and/or alert.

The example measurement settings user interface 3130 displays a toggle component 3132 relating to RRp display. A user may select the toggle component 3132 to enable or disable the display of RRp physiological parameter measurements in any of the user interfaces discussed herein, for example user interfaces 29 or 30A-30H. A toggle component or other means similar to the toggle component 3132 shown in user interface 3130 may be displayed in other user interfaces relating to other physiological parameters. For example, a similar toggle component may be displayed in user interface 3120 to allow a user to enable or disable the display of SpO2 physiological parameter measurement in the user interfaces discussed herein.

FIG. 32 illustrates an example activity user interface 3200 of the health application 2804. The activity user interface 3200 may display a history of activity level of the wearer for any number of activity categories 3202 such as the number of steps taken, distance travelled, and/or calories burned. The activity user interface 3200 may display the activity levels of the wearer throughout a time period such as a 12 hour time period, a 24 hour time period, a week time period or any other time period. For example, the activity user interface 3200 can include a visualization(s) that presents historical trends of wearer activity levels 3202. As shown, the visualization(s) can include one or more graphs with an x-axis of time and a y-axis of activity level. The activity user interface 3200 may display goals of the wearer/user for any of the activity categories 3202 and may display a visualization 3204 corresponding to the goal and/or a wearer's status in achieving the goal.

Figure 33C:
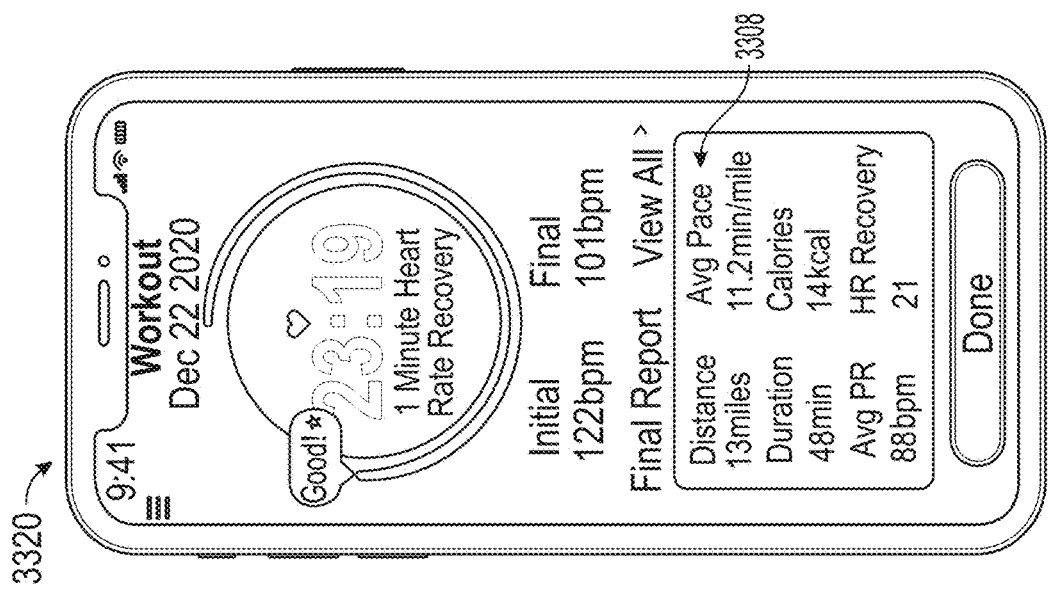
FIGS. 33A-33C illustrate example workout user interfaces of the health application.
Figure 33B:
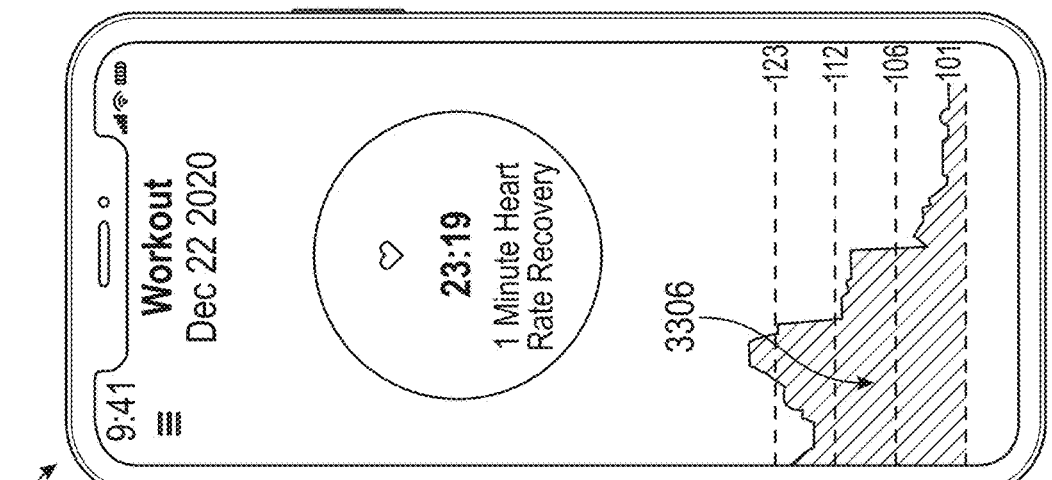
Figure 33A:
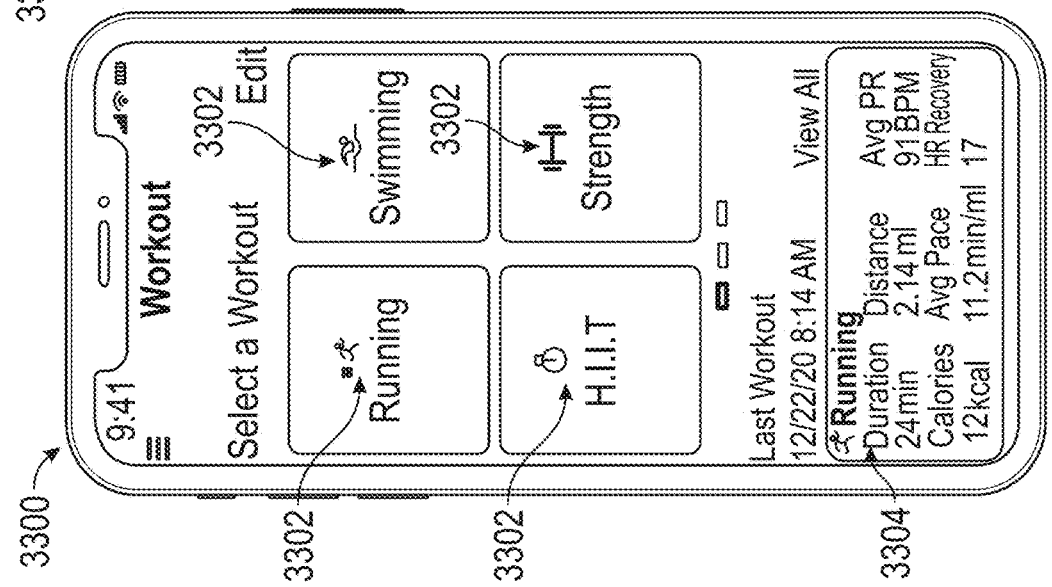

FIG. 33A illustrates an example workout user interface 3300 of the health application 2804. The user may select a selectable component 3302 of the workout user interface 3300 to cause the wearable device to begin monitoring wearer physiological parameters and/or to cause the health application 2804 to begin tracking/logging wearer physiological parameters during the workout. The selectable component 3302 may correspond to the type of workout such as running, swimming, high-intensity interval training (H.I.I.T), strength training and the like. The workout user interface 3300 may display information 3304 relating to a previous workout.

FIG. 33B illustrates an example workout user interface 3310 of the health application 2804. The workout user interface 3310 may be displayed by the health application 2804 during and/or after a workout of the wearer. The workout user interface 3310 may display physiological parameters of the wearer, such as received by the wearable device 10, and other information relating to the workout such as time duration of the workout. The workout user interface 3310 may display historical and/or substantially real-time physiological parameters of the wearer. The workout user interface 3310 may display a visualization(s) 3306 of any of the wearer physiological parameters. For example, the workout user interface 3310 can include a visualization(s) that present historical trends of wearer physiological parameters during the workout. As shown, the visualization(s) can include one or more graphs with an x-axis of time and a y-axis of parameter values.

FIG. 33C illustrates an example workout user interface 3320 of the health application 2804. The workout user interface 3320 may be displayed by the health application 2804 after a workout of the wearer. The workout user interface 3320 may display information 3308 relating to the workout of the wearer.

FIG. 34A illustrates an example sleep user interface 3400 of the health application 2804. The sleep user interface 3400 may display a sleep quality index which may be calculated based, at least in part, on one or more of the physiological parameters of the wearer received from the wearable device 10. The sleep user interface 3400 may display a visualization(s) 3402 of the sleep quality index. For example, the sleep user interface 3400 can include a visualization(s) that present historical trends of the sleep quality index during a time the wearer is asleep. As shown, the visualization(s) can include one or more graphs with an x-axis of time and a y-axis of sleep quality index.

FIG. 34B illustrates an example sleep user interface 3410 of the health application 2804. The sleep user interface 3410 may display a history of events occurring during a time the wearer is asleep. The events may be major or minor events as determined by, for example, a magnitude of the event. For example, the history of events may display all the times during which the wearer was asleep wherein a physiological parameter, such as SpO2, exceeded a threshold. The threshold(s) may be set by the user/wearer as discussed with reference to FIGS. 31C-31D.

FIG. 34C illustrates an example sleep user interface 3420 of the health application 2804. The sleep user interface 3420 may display physiological parameters of the wearer, such as current physiological parameters and/or average physiological parameters of the wearer during a time the wearer was asleep. The sleep user interface 3420 may display a visualization(s) 3404 of the physiological parameters. For example, the sleep user interface 3420 can include a visualization(s) that present historical trends of the physiological parameters during a time the wearer is asleep. As shown, the visualization(s) can include one or more graphs with an x-axis of time and a y-axis of parameter value. The visualization may further include an indication of a threshold(s) and may show all times wherein the physiological parameter exceeded the threshold(s). The threshold(s) may correspond to the threshold(s) discussed with reference to FIG. 34B and may be set by the wearer as discussed with reference to FIGS. 31C-31D.

Figure 35B:
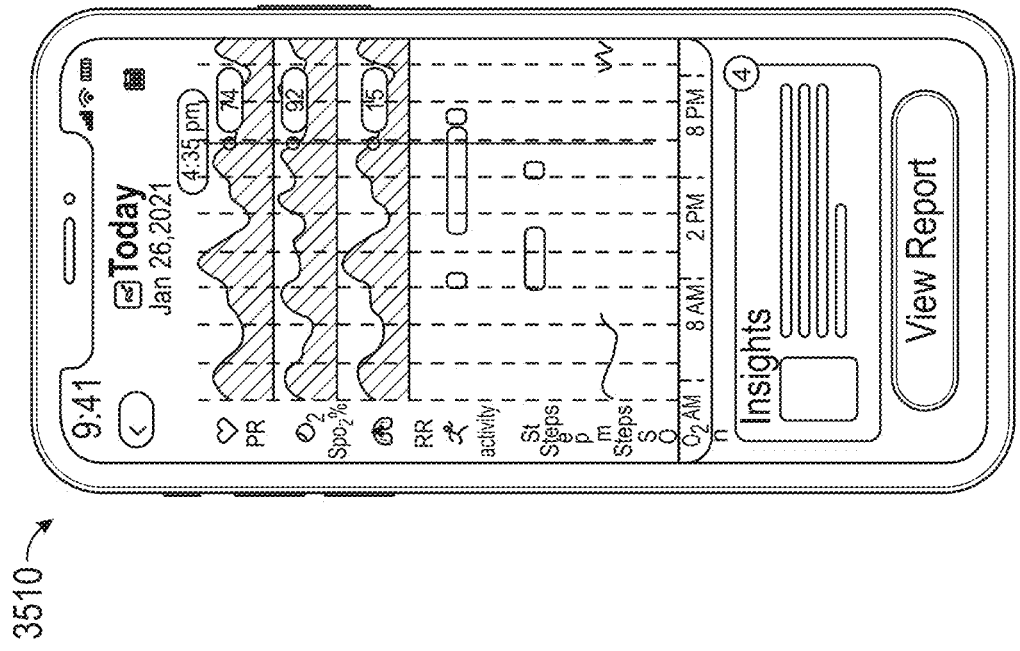
FIGS. 35A-35B illustrate example history user interfaces of the health application.
Figure 35A:
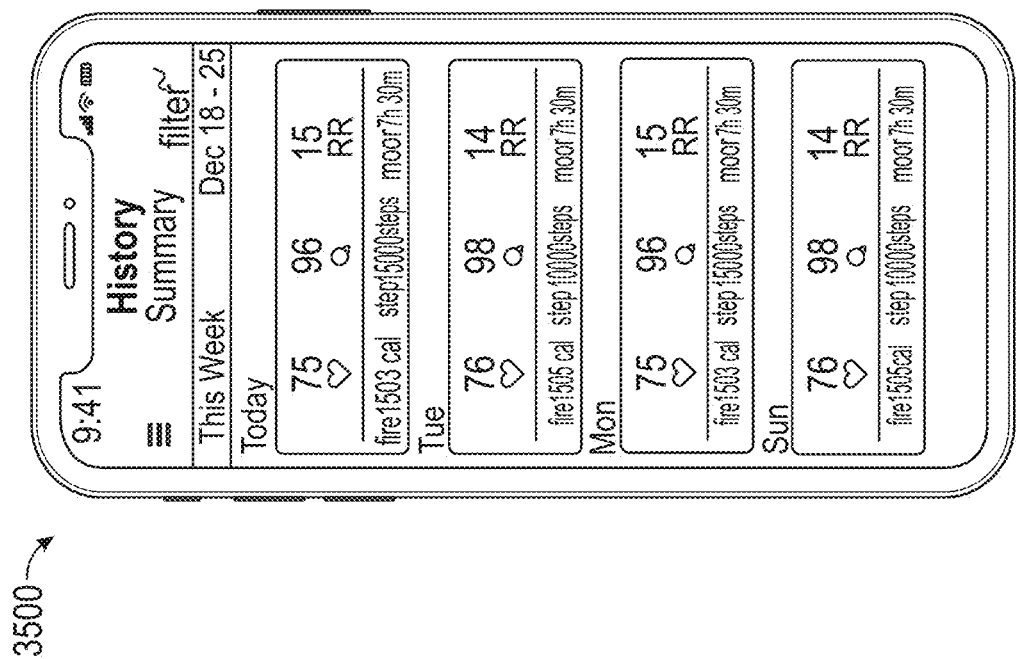

FIG. 35A illustrates an example history user interface 3500 of the health application 2804. The history user interface 3500 may display historical data, for example historical data of the wearer physiological parameters received from the wearable device 10. The history user interface 3500 may display historical data over any range of time, for example historical data for the day and/or historical data for the week. The history user interface 3500 may display historical data grouped according to any time frame, for example historical data grouped by day and/or historical data grouped by hour. As shown in FIG. 35A, the history user interface 3500 may display historical data for the current day and any number of preceding days.

FIG. 35B illustrates an example history user interface 3510 of the health application 2804. The history user interface 3510 may display historical data, such as historical physiological parameter values and/or activity levels of the wearer. The history user interface 3510 can include a visualization(s) that present historical trends of wearer physiological parameters and/or activities, such as calories burned or steps taken. As shown, the visualization(s) can include one or more graphs with an x-axis of time and a y-axis of values, such as physiological parameter values or activity levels. The history user interface 3510 may display the visualization(s) such that the x-axis of time of one graph corresponds with the x-axis of time of any of the other graphs. The history user interface 3510 may further display historical data value(s) of the visualization graph(s) corresponding to the time of the of the visualization graph(s) upon selection by a user such as by adjusting a slider along the x-axis of the graphs as shown in FIG. 35B.

Appendix A that is attached to this specification is hereby incorporated by reference in its entirety and is made a part of this specification. Appendix A shows additional example graphical user interfaces of the health application 2804. A1 illustrates example user interfaces of the wearable device 10 for connecting the wearable device 10 with an external device 2802. A2 illustrates an example user interface for initiating the health application 2804 on an external device 2802. A3-A5 illustrate example user interfaces for creating an account on the health application 2804. A6 illustrates an example user interface of a successful account creation for health application 2804. A7 illustrates example user interfaces of successfully pairing the wearable device 10 with an external device 2802. A8 illustrates example user interfaces for setting goals in the health application 2804. A9 illustrates example user interfaces of unsuccessfully logging in to the health application 2804.

A10 illustrates example user interfaces of a homepage of the health application 2804. A11-A13 illustrate example user interfaces of a dashboard of the health application 2804. A14 illustrates example user interfaces for spot check monitoring of wearer physiological parameters with the wearable device 10. As shown in A14, a user may select a component via the user interface to start a physiological measurement with the wearable device 10. The wearable device 10 may measure physiological parameters and display the measurements to the user interface for a predetermined amount of time (e.g., one minute) and/or until the user selects a component via the user interface to stop the physiological measurement. A15 illustrates an example user interface for displaying physiological parameters measured continuously with the wearable device 10. A16 illustrates example user interfaces for adjusting physiological measurement settings. A17 illustrates an example user interface for displaying physiological parameter measurements.

A18-A19 illustrates example user interfaces for displaying activity of a user. A20-A21 illustrate example user interfaces for displaying workout information of a user. A22-A24 illustrate example user interfaces for displaying sleep information of a user. A25-A26 illustrates example user interfaces for setting sleep settings for a user. A27-A29 illustrate example user interfaces for displaying a history of a user's physiological parameter measurements and activity.

A30-A36 illustrate example user interfaces for setting the settings of the wearable device 10.

A37 illustrates example user interfaces of a dashboard of the health application 2804. A38 illustrates example user interfaces of a history of physiological parameters of a user. A39 illustrates an example user interface for sharing information, such as physiological parameters, from the external device 2802 to another device. A40-A41 illustrate example user interfaces for navigating between interfaces of the health application 2804 using an interactive navigation bar displayed at the bottom of the user interface. A42 illustrates example user interfaces of a dashboard and account homepage of the health application 2804. A43 illustrates example user interfaces for navigating between interfaces of the health application 2804 using an interactive navigation bar displayed at the bottom of the user interface. A44 illustrates example user interfaces of a dashboard of the health application 2804.

Example Graphical User Interfaces of the Wearable Device

As discussed herein, for example, with reference to FIG. 11A, the wearable device 10 can include a display 12, which can include the display screen and touch input from the wearer. For example, the display 12 may comprise a capacitive touchscreen configured to receive touch input from the wearer to control functionality of the wearable device 10. The wearable device 10 can also include user interfaces on the device 10 to receive input from the wearer. As shown in FIG. 1D, example user interfaces can include buttons 13.

FIG. 36A shows an example wearable device 10 including a display 12 and buttons 13. FIGS. 36B-36E show example screens of the display 12 of the wearable device 10. The display 12 may be configured to display many different screens. For example, in some aspects, the display 12 may display a screen with various physiological parameter information (such as values and trends) and in other aspects, the display 12 may display a screen with no physiological parameter information. In some aspects, the display 12 may display a screen with non-physiological related information such as date, time and other notifications.

The display 12 may display various screens in a cyclical manner. For example, the display 12 may display a screen with a first physiological parameter information (such as value and trend) and then may display a screen with a second physiological parameter information and then may display a screen with a third physiological parameter information and so forth. In some aspects, the order of the screens the display 12 displays is constant. The display 12 may cycle through displaying various screens automatically and/or manually. For example, the display 12 may change the screen that is displayed automatically, without user input, every 1 minute, every 30 seconds, every 10 seconds, every 5 seconds, every 3 seconds, every 2 seconds, every 1 second or any other time frame that is required or desired. In some aspects, a wearer/user may select the time frame (e.g., frequency) in which the display 12 will change the screen. In some aspects, a wearer/user may manually change the screen that is displayed by the display 12. For example, a wearer may touch the display 12 to provide touch input to the wearable device 10 and/or may press a button 13 to provide input to the wearable device 10. Upon receiving said input from the wearer, the display 12 may change the screen that is displayed. The display 12 may not change the screen again until another user input, as described, is received.

In some aspects, the display 12 may cycle through displaying various screens automatically and manually, as simultaneous modes of operation. For example, the display 12 may cycle through the various screens automatically without user input (e.g., every 3 seconds, for example) unless or until a wearer/user provides input (via, the display 12 and/or buttons 13) upon which the display 12 will change the screen.

In some aspects, the display 12 may cycle through displaying the various screens automatically or manually, but not both modes of operation at the same time. For example, the display 12 may cycle through the various screens automatically (e.g., every 3 seconds, for example) regardless of user input that is received. As another example, the display 12 may cycle through the various screens manually, only upon receiving user input, regardless of time that has elapsed. In some aspects, the display 12 may toggle between cycling through the displaying the various screens automatically and manually, for example upon adjustment of user settings of the wearable device 10.

FIGS. 36A-36E show example screens of the display 12 of the wearable device 10. FIG. 36A shows a screen without physiological parameter information (such as values and trends). FIG. 36B shows a screen with SpO2 physiological parameter value of the wearer. FIG. 36C shows a screen with RR physiological parameter value of the wearer. FIG. 36D shows a screen with the number of steps taken by the wearer. FIG. 36E shows a screen with PR physiological parameter value of the wearer. The display 12 may cycle through displaying the various screens of FIGS. 36A-36E automatically and/or manually, as described above.

FIGS. 37A-37E show example screens of the display 12 of the wearable device 10. The display 12 may cycle through displaying the various screens of FIGS. 37A-37E automatically and/or manually, as described above.

Figures 38A, 38B:
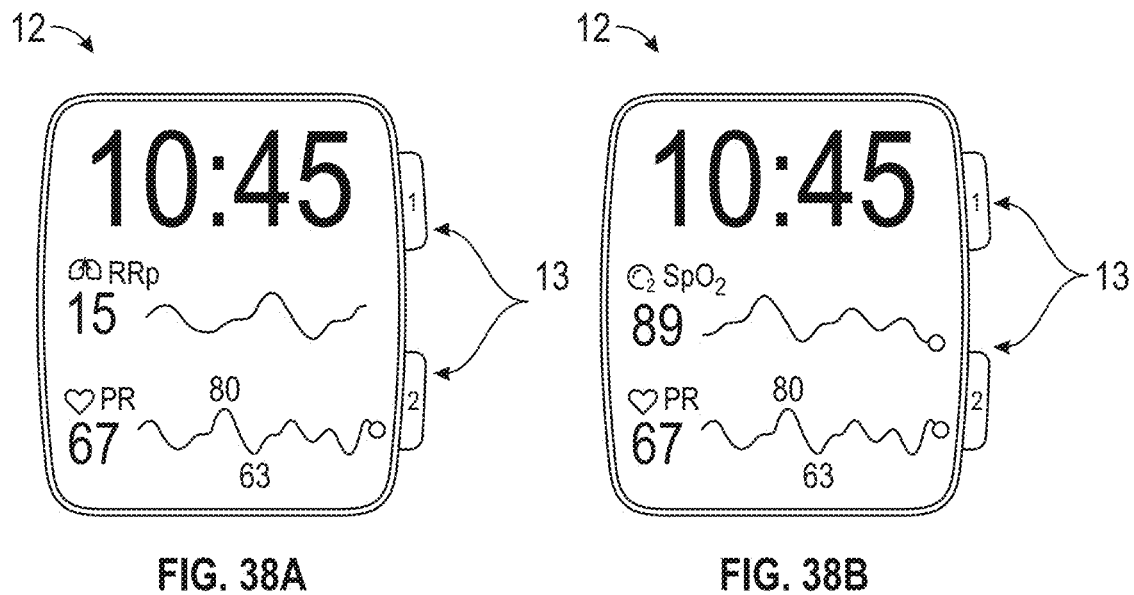

FIG. 38A shows an example screen of the display 12 of the wearable device 10. The display 12 displays a screen with time, and RRp physiological parameter value and trend and PR physiological parameter value and trend. In some aspects, the display 12 may cycle through displaying physiological information (such as values and trends) of other parameters (such as SpO2, steps taken etc.) automatically and/or manually as described above with reference to FIGS. 37A-37E, for example. In some aspects, a user/wearer may select physiological information to be displayed as a default by display 12, for example by adjusting the settings of the wearable device 10.

FIG. 38B shows an example screen of the display 12 of the wearable device 10. The display 12 displays a screen with time, and SpO2 physiological parameter value and trend and PR physiological parameter value and trend. In some aspects, the display 12 may automatically display physiological information (such as value and trend) relating to a parameter if that parameter has exceeded a threshold. For example, if a physiological parameter value exceeds a high or low threshold, the display 12 may automatically display that physiological parameter value and trend. This may be in place of physiological information of another parameter already displayed. For example, as shown in FIG. 38B, the wearer may have an SpO2 parameter value of 89. This value may be below a low limit threshold for SpO2 (for example, as set by a user/wearer as described with reference to FIG. 31C, for example). Upon determining that that the SpO2 has fallen below a low limit threshold, the wearable device 10 may cause the display 12 to display the physiological information (such as value and trend) for SpO2. This may replace physiological information of another parameter already displayed that has not exceeded a threshold. In this example, the display 12 replaces RRp (which has not exceeded any thresholds) in the screen (shown in FIG. 38A) with SpO2 in the screen (shown in FIG. 38B). Physiological parameters that have exceeded a threshold that are displayed in the screen by display 12 may differ in color or some other respect to physiological parameters that have not exceeded a threshold.

Figure 39:
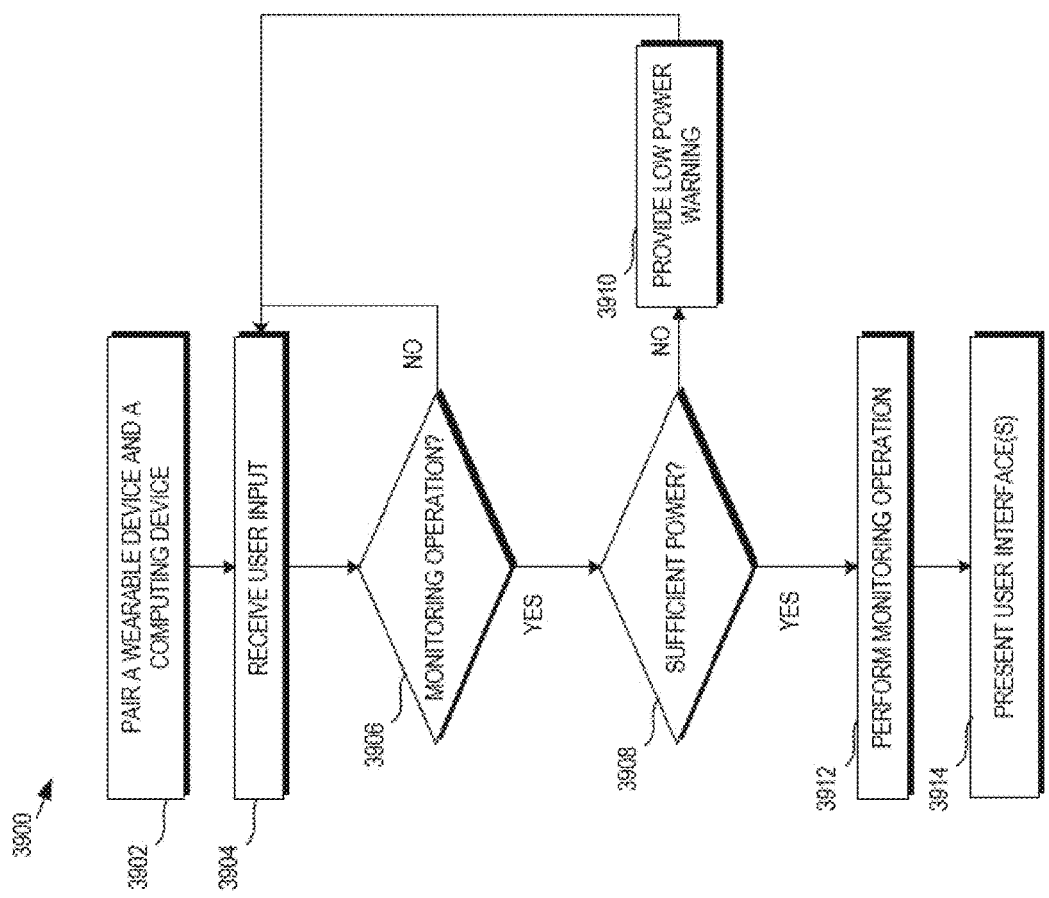

FIG. 39 is a flowchart illustrating an example process 3900 for performing monitoring operation(s) of one or more physiological parameters of a user/wearer. The process 3900 may be performed by a system that includes a wearable device 10 and a computing device 2802. The computing device 2802 may be, for example, any of the devices discussed with reference to FIG. 2, such as a patient monitor 202, a mobile communication device 204, a computer 206, a tablet 208, a nurses' station system 210 or any other device as required or desired. As discussed herein, the wearable device 10 and the computing device 2802 may be in communication with each other, for example, via Bluetooth technology or near-field communication (NFC) technology.

At block 3902, the wearable device 10 and the computing device 2802 may establish communication with each other. For example, the wearable device 10 may be paired with the computing device using Bluetooth or NFC.

At block 3904, the computing device 2802 may receive a user input. For example, a user can provide the user input via an interactive user interface of the computing device 2802. Example user input can include a user selection to initiate a monitoring operation, such as sport check or continuous monitoring. Additionally or alternatively, the wearable device 10 can receive user input, such as a user selection to initiate a monitoring operation, such as sport check or continuous monitoring.

At block 3906, the computing device 2802 may check to determine whether it has received user input corresponding to an instruction to perform a monitoring operation. In response to receiving the user input for a monitoring operation, the computing device 2802 may generate a signal to communicate to the wearable device 10, such as by sending a wireless communication to the wearable device 10. The signal may instruct the wearable device 10 to perform one or more operations according to the user input. For example, via a user interface of the computing device 2802, a user may select a spot check physiological monitoring operation. In response to the user input, the computing device 2802 may generate a signal to wirelessly communicate to the wearable device 10 to instruct the wearable device 10 to perform a spot check monitoring operation.

If the user input is not associated with a monitoring operation, the process 3900 can return to block 3904 to wait for additional input. In some aspects, the computing device 2802 can perform some other operation associated with the non-monitoring operation user input, as described herein.

The wearable device 10 may check to determine whether it has received a signal instructing it to perform a monitoring operation. If no signal has been received to perform a monitoring operation, the wearable device 10 may continue to determine whether it has received a signal at block 3906. If the wearable device 10 has received a signal, for example from the computing device 2802, instructing it to perform a monitoring operation, the process 3900 may continue to step 3908.

At block 3908, it may be determined whether the wearable device 10 has sufficient power to perform the requested monitoring operation. One or more techniques can be used to determine whether a battery has sufficient charge to initiate the particular monitoring operation. For example, the wearable device 10 may determine a current charge status of its battery. In some aspects, the wearable device 10 may include an estimate power consumption rate for respective operations and/or sensors. Additionally or alternatively, the wearable device 10 or another computing device 2802 may log power consumption for particular operations or sensors of wearable device(s) to determine an estimated power consumption rate. A determination of sufficient power for an operation can be based on the particular operation. For example, a spot check operation can use less power than a continuous monitoring operation. Moreover, an estimation of power consumption can be based on the particular operation. The estimation of power consumption can include an estimated duration of the operation. For example, a spot check operation can last a predetermined period of time, such as 1 second, 5 seconds, or 15 seconds, and the estimated power consumption can be based on that duration and the particular sensor(s) involved in the operation. Similarly, a continuous monitoring operation can have an estimated duration that is used for power consumption purposes, such as an estimated runtime for thirty minutes, one hour, four hours, or eight hours. The wearable device 10 or another computing device 2802 can estimate the power consumption for the operation by multiplying the estimated power consumption rate with the predetermined or estimated duration for the particular operation. The estimated power consumption can then be compared to the current battery charge level. For example, if the estimated power operation is greater than the current battery charge or is estimated to leave the battery at less than five percent or ten percent capacity, the wearable device 10 or another computing device 2802 can determine that there is insufficient power for the requested monitoring operation. If the wearable device 10 has sufficient power to perform the requested monitoring operation, the process proceeds to block 3912 to perform the monitoring operation.

If the wearable device 10 does not have sufficient power, the process 3900 proceeds to block 3910 to provide a lower power warning.

At block 3910, a low power warning can be provided. For example, the wearable device 10 may transmit a signal (such as a message) to the computing device 2802 that the wearable device 10 has insufficient power for the monitoring operation. The signal may cause the computing device 2802 to display a lower power warning message to a user.

In some aspects, if the wearable device 10 does not have sufficient power to perform the requested monitoring operation, the wearable device may continue to step 3912 to perform a monitoring operation that is different than the requested monitoring operation. For example, if the wearable device 10 does not have sufficient power to perform the requested operation, the wearable device 10 may determine a modified monitoring operation that may be performed, such as a modified continuous monitoring operation and/or a modified spot check monitoring operation. The determination may be based at least in part on the power of the monitoring device (e.g., remaining battery life). For example, a user may request a continuous monitoring operation and upon determining that there is insufficient power to perform the continuous monitoring operation (e.g., at step 3908) the wearable device 10 may instead perform a spot check operation (which may require less power than continuous monitoring) for an amount of time that is commensurate with the amount of power (e.g., remaining battery life) of the wearable device 10. As another example, a user may request a spot check monitoring operation to be performed for an amount of time and upon determining that there is insufficient power to perform the spot check monitoring operation (e.g., at step 3908) for the duration of the length of time the wearable device 10 may instead perform a spot check operation for an abbreviated length of time (which may require less power than the request spot check monitoring) which may be commensurate with the amount of power (e.g., remaining battery life) of the wearable device 10.

At block 3912, a monitoring operation may be performed. For example, the wearable device 10 may perform the monitoring operation. As described herein, example monitoring operations can include one or more of a spot-check monitoring operation, a continuous monitoring operation, and/or any other monitoring operation as discussed herein. The wearable device 10 may perform the monitoring operation on the wearer/user for one or more of the physiological parameters, such as, but not limited to, SpO2, RR, PR, RRp, etc.

The wearable device 10 may transmit physiological parameter measurement data to the computing device 2802. In some aspects, the wearable device 10 may transmit measurement data during the monitoring operation (such as while the wearable device 10 measures the physiological parameters and/or during a continuous monitoring operation,).

At block 3914, one or more user interfaces may be presented. For example, the computing device 2802 may present the physiological parameter measurement data received from the wearable device 10 in a user interface. Similarly, the wearable device 10 can present the physiological parameter measurement data in a user interface on the wearable device 10. In response to receiving physiological parameter measurement data from the wearable device 10, the computing device 2802 may display the user interfaces described herein, such as with reference to FIGS. 30B, 30C, 30F and/or 30G. The computing device 2802 may display the physiological parameter measurement data in substantially real-time, for example, as the wearable device 10 performs the monitoring operation and measures the one or more physiological parameters.

In some implementations, the wearable device 10 may generate user interface data to display physiological parameter measurement data to a wearer/user of the wearable device 10. For example, the wearable device 10 may display the user interfaces described herein on a display screen 12 of the wearable device 10, such as with reference to FIGS. 38A-38B. The wearable device 10 may display the physiological parameter measurement data in substantially real-time, for example, as the wearable device 10 performs the monitoring operation and measures the one or more physiological parameters.

Additional Implementation Details

Figure 40:
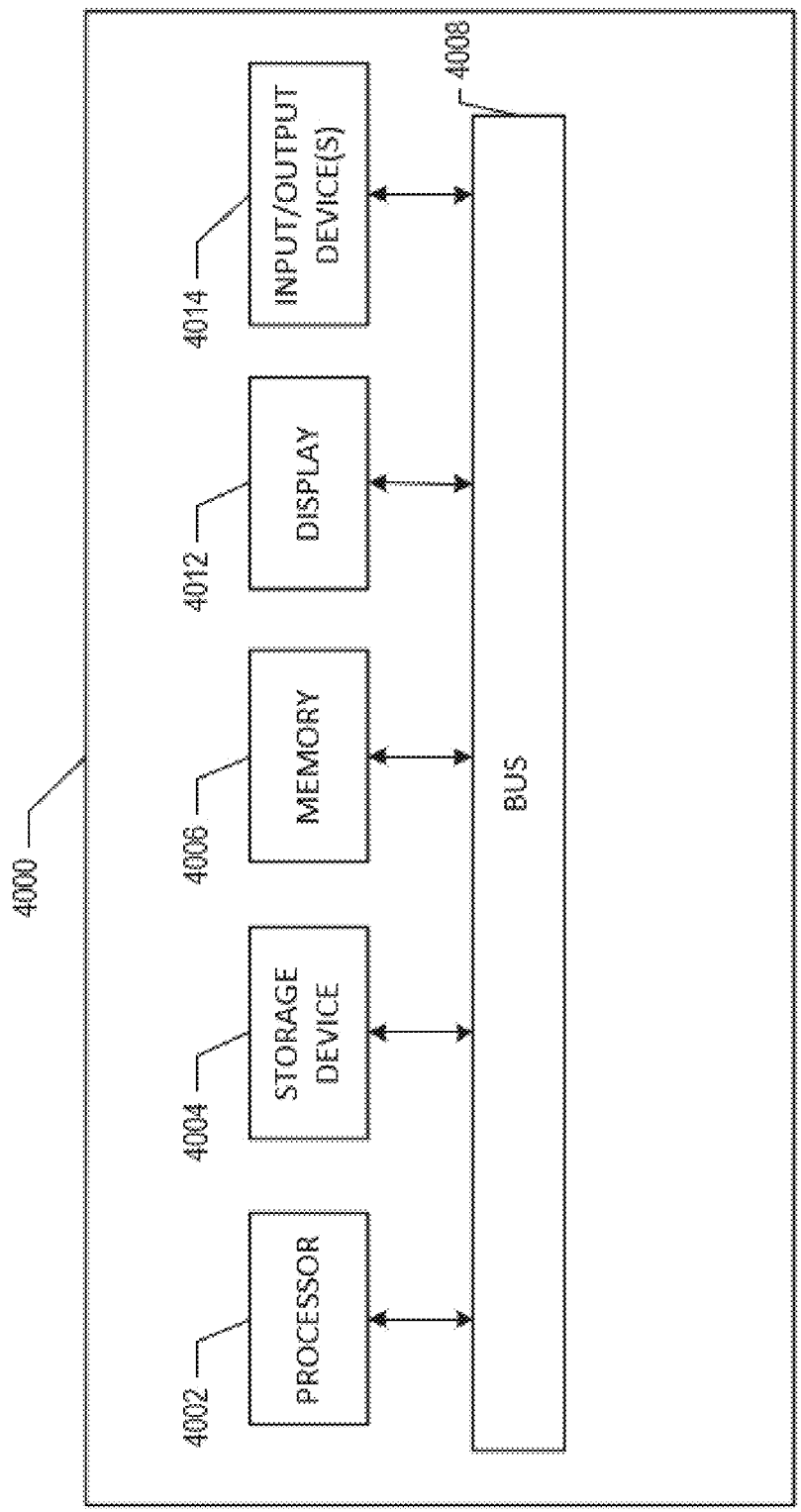

FIG. 40 is a block diagram that illustrates example components of a computing device 4000. The computing device 4000 can implement aspects of the present disclosure, and, in particular, aspects of the wearable device 10 and/or the computing device 2802 of FIG. 28. The computing device 4000 can communicate with other computing devices.

The computing device 4000 can include a hardware processor 4002, a data storage device 4004, a memory device 4006, a bus 4008, a display 4012, and one or more input/output devices 4014. A processor 4002 can also be implemented as a combination of computing devices, e.g., a combination of a digital signal processor and a microprocessor, a plurality of microprocessors, one or more microprocessors in conjunction with a digital signal processor, or any other such configuration. The processor 4002 can be configured, among other things, to process data, execute instructions to perform one or more functions, such as process one or more physiological signals to obtain one or measurements, as described herein. The data storage device 4004 can include a magnetic disk, optical disk, or flash drive, etc., and is provided and coupled to the bus 4008 for storing information and instructions. The memory 4006 can include one or more memory devices that store data, including without limitation, random access memory (RAM) and read-only memory (ROM). The computing device 4000 may be coupled via the bus 4008 to a display 4012, such as an LCD display or touch screen, for displaying information to a user. The computing device 4000 may be coupled via the bus 4008 to one or more input/output devices 4014. The input device 4014 can include, but is not limited to, a keyboard, mouse, digital pen, microphone, touch screen, gesture recognition system, voice recognition system, imaging device (which may capture eye, hand, head, or body tracking data and/or placement), gamepad, accelerometer, or gyroscope.

Terminology

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain aspects, the terms "generally parallel" and "substantially parallel" refer to a value, amount, or characteristic that departs from exactly parallel by less than or equal to 10 degrees, 5 degrees, 3 degrees, or 1 degree. As another example, in certain aspects, the terms "generally perpendicular" and "substantially perpendicular" refer to a value, amount, or characteristic that departs from exactly perpendicular by less than or equal to 10 degrees, 5 degrees, 3 degrees, or 1 degree.

Many other variations than those described herein will be apparent from this disclosure. For example, certain acts, events, or functions of any of the algorithms described herein can be performed in a different sequence, can be added, merged, or left out altogether (for example, not all described acts or events are necessary for the practice of the algorithms). Moreover, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

It is to be understood that not necessarily all such advantages can be achieved in accordance with any particular example of the examples disclosed herein. Thus, the examples disclosed herein can be embodied or carried out in a manner that achieves or optimizes one advantage or group of advantages as taught herein without necessarily achieving other advantages as may be taught or suggested herein.

The various illustrative logical blocks, modules, and algorithm steps described in connection with the examples disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the examples disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry or digital logic circuitry configured to process computer-executable instructions. In another example, a processor can include an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the examples disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The term "substantially" when used in conjunction with the term "real-time" forms a phrase that will be readily understood by a person of ordinary skill in the art. For example, it is readily understood that such language will include speeds in which no or little delay occurs.

Conditional language used herein, such as, among others, "can," "might," "may," "for example," and the like, unless specifically stated otherwise, or otherwise understood within the context as used, is generally intended to convey that certain examples include, while other examples do not include, certain features, elements and/or states. Thus, such conditional language is not generally intended to imply that features, elements and/or states are in any way required for one or more examples or that one or more examples necessarily include logic for deciding, with or without author input or prompting, whether these features, elements and/or states are included or are to be performed in any particular example. The terms "comprising," "including," "having,"

and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain examples require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various examples, it will be understood that various omissions, substitutions, and changes in the form and details of the devices or algorithms illustrated can be made without departing from the spirit of the disclosure. As will be recognized, the inventions described herein can be embodied within a form that does not provide all of the features and benefits set forth herein, as some features can be used or practiced separately from others.

Additionally, all publications, patents, and patent applications mentioned in this specification are herein incorporated by reference to the same extent as if each individual publication, patent, or patent application was specifically and individually indicated to be incorporated by reference.

What is claimed is:

1. An optical physiological sensor integrated into a wearable device, the optical physiological sensor comprising:
   a substrate having an optical center;
   a first emitter group of light emitting diodes (LEDs) positioned adjacent to the optical center of the substrate and spaced at an offset from the optical center;
   a second emitter group of LEDs positioned adjacent to the optical center of the substrate at an offset to the optical center and spaced at an offset from the optical center opposite the first emitter group of LEDs relative to the optical center;
   a plurality of detectors arranged in an annular spatial configuration that surrounds the first emitter group and the second emitter group, wherein each of the plurality of detectors are positioned on the substrate a same distance away from the optical center of the substrate, wherein the annular spatial configuration has a radius of less than 6.75 mm; and
   a light barrier construct mounted on the substrate and defining a first emitter chamber that houses the first emitter group of LEDs, and a second emitter chamber that houses the second emitter group of LEDs, wherein the light barrier construct is configured to optically isolate the first emitter group of LEDs from the second emitter group of LEDs.

2. The sensor of claim 1, wherein the light barrier construct defines a maximum height extending away from the substrate at the optical center of the substrate.

3. The sensor of claim 1, wherein the light barrier construct comprises a light barrier configured to isolate the first emitter group from the second emitter group, wherein a width of the light barrier is less than 1.40 mm.

4. The sensor of claim 1, wherein the first emitter group is configured to emit optical radiation having a same wavelength as optical radiation emitted from the second emitter group.

5. The sensor of claim 1, wherein an arrangement of the LEDs of the first emitter group on the substrate mirrors an arrangement of the LEDs of the second emitter group on the substrate across a centerline of the sensor that bisects the sensor.

6. The sensor of claim 5, wherein the centerline of the sensor bisects at least one of the plurality of detectors.

7. The sensor of claim 6, wherein a distance from the first emitter group to the at least one of the plurality of detectors is the same as a distance from the second emitter group to the at least one of the plurality of detectors.

8. The sensor of claim 1, further comprising a reference electrode and a negative electrode located on the light barrier construct of the optical physiological sensor.

9. The sensor of claim 8, wherein the reference electrode is semi-annular and wherein the negative electrode is semi-annular.

10. The sensor of claim 9, wherein the reference and negative electrodes surround the plurality of detectors.

11. The sensor of claim 1, wherein the plurality of detectors includes a first detector group and a second detector group, wherein the first detector group includes at least two detectors housed in respective detector chambers, and wherein the second detector group includes at least two detectors housed in respective detector chambers.

12. The sensor of claim 11, wherein a distance between the first emitter group and the first detector group is greater than a distance between the second emitter group and the first detector group.

13. The sensor of claim 1, wherein the first emitter group comprises:
   a first LED configured to emit optical radiation having a first wavelength of between 620 nm and 660 nm;
   a second LED configured to emit optical radiation having a third wavelength of between 650 nm and 670 nm; and
   a third LED configured to emit optical radiation having a third wavelength of between 900 nm and 910 nm.

14. The sensor of claim 13, wherein the second emitter group is configured to emit optical radiation having the first, second, and third wavelengths.

15. An optical physiological sensor integrated into a wearable device, the optical physiological sensor comprising:
   a substrate having an optical center;
   a first emitter group of light emitting diodes (LEDs) positioned adjacent to the optical center of the substrate and spaced at an offset from the optical center;
   a second emitter group of LEDs positioned adjacent to the optical center of the substrate at an offset to the optical center and spaced at an offset from the optical center opposite the first emitter group of LEDs relative to the optical center;

a plurality of detectors arranged in a spatial configuration that surrounds the first and the second emitter group, wherein each of the plurality of detectors are positioned on the substrate a same distance away from the optical center of the substrate; and a light barrier construct mounted on the substrate and defining a first emitter chamber that houses the first emitter group of LEDs, and a second emitter chamber that houses the second emitter group of LEDs, wherein the light barrier construct comprises a light barrier configured to optically isolate the first emitter group of LEDs from the second emitter group of LEDs, wherein a width of the light barrier is less than 1.40 mm.

16. The sensor of claim 15, wherein the spatial configuration is annular.

17. The sensor of claim 15, wherein the light barrier construct defines a maximum height extending away from the substrate at the optical center of the substrate.

18. The sensor of claim 15, wherein the first emitter group is configured to emit optical radiation having a same wavelength as optical radiation emitted from the second emitter group.

19. The sensor of claim 15, wherein an arrangement of the LEDs of the first emitter group on the substrate mirrors an arrangement of the LEDs of the second emitter group on the substrate across a centerline of the sensor that bisects the sensor.

20. The sensor of claim 19, wherein the centerline of the sensor bisects at least one of the plurality of detectors.

21. The sensor of claim 20, wherein a distance from the first emitter group to the at least one of the plurality of detectors is the same as a distance from the second emitter group to the at least one of the plurality of detectors.

22. The sensor of claim 15, further comprising a reference electrode and a negative electrode located on the light barrier construct of the optical physiological sensor.

23. The sensor of claim 22, wherein the reference electrode is semi-annular and wherein the negative electrode is semi-annular.

24. The sensor of claim 22, wherein the reference and negative electrodes surround the plurality of detectors.

25. The sensor of claim 15, wherein the plurality of detectors includes a first detector group and a second detector group, wherein the first detector group includes at least two detectors housed in respective detector chambers, and wherein the second detector group includes at least two detectors housed in respective detector chambers.

26. The sensor of claim 25, wherein a distance between the first emitter group and the first detector group is greater than a distance between the second emitter group and the first detector group.

27. The sensor of claim 15, wherein the first emitter group comprises:
a first LED configured to emit optical radiation having a first wavelength of between 620 nm and 660 nm;
a second LED configured to emit optical radiation having a third wavelength of between 650 nm and 670 nm; and
a third LED configured to emit optical radiation having a third wavelength of between 900 nm and 910 nm.

28. The sensor of claim 27, wherein the second emitter group is configured to emit optical radiation having the first, second, and third wavelengths.

* * * * *